US011041176B2

(12) United States Patent
Rush et al.

(10) Patent No.: US 11,041,176 B2
(45) **Date of Patent: *Jun. 22, 2021**

(54) YEAST CELLS HAVING REDUCTIVE TCA PATHWAY FROM PYRUVATE TO SUCCINATE AND OVEREXPRESSING AN EXOGENOUS NAD(P)+ TRANSHYDROGENASE ENZYME

(71) Applicant: Cargill, Incorporated, Wayzata, MN (US)

(72) Inventors: Brian J. Rush, Minneapolis, MN (US); Kevin T. Watts, Minneapolis, MN (US); Vernon L. McIntosh, Jr., Minneapolis, MN (US); Arlene M. Fosmer, Eden Prairie, MN (US); Gregory M. Poynter, St. Paul, MN (US); Thomas W. McMullin, Minnetonka, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/816,779

(22) Filed: Nov. 17, 2017

(65) Prior Publication Data

US 2018/0100170 A1 Apr. 12, 2018

Related U.S. Application Data

(62) Division of application No. 14/416,633, filed as application No. PCT/US2013/052069 on Jul. 25, 2013, now Pat. No. 9,850,507.

(60) Provisional application No. 61/675,788, filed on Jul. 25, 2012.

(51) Int. Cl.

| | |
|---|---|
| ***C12P 7/46*** | (2006.01) |
| ***C12N 1/19*** | (2006.01) |
| ***C12N 9/02*** | (2006.01) |
| ***C12P 7/52*** | (2006.01) |
| ***C12P 5/02*** | (2006.01) |
| ***C12P 7/42*** | (2006.01) |
| ***C12N 15/52*** | (2006.01) |
| ***C12P 7/18*** | (2006.01) |
| ***C12N 9/04*** | (2006.01) |
| ***C12N 9/88*** | (2006.01) |
| ***C12N 9/00*** | (2006.01) |

(52) U.S. Cl.

CPC ................ *C12P 7/52* (2013.01); *C12N 9/001* (2013.01); *C12N 9/0006* (2013.01); *C12N 9/0036* (2013.01); *C12N 9/88* (2013.01); *C12N 9/93* (2013.01); *C12N 15/52* (2013.01); *C12P 5/026* (2013.01); *C12P 7/18* (2013.01); *C12P 7/42* (2013.01); *C12P 7/46* (2013.01); *C12Y 106/01001* (2013.01); *C12Y 101/01* (2013.01); *C12Y 106/01* (2013.01); *C12Y 402/01002* (2013.01); *C12Y 604/01001* (2013.01); *Y02E 50/30* (2013.01)

(58) Field of Classification Search

None

See application file for complete search history.

(56) References Cited

U.S. PATENT DOCUMENTS

| | | | | |
|---|---|---|---|---|
| 4,275,234 | A | 6/1981 | Baniel | |
| 4,771,001 | A | 9/1988 | Bailey | |
| 5,132,456 | A | 7/1992 | King | |
| 5,420,304 | A | 5/1995 | Verser | |
| 5,510,526 | A | 4/1996 | Baniel | |
| 5,641,406 | A | 6/1997 | Sarhaddar | |
| 5,831,122 | A | 11/1998 | Eyal | |
| 5,876,983 | A | 3/1999 | Sugimoto | |
| 6,485,947 | B1 | 11/2002 | Rajgarhia | |
| 9,605,285 | B2 | 3/2017 | Finley | |
| 9,850,507 | B2 * | 12/2017 | Rush | C12P 5/026 |
| 9,885,065 | B2 | 2/2018 | Rush | |
| 2003/0087381 | A1 | 5/2003 | Gokarn | |
| 2004/0199940 | A1 | 10/2004 | Karunanandaa | |
| 2007/0027309 | A1 | 2/2007 | Weinstock | |
| 2007/0118916 | A1 | 5/2007 | Puzio | |
| 2008/0009041 | A1 | 1/2008 | Mizoguchi | |
| 2008/0090273 | A1 | 4/2008 | Winkler | |
| 2008/0148432 | A1 | 6/2008 | Abad | |
| 2008/0293113 | A1 | 11/2008 | Koseki | |
| 2009/0053782 | A1 | 2/2009 | Dundon | |
| 2009/0191599 | A1 | 7/2009 | Devroe | |
| 2009/0226989 | A1 | 9/2009 | Suominen et al. | |
| 2010/0009419 | A1 | 1/2010 | Burk | |
| 2010/0120105 | A1 | 5/2010 | Anthony | |

(Continued)

FOREIGN PATENT DOCUMENTS

| | | | |
|---|---|---|---|
| EP | 17512921 | A | 2/2007 |
| EP | 2495304 | A1 | 9/2012 |

(Continued)

OTHER PUBLICATIONS

Molina, A.M., "Design and Implementation of Metabolic Networks for the Improvement of Products Yields in Cofactor-Limiting Systems in *Escherichia coli*", Doctoral Dissertation, University of Texas, Houston, 2005.

(Continued)

*Primary Examiner* — David Steadman

(57) ABSTRACT

Yeast cells having a reductive TCA pathway from pyruvate or phosphoenolpyruvate to succinate, and which include at least one exogenous gene overexpressing an enzyme in that pathway, further contain an exogenous transhydrogenase gene.

1 Claim, No Drawings

Specification includes a Sequence Listing.

(56) References Cited

U.S. PATENT DOCUMENTS

| | | | |
|---|---|---|---|
| 2010/0184171 | A1 | 7/2010 | Jantama |
| 2010/0280803 | A1 | 11/2010 | Famili |
| 2011/0008861 | A1 | 1/2011 | Berry |
| 2011/0020889 | A1 | 1/2011 | Feldman |
| 2011/0022994 | A1 | 1/2011 | Hu et al. |
| 2011/0129885 | A1 | 6/2011 | Lang |
| 2011/0143405 | A1 | 6/2011 | Verwaal |
| 2011/0201089 | A1 | 8/2011 | Burgard |
| 2011/0207189 | A1 | 8/2011 | Burgard |
| 2011/0300595 | A1 | 12/2011 | Lang |
| 2012/0040422 | A1 | 2/2012 | Jansen |
| 2012/0135482 | A1 | 5/2012 | Jansen |
| 2012/0165569 | A1 | 6/2012 | Verwaal |
| 2013/0302866 | A1 | 11/2013 | Finley |
| 2013/0309736 | A1 | 11/2013 | Finley |
| 2014/0031587 | A1 | 1/2014 | Verwaal |

FOREIGN PATENT DOCUMENTS

| | | | |
|---|---|---|---|
| KR | 101028039 | B1 | 4/2011 |
| WO | 1993000440 | A1 | 1/1993 |
| WO | 1999014335 | A1 | 3/1999 |
| WO | 9953035 | W | 10/1999 |
| WO | 0003021 | A2 | 1/2000 |
| WO | 0003021 | A3 | 1/2000 |
| WO | 2000071738 | A1 | 11/2000 |
| WO | 2002010425 | A2 | 2/2002 |
| WO | 2002042471 | A2 | 5/2002 |
| WO | 2003049525 | A2 | 6/2003 |
| WO | 2003102152 | A2 | 12/2003 |
| WO | 2003102200 | A2 | 12/2003 |
| WO | 2003102201 | A2 | 12/2003 |
| WO | 2007061590 | A1 | 5/2007 |
| WO | 2007106524 | A2 | 9/2007 |
| WO | 2008128522 | A2 | 10/2008 |
| WO | 2008144626 | A1 | 11/2008 |
| WO | 2009011974 | A1 | 1/2009 |
| WO | 2009062190 | A2 | 5/2009 |
| WO | 2009062190 | A3 | 5/2009 |
| WO | 2009065778 | A1 | 5/2009 |
| WO | 2009065780 | A1 | 5/2009 |
| WO | 2009101180 | A2 | 8/2009 |
| WO | 2010003728 | A1 | 1/2010 |
| WO | 2010043197 | A1 | 4/2010 |
| WO | 2010051527 | A2 | 5/2010 |
| WO | 2010051527 | A3 | 5/2010 |
| WO | 2010147920 | A1 | 12/2010 |
| WO | 2011023700 | A2 | 3/2011 |
| WO | 2011041426 | A1 | 4/2011 |
| WO | 20110641511 | W | 6/2011 |
| WO | 2012103261 | A2 | 8/2012 |
| WO | 2013004670 | A1 | 1/2013 |
| WO | 2013112939 | A2 | 8/2013 |
| WO | 2013112939 | A3 | 8/2013 |
| WO | 2014018755 | A1 | 1/2014 |

OTHER PUBLICATIONS

Anderlund et al., "Expression of the *Escherichia coli* pntA and pntB Genes, Encoding Nicotinamide Nucleotide Transhydrogenase, in *Saccharomyces cerevisiae* and its Effets on Products Formation during Anaerobic Glucose Fermentation", Appl. Environ. Microbiol., 65:2333-2340, 1999.

Boonstra et al., "Cofactor Regeneration by a Soluble Pyridine Nucleotide Transhydrogenase for Biological Production of Hydromorphone", Appl. Environ. Microbiol., 66:5161-5166, 2000.

Raab et al., "Oxidative versus reductive succinic acid production in the yeast *Saccharomyces cerevisiae*", Bioengineered Bugs vol. 2, pp. 120-123, Mar. 1, 2011.

Kabir et al., "Fermentation characteristics and protein expression patterns in a recombinant *Escherichia coli* mutant lacking phosphoglucose isomerase for poly(3-hydroxybutyrate) production", Applied Microbiology and Biotechnology vol. 62, pp. 244-255, Aug. 1, 2003.

Cadiere, A. et al., "The *Saccharomyces cerevisiae* zinc factor protein Stb5p is required as a basal regulator of the pentose phosphate pathway", FEMS Yeast Research vol. 10, pp. 819-827, Nov. 1, 2010.

Qiang et al., "Responses of the central merabolism in *Escherichia coli* to Phosphoglucose Isomerase and Glucose-6-Phosphate Dehydrogenase Knockouts", J. Bacteriology vol. 185, pp. 7053-7067, Dec. 2003.

Hall et al., "Structure-function analysis of NADPH: nitrate reductase from Aspergillus nidulans: analysis of altered pyridine nucleotide specificity in vivo", Microbiology (Reading, England), vol. 146, pp. 1399-1406, Jun. 2000.

Dohr et al., "Engineering of a functional human NADH-dependent cytrochrome P450 system", Proceedings of the National Academy of Sciences of the United States of America vol. 98, pp. 81-86, Jan. 2, 2001.

Nakayama et al., "Characteristics of the high malic acid production mechanism in sake yeast strain No. 28", J. Bioscience and Bioengineering, vol. 114, pp. 281-285, Apr. 13, 2012.

Beauprez et al., "Influence of C4-dicarboxylic acid transporters on succinate production", Green Chemistry vol. 13, pp. 2179-2186, Jan. 1, 2011.

Cheng et al., "Biotechnological production of succinic acid: current state and perspectives" Biofuels, Bioproduction & Biorefining, vol. 6, pp. 302-318, Feb. 29, 2012, XP055091914.

Otero et al., "Industrial systems biology of *Saccharomyces cerevisiae* enables novel succinic acid cell factory", PLOS ONE vol. 8(e54144), pp. 1-10, Jan. 21, 2013, XP002750949.

Papagianni, "Recent advances in enginerring the central carbon metabolism of industrially important bacteria", Microbial Cell Factories, vol. 11, pp. 1-13, Apr. 30, 2012, XP021126659.

Raab et al., "Metabolic engineering of *Saccharomyces cerevisiae* for the biotechnological production of succinic acid", Metabolic Engineering, vol. 12, pp. 518-525, 2010, XP055052799.

Thalagala et al., "Study of ethanol fermentation using D-glucose rich fractions obtained from lignocelluloses by a two-step extraction with sulfuric acid and Issatchenkia orientalis MF 121", Journal of Applied Glycoscience, vol. 56, pp. 7-11, 2009, XP002750966.

Camarosa et al, "Investigation by 13C-NMR and tricarboxylic acid (TCA) deletion mutant analysis of pathways for succinate formation in *Saccharamyces cerevisiae* during anaerobic fermentation", Microbiology (2003) 149, 2269-2278.

Nissen et al., "Expression of a Cytoplasmic Transhydrogenase in *Saccharomyces cerevisiae* Results in Formation of 2-Oxoglutarate Due to Depletion of the NADPH pool", Yeast, 2001, 17, pp. 19-32.

Bastian et al., "Engineered Ketol-Acid Reductoisomerase and Alcohol Dehydrogenase Enable Anaerobic 2-Methylpropan-1-ol Production at Theoretical Yield in *Escherichia coli*" Metabolic Engineering, 2011, 13, pp. 345-352.

Guo et al., "Mini-Review: In vitro Metabolic Engineering for Biomanufacturing of High-Value Products", Computational and Structural Biotechnology Journal, 2017, 15, pp. 161-167.

Nakayama, S. et al., "Candida krusei produces ethanol without production of succinic acid; a potential advantage for ethanol recovery by pervaporation membrane separation", FEMS Yeast Res 8, pp. 706-714, 2008.

Zelle, R.M. et al., "Malic Acid Production by *Saccharomyces cerevisiae*: Engineering of Pyruvate Carboxylation, Oxaloacetate Reduction, and Malate Export", Applied and Environmental Microbiology, vol. 74, No. 9, pp. 2766-2777, May 2008.

Abbott, D.A. et al., "Metabolic engineering of *Saccharomyces cerevisiae* for production of carboxylic acids: current status and challenges", FEMS Yeast Res 9, pp. 1123-1136, 2009.

Anonymous: "Candida krusei (Castellani) Berkhout, anamorph ATCC 60585(TM)", Jan. 1, 1982 (Jan. 1, 1982), XP055203286, Retrieved from the Internet: URL:http://www.lgcstandards-atcc.org/products/all/60585.aspx? geo_country=nl#history.

Anonymous: "Pichia fermentans Lodder ATCCc 38617(TM)", Jan. 1, 2978 (Jan. 1, 1978), XP055203287, Retrieved from the Internet: URL:http://www.lgcstandards-atcc.org/Products/All/38617.aspx#history.

(56) References Cited

OTHER PUBLICATIONS

Bioreaction Engineering Principles, 2nd ed., Kluwer Academic/Plenum Publishers, (2003), p. 449.
Broun et al., Catalytic plasticity of fatty acid modification enzymes underlying chemical diversity of plant lipids, Science, 1998, vol. 282: 1315-1317.
Chica, et al., Semi-rational approaches to engineering enzyme activity: combining the benefits of directed evolution and rational design, Curr. Opi. Biotechnol. 16:, 378-384, 2005.
Datta et al., “Technological and economic potential of poly(lactic acid) and lactic acid derivatives,” FEMS Microbioal Rev., 1995, vol. 16, pp. 221-231.
Devos et al., Practical limits of function prediction. Proteins: Structure, Function and Genetics, 2000, vol. 41: 98-107.
Famili et al., “*Saccharomyces cerevisiae* phenotypes can be predicted by using constraint-based analysis of a genome-scale reconstructed metabolic network,” Proc Natl Acad Sci USA, 2003, vol. 100, No. 23, pp. 13134-13139.
Gietz et al., “Transformation of Yeast by Lithium Acetate/Single-Stranded Carrier DNA/Polyethylene Glycol Method,” Met Enzymol, 2002, vol. 350, pp. 87-96.
Gross et al., “Acidophilic and acid-tolerant fungi and yeasts,” Hydrobiologia, 2000, vol. 433, pp. 91-109.
Guccione et al., “Reduction of fumarate, mesaconate and crotonate by Mfr, a novel oxygen-regulated periplasmic reductase in Campylobacter jejuni,” Environ Microbiol, 2010, vol. 12, No. 3, pp. 576-591.
Harder et al., “Microbial Selection in Continuous Culture,” J Appl Bacteriol, 1977, vol. 43, pp. 1-24.
Hjersted et al., “Genome-Scale Analysis of *Saccharomyces cerevisiae* Metabolism and Ethanol Production in Fed-Batch Culture,” Biotechnol Bioeng, 2007, vol. 97, No. 5, pp. 1190-1204.
Kisselev L., Polypeptide release factors in prokaryotes and eukaryotes: same function, different structure. Structure, 2002, vol. 10: 8-9.
Kurtzman; Fell, “The Yeasts, a Taxonomic Study, Section 35”, Issatchenkia Kudryavtsev, (1998), pp. 222-223.
Kurtzman; Robnett, “Identification and Phylogeny of Ascomycetous Yeasts from Analysis of Nuclear Large Subunit (26S) Ribosomal DNA Partial Sequences”, Antonie Van Leeuwenhoek, (1998), vol. 73, pp. 331-371.
Magnuson et al., “Organic Production by Filamentous Fungi,” Advances in Fungal Biotechnology for Industry, Agriculture, and Medicine, 2004, pp. 307-340.
NCBI Accession No. 476733.1, http://www.ncbi.nlm.nih.gov/nuccore/76152006?sat=11&satkey=491535), Sep. 23, 2005.
NCBI Accession No. 476733.1, http://www.ncbi.nlm.nih.gov/nuccore/CH476733#, Apr. 18, 2012.
Novick et al., “Experiments with the Chemostat on Spontaneous Mutations of Bacteria,” Proc Natl Sci USA, 1950, vol. 36, pp. 708-719.
OK Taing et al., “Production of malic and succinic acids by sugar-tolerant yeast *Zygosaccharomyces rouxii*”, European Food Research and Technology; Zeitschrift Fur Lebensmitteluntersuchung Und-Forschung A, Springer, Berlin, DE, vol. 224, No. 3, Mar. 31, 2006, pp. 343-347, XP019458173, ISSN: 1438-2385, DOI:10.1007/S00217-006-0323-Z.
Patil et al., “Evolutionary programming as a platform for in silico metabolic engineering”, BMC Bioinformatics 2005, 6:308.
Pentose Phosphate Pathway, Sigma-Aldrich 2007 [online], Retrieved on Jul. 5, 2012 from the internet <URL: http://www.sigmaaldrich.com/technical-documents/articles/biofiles/pentose-phosphase.html>.
Seffernick et al., Melamine deaminase and Atrazine chlorohydrolase: 98 percent identical but functionally different. J. Bacteriol., 2001, vol. 183(8): 2405-2410.
Sen et al., Developments in directed evolution for improving enzyme functions. Appl. Biochem. Biotechnol., 2007, vol. 143: 212-223.
Souciet et al., Zygosaccharomyces rouxii strain CBS732 chromosome C complete sequence, GenBank Accession No. CU928175.1, Jan. 14, 2010 (Jan. 14, 2010), Retrieved on Jul. 18, 2012, available at <http://www.ncbi.nlm.nih.gov/nuccore/CU928175>.
T.B. Vickory, Comprehensive Biotechnology, 1985, Chapter 38, pp. 761-776.
The Genolevures Consortium, Comparative genomics of protoploid Saccharomycetaseae, Uniprot C5DSS7_ZYGRC, Jul. 28, 2009 (Jul. 28, 2009), Retrieved on Jul. 18, 2012, available at <http://www.uniprot.org/uniprot/C5DSS7.txt?version=3>.
Thomas et al., “Identification of the structural gene for glucose-6-phosphase dehydrogenase in yeast. Inactivation leads to a nutritional requirement for organic sulfur,” EMBO Journal, 1991, vol. 10, pp. 547-553.
Verduyn, C., et al. Effect of benzoic acidon metabolic fluxes in yeasts: A continuous-culture study on the regulation of respiration and alcoholic fermentation. YEAST, vol. 8, Issue 7, pp. 501-517, Jun. 1992.
Whisstock et al., Prediction of protein function from protein sequence. Q. Rev. Biophysics., 2003, vol. 36 (3): 307-340.
Wishart et al., A single mutation converts a novel phophotyrosine binding domain into a dual-specificity phosphatase. J. Biol. Chem., 1995, vol. 270(45): 26782-26785.
Witkowski et al., Conversion of b-ketoacyl synthase to a Malonyl Decarboxylase by replacement of the active cysteine with glutamine. Biochemistry, 1999, vol. 38: 11643-11650.
Zhang et al., Candida glycerinogenese glucose 6-phosphate dehydrogenase gene, partial cds, GenBank Accession No. EF373653, Feb. 11, 2007 (Feb. 7, 2007, Retrieved on Jul. 18, 2012, available at <http://www.ncbi.nim.nih.gov/nuccore/EF373653>.
Zhang et al., “Cloning and characterization of the partial gene CgZWF encoding glucose 6-phosphate dehydrogenase from Candida glycerinogenes,” Uniprot A3FFK8_CANGY Mar. 20, 2007 (Mar. 20, 2007), Retrieved on Jul. 18, 2012, available at <http://www.uniprot.org/uniprot/A3FFK8.text?version=13>.

* cited by examiner

YEAST CELLS HAVING REDUCTIVE TCA PATHWAY FROM PYRUVATE TO SUCCINATE AND OVEREXPRESSING AN EXOGENOUS NAD(P)+ TRANSHYDROGENASE ENZYME

This application is a divisional of U.S. patent application Ser. No. 14/416,633, filed Jan. 22, 2015 (U.S. Pat. No. 9,850,507), which is a U.S. national stage of International Patent Application No. PCT/US2013/052069, filed Jul. 25, 2013, which claims benefit of Provisional Application No. 61/675,788, filed Jul. 25, 2012, each of which is incorporated herein by reference.

The instant application contains a sequence listing which has been submitted electronically in ASCII format and is hereby incorporated by reference in its entirety. Said ASCII copy, created on Dec. 9, 2017, is named "105464_000035_SL.txt" and is 527,808 bytes in size.

This invention relates to recombinant yeast having an active reductive TCA pathway from pyruvate to succinate. The inventions disclosed and claimed herein were made pursuant to a joint research agreement between Cargill Incorporated, Wayzta, Minn., US, and BioAmber S.A.S, Bazancourt, France.

Succinic acid is a chemical intermediate useful as a precursor for making compounds such as 1,4-butanediol, tetrahydrofuran and gamma-butyrolactone. It is also a useful diacid that can be polymerized with a polyol to make polyester resins. Succinic acid can be produced industrially from butane. However, butane is a petrochemical, and there is a strong desire to develop processes for making many chemical compounds from annually renewable resources such as plant or animal feedstocks.

Some microorganisms have evolved the ability to produce succinate from carbohydrate feedstocks. In some cases, these strains have been engineered to improve yield and/or productivity. WO 2007/061590 describes recombinant yeast cells that produce succinate. Some yeast species are of interest as candidates for succinic acid-producing fermentations because they are resistant to low pH conditions, and so can produce acidic fermentation products at a low pH at which the product acid exists mainly in the acid form rather than in the salt form. Producing the acid directly in the acid form simplifies recovery and purification, as salt splitting, with its attendant requirements for raw materials, capital, operating and disposal costs, can be reduced if not eliminated.

There are three primary fermentation pathways for by which a microorganism can produce succinate: oxidative tricarboxylic acid (TCA), glyoxylate shunt, and reductive TCA. The oxidative TCA pathway begins with the conversion of oxaloacetate (OAA) and acetyl-CoA to citrate. OAA can be generated from carboxylation of phosphoenolpyruvate (PEP) or pyruvate, while acetyl-CoA is generated from the decarboxylation of pyruvate by pyruvate dehydrogenase (PDH) or pyruvate formate lyase (PFL). Citrate is converted to isocitrate, isocitrate is converted to α-ketoglutarate, α-ketoglutarate is converted to succinyl-CoA, and succinyl-CoA is converted to succinate.

Like the oxidative TCA pathway, the glyoxylate shunt pathway begins with the generation of citrate from OAA and acetyl-CoA and the conversion of citrate to isocitrate. Isocitrate is converted to glyoxylate and succinate. Glyoxylate is condensed with acetyl-CoA to form malate, and the resultant malate is converted to succinate via a fumarate intermediate.

The reductive TCA pathway begins with carboxylation of phosphoenolpyruvate (PEP) or pyruvate to oxaloacetate (OAA) (by PEP carboxylase (PPC) and pyruvate carboxylase (PYC), respectively). OAA is converted to malate by malate dehydrogenase (MDH), malate is converted to fumarate by fumarase (FUM, also known as fumarate hydratase), and fumarate is converted to succinate by fumarate reductase (FRD). The reductive TCA pathway provides the highest succinate yield of the three succinate fermentation pathways, per mole of glucose consumed, and for that reason offers the best economic potential.

A problem with the reductive TCA pathway is that the MDH enzyme consumes NADH as a cofactor. In addition, certain efficient FRD enzymes also consume NADH. Examples of such NADH-dependent FRD enzymes are described, for example, in WO 2009/065778 and PCT/US2011/022612. Thus, certain efficient metabolic pathways from pyruvate to succinate consume two molecules of NADH. One molecule of NADH is produced when sugars such as glucose are metabolized to pyruvate via the glycolytic pathway, but this still leaves a net deficit of one NADH, which results in a redox imbalance. A living cell must correct this redox balance if it is to remain healthy and continue to metabolize through the reductive TCA pathway. This typically means that the cell must balance the net NADH consumption by replacing the consumed NADH from other metabolic processes that produce NADH. For example, the reductive TCA pathway can be combined with one or both of the oxidative TCA or glyoxylate shunt pathways to help with the redox balance, but the oxidative TCA and glyoxylate shunt pathways produce less succinic acid per mole of starting sugar, and taking this approach therefore results in a loss of yield. It is possible for the cell to use one or more unrelated pathways to produce the needed NADH, but this can have adverse consequences for cell health and productivity, and may create other imbalances within the cell.

Therefore, there remains a desire to provide a yeast strain that efficiently produces succinic acid (or its salts).

In one aspect, this invention is a recombinant yeast cell having an active reductive TCA metabolic pathway from pyruvate to succinate and which further overexpresses a $NAD(P)^+$ transhydrogenase enzyme.

In particular embodiments, the yeast cell of the invention has integrated into its genome at least one exogenous NAD(P)+ transhydrogenase gene that encodes for the NAD(P)+ transhydrogenase enzyme.

In other particular embodiments, the recombinant yeast cell of the invention (a) expresses an NADPH-dependent malate dehydrogenase enzyme, (b) has at least one exogenous NADPH-dependent malate dehydrogenase gene integrated into its genome, (c) expresses an NADPH-dependent fumarate reductase enzyme, (d) has at least one exogenous NADPH-dependent fumarate reductase gene integrated into its genome or (e) has a combination of any two or more of (a), (b), (c) and (d).

The recombinant yeast cell of the invention in some embodiments has integrated into its genome one or more of (i) an exogenous pyruvate carboxylase gene that encodes for an enzyme which catalyzes the conversion of pyruvate to oxaloacetate, (ii) an exogenous malate dehydrogenase gene which encodes for an enzyme that catalyzes the conversion of oxaloacetate to malate, (iii) an exogenous fumarase gene that encodes for an enzyme which catalyzes the conversion of malate to fumarate and (iv) an exogenous fumarate reductase gene that encodes an enzyme which catalyzes the conversion of fumarate to succinate. In some embodiments, the recombinant cell of the invention has integrated into its genome one or more of (i) a non-native pyruvate carboxylase gene that encodes for an enzyme which catalyzes the conversion of pyruvate to oxaloacetate, (ii) a non-native malate dehydrogenase gene which encodes for an enzyme that catalyzes the conversion of oxaloacetate to malate, (iii) a non-native exogenous fumarase gene that encodes for an enzyme which catalyzes the conversion of malate to fumarate and (iv) a non-native exogenous fumarate reductase gene which encodes an enzyme which catalyzes the conversion of fumarate to succinate.

In preferred embodiments, the recombinant cell of the invention has integrated into its genome at least one exogenous malate dehydrogenase gene which encodes for an NADH-dependent enzyme that catalyzes the conversion of oxaloacetate to malate. In other preferred embodiments, the recombinant cell of the invention has integrated into its genome at least one exogenous fumarate reductase gene which encodes for an NADH-dependent enzyme that catalyzes the conversion of fumarate to succinate. In especially preferred embodiments, the recombinant cell of the invention has both of these features.

In other specific embodiments, the recombinant cell of the invention overexpresses at least one enzyme which catalyzes a reaction that includes the reduction of NADP+ to NADPH. This reaction may be a reaction in the pentose phosphate pathway. The enzyme catalyzing that reaction may be, for example, a 6-phosphogluconate dehydrogenase (6PDGH) enzyme and/or a glucose 6-phosphate dehydrogenase (G6PDH) enzyme.

In still other specific embodiments, the recombinant cell of the invention overexpresses at least one Stb5p protein, and/or has at least one exogenous Stb5p gene (i.e., a gene that encodes for the Stb5p protein) integrated into its genome.

In still other specific embodiments, the recombinant cell of the invention has a deletion or disruption of a native phosphoglucose isomerase gene.

In the cells of any of the foregoing aspects of the invention, the NADH/NAD+ redox imbalance that is produced in the reductive TCA pathway to succinate is compensated for, at least in part, by converting NADPH formed in other cellular metabolic processes to NADH, which can be consumed in the succinate-producing pathway. This is a beneficial approach to solving the NADH/NAD+ redox imbalance, because yeast cells typically have, or can be easily engineered to have, active metabolic pathways that produce NADPH. A yeast cell's native pentose phosphate pathway is an example of a metabolic pathway that produces NADPH. Thus, NADPH can be produced in the cell by directing carbon flux through a pentose phosphate pathway, and all or a portion of the NADPH so produced can be converted to NADH by action of the overexpressed $NAD(P)^+$ transhydrogenase enzyme. Some or all of the NADH so produced can alleviate or even eliminate the NADH/NAD+ redox imbalance that results from succinate production through the reductive TCA pathway.

NADPH production can be increased (relative to the wild-type host cell), for example, by increasing carbon flux through the pentose phosphate pathway and/or by overexpressing at least one enzyme (including an enzyme in the pentose phosphate pathway) which catalyzes a reaction that includes the reduction of NADP+ to NADPH. Again, the increased NADPH so produced can be converted to NADH by action of the $NAD(P)^+$ transhydrogenase enzyme. As before, some or all of the NADH so produced can alleviate or even eliminate the NADH/NAD+ redox imbalance that results from succinate production through the reductive TCA pathway.

This, in some embodiments, the recombinant cell of the invention includes one or more genetic modifications that (1) increase flux through the pentose phosphate pathway and/or (2) overexpress one or more enzymes in the pentose phosphate pathway that catalyze a reaction that includes the reduction of NADP+ to NADPH. In certain embodiments, therefore, the recombinant cell of the invention also (a) overexpresses at least one Stb5p protein (b) has at least one exogenous Stb5p gene integrated into its genome, (c) produces a severely reduced quantity of an active phosphoglucose isomerase (PGI) enzyme, (d) produces a PGI enzyme that has a severely reduced activity, (e) has a deletion or disruption of a native PGI gene, (f) overexpresses at least one 6-phosphogluconate dehydrogenase (6PGDH) enzyme, (g) has at least one exogenous 6PGDH gene integrated into its genome, (h) overexpresses at least one glucose-6-phosphate dehydrogenase (G6PDH) enzyme, (i) has at least one exogenous G6PDH gene integrated into its genome, or (j) an combination of any two or more of (a)-(i).

The cell of the invention may produce succinate and transport it from the cell. In some embodiments, the cell may further metabolize some or all of the succinate into one or more other succinate metabolization products, and transport one or more of such succinate metabolization products from the cell. In such embodiments, the cell contains native or non-native metabolic pathways which perform the further metabolization of succinate into such succinate metabolization product(s).

In yet other aspects, the invention is a method of producing succinate or a metabolization product of succinate, comprising culturing a cell of any of the foregoing aspects in a fermentation medium that includes at least one carbon source. The cells of the invention are capable of producing succinate or metabolization products of succinate in high yields at commercially reasonable production rates.

The term "NADH-dependent" as used herein refers to the property of an enzyme to preferentially use NADH as the redox cofactor. An NADH-dependent enzyme has a higher specificity constant ($k_{cat}/K_M$) with the cofactor NADH than with other cofactors, including the cofactor NADPH, as determined by in vitro enzyme activity assays.

For purposes of this application, "native" as used herein with regard to a metabolic pathway refers to a metabolic pathway that exists and is active in the wild-type host strain. Genetic material such as genes, promoters and terminators is "native" for purposes of this application if the genetic material has a sequence identical to (apart from individual-to-individual mutations which do not affect function) a genetic component that is present in the genome of the wild-type host cell (i.e., the exogenous genetic component is identical to an endogenous genetic component).

For purposes of this application, genetic material such as a gene, a promoter and a terminator is "endogenous" to a cell if it is (i) native to the cell, (ii) present at the same location as that genetic material is present in the wild-type cell and (iii) under the regulatory control of its native promoter and its native terminator.

For purposes of this application, genetic material such as genes, promoters and terminators is "exogenous" to a cell if it is (i) non-native to the cell and/or (ii) is native to the cell, but is present at a location different than where that genetic material is present in the wild-type cell and/or (iii) is under the regulatory control of a non-native promoter and/or non-native terminator. Extra copies of native genetic material are considered as "exogenous" for purposes of this invention, even if such extra copies are present at the same locus as that genetic material is present in the wild-type host strain.

As used herein, the term "promoter" refers to an untranslated sequence located upstream (i.e., 5') to the translation start codon of a gene (generally a sequence of about 1 to 1500 base pairs (bp), preferably about 100 to 1000 bp and especially of about 200 to 1000 bp) which controls the start of transcription of the gene. The term "terminator" as used herein refers to an untranslated sequence located downstream (i.e., 3') to the translation finish codon of a gene (generally a sequence of about 1 to 1500 bp, preferably of about 100 to 1000 bp, and especially of about 200 to 500 bp) which controls the end of transcription of the gene. A promoter or terminator is "operatively linked" to a gene if its position in the genome relative to that of the gene is such that the promoter or terminator, as the case may be, performs its transcriptional control function.

"Identity" for nucleotide or amino acid sequences are for purposes of this invention calculated using BLAST (National Center for Biological Information (NCBI) Basic Local Alignment Search Tool) version 2.2.13 software with default parameters. A sequence having an identity score of XX % with regard to a reference sequence using the BLAST version 2.2.13 algorithm with default parameters is considered to be at least XX % identical or, equivalently, have XX % sequence identity to the reference sequence.

"Deletion or disruption" with regard to a gene means that either the entire coding region of the gene is eliminated (deletion) or the coding region of the gene, its promoter, and/or its terminator region is modified (such as by deletion, insertion, or mutation) such that the gene no longer produces an active enzyme, produces a severely reduced quantity (at least 75% reduction, preferably at least 85% reduction, more preferably at least 95% reduction) of the enzyme, or produces an enzyme with severely reduced (at least 75% reduced, preferably at least 85% reduced, more preferably at least 95% reduced) activity. A deletion or disruption of a gene can be accomplished by, for example, forced evolution, mutagenesis or genetic engineering methods, followed by appropriate selection or screening to identify the desired mutants.

"Overexpress" means the artificial expression of an enzyme in increased quantity by a gene. Overexpression of an enzyme may result from the presence of one or more exogeneous gene(s), or from other conditions. For purposes of this invention, a yeast cell containing at least one exogenous gene is considered to overexpress the enzyme(s) encoded by such exogenous gene(s).

The recombinant yeast of the invention is made by performing certain genetic modifications to a host yeast cell. The host yeast cell is one which as a wild-type strain is natively capable of metabolizing at least one sugar to pyruvate. Suitable host yeast cells include (but are not limited to) yeast cells classified under the genera *Candida, Pichia, Saccharomyces, Schizosaccharomyces, Zygosaccharomyces, Kluyveromyces, Debaryomyces, Pichia, Issatchenkia, Yarrowia* and *Hansenula. Examples of specific host yeast cells include C. sonorensis, K. marxianus, K. thermotolerans, C. methanesorbosa, Saccharomyces bulderi* (*S. bulderi*), *I. orientalis, C. lambica, C. sorboxylosa, C. zemplinina, C. geochares, P. membranifaciens, Z. kombuchaensis, C. sorbosivorans, C. vanderwaltii, C. sorbophila, Z. bisporus, Z. lentus, Saccharomyces bayanus* (*S. bayanus*), *D. castellii, C, boidinii, C. etchellsii, K. lactis, P. jadinii, P. anomala, Saccharomyces cerevisiae* (*S. cerevisiae*) *Pichia galeiformis, Pichia* sp. YB-4149 (NRRL designation), *Candida ethanolica, P. deserticola, P. membranifaciens, P. fermentans* and *Saccharomycopsis crataegensis* (*S. crataegensis*). Suitable strains of *K. marxianus* and *C. sonorensis* include those described in WO 00/71738 A1, WO 02/42471 A2, WO 03/049525 A2, WO 03/102152 A2 and WO 03/102201A2. Suitable strains of *I. orientalis* are ATCC strain 32196 and ATCC strain PTA-6648.

In some embodiments of the invention the host cell is Crabtree negative as a wild-type strain. The Crabtree effect is defined as the occurrence of fermentative metabolism under aerobic conditions due to the inhibition of oxygen consumption by a microorganism when cultured at high specific growth rates (long-term effect) or in the presence of high concentrations of glucose (short-term effect). Crabtree negative phenotypes do not exhibit this effect, and are thus able to consume oxygen even in the presence of high concentrations of glucose or at high growth rates.

In some embodiments, the host cell is succinate-resistant as a wild-type strain. A cell is considered to be "succinate-resistant" if the cell exhibits a growth rate in media containing 75 g/L or greater succinate at pH 2.8 that is at least 50% as high as its growth rate in the same media containing 0 g/L succinate, according to the test method described in Example 1A of WO 2012/103261.

In some embodiments, the host cell exhibits a volumetric glucose consumption rate of at least 3, at least 5 or at least 8 grams of glucose per liter of broth per hour, as a wild-type strain.

In some embodiments, the host cell exhibits a specific glucose consumption rate of at least 0.5, at least 1.0 or at least 1.5 gram of glucose per gram dry weight of cells per hour, as a wild-type strain.

Volumetric and specific glucose consumption can be measured by cultivating the cells in shake flasks yeast in extract peptone dextrose (YPD) media containing 0 g/l 75 g/L succinate at pH 3.0 a described in Example 1 of WO 2012/103261. The flasks are inoculated with biomass harvested from seed flasks grown overnight to an $OD_{600}$ of 6 to 10. 250 mL baffled glycolytic assay flasks (50 mL working volume) are inoculated to an $OD_{600}$ of 0.1 and grown at 250 RPM and 30° C. Samples are taken throughout the time course for the assay and analyzed for glucose consumption by electrophoretic methods (such as by using a 2700 Biochemistry Analyzer from Yellow Springs Instruments or equivalent device). The data is plotted and volumetric glucose consumption rate calculated. Specific glucose consumption rate is calculated by dividing the glucose consumption by the cell dry weight at the end of fermentation.

The genetically modified yeast cells provided herein have an active reductive TCA active pathway from pyruvate to succinate. Such an active reductive TCA pathway includes a step of converting pyruvate or phosphoenolpyruvate (PEP) (or each) to oxaloacetate (OAA), a step of converting oxaloacetate to malate, a step of converting malate to fumarate, and a step of converting fumarate to succinate.

The step of converting pyruvate to OAA is catalyzed by a PYC (pyruvate carboxylase) enzyme, i.e., an enzyme having the ability to catalyze the conversion of pyruvate to OAA. A PYC enzyme is encoded by a PYC (pyruvate carboxylase) gene integrated into the genome of the recombinant yeast cell. The PYC gene may be native or non-native to the host cell, and may be endogenous (if native) or exogenous (if non-native or if additional copies of a native gene are present). In certain embodiments, a PYC gene may be a yeast gene. For example, the PYC gene may be an *I. orientalis* PYC gene encoding for an enzyme having amino acid sequence SEQ ID NO: 94, an *S. cerevisiae* PYC1 gene encoding for an enzyme having amino acid sequence SEQ ID NO: 95, or a *K. marxianus* PYC1 gene encoding for an enzyme having amino acid SEQ ID NO: 96. In other embodiments, the gene may encode for an enzyme having an amino acid sequence with at least 50%, at least 60%, at least 70%, at least 80%, at least 85%, at least 90%, at least 95%, at least 97%, or at least 99% sequence identity to any of SEQ ID NOs: 94, 95 or 96. In certain embodiments, the gene may have the nucleotide sequence set forth in SEQ ID NOs: 4, 45 or 46, or a nucleotide sequence with at least 50%, at least 60%, at least 70%, at least 80%, at least 85%, at least 90%, at least 95%, at least 97%, or at least 99% sequence identity to any of SEQ ID NOs: 4, 45 or 46. In other embodiments, the PYC gene may be fungal.

The step of converting PEP to OAA is catalyzed by a PPC (phosphoenolpyruvate carboxylase) enzyme, i.e., an enzyme having the ability to catalyze the conversion of PEP to OAA. A PPC enzyme is encoded by a PPC (phosphoenolpyruvate carboxylase) gene integrated into the genome of the recombinant yeast cell. The PPC gene may be native or non-native to the host cell, and may be endogenous (if native) or exogenous (if non-native or if additional copies of a native gene are present). The PPC gene may encode for an enzyme having either of amino acid sequences SEQ ID NO: 97 or 115, or for an enzyme having an amino acid sequence with at least 50%, at least 60%, at least 70%, at least 80%, at least 85%, at least 90%, at least 95%, at least 97%, or at least 99% sequence identity to either of SEQ ID NOs: 97 or 115. In certain embodiments, the PPC gene may have the nucleotide sequence set forth in either of SEQ ID NOs: 49 or 50, or a nucleotide sequence with at least 50%, at least 60%, at least 70%, at least 80%, at least 85%, at least 90%, at least 95%, at least 97%, or at least 99% sequence identity to either of SEQ ID NOs: 49 or 50.

The step of converting OAA to malate is catalyzed by a MDH (malate dehydrogenase) enzyme, i.e., an enzyme having the ability to catalyze the conversion of OAA to malate. A MDH enzyme is encoded by a MDH (malate dehydrogenase) gene present in the genome of the recombinant yeast cell. The MDH gene may be native or non-native to the host cell, and may be endogenous (if native) or exogenous (if non-native or if additional copies of a native gene are present). The MDH enzyme preferably is NADH-dependent, i.e., one which uses NADH preferentially as a cofactor, and in converting OAA to malate also oxidizes NADH to NAD+. In the cells of this invention, the MDH enzyme preferably is overexpressed, by integrating one or more copies of an exogenous MDH gene (preferably at least two copies) into the genome of the cell. Preferred MDH genes encode for NADH-dependent MDH enzymes.

In certain embodiments, the MDH gene is a yeast MDH gene that encodes for an NADH-dependent MDH enzyme. For example, the MDH gene may be an *I. orientalis* MDH1, MDH2, or MDH3 gene encoding for an enzyme having any of the amino acid sequences SEQ ID NOs: 98, 99 or 100, respectively, a *Z. rouxii* MDH gene encoding for an enzyme having amino acid sequence SEQ ID NO: 101, a *K. marxianus* MDH1, MDH2, or MDH3 gene encoding for an enzyme having any of amino acid sequences SEQ ID NOs: 102, 103 or 104, respectively, or a gene encoding for an enzyme having an amino acid sequence with at least 50%, at least 60%, at least 70%, at least 80%, at least 85%, at least 90%, at least 95%, at least 97%, or at least 99% sequence identity to any thereof. In certain embodiments, the yeast MDH gene has the nucleotide sequence set forth in any of SEQ ID NOs: 58, 59, 60, 61, 62, 63 or 64 or a nucleotide sequence with at least 50%, at least 60%, at least 70%, at least 80%, at least 85%, at least 90%, at least 95%, at least 97%, or at least 99% sequence identity to any thereof.

In certain embodiments, the MDH gene is a bacterial MDH gene that encodes for an NADH-dependent MDH enzyme. For example, the MDH gene is in some embodiments an *Escherichia coli* (*E. coli*) MDH gene encoding for an enzyme having amino acid sequence SEQ ID NO: 105 or a gene that encodes for an enzyme having an amino acid sequence with at least 50%, at least 60%, at least 70%, at least 80%, at least 85%, at least 90%, at least 95%, at least 97%, or at least 99% sequence identity thereto. In certain embodiments, the bacterial MDH gene has the nucleotide sequence SEQ ID NO: 66 or a nucleotide sequence with at least 50%, at least 60%, at least 70%, at least 80%, at least 85%, at least 90%, at least 95%, at least 97%, or at least 99% sequence identity to either of those.

In certain embodiments, an MDH gene is a fungal MDH gene that encodes for an NADH-dependent MDH enzyme. For example, the MDH gene in some embodiments is a *Rhizopus. oryzae* (*R. oryzae*) MDH gene or a *Rhizopus delemar* (*R. delemar*) MDH gene encoding for an enzyme having amino acid sequence SEQ ID NO: 106 or 128 or a gene which encodes for an enzyme having amino acid sequence with at least 50%, at least 60%, at least 70%, at least 80%, at least 85%, at least 90%, at least 95%, at least 97%, or at least 99% sequence identity to either thereof. In certain embodiments, the fungal MDH gene has nucleotide sequence SEQ ID NO: 68 or 13 or a nucleotide sequence with at least 50%, at least 60%, at least 70%, at least 80%, at least 85%, at least 90%, at least 95%, at least 97%, or at least 99% sequence identity thereto.

The step of converting malate to fumarate is catalyzed by a FUM (fumarase) enzyme, i.e., an enzyme having the ability to catalyze the conversion of malate to fumarate. A FUM (fumarase) enzyme is encoded by a FUM (fumarase) gene integrated into the genome of the recombinant yeast cell. The FUM gene may be native or non-native to the host cell, and may be endogenous (if native) or exogenous (if non-native or if additional copies of a native gene are present). In certain embodiments, a FUM gene is a yeast gene. The FUM gene is in some embodiments an *I. orientalis* FUM gene encoding an enzyme having amino acid sequence SEQ ID NO: 107, or for an enzyme having an amino acid sequence with at least 50%, at least 60%, at least 70%, at least 80%, at least 85%, at least 90%, at least 95%, at least 97%, or at least 99% sequence identity to SEQ ID NO: 107. In certain embodiments, the FUM gene may have nucleotide sequence SEQ ID NO: 70 or a nucleotide sequence with at least 50%, at least 60%, at least 70%, at least 80%, at least 85%, at least 90%, at least 95%, at least 97%, or at least 99% sequence identity to SEQ ID NO: 70. In other embodiments, a FUM gene may be a bacterial gene.

The step of converting fumarate to succinate is catalyzed by a FRD (fumarate reductase) enzyme, i.e., an enzyme having the ability to catalyze the conversion of fumarate to succinate. A FRD (fumarate reductase) enzyme is encoded by a FRD (fumarate reductase) gene present in the genome of the recombinant yeast cell. The FRD gene may be native or non-native to the host cell, and may be endogenous (if native) or exogenous (if non-native or if additional copies of a native gene are present). The FRD enzyme preferably is NADH-dependent, i.e., one which uses NADH preferentially as a cofactor, and in converting fumarate to succinate also oxidizes NADH to NAD+. In the cells of this invention, the FRD enzyme preferably is overexpressed, by integrating one or more copies of an exogenous FRD gene (preferably at least two copies) into the genome of the cell. The FRD gene preferably encodes for an NADH-dependent FRD enzyme.

In certain embodiments, the FRD gene is a yeast FRD gene that encodes for an NADH-dependent FRD enzyme. For example, the FRD gene may be an *S. cerevisiae* FRD1 gene encoding for an enzyme having amino acid sequence SEQ ID NO: 108, a *Saccharomyces mikatae* (*S. mikatae*) FRD1 gene encoding for an enzyme having amino acid sequence SEQ ID NO: 109, a *K. polyspora* FRD1 gene encoding for an enzyme having amino acid sequence SEQ ID NO: 110, a *K. marxianus* FRD1 gene encoding for an enzyme having amino acid sequence SEQ ID NO: 111, or a gene encoding for an enzyme having an amino acid sequence with at least 50%, at least 60%, at least 70%, at least 80%, at least 85%, at least 90%, at least 95%, at least 97%, or at least 99% sequence identity to any thereof. In certain embodiments, the yeast FRD gene may have any of nucleotide sequences SEQ ID NOs: 75, 76, 77 or 78, or have a nucleotide sequence with at least 50%, at least 60%, at least 70%, at least 80%, at least 85%, at least 90%, at least 95%, at least 97%, or at least 99% sequence identity to any thereof.

In certain embodiments, the FRD gene may be a protozoan gene that encodes for an NADH-dependent FRD enzyme. For example, the FRD gene may be a *Trypanosoma brucei* (*T. brucei*) FRD gene encoding for an enzyme having amino acid sequence SEQ ID NO: 112, a *Trypanosoma cruzi* (*T. cruzi*) FRD gene encoding for an enzyme having amino acid sequence SEQ ID NO: 113, a *Leishmania braziliensis* (*L. braziliensis*) FRD gene encoding for an enzyme having amino acid sequence SEQ ID NO: 114, a *Leishmania mexicana* (*L. mexicana*) FRD gene encoding for an enzyme having amino acid sequence SEQ ID NO: 82, or a gene encoding for an enzyme having an amino acid sequence having at least 50%, at least 60%, at least 70%, at least 80%, at least 85%, at least 90%, at least 95%, at least 97%, or at least 99% sequence identity to any thereof. In certain embodiments, the FRD gene may have a nucleotide sequence as set forth in any of SEQ ID NOs: 42, 43, 44 or 10, or a nucleotide sequence with at least 50%, at least 60%, at least 70%, at least 80%, at least 85%, at least 90%, at least 95%, at least 97%, or at least 99% sequence identity to any thereof.

In this invention, it is preferred that the reaction of OAA to malate and the reaction of fumarate to succinate each oxidizes NADH to NAD+. The oxidation of NADH to NAD+ typically occurs in cases in which the reaction in any one or more of these steps is catalyzed by an NADH-dependent enzyme as described before.

The recombinant cell of the invention overexpresses an active NAD(P)+ transhydrogenase enzyme and/or includes one or more exogenous NAD(P)+ transhydrogenase genes, which may be native or non-native to the host cell. A "NAD(P)+ transhydrogenase" (SthA) gene refers to any gene that encodes a polypeptide that catalyzes the reaction of NADP(H) to form NAD(H). The NAD(P)+ transhydrogenase (SthA) enzyme preferably is soluble in the cytosol of the recombinant cell. The exogenous SthA gene may be of bacterial, fungal, yeast or other origin. The exogenous SthA gene in some embodiments is an *E. coli, Azotobacter vinelandii* (*A. vinelandii*) or *Pseudomona flourescens* SthA gene. The exogenous SthA gene in some embodiments encodes for an enzyme having any of amino acid sequences SEQ ID NOs: 117, 118, 119, or 146, or which is at least 50%, at least 60%, at least 70%, at least 80%, at least 85%, at least 90%, at least 95%, at least 97%, or at least 99% identical to any thereof. In certain embodiments, the exogenous SthA gene has any of nucleotide sequences SEQ ID NOs: 21, 24, 27, or 139, or a nucleotide sequence with at least 50%, at least 60%, at least 70%, at least 80%, at least 85%, at least 90%, at least 95%, at least 97%, or at least 99% sequence identity to any thereof.

In some embodiments, the recombinant cell exhibits increased flux (relative to the wild-type host strain) through the pentose phosphate pathway and/or overexpresses at least one enzyme which catalyzes a reaction that includes the reduction of NADP+ to NADPH.

The overexpressed enzyme may be an enzyme that catalyzes a reaction in the pentose phosphate pathway. The pentose phosphate pathway metabolizes glucose-6-phosphate to glyceraldehyde-3-phosphate through 6-phosphogluconolactone, 6-phosphogluconate and ribulose 5-phosphate intermediates. The conversion of glucose-6-phosphate to 6-phosphogluconolactone is catalyzed by a glucose-6-phosphate dehydrogenase (G6PDH) enzyme that uses NADP+ as a cofactor, thereby reducing NADP+ to NADPH. Similarly, the conversion of 6-phosphogluconate to ribulose-5-phosphate is catalyzed by a 6-phosphogluconate dehydrogenase (6PGDH) enzyme that uses NADP+ as a cofactor, thereby reducing NADP+ to NADPH. Overexpessing one or both of these enzymes, or increasing flux through the pentose phosphate pathway, produces NADPH, which can be converted to NADH by action of the NAD(P)+ transhydrogenase enzyme, helping to maintain cofactor balance in the cell.

One way of increasing flux through the pentose phosphate pathway is to disrupt the glycolytic pathway from glucose to pyruvate. This can be done, for example, by disrupting or removing the step of isomerising glucose-6-phosphate to fructose-6-phosphate, which is catalyzed by a phosphoglucose (PGI) enzyme. Therefore, in certain embodiments, the recombinant cell of the invention produces a severely reduced quantity (at least 75% reduction, preferably at least 85% reduction, more preferably at least 95% reduction) of an active phosphoglucose isomerase (PGI) enzyme, or produces a PGI enzyme with severely reduced (at least 75% reduced, preferably at least 85% reduced, more preferably at least 95% reduced) activity. In some embodiments, the recombinant cell includes a deletion or disruption of at least one native phosphoglucose isomerase (PGI) gene. If the host cell contains multiple alleles of the PGI gene, all such alleles may be deleted or disrupted.

The overexpressed enzyme which catalyzes a reaction that includes the reduction of NADP+ to NADPH may be an enzyme that catalyzes a reaction in the pentose phosphate pathway. The pentose phosphate pathway metabolizes glucose-6-phosphate to glyceraldehyde-3-phosphate through 6-phosphogluconolactone, 6-phosphogluconate and ribulose 5-phosphate intermediates. The conversion of glucose-6-phosphate to 6-phosphogluconolactone is catalyzed by a glucose-6-phosphate dehydrogenase (G6PDH) enzyme that uses NADP+ as a cofactor, thereby reducing NADP+ to NADPH. Similarly, the conversion of 6-phosphogluconate to ribulose-5-phosphate is catalyzed by a 6-phosphogluconate dehydrogenase (6PGDH) enzyme that uses NADP+ as a cofactor, thereby reducing NADP+ to NADPH.

Therefore, in certain embodiments, the yeast cell of the invention overexpresses a G6PDH enzyme. Such a yeast cell in some embodiments includes one or more exogenous G6PDH genes, which may be native or non-native to the strain, integrated into its genome. In certain of these embodiments, the exogenous G6PDH gene may be an *I. orientalis* G6PDH gene (ZWF1) that encodes for an enzyme having amino acid sequence SEQ ID NO: 121 or which encodes for an enzyme having with at least 50%, at least 60%, at least 70%, at least 80%, at least 85%, at least 90%, at least 95%, at least 97%, or at least 99% sequence identity SEQ ID NO: 121. In certain embodiments, the G6PDH gene may have nucleotide sequence SEQ ID NO: 87 or a nucleotide sequence with at least 50%, at least 60%, at least 70%, at least 80%, at least 85%, at least 90%, at least 95%, at least 97%, or at least 99% sequence identity to nucleotide sequence SEQ ID NO: 87.

Similarly, in other embodiments, the recombinant yeast cells provided herein contains one or more exogenous 6PGDH genes, which may be native or non-native to the host strain, integrated into its genome. In certain embodiments, a 6PGDH gene may be a yeast 6PGDH gene such as an *I. orientalis* 6PGDH gene. In certain embodiments, the exogenous 6PGDH gene encodes for an enzyme having amino acid sequence SEQ ID NO: 88, or an amino acid sequence with at least 50%, at least 60%, at least 70%, at least 80%, at least 85%, at least 90%, at least 95%, at least 97%, or at least 99% sequence identity to SEQ ID NO: 88. In certain embodiments, the exogenous 6PGDH gene has the nucleotide sequence of SEQ ID NO: 89, or a nucleotide sequence with at least 50%, at least 60%, at least 70%, at least 80%, at least 85%, at least 90%, at least 95%, at least 97%, or at least 99% sequence identity to the nucleotide sequence of SEQ ID NO: 89.

In certain embodiments, the recombinant cell of the invention overexpresses an oxidative stress-activated zinc cluster protein Stb5p. This zinc cluster protein regulates genes involved in certain NADPH-producing reactions, including the G6PDH and 6PGDH genes. In certain embodiments, the recombinant cell includes one or more exogenous Stb5p genes, which may be native or non-native to the host cell, integrated into its genome. In certain embodiments, the exogenous Stb5p gene encodes for an enzyme having amino acid sequence SEQ ID NO: 83, or an amino acid sequence with at least 50%, at least 60%, at least 70%, at least 80%, at least 85%, at least 90%, at least 95%, at least 97%, or at least 99% sequence identity to SEQ ID NO: 83. In certain embodiments, the exogenous Stb5p gene has the nucleotide sequence of SEQ ID NO: 30, or a nucleotide sequence with at least 50%, at least 60%, at least 70%, at least 80%, at least 85%, at least 90%, at least 95%, at least 97%, or at least 99% sequence identity to the nucleotide sequence of SEQ ID NO: 30.

The recombinant cell of the invention may further include one or more exogenous succinate exporter genes, which may be native or non-native to the host cell. A "succinate exporter gene" as used herein refers to any gene that encodes a polypeptide with succinate export activity, meaning the ability to transport succinate out of a cell and into the extracellular environment. The exogenous succinate exporter gene may be a fungal succinate exporter gene such as a *Schizosaccharomyces pombe* (*S. pombe*) succinate exporter gene or *Aspergillus oryzae* (*A. oryzae*) source succinate exporter gene. The exogenous succinate exporter gene in some embodiments encodes for an enzyme having amino acid sequence SEQ ID NOs: 90 or 91, or at least 50%, at least 60%, at least 70%, at least 80%, at least 85%, at least 90%, at least 95%, at least 97%, or at least 99% sequence identity to either of SEQ ID NOs: 90 or 91. In certain embodiments, the exogenous succinate exporter gene has either of nucleotide sequence SEQ ID NOs: 92 or 93, or a nucleotide sequence with at least 50%, at least 60%, at least 70%, at least 80%, at least 85%, at least 90%, at least 95%, at least 97%, or at least 99% sequence identity to either SEQ ID NOs: 92 or 93.

In certain embodiments, the recombinant yeast cells provided herein may have a deletion or disruption of one or more other endogenous genes. The other deleted or disrupted genes may include genes which produce enzymes that catalyze the reaction of pyruvate or phosphoenolpyruvate (or their metabolizes) to downstream products other than succinate. Among such genes are, for example, native pyruvate decarboxylase, alcohol dehydrogenase 1 (ADH1, catalyzes the conversion of acetaldehyde to ethanol), alcohol dehydrogenase 2 (ADH2, catalyzes the conversion of ethanol to acetaldehyde), glycerol-3-phosphate dehydrogenase (GPD, systematic name sn-glycerol-3-phosphate:NAD+2-oxidoreductase, EC 1.1.1.8), and glycerol-3-phosphatase enzyme (GPP, systematic name glycerol-1-phosphate phosphohydrolase, EC 3.1.3.21) and $NADH^+$-dependent glycerol dehydrogenase (systematic name glycerol:NAD+2-oxidoreductase, EC 1.1.1.6) genes.

Other endogenous genes that may be deleted in certain embodiments of the invention include genes which encode for enzymes that catalyze a reaction that consumes PEP, pyruvate, succinate or any intermediates produced in the reductive TCA pathway (other than the TCA pathway reactions leading to succinate). Examples of such genes include a native pyruvate carboxylase gene (which encodes an enzyme that converts OAA to pyruvate), a native PEP carboxykinase (PCK) gene (which encodes an enzyme that converts OAA to PEP), a native malic enzyme (MAE) gene (which encodes an enzyme that converts malate to pyruvate) and a native succinate dehydrogenase (SDH) gene (which encodes an enzyme that catalyzes the back-reaction of succinate to fumarate).

In some embodiments, the modified yeast cells provided herein have a deletion or disruption of a native succinate importer gene, which as used herein refers to any gene that encodes a polypeptide that allows for growth on and consumption of succinate.

In certain embodiments, the cells may contain all or part of an active oxidative TCA or glyoxylate shunt succinate fermentation pathway. In these embodiments, the cells comprise one or more genes encoding enzymes selected from the group consisting of citrate synthase, PDH (pyruvate dehydrogenase), PFL (pyruvate formate lyase), aconitase, IDH (isocitrate dehydrogenase), α-KGDH (α-ketoglutarate dehydrogenase), succinate thiokinase, isocitrate lyase, and malate synthase.

The recombinant cell of the invention may further include one or more modifications which individually or collectively confers to the cell the ability to ferment pentose sugars to xylulose 5-phosphate. Among such modifications are (1) insertion of a functional xylose isomerase gene, (2) a deletion or disruption of a native gene that produces an enzyme that catalyzes the conversion of xylose to xylitol, (3) a deletion or disruption of a functional xylitol dehydrogenase gene and/or (4) modifications that cause the cell to overexpress a functional xylulokinase. Methods for introducing those modifications into yeast cells are described, for example, in WO 04/099381, incorporated herein by reference. Suitable methods for inserting a functional xylose isomerase gene, deleting or disrupting a native gene that produces an enzyme that catalyzes the conversion of xylose to xylitol, deleting or disrupting a functional xylitol dehydrogenase gene, and modifying the cell to overexpress a functional xylulokinase are described, for example, in WO 04/099381, incorporated herein by reference.

In this invention, any exogenous gene, including without limitation any of the exogeneous genes in the reductive TCA pathway from pyruvate to succinate, any succinate exporter gene, any G6PDH gene, any 6PGDH gene, any SthA gene, or any other exogenous gene introduced into the host cell, is operatively linked to one or more regulatory elements, and in particular to a promoter sequence and a terminator sequence that each are functional in the host cell. Such regulatory elements may be native or non-native to the host cell.

Examples of promoters that may be linked to one or more exogenous genes in the yeast cells provided herein include, but are not limited to, promoters for pyruvate decarboxylase (PDC1), phosphoglycerate kinase (PGK), xylose reductase (XR), xylitol dehydrogenase (XDH), L-(+)-lactate-cytochrome c oxidoreductase (CYB2), translation elongation factor-1 or -2 (TEF1, TEF2), enolase (ENO1), glyceraldehyde-3-phosphate dehydrogenase (GAPDH), orotidine 5'-phosphate decarboxylase (URA3) genes, as well as any of those described in the various Examples that follow. Where the promoters are non-native, they may be identical to or share a high degree of sequence identity (i.e., at least about 80%, at least about 85%, at least about 90%, at least about 95%, or at least about 99%) with one or more native promoters. Other suitable promoters and terminators include those described, for example, in WO99/14335, WO00/71738, WO02/42471, WO003/102201, WO03/102152 and WO03/049525.

Examples of terminators that may be linked to one or more exogenous genes in the yeast cells provided herein include, but are not limited to, terminators for PDC1, XR, XDH, transaldolase (TAL), transketolase (TKL), ribose 5-phosphate ketol-isomerase (RKI), CYB2, or iso-2-cytochrome c (CYC) genes or the galactose family of genes (especially the GAL10 terminator), as well as any of those described in the various Examples that follow. Where the terminators are non-native, they may be identical to or share a high degree of sequence identity (i.e., at least about 80%, at least about 85%, at least about 90%, at least about 95%, or at least about 99%) with one or more native terminators.

Modifications (insertion, deletions and/or disruptions) to the genome of the host cell described herein can be performed using methods known in the art. Exogeneous genes may be integrated into the genome in a targeted or a random manner using, for example, well known electroporosis and chemical methods (including calcium chloride and/or lithium acetate methods). In those embodiments where an exogenous gene is integrated in a targeted manner, it may be integrated into the locus for a particular native gene, such that integration of the exogenous gene is coupled with deletion or disruption of a native gene. Alternatively, the exogenous gene may be integrated into a portion of the native genome that does not correspond to a gene. Methods for transforming a yeast cell with an exogenous construct are described in, for example, WO99/14335, WO00/71738, WO02/42471, WO03/102201, WO003/102152, WO03/049525, WO2007/061590, WO 2009/065778 and PCT/US2011/022612.

Insertion of exogenous genes is generally performed by transforming the cell with one or more integration constructs or fragments. The terms "construct" and "fragment" are used interchangeably herein to refer to a DNA sequence that is used to transform a cell. The construct or fragment may be, for example, a circular plasmid or vector, a portion of a circular plasmid or vector (such as a restriction enzyme digestion product), a linearized plasmid or vector, or a PCR product prepared using a plasmid or genomic DNA as a template. An integration construct can be assembled using two cloned target DNA sequences from an insertion site target. The two target DNA sequences may be contiguous or non-contiguous in the native host genome. In this context, "non-contiguous" means that the DNA sequences are not immediately adjacent to one another in the native genome, but are instead are separated by a region that is to be deleted. "Contiguous" sequences as used herein are directly adjacent to one another in the native genome. Where targeted integration is to be coupled with deletion or disruption of a target gene, the integration construct also functions as a deletion construct. In such an integration/deletion construct, one of the target sequences may include a region 5' to the promoter of the target gene, all or a portion of the promoter region, all or a portion of the target gene coding sequence, or some combination thereof. The other target sequence may include a region 3' to the terminator of the target gene, all or a portion of the terminator region, and/or all or a portion of the target gene coding sequence. Where targeted integration is not to be coupled to deletion or disruption of a native gene, the target sequences are selected such that insertion of an intervening sequence will not disrupt native gene expression. An integration or deletion construct is prepared such that the two target sequences are oriented in the same direction in relation to one another as they natively appear in the genome of the host cell. The gene expression cassette is cloned into the construct between the two target gene sequences to allow for expression of the exogenous gene. The gene expression cassette contains the exogenous gene, and may further include one or more regulatory sequences such as promoters or terminators operatively linked to the exogenous gene.

It is usually desirable that the deletion construct may also include a functional selection marker cassette. When a single deletion construct is used, the marker cassette resides on the vector downstream (i.e., in the 3' direction) of the 5' sequence from the target locus and upstream (i.e., in the 5' direction) of the 3' sequence from the target locus. Successful transformants will contain the selection marker cassette, which imparts to the successfully transformed cell some characteristic that provides a basis for selection.

A "selection marker gene" may encode for a protein needed for the survival and/or growth of the transformed cell in a selective culture medium. Typical selection marker genes encode proteins that (a) confer resistance to antibiotics or other toxins, (such as, for example, zeocin (*Streptoalloteichus hindustanus* ble bleomycin resistance gene), G418 (kanamycin-resistance gene of Tn903) or hygromycin (aminoglycoside antibiotic resistance gene from *E. coli*)), (b) complement auxotrophic deficiencies of the cell (such as, for example, amino acid leucine deficiency (*K. marxianus* LEU2 gene) or uracil deficiency (e.g., *K. marxianus* or *S. cerevisiae* URA3 gene)); (c) enable the cell to synthesize critical nutrients not available from simple media, or (d) confer ability for the cell to grow on a particular carbon source, (such as a MEL5 gene from *S. cerevisiae*, which encodes the alpha-galactosidase (melibiase) enzyme and confers the ability to grow on melibiose as the sole carbon source). Preferred selection markers include the zeocin resistance gene, G418 resistance gene, a MEL5 gene, a URA3 gene and hygromycin resistance gene. Another preferred selection marker is an L-lactate:ferricytochrome c oxidoreductase (CYB2) gene cassette, provided that the host cell either natively lacks such a gene or that its native CYB2 gene(s) are first deleted or disrupted.

The construct may be designed so that the selection marker cassette can become spontaneously deleted as a result of a subsequent homologous recombination event. A convenient way of accomplishing this is to design the vector such that the selection marker gene cassette is flanked by direct repeat sequences. Direct repeat sequences are identical DNA sequences, native or not native to the host cell, and oriented on the construct in the same direction with respect to each other. The direct repeat sequences are advantageously about 50-1500 bp in length. It is not necessary that the direct repeat sequences encode for anything. This construct permits a homologous recombination event to occur. This event occurs with some low frequency, resulting in cells containing a deletion of the selection marker gene and one of the direct repeat sequences. It may be necessary to grow transformants for several rounds on nonselective or selective media to allow for the spontaneous homologous recombination to occur in some of the cells. Cells in which the selection marker gene has become spontaneously deleted can be selected or screened on the basis of their loss of the selection characteristic imparted by the selection marker gene, or by using PCR or Southern Analysis methods to confirm the loss of the selection marker.

In some embodiments, an exogenous gene may be inserted using DNA from two or more integration fragments, rather than a single fragment. In these embodiments, the 3' end of one integration fragment contains a region of homology with the 5' end of another integration fragment. One of the fragments will contain a first region of homology to the target locus and the other fragment will contain a second region of homology to the target locus. The gene cassette to be inserted can reside on either fragment, or be divided among the fragments, with a region of homology at the 3' and 5' ends of the respective fragments, so the entire, functional gene cassette is produced upon a crossover event. The cell is transformed with these fragments simultaneously. A selection marker may reside on any one of the fragments or may be divided between the fragments with a region of homology as described. In other embodiments, transformation from three or more constructs can be used in an analogous way to integrate exogenous genetic material.

Deletions and/or disruptions of native genes can be performed by transformation methods, by mutagenesis and/or by forced evolution methods. In mutagenesis methods cells are exposed to ultraviolet radiation or a mutagenic substance, under conditions sufficient to achieve a high kill rate (60-99.9%, preferably 90-99.9%) of the cells. Surviving cells are then plated and selected or screened for cells having the deleted or disrupted metabolic activity. Disruption or deletion of the desired native gene(s) can be confirmed through PCR or Southern analysis methods.

Cells of the invention can be cultivated to produce succinic acid, either in the free acid form or in salt form (or both), or a metabolization product of succinate. The recombinant cell is cultured in a medium that includes at least one carbon source that can be fermented by the cell. Examples include, but are not limited to, twelve carbon sugars such as sucrose, hexose sugars such as glucose or fructose, glycan, starch, or other polymer of glucose, glucose oligomers such as maltose, maltotriose and isomaltotriose, panose, and fructose oligomers, and pentose sugars such as xylose, xylan, other oligomers of xylose, or arabinose.

The medium will typically contain, in addition to the carbon source, nutrients as required by the particular cell, including a source of nitrogen (such as amino acids, proteins, inorganic nitrogen sources such as ammonia or ammonium salts, and the like), and various vitamins, minerals and the like. In some embodiments, the cells of the invention can be cultured in a chemically defined medium.

Other cultivation conditions, such as temperature, cell density, selection of substrate(s), selection of nutrients, and the like are not considered to be critical to the invention and are generally selected to provide an economical process. Temperatures during each of the growth phase and the production phase may range from above the freezing temperature of the medium to about 50° C., although this depends to some extent on the ability of the strain to tolerate elevated temperatures. A preferred temperature, particularly during the production phase, is about 30 to 45° C.

During cultivation, aeration and agitation conditions may be selected to produce a desired oxygen uptake rate. The cultivation may be conducted aerobically, microaerobically, or anaerobically, depending on pathway requirements. In some embodiments, the cultivation conditions are selected to produce an oxygen uptake rate of around 2-25 mmol/L/hr, preferably from around 5-20 mmol/L/hr, and more preferably from around 8-15 mmol/L/hr. "Oxygen uptake rate" or "OUR" as used herein refers to the volumetric rate at which oxygen is consumed during the fermentation. Inlet and outlet oxygen concentrations can be measured with exhaust gas analysis, for example by mass spectrometers. OUR can be calculated using the Direct Method described in Bioreaction Engineering Principles 2nd Edition, 2003, Kluwer Academic/Plenum Publishers, p. 449, equation 1.

The culturing process may be divided up into phases. For example, the cell culture process may be divided into a cultivation phase, a production phase, and a recovery phase.

The pH may be allowed to range freely during cultivation, or may be buffered if necessary to prevent the pH from falling below or rising above predetermined levels. For example, the medium may be buffered to prevent the pH of the solution from falling below around 2.0 or above about 8.0 during cultivation. In certain of these embodiments, the medium may be buffered to prevent the pH of the solution from falling below around 3.0 or rising above around 7.0, and in certain of these embodiments the medium may be buffered to prevent the pH of the solution from falling below around 3.0 or rising above around 4.5. Suitable buffering agents include basic materials that neutralize the acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like.

In a buffered fermentation, acidic fermentation products are neutralized to the corresponding salt as they are formed. Recovery of the acid therefore involves regenerating the free acid. This is typically done by removing the cells and acidulating the fermentation broth with a strong acid such as sulfuric acid. A salt by-product is formed (gypsum in the case where a calcium salt is the neutralizing agent and sulfuric acid is the acidulating agent), which is separated from the broth.

In other embodiments, the pH of the fermentation medium may be permitted to drop during cultivation from a starting pH that is at or above the lower pKa (4.207) of succinate, typically 8 or higher, to at or below the lower pKa of the acid fermentation product, such as in the range of about 2.0 to about 4.2, in the range of from about 3.0 to about 4.2, or in the range from about 3.8 to about 4.2.

In still other embodiments, fermentation may be carried out to produce a product acid by adjusting the pH of the fermentation broth to at or below the lower pKa of the product acid prior to or at the start of the fermentation process. The pH may thereafter be maintained at or below the lower pKa of the product acid throughout the cultivation. In certain embodiments, the pH may be maintained at a range of about 2.0 to about 4.2, in the range of from about 3.0 to about 4.2, or in the range from about 3.8 to about 4.2.

When the pH of the fermentation broth is low enough that the succinate is present in acid form, the acid can be recovered from the broth through techniques such as liquid-liquid extraction, distillation, absorption, etc., such as are described in T. B. Vickroy, Vol. 3, Chapter 38 of *Comprehensive Biotechnology*, (ed. M. Moo-Young), Pergamon, Oxford, 1985; R. Datta, et al., FEMS Microbiol. Rev., 1995, 16:221-231; U.S. Pat. Nos. 4,275,234, 4,771,001, 5,132,456, 5,420,304, 5,510,526, 5,641,406, and 5,831,122, and WO 93/00440.

The cultivation may be continued until a yield of succinate on the carbon source is, for example, at least 10%, at least 20%, at least 30%, at least 40%, at least 50%, or greater than 50% of the theoretical yield. The yield to succinate may at least 80% or at least 90% of the theoretical yield. The concentration, or titer, of succinate produced in the cultivation will be a function of the yield as well as the starting concentration of the carbon source. In certain embodiments, the titer may reach at least 1, at least 3, at least 5, at least 10, at least 20, at least 30, at least 40, at least 50, or greater than 50 g/L at some point during the fermentation, and preferably at the end of the fermentation.

In certain embodiments, the genetically modified yeast cells produce ethanol in a yield of 10% or less, preferably in a yield of 2% or less of the theoretical yield. In certain of these embodiments, ethanol is not detectably produced. In other embodiments, however, succinate and ethanol may be co-produced. In these embodiments, ethanol may be produced at a yield of greater than 10%, greater than 25%, or greater than 50% of the theoretical yield.

The recombinant cell of the invention may exhibit a volumetric glucose consumption rate of at least 0.5 gram, at least 0.75 gram, or at least 0.9 gram of glucose per liter of broth per hour, when cultivated under the conditions described in Examples 253-255.

The cell of the invention may produce succinate as an end-product of the fermentation process. In such a case, the cell preferably transports succinate out of the cell and into the surrounding culture medium.

In some embodiments, the cell may further metabolize some or all of the succinate into one or more succinate metabolization products, i.e., a compound formed in the further metabolization of succinate by the cell. Examples of such downstream succinate metabolization products include, for example, 1,4-butanediol, 1,3-butadiene, propionic acid, and 3-hydroxyisobutryic acid. In such embodiments, the cell contains native or non-native metabolic pathways which perform the such a further metabolization of succinate into such downstream succinate metabolization product(s). The cell may then transport such downstream succinate metabolization products out of the cell and into the surrounding medium. In some embodiments, the cell may transport one or more succinate metabolization products, but not succinate, out of the cell. In other embodiments, the cell may transport both succinate itself and one or more succinate metabolization products out of the cell. For example, the cell may transport less than 10% by weight of succinate from the cell, based on the combined weight of succinate and succinate metabolization products exported from the cell.

The following examples are provided to illustrate the invention, but are not intended to limit the scope thereof. All parts and percentages are by weight unless otherwise indicated.

EXAMPLES

Construction of Preparatory Examples

P-1. An *I. orientalis* strain host strain is generated by evolving *I. orientalis* strain ATCC PTA-6658 for 91 days in a glucose-limited chemostat. The system is fed 15 g/L glucose in a defined medium and operated at a dilution rate of 0.06 $h^{-1}$ at pH=3 with added lactic acid in the feed medium. The conditions are maintained with an oxygen transfer rate of approximately 2 mmol $L^{-1}h^{-1}$, and dissolved oxygen concentration remains constant at 0% of air saturation. Single colony isolates from the final time point are characterized in two shake flask assays. In the first assay, the isolates are characterized for their ability to ferment glucose to ethanol in the presence of 25 g/L total lactic acid with no pH adjustment in the defined medium. In the second assay, the growth rate of the isolates is measured in the presence of 45 g/L of total lactic acid, with no pH adjustment in the defined medium. Strain P-1 is a single isolate exhibiting the highest glucose consumption rate in the first assay and the highest growth rate in the second assay.

P-2. Strain P-1 is transformed with linearized integration fragment P2 (having nucleotide sequence SEQ ID NO: 1) designed to disrupt the URA3 gene, using a LiOAc transformation method as described by Gietz et al., in Met. Enzymol. 350:87 (2002). Integration fragment P2 includes a MEL5 selection marker gene. Transformants are selected on YNB-melibiose plates and screened by PCR to confirm the integration of the integration piece and deletion of a copy of the URA3 gene. A URA3-deletant strain is grown for several rounds until PCR screening identifies an isolate in which the MEL5 selection marker gene has looped out. The PCR screening is performed using primers having nucleotide sequences SEQ ID NOs: 47 and 48 to confirm the 5'-crossover and primers having nucleotide sequences SEQ ID NOs: 51 and 52 to confirm the 3' crossover. That isolate is again grown for several rounds on 5-fluoroorotic acid (FOA) plates to identify a strain in which the URA3 marker has looped out. PCR screening is performed on this strain using primers having nucleotide sequences SEQ ID NOs: 56 and 124, identifies an isolate in which both URA3 alleles have been deleted. This isolate is named strain P-2.

P-3. Strain P-2 is transformed with integration fragment P3 (having the nucleotide sequence SEQ ID NO: 2), which is designed to disrupt the PDC gene. Integration fragment P3 contains the following elements, 5' to 3': a DNA fragment with homology for integration corresponding to the region immediately upstream of the *I. orientalis* PDC open reading frame, a PDC transcriptional terminator, the URA3 promoter, the *I. orientalis* URA3 gene, an additional URA3 promoter direct repeat for marker recycling and a DNA fragment with homology for integration corresponding to the region directly downstream of the *I. orientalis* PDC open reading frame. A successful integrant (and single-copy PDC deletant) is identified on selection plates lacking uracil and confirmed by PCR using primers having nucleotide sequences SEQ ID NOS: 53 and 54 to confirm the 5'-crossover and primers having nucleotide sequences SEQ ID NOs: 55 and 122 to confirm the 3'-crossover. That integrant is grown for several rounds and plated on 5-fluoroorotic acid (FOA) plates to identify a strain in which the URA3 marker has looped out. Loopout of the URA3 marker is confirmed by PCR. That strain is again transformed with integration fragment P3 (SEQ ID NO: 2) to delete the second copy of the native PDC gene. A successful transformant is again identified by selection on selection plates lacking uracil, and further confirmed by culturing the strain over two days and measuring ethanol production. Lack of ethanol production further demonstrates a successful deletion of both copies of the PDC gene in a transformant. That transformant is grown for several rounds and plated on FOA plates until PCR identifies a strain in which the URA3 marker has looped out. The PCR screening is performed using primers having nucleotide sequences SEQ ID NOs: 53 and 54 to confirm the 5'-crossover and SEQ ID NOs: 55 and 122 to confirm the 3'-crossover. That strain is plated on selection plates lacking uracil to confirm the loss of the URA3 marker, and is designated strain P-3.

P-4. Integration fragment P4-1, having nucleotide sequence SEQ ID NO: 3, contains the following elements, 5' to 3': a DNA fragment with homology for integration corresponding to the region immediately upstream of the *I. orientalis* ADH9091 open reading frame, an *I. orientalis* PDC1 promoter, the *I. orientalis* PYC gene (having the nucleotide sequence SEQ ID NO: 4), the *I. orientalis* TAL terminator, the *I. orientalis* URA3 promoter, and the first 530 bp of the *I. orientalis* URA3 open reading frame.

Integration fragment P4-2, having nucleotide sequence SEQ ID NO: 5, contains the following elements, 5' to 3': a DNA fragment corresponding to the last 568 bp of the *I. orientalis* URA3 open reading frame, the *I. orientalis* URA3 terminator, the *I. orientalis* URA3 promoter, the *I. orientalis* TDH3 promoter, the *S. pombe* MAE gene (having the nucleotide sequence SEQ ID NO: 6), the *I. orientalis* TKL terminator, and a DNA fragment with homology for integration corresponding to the region immediately downstream of the *I. orientalis* ADH9091 open reading frame.

Strain P-3 is transformed simultaneously with integration fragments P4-1 and P4-2, using lithium acetate methods, to insert the *I. orientalis* PYC gene and the *S. pombe* MAE gene at the ADH9091 locus. Integration occurs via three cross-over events: in the regions of the ADH9091 upstream homology, in the regions of the ADH9091 downstream homology and in the region of URA3 homology between SEQ ID NO: 3 and SEQ ID NO: 5. Transformants are streaked to isolates and the correct integration of the cassette at the AHD9091 locus is confirmed in a strain by PCR. The PCR screening is performed using primers having nucleotide sequences SEQ ID NOs: 65 and 69 to confirm the 5'-crossover and SEQ ID NOs: 67 and 71 to confirm the 3'-crossover. That strain is grown and plated on FOA as before until the loopout of the URA3 marker from an isolate is confirmed by PCR.

That isolate is then transformed simultaneously with integration fragments P4-3 and P4-4 using LiOAc transformation methods, to insert a second copy of each of the *I. orientalis* PYC gene and the *S. pombe* MAE gene at the ADH9091 locus.

Integration fragment P4-3, having the nucleotide sequence SEQ ID NO: 7, contains the following elements, 5' to 3': a DNA fragment with homology for integration corresponding to the region immediately downstream of the *I. orientalis* ADH9091 open reading frame, an *I. orientalis* PDC1 promoter, the *I. orientalis* PYC gene as found in SEQ ID NO: 4, the *I. orientalis* TAL terminator, the *I. orientalis* URA3 promoter, and the first 530 bp of the *I. orientalis* URA3 open reading frame.

Integration fragment P4-4, having the nucleotide sequence SEQ ID NO: 8, contains the following elements, 5' to 3': a DNA fragment corresponding to the last 568 bp of the *I. orientalis* URA3 open reading frame, the *I. orientalis* URA3 terminator, the *I. orientalis* URA3 promoter, the *I. orientalis* TDH3 promoter, the *S. pombe* MAE gene (having a nucleotide sequences SEQ ID NO: 6), the *I. orientalis* TKL terminator, and a DNA fragment with homology for integration corresponding to the region immediately upstream of the *I. orientalis* ADH9091 open reading frame.

Integration again occurs via three crossover events. Transformants are streaked to isolates and screened by PCR to identify a strain containing both copies of the *I. orientalis* PYCI and *S. pombe* MAE genes at the ADH9091 locus by PCR. The PCR screening to confirm the first copy is performed using primers having nucleotide sequences SEQ ID NOs: 65 and 69 to confirm the 5'-crossover and SEQ ID NOs: 67 and 71 to confirm the 3'-crossover. The PCR screening to confirm the second copy is performed using primers having nucleotide sequences SEQ ID NOs: 65 and 67 to confirm the 5'-crossover and SEQ ID NOs: 69 and 71 to confirm the 3'-crossover. That strain is grown and replated on FOA until a strain in which the URA3 marker has looped out is identified. That strain is designated strain P-4.

P-5. Strain P-4 is transformed with integration fragment P5-1 (having the nucleotide sequence SEQ ID NO: 9) using LiOAc transformation methods as described in previous examples, to integrate the *L. mexicana* FRD gene at the locus of the native CYB2b open reading frame. The integration fragment P5-1 contains the following elements, 5' to 3': a DNA fragment with homology for integration corresponding to the region immediately downstream of the *I. orientalis* CYB2b open reading frame, an *I. orientalis* PDC1 promoter, the *L. mexicana* FRD gene (having nucleotide sequence SEQ ID NO: 10, and encoding for an enzyme having amino acid sequence SEQ ID NO: 82), the *I. orientalis* PDC1 Terminator, the *I. orientalis* URA3 promoter, gene, and terminator in succession, followed by an additional URA3 promoter which serves as a direct repeat for marker recycling, and a region immediately upstream of the *I. orientalis* CYB2b open reading frame.

Successful integration of a single copy of the *L. mexicana* FRD gene in one isolate is identified by selection on a selection plates lacking uracil and confirmed by PCR. The PCR screening is performed using primers having nucleotide sequences SEQ ID NOs: 72 and 73 to confirm the 5'-crossover and SEQ ID NOs: 69 and 79 to confirm the 3'-crossover. That isolate is grown and plated on FOA as before until a strain in which the URA3 promoter has looped out is identified by PCR. That isolate is transformed with integration fragment P5-2 in the same manner as before, to integrate a second copy of the *L. mexicana* FRD gene at the native locus of the CYB2b open reading frame.

Integration fragment P5-2 (having nucleotide sequence SEQ ID NO: 11), contains the following elements, 5' to 3': a DNA fragment with homology for integration corresponding to the region immediately upstream of the *I. orientalis* CYB2b open reading frame, an *I. orientalis* PDC1 promoter, the *L. mexicana* FRD gene (having the nucleotide sequence SEQ ID NO: 10), the *I. orientalis* PDC1 terminator, the *I. orientalis* URA3 promoter, gene, and terminator in succession, followed by an additional URA3 promoter which serves as a direct repeat for marker recycling, and a region immediately downstream of the *I. orientalis* CYB2b open reading frame.

Correct integration of the second copy of the *L. mexicana* FRD gene in one isolate is confirmed by PCR using primers having nucleotide sequences SEQ ID NOs: 69 and 73 to confirm the 5'-crossover and SEQ ID NOs: 72 and 79 to confirm the 3'-crossover. Retention of the first integration is reconfirmed by repeating the PCR reactions used to verify proper integration of fragment P5-1 above. The confirmed isolate is grown and plated on FOA as before until the loop out of the URA3 marker is confirmed by PCR in one isolate. That isolate is designated strain P-5.

P-6. Integration fragment P6-1 (having nucleotide sequence SEQ ID NO: 12) contains the *Rhizopus delemar* MDH (RdMDH) gene (having the nucleotide sequence SEQ ID NO: 13), an ADHb upstream integration arm, ENO promoter, RKI terminator, URA3 promoter and the first 583 base pairs of the URA3 marker.

Integration fragment P6-2 (having nucleotide sequence SEQ ID NO: 14) contains the *Actinobacillus succinogenes* FUM (AsFUM) gene (nucleotide sequence SEQ ID NO: 15), the last 568 base pairs of the URA3 marker, URA3 promoter, PGK promoter, PDC terminator and ADHb downstream integration arm.

Strain P-5 is simultaneously transformed with each of integration fragments P6-1 and P6-2 using the standard lithium acetate process described before. Successful transformants are identified by PCR, and grown and plated until a strain in which the URA3 marker has looped out is identified as before. This strain is designated as strain P-6.

Second *Rhizopus delemar* MDH integration fragment P6-3 (having the nucleotide sequence SEQ ID NO: 16) contains the *Rhizopus delemar* MDH gene (having nucleotide sequence SEQ ID NO: 13), ADHb downstream integration arm, ENO promoter, RKI terminator, URA3 promoter and the first 583 base pairs of the URA3 marker.

Second *A. succinogenes* FUM (AsFUM) integration fragment P6-4 (having nucleotide sequence SEQ ID NO: 17) contains the truncated AsFUM gene (nucleotide sequence SEQ ID NO: 15) the last 568 base pairs of the URA3 marker, URA3 promoter, PGK promoter, PDC terminator and ADHb upstream integration arm.

Strain P-6 is simultaneously transformed with integration fragments P6-3 and P6-4, using the standard lithium acetate process described before. Successful transformants are identified by PCR, and grown and plated on FOA as before until a strain in which the URA3 marker has looped out is identified. This strain is designated as strain P-7.

TABLE 1

Preparatory Strains P-1 through P-7

| Strain name | Description | Parent strain |
|---|---|---|
| P-1 | Organic acid tolerant *I. orientalis* isolate | Wild-type |
| P-2 | URA3 deletion (2) | P-1 |
| P-3 | URA3 deletion (2)<br>PDC deletion (2) | P-2 |
| P-4 | URA deletion (2)<br>PDC deletion (2)<br>*I. orientalis* PYC1 insertion at ADHa (2)<br>*S. pombe* MAE insertion at ADHa (2) | P-3 |
| P-5 | URA deletion (2)<br>PDC deletion (2)<br>*I. orientalis* PYC1 insertion at ADHa (2)<br>*S. pombe* MAE insertion at ADHa (2)<br>*L. mexicana* FRD insertion at CYB2b (2) | P-4 |
| P-6 | URA deletion (2)<br>PDC deletion (2)<br>*I. orientalis* PYC1 insertion at ADHa (2)<br>*S. pombe* MAE insertion at ADHa (2)<br>*L. mexicana* FRD insertion at CYB2b (2)<br>*R. delemar* MDH insertion at ADHb (1)<br>*A. succinogenes* FUM insertion at ADHb (1) | P-5 |
| P-7 | URA deletion (2)<br>PDC deletion (2)<br>*I. orientalis* PYC1 insertion at ADHa (2)<br>*S. pombe* MAE insertion at ADHa (2)<br>*L. mexicana* FRD insertion at CYB2b (2)<br>*R. delemar* MDH insertion at ADHb (2)<br>*A. succinogenes* FUM insertion at ADHb (2) | P-6 |

Examples 1-9: Integration of Soluble Transhydrogenase

General procedure for producing Examples 1-9: The host strain (as indicated in Table 2 below) is simultaneously transformed with each of two integration fragments, as indicated in Table 2 below, using the standard lithium acetate process described before. The integration fragments are designed for targeted insertion at the native MAE1 gene of the host strain. Integration occurs via three cross-over events: the MAE1 upstream homology, the MAE1 downstream homology and homology between portions of the URA3 gene that are present in each of the integration fragments. Transformants are streaked to isolates and the correct integration of the cassette at the MAE1 locus is confirmed by PCR using primers having nucleotide sequences SEQ ID NOs: 80 and 81 to confirm the 5'-cross-over and SEQ ID NOs: 85 and 126 to confirm the 3'-cross-over. That strain is grown and plated on FOA as before until the loopout of the URA3 marker from an isolate is confirmed by PCR.

The integration fragments used to produce strain Examples 1-9 are as follows:

Integration Fragment 1A: Left Hand Integration Fragment—Marker Only

Integration fragment 1A, having the nucleotide sequence SEQ ID NO: 18, contains the following elements, 5' to 3': a DNA fragment with homology for integration corresponding to the region immediately upstream of the *I. orientalis* MAE1 open reading frame, an *I. orientalis* PDC1 promoter, the *I. orientalis* TAL terminator, the *I. orientalis* ENO promoter, *I. orientalis* RKI terminator, URA3 promoter, and the first 582 bp of the *I. orientalis* URA3 open reading frame.

Integration Fragment 1B: Right Hand Integration Fragment—Marker Only

Integration fragment 1B having the nucleotide sequence SEQ ID NO: 19, contains the following elements, 5' to 3': a DNA fragment corresponding to the last 567 bp of the *I. orientalis* URA3 open reading frame, the *I. orientalis* URA3 terminator, the *I. orientalis* URA3 promoter, the *I. orientalis* TDH3 promoter, the *I. orientalis* TKL terminator, the *I. orientalis* PGK promoter, the *I. orientalis* PDC terminator and a DNA fragment with homology for integration corresponding to the region immediately downstream of the *I. orientalis* MAE1 open reading frame.

Integration Fragment 1C: Left Hand Integration Fragment with the *E. coli* SthA Gene Integration fragment 1C, having the nucleotide sequence SEQ ID NO: 20, contains the following elements, 5' to 3': a DNA fragment with homology for integration corresponding to the region immediately upstream of the *I. orientalis* MAE1 open reading frame, an *I. orientalis* PDC1 promoter, the *I. orientalis* TAL terminator, the *I. orientalis* ENO promoter, the *E. coli* SthA gene (having nucleotide sequence SEQ ID NO: 21), *I. orientalis* RKI terminator, URA3 promoter, and the first 582 bp of the *I. orientalis* URA3 open reading frame.

Integration Fragment 1D: Right Hand Integration Fragment with the *E. coli* SthA Gene Integration fragment 1D, having nucleotide sequence SEQ ID NO: 22, contains the following elements, 5' to 3': a DNA fragment corresponding to the last 567 bp of the *I. orientalis* URA3 open reading frame, the *I. orientalis* URA3 terminator, the *I. orientalis* URA3 promoter, the *I. orientalis* TDH3 promoter, the *I. orientalis* TKL terminator, the *I. orientalis* PGK promoter, the *E. coli* SthA gene (having nucleotide sequence SEQ ID NO: 21), the *I. orientalis* PDC terminator and a DNA fragment with homology for integration corresponding to the region immediately downstream of the *I. orientalis* MAE1 open reading frame.

Integration Fragment 1E: Left Hand Integration Fragment with a Codon Optimized *E. coli* SthA Gene Integration fragment 1E, having the nucleotide sequence SEQ ID NO: 23, contains the following elements, 5' to 3': a DNA fragment with homology for integration corresponding to the region immediately upstream of the *I. orientalis* MAE1 open reading frame, an *I. orientalis* PDC1 promoter, the *I. orientalis* TAL terminator, the *I. orientalis* ENO promoter, the codon optimized *E. coli* SthA gene (having nucleotide sequence SEQ ID NO: 24), *I. orientalis* RKI terminator, URA3 promoter, and the first 582 bp of the *I. orientalis* URA3 open reading frame.

Integration Fragment 1F: Right Hand Integration Fragment with the Codon Optimized *E. coli* SthA Gene Integration fragment 1F, having the nucleotide sequence SEQ ID NO: 25, contains the following elements, 5' to 3': a DNA fragment corresponding to the last 567 bp of the *I. orientalis* URA3 open reading frame, the *I. orientalis* URA3 terminator, the *I. orientalis* URA3 promoter, the *I. orientalis* TDH3 promoter, the *I. orientalis* TKL terminator, the *I. orientalis* PGK promoter, the codon-optimized *E. coli* SthA gene (having nucleotide sequence SEQ ID NO: 24), the *I. orientalis* PDC terminator and a DNA fragment with homology for integration corresponding to the region immediately downstream of the *I. orientalis* MAE1 open reading frame.

Integration Fragment 1G: Left Hand Integration Fragment with the *A. vinelandii* SthA Gene Integration fragment 1G, having the nucleotide sequence SEQ ID NO: 26, contains the following elements, 5' to 3': a DNA fragment with homology for integration corresponding to the region immediately upstream of the *I. orientalis* MAE1 open reading frame, an *I. orientalis* PDC1 promoter, the *I. orientalis* TAL terminator, the *I. orientalis* ENO promoter, the *A. vinelandii* SthA gene (having nucleotide sequence, SEQ ID NO: 27), *I. orientalis* RKI terminator, URA3 promoter, and the first 582 bp of the *I. orientalis* URA3 open reading frame.

Integration Fragment 1H: Right Hand Integration Fragment with the *A. vinelandii* SthA Gene Integration fragment 1H, having the nucleotide sequence SEQ ID NO: 28, contains the following elements, 5' to 3': a DNA fragment corresponding to the last 567 bp of the *I. orientalis* URA3 open reading frame, the *I. orientalis* URA3 terminator, the *I. orientalis* URA3 promoter, the *I. orientalis* TDH3 promoter, the *I. orientalis* TKL terminator, the *I. orientalis* PGK promoter, the *A. vinelandii* SthA gene (having nucleotide sequence SEQ ID NO: 27), the *I. orientalis* PDC terminator and a DNA fragment with homology for integration corresponding to the region immediately downstream of the *I. orientalis* MAE1 open reading frame.

Integration Fragment 1I: Left Hand Integration Fragment with the *S. Cerevisiae* Stb5p Gene Integration fragment 1I, having nucleotide sequence SEQ ID NO: 29, contains the following elements, 5' to 3': a DNA fragment with homology for integration corresponding to the region immediately upstream of the *I. orientalis* MAE1 open reading frame, an *I. orientalis* PDC1 promoter, the *S. cerevisiae* Stb5p gene (having nucleotide sequence SEQ ID NO: 30), the *I. orientalis* TAL terminator, the *I. orientalis* ENO promoter, the *I. orientalis* RKI terminator, URA3 promoter, and the first 582 bp of the *I. orientalis* URA3 open reading frame.

TABLE 2

| *I. orientalis* Insertion Strains | | | |
|---|---|---|---|
| Designation | Description (in addition to those in strain P-7) | Integration Fragments | Parent strain |
| Ex. 1 | *E. coli* SthA insertion at MAE1 (1) | 1C/1B | P-7 |
| Ex. 2 | *E. coli* SthA insertion at MAE1 (2) | 1D/1A | Ex. 1 |
| Ex. 3 | *A. vinelandii* SthA insertion at MAE1 (1) | 1G/1B | P-7 |
| Ex. 4 | *A. vinelandii* SthA insertion at MAE1 (2) | 1H/1A | Ex. 3 |
| Ex. 5 | Codon optimized *E. coli* SthA insertion at MAE1 (1) | 1E/1B | P-7 |
| Ex. 6 | Codon optimized *E. coli* SthA insertion at MAE1 (2) | 1F/1A | Ex. 5 |
| P-8 | *S. cerevisiae* Stb5p insertion at MAE1 (1) | 1I/1B | P-7 |
| Ex. 7 | *S. cerevisiae* Stb5p insertion at MAE1 (1) *E. coli* SthA insertion at MAE1 (1) | 1I/1D | P-8 |
| Ex. 8 | *S. cerevisiae* Stb5p insertion at MAE1 (1) Codon optimized *E. coli* SthA insertion at MAE1 (1) | 1I/1F | P-8 |
| Ex. 9 | *S. cerevisiae* Stb5p insertion at MAE1 (1) *A. vinelandii* SthA insertion at MAE1 (1) | 1I/1H | P-8 |

Examples 9-63

Strains P-9 through P-13 are prepared in the same manner as strain P-7, except the *L. mexicana* FRD gene in each case has been mutated to render it NADPH-dependent. In each case, the *L. mexicana* FRD gene having the nucleotide sequence SEQ ID NO: 10 is used as a template to modify the coding sequence to introduce substitutions of amino acid residues of the putative NADH binding domain of the enzyme.

The FRD gene used to prepare strain P-9 is prepared by performing site-directed substitutions at amino acids 219 (glutamic acid) and 220 (tryptophan) to produce a mutated gene having the nucleotide sequence SEQ ID NO. 32.

The FRD gene used to prepare strain P-10 is prepared by performing a site-directed substitution at amino acid 417 (glutamic acid) to produce a mutated gene having nucleotide sequence SEQ ID NO: 33.

The FRD gene used to prepare strain P-11 is prepared by performing a site-directed substitution at amino acid 641 (aspartic acid) to produce a mutated gene having nucleotide sequence SEQ ID NO: 34.

The FRD gene used to prepare strain P-12 is prepared by performing site-directed substitutions at amino acids 861 (glutamic acid) and 862 (cysteine) to produce a mutated gene having nucleotide sequence SEQ ID NO: 35.

The FRD gene used to prepare strain P-13 is prepared by performing site-directed substitutions at amino acids 1035 (aspartic acid) and 1036 (serine) to produce a mutated gene having nucleotide sequence SEQ ID NO: 36.

The FRD gene used to prepare strain P-14 is prepared by performing site-directed substitutions at amino acid 411 of a *T. brucei* FRD gene having SEQ ID NO: 42 to produce a mutated gene having nucleotide sequence SEQ ID NO: 37.

Examples 10-18 are made in the same manner as Examples 1-9, respectively, except Examples 10-18 are made starting from strain P-9 instead of strain P-7. Examples 10-18 correspond to Examples 1-9, respectively, except the FRD gene in Examples 10-18 is the mutated *L. mexicana* FRD gene having the nucleotide sequence SEQ ID NO: 32.

Examples 19-27 are made in the same manner as Examples 1-9, respectively, except Examples 19-27 are made starting from strain P-10 instead of strain P-7. Examples 23-33 correspond to Examples 1-9, respectively, except the FRD gene in Examples 19-27 is the mutated *L. mexicana* FRD gene having the nucleotide sequence SEQ ID NO: 33.

Examples 28-36 are made in the same manner as Examples 1-9, respectively, except Examples 28-36 are made starting from strain P-11 instead of strain P-7. Examples 28-36 correspond to Examples 1-9, respectively, except the FRD gene in Examples 28-36 is the mutated *L. mexicana* FRD gene having the nucleotide sequence SEQ ID NO: 34.

Examples 37-45 are made in the same manner as Examples 1-9, respectively, except Examples 37-45 are made starting from strain P-12 instead of strain P-7. Examples 37-45 correspond to Examples 1-9, respectively, except the FRD gene in Examples 37-45 is the mutated *L. mexicana* FRD gene having the nucleotide sequence SEQ ID NO: 35.

Examples 46-54 are made in the same manner as Examples 1-9, respectively, except Examples 46-54 are made starting from strain P-13 instead of strain P-7. Examples 46-54 correspond to Examples 1-9, respectively, except the FRD gene in Examples 46-54 is the mutated *L. mexicana* FRD gene having the nucleotide sequence SEQ ID NO: 36.

Examples 55-63 are made in the same manner as Examples 1-9, respectively, except Examples 55-63 are made starting from strain P-14 instead of stain P-7. Examples 55-63 correspond to Examples 1-9, respectively, except the FRD gene in Examples 55-63 is the mutated *T. brucei* FRD gene having the nucleotide sequence SEQ ID NO: 37.

Examples 64-126—Deletion of Native GPD Gene

Examples 1-63 each are transformed with an integration fragment having nucleotide sequence SEQ ID NO: 38 using lithium acetate methods as described before. This integration fragment contains the following elements, 5' to 3': a DNA fragment with homology for integration corresponding to the region immediately upstream of the *I. orientalis* GPD1 open reading frame, a PDC transcriptional terminator, the URA3 promoter, the *I. orientalis* URA3 gene, a URA3 terminator, an additional URA3 promoter direct repeat for marker recycling and a DNA fragment with homology for integration corresponding to the region directly downstream of the *I. orientalis* GPD1 open reading frame. Successful transformants are selected on selection plates lacking uracil, confirmed by PCR using primers having nucleotide sequences SEQ ID NOs: 129 and 130 to confirm the 5'-crossover and SEQ ID NOs: 131 and 132 to confirm the 3'-crossover), and are then grown and plated on FOA as before until a strain in which the URA3 marker has looped out is identified. This strain is then transformed with an integration fragment having nucleotide sequence SEQ ID NO: 39. This integration fragment contains the following elements, 5' to 3': a DNA fragment with homology for integration corresponding to the region immediately upstream of the *I. orientalis* GPD1 open reading frame, the URA3 promoter, the *I. orientalis* URA3 gene, a URA3 terminator an additional URA3 promoter direct repeat for marker recycling a PDC transcriptional terminator, and a DNA fragment with homology for integration corresponding to the region directly downstream of the *I. orientalis* GPD1 open reading frame. Successful transformants are again selected on selection plates lacking uracil and confirmed by PCR, using primers having nucleotide sequences SEQ ID NOs: 130 and 132) to confirm the 5'-crossover and SEQ ID NOs: 129 and 131 to confirm the 3'-crossover). Retention of the first GPD1 deletion construct is also reconfirmed by repeating the PCR reactions used to verify proper integration of SEQ ID NO: 38 above. Confirmed isolates are grown and plated on FOA as before until a strain in which the URA3 marker has looped out is identified. The strains resulting from the transformations of Examples 1-63 are designated Examples 64-126, respectively.

Example 127-252—Deletion of Native PGI Gene

Integration fragment 5-1 (having SEQ ID NO: 40) for the deletion of the first copy of the *I. orientalis* PGI gene, contains the following elements, 5' to 3': a DNA fragment with homology for integration corresponding to the region immediately upstream of the *I. orientalis* PGI open reading frame, a PDC1 transcriptional terminator, the *I. orientalis* URA3 promoter, gene, and terminator in succession, followed by an additional URA3 promoter which serves as a direct repeat for marker recycling, and a region immediately downstream of the *I. orientalis* PGI open reading frame.

Integration fragment 5-2 (having SEQ ID NO: 41) for the deletion of the second copy of the *I. orientalis* PGI gene, contains the following elements, 5' to 3': a DNA fragment with homology for integration corresponding to the region immediately downstream of the *I. orientalis* PGI open reading frame, a PDC1 transcriptional terminator, the *I. orientalis* URA3 promoter, gene, and terminator in succession, followed by an additional URA3 promoter which serves as a direct repeat for marker recycling, and a region immediately upstream of the *I. orientalis* PGI open reading frame.

Examples 1-127 each are transformed with integration fragment 5-1 using the lithium acetate process described before. Successful transformants are selected on PGI deletion selection plates lacking uracil (SC −ura, +20 g/L fructose, +0.5 g/L glucose) incubated 3-5 days, confirmed by PCR using primers having nucleotide sequences SEQ ID NOs: 84 and 85 to confirm the 5'-crossover and SEQ ID NOs: 72 and 86 to confirm the 3'-crossover. Successful transformants are grown and plated on FOA as before until a strain in which the URA3 marker has looped out is identified. In each case, the resulting strain is then transformed with integration fragment 5-2 in the same manner and successful transformants selected on PGI deletion selection plates lacking uracil (SC −ura, +20 g/L fructose, +0.5 g/L glucose) incubated 3-5 days and confirmed by PCR using primers having nucleotide sequences SEQ ID NOs: 72 and 84 to confirm the 5'-crossover and SEQ ID NOs: 85 and 86 to confirm the 3'-crossover. A successful deletant in which the URA3 marker has looped out is again identified as before. The strains resulting from the transformations of Examples 1-126 are designated Examples 127-252, respectively.

Shake Flask Evaluation for Succinate Production

Example 1-1 is streaked out for single colonies on URA selection plates and incubated at 30° C. until single colonies are visible (1-2 days). Cells from plates are scraped into sterile growth medium and the optical density ($OD_{600}$) is measured. Optical density is measured at wavelength of 600 nm with a 1 cm pathlength using a model Genesys20 spectrophotometer (Thermo Scientific). Dry cell mass is calculated from the measured $OD_{600}$ value using an experimentally derived conversion factor of 1.7 $OD_{600}$ units per 1 g dry cell mass.

A shake flask is inoculated with the cell slurry to reach an initial $OD_{600}$ of 0.1-0.3. Prior to inoculation, the 250 mL baffled shake flasks containing 1.75 g/L dry $CaCO_3$ are sterilized. Immediately prior to inoculating, 50 mL of shake flask medium is added to the dry calcium carbonate. The shake flask medium is a sterilized, 5.5 pH aqueous solution of urea (2.3 g/L), magnesium sulfate heptahydrate (0.5 g/L), potassium phosphate monobasic (3.0 g/L), trace element solution (1 mL/L) and vitamin solution (1 mL/L), glucose (120.0 g/L), glycerol (0.1 g/L), 2-(N-Morpholino) ethanesulfonic acid (MES) (4.0 g/L). For strains lacking the URA3 gene (URA−) 20 mg/L uracil is added to the media. The trace element solution is an aqueous solution of EDTA (15.0 g/L), zinc sulfate heptahydrate (4.5 g/L), manganese chloride dehydrate (1.0 g/L), cobalt(II) chloride hexahydrate (0.3 g/L), copper(II)sulfate pentahydrate (0.3 g/L), disodium molybdenum dehydrate (0.4 g/L), calcium chloride dehydrate (4.5 g/L), iron sulphate heptahydrate (3 g/L), boric acid (1.0 g/L), and potassium iodide (0.1 g/L). The vitamin solution is an aqueous solution of biotin (D−; 0.05 g/L), calcium pantothenate (D+; 1 g/L), nicotinic acid (5 g/L), myo-inositol (25 g/L), pyridoxine hydrochloride (1 g/L), p-aminobenzoic acid (0.2 g/L).

The inoculated flask is incubated at 30° C. with shaking at 150 rpm for 72 hours and taken to analysis. Succinate concentration in the broth at the end of 72 hours fermentation is determined by gas chromatography with flame ionization detector and glucose by high performance liquid chromatography with refractive index detector.

Examples 2 through 252 are cultured in shake flasks in similar manner and found to produce succinate. The succinate concentration in the broth is measured and yield and titer are calculated.

Examples 253-255

Integration fragment P6-2a (having nucleotide sequence SEQ ID NO: 116) contains the *I. orientalis* FUM (IoFUM) gene (nucleotide sequence SEQ ID NO: 70), the last 568 base pairs of the URA3 marker, URA3 promoter, PGK promoter, PDC terminator and ADHb downstream integration arm.

Integration fragment P6-4a (having nucleotide sequence SEQ ID NO: 125) contains the *I. orientalis* FUM (IoFUM) gene (nucleotide sequence SEQ ID NO: 70) the last 568 base pairs of the URA3 marker, URA3 promoter, PGK promoter, PDC terminator and ADHb upstream integration arm.

Strain P-5 is simultaneously transformed with each of integration fragments P6-1 and P6-2a using the standard lithium acetate process described before. Successful transformants are identified by PCR, the transformants are grown and plated on 5FOA plates until a strain in which the URA3 marker has looped out is identified as before. This strain is designated strain P-6a.

Strain P-6a is simultaneously transformed with each of integration fragments P6-3 and P6-4a and using the standard lithium acetate process described before. Successful transformants are identified by PCR, the transformants are grown and plated on 5FOA plates until a strain in which the URA3 marker has looped out is identified as before. This strain is designated strain P-7a.

Strain P-7a is transformed with an integration fragments having nucleotide sequences SEQ ID NO: 38 and SEQ ID NO: 39, deleting the GPD gene as described with respect to Example 64-126 above. The resulting strain is named P-8a. Strain P-8a is grown and plated on 5FOA plates until a strain in which the URA3 marker has looped out is identified as before. The resulting strain is named P-8b.

Construction of Strains 253, 254, and 255

Integration fragment 6-1, having nucleotide sequence SEQ ID NO: 133, contains the following elements, 5' to 3': a DNA fragment with homology for integration corresponding to the region immediately downstream of the *I. orientalis* GPD1 open reading frame, an *I. orientalis* ENO1 promoter, the *E. coli* SthA gene (having the nucleotide sequence SEQ ID NO: 24), the *I. orientalis* PDC terminator, a LoxP site, the *I. orientalis* PGK promoter, the *S. cerevisiae* MEL5 gene and terminator (having the nucleotide sequence SEQ ID NO: 134), another LoxP site, and a DNA fragment with homology for integration corresponding to the region directly upstream of the *I. orientalis* GPD1 open reading frame.

Integration fragment 6-2, having nucleotide sequence SEQ ID NO: 135, contains the following elements, 5' to 3': a DNA fragment with homology for integration corresponding to the region immediately upstream of the *I. orientalis* GPD1 open reading frame, an *I. orientalis* ENO1 promoter, the *E. coli* SthA gene (having the nucleotide sequence SEQ ID NO: 24), the *I. orientalis* PDC terminator, the URA3 promoter, the *I. orientalis* URA3 gene, an additional URA3 promoter direct repeat for marker recycling and a DNA fragment with homology for integration corresponding to the region directly downstream of the *I. orientalis* GPD1 open reading frame.

Integration fragment 6-3, having nucleotide sequence SEQ ID NO: 136 contains the following elements, 5' to 3': a DNA fragment with homology for integration corresponding to the region immediately downstream of the *I. orientalis* GPD1 open reading frame, an *I. orientalis* ENO1 promoter, the *A. vinelandii* SthA gene (having the nucleotide sequence SEQ ID NO: 27), the *I. orientalis* PDC terminator, a LoxP site, the *I. orientalis* PGK promoter, the *S. cerevisiae* MEL5 gene and terminator (having the nucleotide sequence SEQ ID NO: 134), another LoxP site, and a DNA fragment with homology for integration corresponding to the region directly upstream of the *I. orientalis* GPD1 open reading frame.

Integration fragment 6-4, having nucleotide sequence SEQ ID NO: 137, contains the following elements, 5' to 3': a DNA fragment with homology for integration corresponding to the region immediately upstream of the *I. orientalis* GPD1 open reading frame, an *I. orientalis* ENO1 promoter, the *A. vinelandii* SthA gene (having the nucleotide sequence SEQ ID NO: 27), the *I. orientalis* PDC terminator, the URA3 promoter, the *I. orientalis* URA3 gene, an additional URA3 promoter direct repeat for marker recycling and a DNA fragment with homology for integration corresponding to the region directly downstream of the *I. orientalis* GPD1 open reading frame.

Integration fragment 6-5, having nucleotide sequence SEQ ID NO: 138, contains the following elements, 5' to 3': a DNA fragment with homology for integration corresponding to the region immediately downstream of the *I. orientalis* GPD1 open reading frame, an *I. orientalis* ENO1 promoter, the *P. fluorescens* SthA gene (having the nucleotide sequence SEQ ID NO: 139), the *I. orientalis* PDC terminator, a LoxP site, the *I. orientalis* PGK promoter, the *S. cerevisiae* MEL5 gene and terminator (having the nucleotide sequence SEQ ID NO: 134), another LoxP site, and a DNA fragment with homology for integration corresponding to the region directly upstream of the *I. orientalis* GPD1 open reading frame.

Integration fragment 6-6, having nucleotide sequence SEQ ID NO: 140, contains the following elements, 5' to 3': a DNA fragment with homology for integration corresponding to the region immediately upstream of the *I. orientalis* GPD1 open reading frame, an *I. orientalis* ENO1 promoter, the *P. fluorescens* SthA gene (having the nucleotide sequence SEQ ID NO: 139), the *I. orientalis* PDC terminator, the URA3 promoter, the *I. orientalis* URA3 gene, an additional URA3 promoter direct repeat for marker recycling and a DNA fragment with homology for integration corresponding to the region directly downstream of the *I. orientalis* GPD1 open reading frame.

Examples 253, 254 and 255 are constructed in the following manner. Strain P-8b is co-transformed with the integration fragments listed in the second column of Table 3. Successful integrants in each case are identified as blue colonies on selection plates with 5-bromo-4-chloro-3-indolyl-alpha-D-galactopyranoside and lacking uracil, and confirmed by PCR. PCR oligos used to test the 3' and 5' crossovers of each integration fragment are listed in the third through sixth columns of Table 3. In each case, successful transformants are grown for several rounds and plated on 5-fluoroorotic acid (FOA) plates to identify a strain in which the URA3 marker has looped out. Loopout of the URA3 marker is confirmed by PCR.

TABLE 3

| Strain name | Integration Fragments | 1st integration 3' crossover oligos SEQ ID | 1st integration 5' crossover oligos SEQ ID | 2nd integration 3' crossover oligos SEQ ID | 2nd integration 5' crossover oligos SEQ ID |
|---|---|---|---|---|---|
| Example 253 | 6-1 and 6-2 | NO: 130 and 145 | NO: 131 and 143 | NO: 130 and 143 | NO: 131 and 144 |
| Example 254 | 6-3 and 6-4 | NO: 130 and 145 | NO: 131 and 141 | NO: 130 and 141 | NO: 131 and 144 |
| Example 255 | 6-5 and 6-6 | NO: 130 and 145 | NO: 131 and 142 | NO130 and 142 | NO: 131 and 144 |

Table 4 summarizes the genetic modifications to Strains 253, 254 and 255 (relative to the wild-type strain):

TABLE 4

| Strains 253, 254 and 255 | |
|---|---|
| Strain name | Description |
| 253 | URA deletion (2)<br>PDC deletion (2)<br>*I. orientalis* PYC1 insertion at ADHa (2)<br>*S. pombe* MAE insertion at ADHa (2)<br>*L. mexicana* FRD insertion at CYB2b (2)<br>*R. delemar* MDH insertion at ADHb (2)<br>*I. orientalis* FUM insertion at ADMb (2)<br>GPD deletion<br>*E. coli* SthA insertion at GPD (2) |
| 254 | URA deletion (2)<br>PDC deletion (2)<br>*I. orientalis* PYC1 insertion at ADHa (2)<br>*S. pombe* MAE insertion at ADHa (2)<br>*L. mexicana* FRD insertion at CYB2b (2)<br>*R. delemar* MDH insertion at ADHb (2)<br>*I. orientalis* FUM insertion at ADHb (2)<br>GPD deletion<br>*A. vinelandii* SthA insertion at GPD (2) |
| 255 | URA deletion (2)<br>PDC deletion (2)<br>*I. orientalis* PYC1 insertion at ADHa (2)<br>*S. pombe* MAE insertion at ADHa (2)<br>*L. mexicana* FRD insertion at CYB2b (2)<br>*R. delemar* MDH insertion at ADHb (2)<br>*I. orientalis* FUM insertion at ADHb (2)<br>GPD deletion<br>*P. fluorescens* SthA insertion at GPD (2) |

Shake Flask Evaluation for Succinate Production for Strains 253-255

Strains P-8, 253, 254 and 255 are separately evaluated for succinate production. In each case, the strain is streaked out for single colonies on plates lacking uracil and incubated at 30° C. until single colonies are visible (1-2 days). Cells from plates are scraped into sterile growth medium and the optical density ($OD_{600}$) is measured. Optical density is measured at wavelength of 600 nm with a 1 cm pathlength using a model Genesys20 spectrophotometer (Thermo Scientific). Dry cell mass is calculated from the measured $OD_{600}$ value using an experimentally derived conversion factor of 1.7 $OD_{600}$ units per 1 g dry cell mass.

A shake flask is inoculated with the cell slurry to reach an initial $OD_{600}$ of 0.1-0.3. Prior to inoculation, the 250 mL baffled shake flasks containing 1.28 g/L dry $CaCO_3$ are sterilized. Immediately prior to inoculating, 50 mL of shake flask medium is added to the dry calcium carbonate. The shake flask medium is a sterilized, 4.5 pH aqueous solution of urea (2.3 g/L), magnesium sulfate heptahydrate (0.5 g/L), potassium phosphate monobasic (3.0 g/L), trace element solution (1 mL/L) and vitamin solution (1 mL/L), glucose (120.0 g/L), glycerol (0.1 g/L), 2-(N-Morpholino) ethanesulfonic acid (MES) (4.0 g/L). The trace element solution is an aqueous solution of EDTA (15.0 g/L), zinc sulfate heptahydrate (4.5 g/L), manganese chloride dehydrate (1.0 g/L), cobalt(II) chloride hexahydrate (0.3 g/L), copper(II)sulfate pentahydrate (0.3 g/L), disodium molybdenum dehydrate (0.4 g/L), calcium chloride dehydrate (4.5 g/L), iron sulphate heptahydrate (3 g/L), boric acid (1.0 g/L), and potassium iodide (0.1 g/L). The vitamin solution is an aqueous solution of biotin (D−; 0.05 g/L), calcium pantothenate (D+; 1 g/L), nicotinic acid (5 g/L), myo-inositol (25 g/L), pyridoxine hydrochloride (1 g/L), p-aminobenzoic acid (0.2 g/L).

The inoculated flask is incubated at 30° C. with shaking at 150 rpm for 96 hours and taken to analysis. Succinate and glucose concentrations in the broth at the end of 96 hours fermentation are determined by high performance liquid chromatography with refractive index detector. Results are as indicated in Table 5:

TABLE 5

| Strain | Glucose after 96 hr, g/L | Average glucose consumption rate, g/L/hr | Succinate after 96 hr, g/L | Average succinate production rate, g/L/hr |
|---|---|---|---|---|
| P-8a | 5.46 | 1.190 | 57.6 | 0.60 |
| 253 | 6.20 | 1.185 | 88.4 | 0.92 |
| 255 | 6.10 | 1.186 | 84.1 | 0.88 |
| 257 | 8.58 | 1.161 | 89.0 | 0.93 |

As can be seen from the data in Table 5, all strains produce succinate. However, Examples 253-255 produce more succinate, at a 50% greater rate, than Strain P-8a.

Example 256

The URA3 gene is deleted from a wild type strain of *S. cerevisiae* (CEN-PK 113-7D) to create a strain with a uracil auxotrophy. This strain is called S-1.

Ethanol production is eliminated in S-1 by deletion of the three PDC genes (PDC1, PDC5, and PDC6), using conventional methods, to produce a strain (S-2) that does not produce ethanol. A pathway from pyruvate to succinate is introduced into strain S-2 by the integration of the following exogenous genes driven by strong promoters: the *I. orientalis* PYC gene, the *R. delemar* MDH gene, the *I. orientalis* FUM (fumarase), the L. *Mexicana* FRD gene, and the *S. pombe* MAE gene. The various promoters include the *S. cerevisiae* CYC1 promoter, the *S. cerevisiae* ADH1 promoter and the *S. cerevisiae* GPD1 promoter.

Strain S-3 is transformed with the *E. coli* soluble transhydrogenase (SthA) gene (SEQ ID NO: 21) under the control of the *S. cerevisiae* CYC1 promoter. The resulting strain (which still is prototrophic for uracil) is called S-4. Strain S-4 cannot produce ethanol, has an active metabolic pathway to succinate, overexpresses the soluble transhydrogenase enzyme and is prototrophic for uracil.

After deletion of the PDC genes from *S. cerevisiae*, it becomes necessary to supplement the growth medium with a C2 carbon source to support growth. Additionally, glucose is known to suppress growth of *S. cerevisiae* strains lacking adequate PDC activity. Therefore, Strains S-3 and S-4 are grown on a medium containing ethanol as a sole carbon source to a suitable cell density in a shake flask. The cells are collected by centrifugation and the ethanol media discarded. The cells are resuspended in a glucose containing medium in a shake flask and cultivated under aeration at 30° in a stirred shake flask, and succinate formation is monitored until glucose depletion. Strain S-4, which exhibits transhydrogenase activity, shows improved succinate production compared with strain S-3, which lacks transhydrogenase activity.

The invention claimed is:

1. A fermentation broth comprising at least one carbon source and recombinant yeast cells engineered to produce succinate through an active reductive tricarboxylic acid (TCA) pathway from pyruvate or phosphoenolpyruvate, wherein the recombinant yeast cells are genetically modified to express a soluble nicotinamide adenine dinucleotide phosphate (NAD(P)+) transhydrogenase enzyme in the cytosol of the yeast cells by having integrated into their genomes an exogenous gene encoding the soluble NAD(P)+ transhydrogenase enzyme, wherein the recombinant yeast cells are further modified by having integrated into their genomes at least one of:

(i) an exogenous pyruvate carboxylase gene that encodes an enzyme which catalyzes the conversion of pyruvate to oxaloacetate;

(ii) an exogenous malate dehydrogenase gene which encodes an enzyme that catalyzes the conversion of oxaloacetate to malate;

(iii) an exogenous fumarase gene that encodes an enzyme which catalyzes the conversion of malate to fumarate; and (iv) an exogenous fumarate reductase gene which encodes an enzyme which catalyzes the conversion of fumarate to succinate, and wherein the recombinant yeast cells produce more succinate through the active reductive TCA pathway as compared to a corresponding parent yeast cell lacking the soluble NAD(P)+ transhydrogenase enzyme.

* * * * *

SEQUENCE LISTING

```
<160> NUMBER OF SEQ ID NOS: 146

<210> SEQ ID NO 1
<211> LENGTH: 4910
<212> TYPE: DNA
<213> ORGANISM: Artificial
<220> FEATURE:
<223> OTHER INFORMATION: URA 3 gene disruption fragment
<220> FEATURE:
<221> NAME/KEY: misc_feature
<222> LOCATION: (1656)..(1656)
<223> OTHER INFORMATION: n is a, c, g, or t
<220> FEATURE:
<221> NAME/KEY: misc_feature
<222> LOCATION: (4312)..(4312)
<223> OTHER INFORMATION: n is a, c, g, or t

<400> SEQUENCE: 1

ctcaaaacta tttaattagt taattgtata aactgtatgt cattataaac agggaaggtt      60

gacattgtct agcggcaatc attgtctcat ttggttcatt aactttggtt ctgttcttgg     120

aaacgggtac caactctctc agagtgcttc aaaaattttt cagcacattt ggttagacat     180

gaactttctc tgctggttaa ggattcagag gtgaagtctt gaacacaatc gttgaaacat     240

ctgtccacaa gagatgtgta tagcctcatg aaatcagcca tttgcttttg ttcaacgatc     300

ttttgaaatt gttgttgttc ttggtagtta agttgatcca tcttggctta tgttgtgtgt     360

atgttgtagt tattcttagt atattcctgt cctgagttta gtgaaacata atatcgcctt     420

gaaatgaaaa tgctgaaatt cgtcgacata caatttttca aacttttttt ttttcttggt     480
```

```
gcacggacat gtttttaaag gaagtactct ataccagtta ttcttcaccc tgcagggtac    540
gtagcatgca ctcgcaagct gtgccatcgc ccaacggtta attataagaa atcaacatca    600
gccaacaact attttcgtcc ccctcttttc agtggtaacg agcaattaca ttagtaagag    660
actattttct tcagtgattt gtaatttttt ttcagtgatt tgtaattctt tctcgaaata    720
tgcgggctta acttatccgg acattcacta catgcaagga aaaacgagaa ccgcggagat    780
ttcctcagta agtaacaatg atgatctttt tacgcttcat catcactttc caaagttcta    840
agctataagt tcaagcctag atacgctgaa aaactcctga ccaacaatgt aaagaaaaca    900
attacaattg taaggttgaa aacatctaaa aatgaaatat tttattgtac atgcacaccc    960
tgatagtcat tctcttactt catccctgaa agacgtggct gtacaagagt tggaatcgca   1020
aggtcatgag gttaaagtta gtgatcttta tgctcaaaag tggaaggcct caatagaccg   1080
tgacgacttc gagcagcttt tcgcaagaag agaggttaaa aataccccaa gcttcttatg   1140
aagcgtatgc cagaggagca ttaacaaaag acgtaaatca ggaacaggaa aaacttattt   1200
gggcggactt tgtcattttg tcgtttccta tatggtggtc ttctatgccg gctagtcgac   1260
cccctcgacc ccctcgagcg atctcgagat ttgctgcaac ggcaacatca atgtccacgt   1320
ttacacacct acatttatat ctatatttat atttatattt atttatttat gctacttagc   1380
ttctatagtt agttaatgca ctcacgatat tcaaaattga cacccttcaa ctactcccta   1440
ctattgtcta ctactgtcta ctactcctct ttactatagc tgctcccaat aggctccacc   1500
aataggctct gtcaatacat tttgcgccgc cacctttcag gttgtgtcac tcctgaagga   1560
ccatattggg taatcgtgca atttctggaa gagagtgccg cgagaagtga ggccccccact   1620
gtaaatcctc gagggggcat ggagtatggg gcatgnagga tggaggatgg gggggggggg   1680
ggaaaatagg tagcgaaagg acccgctatc accccacccg gagaactcgt tgccgggaag   1740
tcatatttcg acactccggg gagtctataa aaggcgggtt ttgtcttttg ccagttgatg   1800
ttgctgagag gacttgtttg ccgtttcttc cgatttaaca gtatagaatc aaccactgtt   1860
aattatacac gttatactaa cacaacaaaa acaaaaacaa cgacaacaac aacaacaatg   1920
tttgctttct actttctcac cgcatgcacc actttgaagg gtgttttcgg agtttctccg   1980
agttacaatg gtcttggtct caccccacag atgggttggg acagctggaa tacgtttgcc   2040
tgcgatgtca gtgaacagct acttctagac actgctgata gaatttctga cttggggcta   2100
aaggatatgg gttacaagta tgtcatccta gatgactgtt ggtctagcgg cagggattcc   2160
gacggtttcc tcgttgcaga caagcacaaa tttcccaacg gtatgggcca tgttgcagac   2220
cacctgcata ataacagctt tcttttcggt atgtattcgt ctgctggtga gtacacctgt   2280
gctgggtacc ctgggtctct ggggcgtgag gaagaagatg ctcaattctt tgcaaataac   2340
cgcgttgact acttgaagta tgataattgt tacaataaag gtcaatttgg tacaccagac   2400
gtttcttacc accgttacaa ggccatgtca gatgctttga ataaaactgg taggcctatt   2460
ttctattctc tatgtaactg ggtcaggat ttgacatttt actggggctc tggtatcgcc   2520
aattcttgga gaatgagcgg agatattact gctgagttca cccgtccaga tagcagatgt   2580
ccctgtgacg gtgacgaata tgattgcaag tacgccggtt tccattgttc tattatgaat   2640
attcttaaca aggcagctcc aatggggcaa aatgcaggtg ttggtggttg gaacgatctg   2700
gacaatctag aggtcggagt cggtaatttg actgacgatg aggaaaaggc ccatttctct   2760
atgtgggcaa tggtaaagtc cccacttatc attggtgccg acgtgaatca cttaaaggca   2820
tcttcgtact cgatctacag tcaagcctct gtcatcgcaa ttaatcaaga tccaaagggt   2880
```

```
attccagcca caagagtctg gagatattat gtttcagaca ccgatgaata tggacaaggt   2940
gaaattcaaa tgtggagtgg tccgcttgac aatggtgacc aagtggttgc tttattgaat   3000
ggaggaagcg tagcaagacc aatgaacacg accttggaag agatttcttt tgacagcaat   3060
ttgggttcaa aggaactgac atcgacttgg gatatttacg acttatgggc caacagagtt   3120
gacaactcta cggcgtctgc tatccttgaa cagaataagg cagccaccgg tattctctac   3180
aatgctacag agcagtctta taaagacggt ttgtctaaga atgatacaag actgtttggc   3240
cagaaaattg gtagtctttc tccaaatgct atacttaaca caactgttcc agctcatggt   3300
atcgccttct ataggttgag accctcggct taagctcaat gttgagcaaa gcaggacgag   3360
aaaaaaaaaa ataatgattg ttaagaagtt catgaaaaaa aaaaggaaaa atactcaaat   3420
acttataaca gagtgattaa ataataaacg gcagtatacc ctatcaggta ttgagatagt   3480
tttatttttg taggtatata atctgaagcc tttgaactat tttctcgtat atatcatgga   3540
gtatacattg cattagcaac attgcatact agtcactcgc aagctgtgcc atcgcccaac   3600
ggttaattat aagaaatcaa catcagccaa caactatttt cgtcccccctc ttttcagtgg   3660
taacgagcaa ttacattagt aagagactat tttcttcagt gatttgtaat ttttttcag   3720
tgatttgtaa ttctttctcg aaatatgcgg gctwaamtaa tccggacatt cactacatgc   3780
aaggaaaaac gagaaccgcg gagatttcct cagtaagtaa caatgatgat ctttttacgc   3840
ttcatcatca ctttccaaag ttctaagcta taagttcaag cctagatacg ctgaaaaact   3900
cctgaccaac aatgtaaaga aaacaattac aattgtaagg ttgaaaacat ctaaaaatga   3960
aatattttat tgtacatgca caccctgata gtcattctct tacttcatcc ctgaaagacg   4020
tggctgtaca agagttggaa tcgcaaggtc atgaggttaa agttagtgat ctttatgctc   4080
aaaagtggaa ggcctcaata gaccgtgacg acwwmaaaaa amaaamrmaa gaagagaggt   4140
taaaaatacc ccaagcttct tatgaagcgt atgccagagg agcattaaca aaagacgtaa   4200
atcaggaaca ggaaaaactt atttgggcgg actttgtcat tttgtcgttt cctatatggt   4260
ggtcttctat gccggctagc ggccgggcaa caaagcctcc cagatttgat anattttcaa   4320
tttgtgcttt gaatcatgac ttccacctgt ttggtccgca agaacacgta aatgcgcaat   4380
ttgtttctcc cttctgctta aaaaccatgc acctttaata ttatctggaa agataaagaa   4440
cagaattgtt gcgtagaaac aagtagcaga gccgtaaatg agaaaaatat acttccaagc   4500
tggtaatttc ccctttatta gtccaataca gtgtccgaag accccaccaa gaataccagc   4560
aagggtgttg aaatataatg tagatcttag tggttgttct gatttcttcc accacattcc   4620
gctaataatc ataaaagacg gtaatattcc ggcttcaaat acgccaagaa aaaacctcac   4680
ggtaaccaaa ccaccaaagc tatgacatgc agccatgcac ataagtaagc cgccccaaat   4740
gaacaaacaa atagacacaa atttgccaat tctaactcgt ggcaacaaaa aaaaggatat   4800
gaactcacct aataaataac cgaaataaaa agtagaagca actgtggaaa attgagaacc   4860
atgtaaattt gtgtcttctt tcaatgtata aacagccgca atacctaggg              4910
```

<210> SEQ ID NO 2
<211> LENGTH: 3704
<212> TYPE: DNA
<213> ORGANISM: Artificial
<220> FEATURE:
<223> OTHER INFORMATION: PDC gene disruption fragment

<400> SEQUENCE: 2

```
cccccagttg ttgttgcaat taacaaattt gctaccgaca ccgagaagga aattgagacc     60
attagagaag aagccatcaa ggctggtgca tttgatgctg ttgagtcaga ccattggtca    120
caaggtggta agggtgcaat caagttagct gaggcaattg tacgtgctac cgaggaaaga    180
ccgttggaag aaagtcaacc tcctaactat ctttattcat tagatggttc gttagaagat    240
agactaagaa caattgccac caagatgtat ggagcaaaag atattgaact atctgagttg    300
gccaagaaac agattgaaga gtatgagagt caaggttttg gcaagctgcc tgtttgtatt    360
gcaaagacgc aatattctct ctcccatgat ccaacattga aaggtgttcc aaaggatttc    420
atcttcccaa tcagagaagt tagaataagt gcaggagcag gatatttata tgcactagct    480
gcaaagatca tgacaattcc aggtctatca acttatgccg gatttatgaa tgttgaagtc    540
aacgaagatg gtgagattga tggattgttt tagtttttat tataaaatta tatattattc    600
ttaattacat atcacccttc tatcagggaa gggagaaacg aaaatagaga gtgacctatc    660
caagctcggg ggtctaagtt ttaatggccc agggaatcat tacttttttt tctcaatcct    720
tgatggataa aagtattaca tacgtacagg attgtgtatt agtgtatttc gttatatgat    780
taaacaaagt ttatagattg taaagtagac gtaaagttta gtaattcatt ttaatgttca    840
ttttacattc agatggcggc cgcggatcca gatcccccgg ggcgttgaag atctattctc    900
cagcaattaa atttgtgaag aataactggt atagagtact tcctttaaaa acatgtccgt    960
gcaccaagaa aaaaaaaaag tttgaaaaat tgtatgtcga cgaatttcag cattttcatt   1020
tcaaggcgat attatgtttc actaaactca ggacaggaat atactaagaa taactacaac   1080
atacacacaa cataagccaa gatggatcaa cttaactacc aagaacaaca acaatttcaa   1140
aagatcgttg aacaaaagca aatggctgat ttcatgaggc tatctgcaga tacgcggaac   1200
aatcaatcga taatgatttg actgataaag aaaaccatac ttttgtttat gtttattagt   1260
tatcgctttg ctacattaaa aattcacata ctaaagcctt tgttaaacaa ctttttctaa   1320
atcttaagat tttactctat ctagtttttt tggttgtagg tgaacgtaaa gtacctcatt   1380
tatttttttt tttttgcttg tgtaattctt ttcatgctta tttaaactag tgtacatgta   1440
tcaaatcttt gtgtaagaat catttaaatc tgtttaaata agcattccaa ccagcttgtt   1500
ggtatctttt agcttgctct ataggatctc ttccttgacc gtacaaacct ctaccaacaa   1560
ttatgatatc cgttccagtc tttacaactt catcaacagt tctatattgt tgaccaagtg   1620
catcaccttt gtcatctaaa ccaacccctg gagtcataat gatccagtca aaaccttctt   1680
ctctaccgcc catatcgtgt tgcgcaataa aaccaatgac aaactcttta tcagatttag   1740
caatttctac tgtttttttct gtatattcac catatgctaa agaacccttt gatgataact   1800
cagcaagcat tagcaaacct ctaggttcac tggttgtttc ttgggctgcc tccttcaagc   1860
cagaaacaat acctgcaccc gttacaccat gtgcattagt gatgtcagcc cattcggcaa   1920
tacggaagac accagattta tattgatttt taacagtgtt accaatatca gcaaattttc   1980
tatcttcaaa aatcataaaa ttatgtttct tggcaagctc cttcaaaggc aacacagttc   2040
cttcatacgt aaaatcagaa acaatatcga tgtgtgtttt aactagacag atgtaaggac   2100
caatagtgtc caaaatagag agaagctttt cagtttcagt aatatccaat gatgcacaaa   2160
ggttagactt cttttcctcc atgatggaga aaagtctcct agcaacaggg gaagtgtgtg   2220
attctgatct ttctttgtat gacgccatcc ttgacaaaca aactacttta ttaaagcgtt   2280
gaagatctat tctccagcaa ttaaatttgt gaagaataac tggtatagag tacttccttt   2340
aaaaacatgt ccgtgcacca agaaaaaaaa aaagtttgaa aaattgtatg tcgacgaatt   2400
```

```
tcagcatttt catttcaagg cgatattatg tttcactaaa ctcaggacag gaatatacta   2460

agaataacta caacatacac acaacataag ccaagatgga tcaacttaac taccaagaac   2520

aacaacaatt tcaaaagatc gttgaacaaa agcaaatggc tgatttcatg aggctatgaa   2580

ttcttttatt ataaaattat atattattct taattacata tcacccttct atcagggaag   2640

ggagaaacga aaatagagag tgacctatcc aagcttgggg gtctaagttt taatggccca   2700

gggaatcatt actttttttt ctcaatcctt gatggataaa agtattacat acgtacagga   2760

ttgtgtatta gtgtatttcg ttatatgatt aaacaaagtt tatagattgt aaagtagacg   2820

taaagtttag taattcattt taatgttcat tttacattca gatgttaatt aaggcctcga   2880

gggatccgcg gccgctattt ttgtgttttg ctgtgttttg ttttattttg ttttattggg   2940

aagaaaatat ataataatag aatattatat taacaaataa ttaaagaagc tcaactgtta   3000

ttagaataaa tgggttctcc gtgtcctttt tatacgcctt ctccgaaaag aaaaaaacca   3060

tcgtatcatt tgtagcccac gccacccgga aaaaccacca ttgtcctcag cagtccgcaa   3120

aaatatggat gcgctcaatc aatttccctc ccccgtcaat gccaaaagga taacgacaca   3180

ctattaagag cgcatcattt gtaaaagccg aggaaggggg atacgctgac cgagacgtct   3240

cgcctcactc tcggagctga gccgccctcc ttaagaaatt catgggaaga acacccttcg   3300

cggcttctga acggctcgcc ctcgtccatt ggtcacctca cagtggcaac taataaggac   3360

attatagcaa tagaaattaa aatggtgcac agaaatacaa taggatcgaa taggatagga   3420

tacaataaga tacggaatat tagactatac tgtgatacgg tacgctacga tacgctacga   3480

tacgatacga tagaggatac cacggatata acgtagtgtt atttttcatt attggggttt   3540

tttttctgtt tgaattttcc acgtcaagag tatcccatct gacaggaacc gatggactcg   3600

tcacagtacc tatcgcccga gttcaatcca tggacgctgc gggtgaagga tcttcgcccg   3660

ctgttggcaa gccatgggat cagggcgtcg ccaagggacg ggcc                    3704
```

```
<210> SEQ ID NO 3
<211> LENGTH: 6392
<212> TYPE: DNA
<213> ORGANISM: Artificial
<220> FEATURE:
<223> OTHER INFORMATION: PYC gene integration fragment

<400> SEQUENCE: 3
```

```
ctaagtagtg gtgttggtga actcaagatg gactctttag gtaattatat tcttgaatag     60

ttgtgtaaag cgaatatgca aatagatttg ttttataatt atgcatctct ttgaaagagg    120

tttagaggca aagttcttgc atacaatatt gtgattgttt taatgtcatt cttgattttc    180

ataaagagat taaaaaaaaa aaaaaaaaac ttataaaatt gagtagaacc atttatatat    240

aagacaaaga ttgtctgtat tagtcctcaa cacactaaac cttacatact tagggtaaat    300

ttgctaatag agtgatatgt tcatgagaac tccaacgaca acacaaccac ctatttgcac    360

aacaaacacc attgtcgcac gctgcgcgcc ctagaagtag aaagaaaggg aaatgacatt    420

aagagaatca taccccgtgc ccgtaacgcc gaaaaaatca caccccgtcc cccacacctt    480

aaaacctcaa ccgcttaaca ccgccacacc ctttctcttt ataaacgccg tttgcattac    540

tcattcttct tataaaccgc accccccaaa acgcggaata gcttcaaccc cccaatcaga    600

tatgagtttc ccgggaaacc cgcttttccc gacagcccca caaggggttg gtctataaaa    660

gaggacgttt tccccgtcat cgagattgaa gattcttaca ggcccattta ttcaaattgg    720
```

-continued

```
agttgattct tcttgtcttt actttctttc tctctttttc ttccttttttt aatattatct    780
tttgtcaagc ctggttccct aagttgaact ctcttttctt gtgatcctcc tatatagata    840
cgccttgcca aatgcggccg cgagtccatc ggttcctgtc agatgggata ctcttgacgt    900
ggaaaattca aacagaaaaa aaaccccaat aatgaaaaat aacactacgt tatatccgtg    960
gtatcctcta tcgtatcgta tcgtagcgta tcgtagcgta ccgtatcaca gtatagtcta   1020
atattccgta tcttattgta tcctatccta ttcgatccta ttgtatttca gtgcaccatt   1080
ttaatttcta ttgctataat gtccttatta gttgccactg tgaggtgacc aatggacgag   1140
ggcgagccgt tcagaagccg cgaagggtgt tcttcccatg aatttcttaa ggagggcggc   1200
tcagctccga gagtgaggcg agacgtctcg gtcagcgtat ccccccttcct cggcttttac   1260
aaatgatgcg ctcttaatag tgtgtcgtta tccttttggc attgacgggg gagggaaatt   1320
gattgagcgc atccatattt ttgcggactg ctgaggacaa tggtggtttt tccgggtggc   1380
gtgggctaca aatgatacga tggttttttt cttttcggag aaggcgtata aaaaggacac   1440
ggagaaccca tttattctaa aaacagttga gcttctttaa ttattttttg atataatatt   1500
ctattattat atattttctt cccaataaaa caaaataaaa caaaacacag caaaacacaa   1560
aaattctaga taaaatgtca actgtggaag atcactcctc cctacataaa ttgagaaagg   1620
aatctgagat tctttccaat gcaaacaaaa tcttagtggc taatagaggt gaaattccaa   1680
ttagaatttt caggtcagcc catgaattgt caatgcatac tgtggcgatc tattcccatg   1740
aagatcggtt gtccatgcat aggttgaagg ccgacgaggc ttatgcaatc ggtaagactg   1800
gtcaatattc gccagttcaa gcttatctac aaattgacga aattatcaaa atagcaaagg   1860
aacatgatgt ttccatgatc catccaggtt atggtttctt atctgaaaac tccgaattcg   1920
caaagaaggt tgaagaatcc ggtatgattt gggttgggcc tcctgctgaa gttattgatt   1980
ctgttggtga caaggtttct gcaagaaatt tggcaattaa atgtgacgtt cctgttgttc   2040
ctggtaccga tggtccaatt gaagacattg aacaggctaa acagtttgtg gaacaatatg   2100
gttatcctgt cattataaag gctgcatttg gtggtggtgg tagaggtatg agagttgtta   2160
gagaaggtga tgatatagtt gatgctttcc aaagagcgtc atctgaagca aagtctgcct   2220
ttggtaatgg tacttgtttt attgaaagat tttggataa gccaaaacat attgaggttc    2280
aattattggc tgataattat ggtaacacaa tccatctctt tgaaagagat tgttctgttc   2340
aaagaagaca tcaaaaggtt gttgaaattg cacctgccaa aactttacct gttgaagtta   2400
gaaatgctat attaaaggat gctgtaacgt tagctaaaac cgctaactat agaaatgctg   2460
gtactgcaga atttttagtt gattcccaaa acagacatta ttttattgaa attaatccaa   2520
gaattcaagt tgaacataca attactgaag aaatcacggg tgttgatatt gttgccgctc   2580
aaattcaaat tgctgcaggt gcatcattgg aacaattggg tctattacaa aacaaaatta   2640
caactagagg ttttgcaatt caatgtagaa ttacaaccga ggatcctgct aagaattttg   2700
ccccagatac aggtaaaatt gaggtttata gatctgcagg tggtaacggt gtcagattag   2760
atggtggtaa tgggtttgcc ggtgctgtta tatctcctca ttatgactcg atgttggtta   2820
aatgttcaac atctggttct aactatgaaa ttgccagaag aaagatgatt agagctttag   2880
ttgaatttag aatcagaggt gtcaagacca atattccttt cttattggca ttgctaactc   2940
atccagtttt catttcgggt gattgttgga caacttttat tgatgatacc ccttcgttat   3000
tcgaaatggt ttcttcaaag aatagagccc aaaaattatt ggcatatatt ggtgacttgt   3060
gtgtcaatgg ttcttcaatt aaaggtcaaa ttggtttccc taaattgaac aaggaagcag   3120
```

```
aaatcccaga tttgttggat ccaaatgatg aggttattga tgtttctaaa ccttctacca   3180
atggtctaag accgtatcta ttaaagtatg gaccagatgc gttttccaaa aaagttcgtg   3240
aattcgatgg ttgtatgatt atggatacca cctggagaga tgcacatcaa tcattattgg   3300
ctacaagagt tagaactatt gatttactga gaattgctcc aacgactagt catgccttac   3360
aaaatgcatt tgcattagaa tgttggggtg gcgcaacatt tgatgttgcg atgaggttcc   3420
tctatgaaga tccttgggag agattaagac aacttagaaa ggcagttcca aatattcctt   3480
tccaaatgtt attgagaggt gctaatggtg ttgcttattc gtcattacct gataatgcaa   3540
ttgatcattt tgttaagcaa gcaaaggata atggtgttga tattttcaga gtctttgatg   3600
ctttgaacga tttggaacaa ttgaaggttg gtgttgatgc tgtcaagaaa gccggaggtg   3660
ttgttgaagc tacagtttgt tactcaggtg atatgttaat tccaggtaaa aagtataact   3720
tggattatta tttagagact gttggaaaga ttgtggaaat gggtacccat attttaggta   3780
ttaaggatat ggctggcacg ttaaagccaa aggctgctaa gttgttgatt ggctcgatca   3840
gatcaaaata ccctgacttg gttatccatg tccataccca tgactctgct ggtaccggta   3900
tttcaactta tgttgcatgc gcattggcag gtgccgacat tgtcgattgt gcaatcaatt   3960
cgatgtctgg tttaacctct caaccttcaa tgagtgcttt tattgctgct ttagatggtg   4020
atatcgaaac tggtgttcca gaacattttg caagacaatt agatgcatac tgggcagaaa   4080
tgagattgtt atactcatgt ttcgaagccg acttgaaggg accagaccca gaagtttata   4140
aacatgaaat tccaggtgga cagttgacta acctaatctt ccaagcccaa caagttggtt   4200
tgggtgaaca atgggaagaa actaagaaga agtatgaaga tgctaacatg ttgttgggtg   4260
atattgtcaa ggttacccca acctccaagg ttgttggtga tttagcccaa tttatggttt   4320
ctaataaatt agaaaaagaa gatgttgaaa aacttgctaa tgaattagat ttcccagatt   4380
cagttcttga tttctttgaa ggattaatgg gtacaccata tggtggattc ccagagcctt   4440
tgagaacaaa tgtcatttcc ggcaagagaa gaaaattaaa gggtagacca ggtttagaat   4500
tagaaccttt caacctcgag gaaatcagag aaaatttggt ttccagattt ggtccaggta   4560
ttactgaatg tgatgttgca tcttataaca tgtatccaaa ggtttacgag caatatcgta   4620
aggtggttga aaaatatggt gatttatctg ttttaccaac aaaagcattt ttggctcctc   4680
caactattgg tgaagaagtt catgtggaaa ttgagcaagg taagactttg attattaagt   4740
tattagccat ttctgacttg tctaaatctc atggtacaag agaagtatac tttgaattga   4800
atggtgaaat gagaaaggtt acaattgaag ataaaacagc tgcaattgag actgttacaa   4860
gagcaaaggc tgacggacac aatccaaatg aagttggtgc gccaatggct ggtgtcgttg   4920
ttgaagttag agtgaagcat ggaacagaag ttaagaaggg tgatccatta gccgttttga   4980
gtgcaatgaa aatggaaatg gttatttctg ctcctgttag tggtagggtc ggtgaagttt   5040
ttgtcaacga aggcgattcc gttgatatgg gtgatttgct tgtgaaaatt gccaaagatg   5100
aagcgccagc agcttaatta attctgtctt tgattttctt atgttattca aaacatctgc   5160
cccaaaatct aacgattata tatattccta cgtataactg tatagctaat tattgattta   5220
tttgtacata aaaaccacat aaatgtaaaa gcaagaaaaa aaataactaa ggagaaggat   5280
caatatctca tttataatgc tcgccaaagc agcgtacgtg aattttaatc aagacatcaa   5340
caaatcttgc aacttggtta tatcgcttct tcacccactc acccgctttt ctacattgtt   5400
gaacacaaat atatacaggg gtatgtctca aggtcaagtg cagtttcaac agagactacc   5460
```

```
tcaaggtacc tcttcagaaa tgcagaactt cactcttgat cagattttct ccgaattaaa   5520

ggtttaaaca tagcctcatg aaatcagcca tttgcttttg ttcaacgatc ttttgaaatt   5580

gttgttgttc ttggtagtta agttgatcca tcttggctta tgttgtgtgt atgttgtagt   5640

tattcttagt atattcctgt cctgagttta gtgaaacata atatcgcctt gaaatgaaaa   5700

tgctgaaatt cgtcgacata caatttttca aactttttt ttttcttggt gcacggacat   5760

gtttttaaag gaagtactct ataccagtta ttcttcacaa atttaattgc tggagaatag   5820

atcttcaacg ctttaataaa gtagtttgtt tgtcaaggat ggcgtcatac aaagaaagat   5880

cagaatcaca cacttcccct gttgctagga gacttttctc catcatggag gaaaagaagt   5940

ctaacctttg tgcatcattg gatattactg aaactgaaaa gcttctctct attttggaca   6000

ctattggtcc ttacatctgt ctagttaaaa cacacatcga tattgtttct gattttacgt   6060

atgaaggaac tgtgttgcct ttgaaggagc ttgccaagaa acataatttt atgatttttg   6120

aagatagaaa atttgctgat attggtaaca ctgttaaaaa tcaatataaa tctggtgtct   6180

tccgtattgc cgaatgggct gacatcacta atgcacatgg tgtaacgggt gcaggtattg   6240

tttctggctt gaaggaggca gcccaagaaa caaccagtga acctagaggt ttgctaatgc   6300

ttgctgagtt atcatcaaag ggttctttag catatggtga atatacagaa aaaacagtag   6360

aaattgctaa atctgataaa gagtttgttg ag                                  6392
```

```
<210> SEQ ID NO 4
<211> LENGTH: 3543
<212> TYPE: DNA
<213> ORGANISM: Issatchenkia orientalis

<400> SEQUENCE: 4

atgtcaactg tggaagatca ctcctcccta cataaattga gaaaggaatc tgagattctt     60

tccaatgcaa acaaaatctt agtggctaat agaggtgaaa ttccaattag aattttcagg    120

tcagcccatg aattgtcaat gcatactgtg gcgatctatt cccatgaaga tcggttgtcc    180

atgcataggt tgaaggccga cgaggcttat gcaatcggta agactggtca atattcgcca    240

gttcaagctt atctacaaat tgacgaaatt atcaaaatag caaaggaaca tgatgtttcc    300

atgatccatc caggttatgg tttcttatct gaaaactccg aattcgcaaa gaaggttgaa    360

gaatccggta tgatttgggt tgggcctcct gctgaagtta ttgattctgt tggtgacaag    420

gtttctgcaa gaaatttggc aattaaatgt gacgttcctg ttgttcctgg taccgatggt    480

ccaattgaag acattgaaca ggctaaacag tttgtggaac aatatggtta tcctgtcatt    540

ataaaggctg catttggtgg tggtggtaga ggtatgagag ttgttagaga aggtgatgat    600

atagttgatg ctttccaaag agcgtcatct gaagcaaagt ctgcctttgg taatggtact    660

tgttttattg aaagattttt ggataagcca aaacatattg aggttcaatt attggctgat    720

aattatggta acacaatcca tctctttgaa agagattgtt ctgttcaaag aagacatcaa    780

aaggttgttg aaattgcacc tgccaaaact ttacctgttg aagttagaaa tgctatatta    840

aaggatgctg taacgttagc taaaaccgct aactatagaa atgctggtac tgcagaattt    900

ttagttgatt cccaaaacag acattatttt attgaaatta atccaagaat tcaagttgaa    960

catacaatta ctgaagaaat cacgggtgtt gatattgttg ccgctcaaat tcaaattgct   1020

gcaggtgcat cattggaaca attgggtcta ttacaaaaca aaattacaac tagaggtttt   1080

gcaattcaat gtagaattac aaccgaggat cctgctaaga attttgcccc agatacaggt   1140

aaaattgagg tttatagatc tgcaggtggt aacggtgtca gattagatgg tggtaatggg   1200
```

```
tttgccggtg ctgttatatc tcctcattat gactcgatgt tggttaaatg ttcaacatct   1260
ggttctaact atgaaattgc cagaagaaag atgattagag ctttagttga atttagaatc   1320
agaggtgtca agaccaatat tcctttctta ttggcattgc taactcatcc agttttcatt   1380
tcgggtgatt gttggacaac ttttattgat gataccctt cgttattcga aatggtttct    1440
tcaaagaata gagcccaaaa attattggca tatattggtg acttgtgtgt caatggttct   1500
tcaattaaag gtcaaattgg tttccctaaa ttgaacaagg aagcagaaat cccagatttg   1560
ttggatccaa atgatgaggt tattgatgtt tctaaacctt ctaccaatgg tctaagaccg   1620
tatctattaa agtatggacc agatgcgttt tccaaaaaag ttcgtgaatt cgatggttgt   1680
atgattatgg ataccacctg gagagatgca catcaatcat tattggctac aagagttaga   1740
actattgatt tactgagaat tgctccaacg actagtcatg ccttacaaaa tgcatttgca   1800
ttagaatgtt ggggtggcgc aacatttgat gttgcgatga ggttcctcta tgaagatcct   1860
tgggagagat taagacaact tagaaaggca gttccaaata ttcctttcca aatgttattg   1920
agaggtgcta atggtgttgc ttattcgtca ttacctgata atgcaattga tcattttgtt   1980
aagcaagcaa aggataatgg tgttgatatt ttcagagtct ttgatgcttt gaacgatttg   2040
gaacaattga aggttggtgt tgatgctgtc aagaaagccg gaggtgttgt tgaagctaca   2100
gtttgttact caggtgatat gttaattcca ggtaaaaagt ataacttgga ttattattta   2160
gagactgttg gaaagattgt ggaaatgggt acccatattt taggtattaa ggatatggct   2220
ggcacgttaa agccaaaggc tgctaagttg ttgattggct cgatcagatc aaaataccct   2280
gacttggtta tccatgtcca tacccatgac tctgctggta ccggtatttc aacttatgtt   2340
gcatgcgcat tggcaggtgc cgacattgtc gattgtgcaa tcaattcgat gtctggttta   2400
acctctcaac cttcaatgag tgcttttatt gctgctttag atggtgatat cgaaactggt   2460
gttccagaac attttgcaag acaattagat gcatactggg cagaaatgag attgttatac   2520
tcatgtttcg aagccgactt gaagggacca gacccagaag tttataaaca tgaaattcca   2580
ggtggacagt tgactaacct aatcttccaa gcccaacaag ttggtttggg tgaacaatgg   2640
gaagaaacta agaagaagta tgaagatgct aacatgttgt tgggtgatat tgtcaaggtt   2700
accccaacct ccaaggttgt tggtgattta gcccaattta tggtttctaa taaattagaa   2760
aaagaagatg ttgaaaaact tgctaatgaa ttagatttcc cagattcagt tcttgatttc   2820
tttgaaggat taatgggtac accatatggt ggattcccag agcctttgag aacaaatgtc   2880
atttccggca agagaagaaa attaaagggt agaccaggtt tagaattaga acctttcaac   2940
ctcgaggaaa tcagagaaaa tttggtttcc agatttggtc caggtattac tgaatgtgat   3000
gttgcatctt ataacatgta tccaaaggtt tacgagcaat atcgtaaggt ggttgaaaaa   3060
tatggtgatt tatctgtttt accaacaaaa gcatttttgg ctcctccaac tattggtgaa   3120
gaagttcatg tggaaattga gcaaggtaag actttgatta ttaagttatt agccatttct   3180
gacttgtcta aatctcatgg tacaagagaa gtatactttg aattgaatgg tgaaatgaga   3240
aaggttacaa ttgaagataa aacagctgca attgagactg ttacaagagc aaaggctgac   3300
ggacacaatc caaatgaagt tggtgcgcca atggctggtg tcgttgttga agttagagtg   3360
aagcatggaa cagaagttaa gaagggtgat ccattagccg ttttgagtgc aatgaaaatg   3420
gaaatggtta tttctgctcc tgttagtggt agggtcggtg aagtttttgt caacgaaggc   3480
gattccgttg atatgggtga tttgcttgtg aaaattgcca aagatgaagc gccagcagct   3540
```

```
taa                                                               3543

<210> SEQ ID NO 5
<211> LENGTH: 4886
<212> TYPE: DNA
<213> ORGANISM: Artificial
<220> FEATURE:
<223> OTHER INFORMATION: MAE gene integration fragment

<400> SEQUENCE: 5

ctttgaagga gcttgccaag aaacataatt ttatgatttt tgaagataga aaatttgctg      60
atattggtaa cactgttaaa aatcaatata aatctggtgt cttccgtatt gccgaatggg     120
ctgacatcac taatgcacat ggtgtaacgg gtgcaggtat tgtttctggc ttgaaggagg     180
cagcccaaga aacaaccagt gaacctagag gtttgctaat gcttgctgag ttatcatcaa     240
agggttcttt agcatatggt gaatatacag aaaaaacagt agaaattgct aaatctgata     300
aagagtttgt cattggtttt attgcgcaac acgatatggg cggtagagaa gaaggttttg     360
actggatcat tatgactcca ggggttggtt tagatgacaa aggtgatgca cttggtcaac     420
aatatagaac tgttgatgaa gttgtaaaga ctggaacgga tatcataatt gttggtagag     480
gtttgtacgg tcaaggaaga gatcctatag agcaagctaa aagataccaa caagctggtt     540
ggaatgctta tttaaacaga tttaaatgat tcttacacaa agatttgata catgtacact     600
agtttaaata agcatgaaaa gaattacaca agcaaaaaaa aaaaaaataaa tgaggtactt   660
tacgttcacc tacaaccaaa aaaactagat agagtaaaat cttaagattt agaaaaagtt     720
gtttaacaaa ggctttagta tgtgaatttt taatgtagca aagcgataac taataaacat     780
aaacaaaagt atggttttct ttatcagtca aatcattatc gattgattgt tccgcgtatc     840
tgcagatagc ctcatgaaat cagccatttg cttttgttca acgatctttt gaaattgttg     900
ttgttcttgg tagttaagtt gatccatctt ggcttatgtt gtgtgtatgt tgtagttatt     960
cttagtatat tcctgtcctg agtttagtga aacataatat cgccttgaaa tgaaaatgct    1020
gaaattcgtc gacatacaat tttcaaact tttttttttt cttggtgcac ggacatgttt     1080
ttaaaggaag tactctatac cagttattct tcacaaattt aattgctgga gaatagatct    1140
tcaacgcgtt taaacagcaa tttgaggaag gaataggaga aggagaagca atttctagga    1200
aagagcaagg tgtgcaacag catgctctga atgatatttt cagcaatagt tcagttgaag    1260
aacctgttgg cgtatctaca tcacttccta caaacaacac cacgaattgc gtccgtggtg    1320
acgcaactac gaatggcatt gtcaatgcca atgccagtgc acatacacgt gcaagtccca    1380
ccggttccct gcccggctat ggtagagaca agaaggacga taccggcatc gacatcaaca    1440
gtttcaacag caatgcgttt ggcgtcgacg cgtcgatggg gctgccgtat ttggatttgg    1500
acgggctaga tttcgatatg gatatggata tggatatgga tatggagatg aatttgaatt    1560
tagatttggg tcttgatttg gggttggaat taaaagggga taacaatgag ggttttcctg    1620
ttgatttaaa caatggacgt gggaggtgat tgatttaacc tgatccaaaa ggggtatgtc    1680
tattttttag agtgtgtctt tgtgtcaaat tatggtagaa tgtgtaaagt agtataaact    1740
ttcctctcaa atgacgaggt ttaaaacacc ccccgggtga gccgagccga gaatggggca    1800
attgttcaat gtgaaataga agtatcgagt gagaaacttg ggtgttggcc agccaagggg    1860
gaaggaaaat ggcgcgaatg ctcaggtgag attgttttgg aattgggtga agcgaggaaa    1920
tgagcgaccc ggaggttgtg actttagtgg cggaggagga acgggaggaa aaggccaaga    1980
gggaaagtgt atataagggg gagcaatttg ccaaccagga tagaattgga tgagttataa    2040
```

```
ttctactgta tttattgtat aatttatttc tccttttata tcaaacacat tacaaaacac   2100
acaaaacata caaacataca cagctagcat gggtgaattg aaagagattt tgaaacaaag   2160
atatcatgaa ttacttgatt ggaatgttaa ggcaccacat gtccctttat cccagagatt   2220
gaagcacttt acttggtcat ggtttgcttg tactatggca accggtggtg ttggtttgat   2280
cattggttcc ttcccattca gattctacgg tttgaacacc attggcaaga ttgtttacat   2340
cttacaaatc tttttgtttt ctctttttgg ctcttgtatg ttgtttcgtt tcatcaagta   2400
tccatctacc attaaggact cttggaatca tcacttggaa aagttgttta tcgcaacttg   2460
tttgttatct atttccacat tcatcgacat gttagctatc tatgcttatc cagataccgg   2520
tgaatggatg gtctgggtca ttagaatctt atactacatc tatgtcgctg tctctttcat   2580
ctactgtgtt atggcctttt tcaccatttt caacaatcat gtttacacta ttgaaactgc   2640
ttctccagct tggattttgc caatcttccc tccaatgatc tgtggtgtca ttgctggtgc   2700
tgttaactcc acccaacctg ctcaccaatt gaaaaacatg gtcattttcg gtatcttgtt   2760
tcaaggttta ggtttttggg tttacctttt acttttcgcc gttaatgttt tgagattctt   2820
cacagtcggt ttagcaaagc cacaagatag accaggtatg tttatgttcg ttggtccacc   2880
agctttctct ggtttagcat tgattaacat tgcaagaggt gcaatgggct caagacctta   2940
cattttcgtt ggtgcaaact cttccgaata cttaggtttt gtctcaacct tcatggccat   3000
tttcatctgg ggtttagccg catggtgtta ttgcttagct atggtttcct tccttgccgg   3060
ctttttcact agagcaccat tgaaattcgc ttgtggttgg ttcgctttca tctttccaaa   3120
tgttggtttt gttaactgta ctatcgaaat cggcaagatg attgattcta aggcttttca   3180
aatgtttggt cacatcattg gtgttatctt gtgtattcaa tggattttgt taatgtactt   3240
aatggttaga gcattccttg ttaatgactt gtgctatcct ggtaaagacg aagatgcaca   3300
cccaccacca aagccaaaca ctggtgtctt aaacccaact ttcccaccag agaaggctcc   3360
agcatcatta gagaaggttg atactcatgt tacatcaaca ggtggtgaat ccgatcctcc   3420
atcttccgaa catgaatccg tttaaggcgc gccatctaat agtttaatca cagcttatag   3480
tctactatag ttttcttttt taaacattgt tgtattttgt cccccccctc taattgatga   3540
tgattatcct ataagaatcc aataaaacga tggaaactaa taccctctcc tttgtcatgt   3600
ggtctttagt atttcttgaa cattggctct gatttctcga ctttatagtc ctattaaaat   3660
cgctgttagt tctcgatcgt tgtatctcgt ttcttgtctc tttggtggat gattttgcgt   3720
gcgaacatgt ttttttccct ttctctcacc atcatcgtgt agttcttgtc accatccccc   3780
ccaccccttc cttctctcat tgattctata agagcttatc cacagaggtg cagtaacgag   3840
gtagtttaac cttcgagtgg atcaaaatgt cacacaggcc tgcggccgct accataatgt   3900
atgcgttgag cctcttgcac cttctttatt aggaaatcag ttgaaaaatt tccggattgt   3960
ctttattatt ggcccatttt tttttggtca cacctttatt tttgtacact tctcgggcaa   4020
agcaaaaact atagtaccgg ataggccttt ataaaactcc agtgtgtatg attttagttg   4080
gtgtgccatc tacacgttct cttagtttct ttatcatgtc acagaaagca agcatgcaaa   4140
cccttacaaa aaataacaac atacaaatgc ctaaacaact ggactataat gatggtgagt   4200
cagttacgaa aagagcaagt gggttaatac gatttcgtaa gggacagtct gaggaagact   4260
acaattttca aaaggagcag ttctggtcca cgggtccttt agtacagaat cacacatttg   4320
tgactgaatt tgttgaaaag tttattgaaa acacaattag tgaagattat tcaatcacag   4380
```

```
atagatcgaa aatagaacgt gaaacaatca tacacggatt ggagaagctg tattttcaaa   4440

gggaatatga gcgatgtcta aaagatgttc aactattgaa ggacaatatc gataagttca   4500

atcctaattt ggatcttaat gaaaagaatt tataatgagc tgaattatat ttcttggatg   4560

tgcatcaaaa agatccatga gagtaacgaa aagaaactgg gggaaatcta ataatttaca   4620

atttcaatat acacttctat atcctttaat gtaatggctt tataaataaa cacgaacttc   4680

tacagcaccg acgtttcttt ttcttaccag ctcctcttct tcttcttctt cttcttcttc   4740

ttcttcttct tcttcttctt cttcttcttc ttcttcttct ttcttaccat cattgccatt   4800

ttcctttttt cttatttgct cttgatcctc tgttttttca atttggacaa actcatctaa   4860

tacaccaaca cttttagggc ccccgc                                        4886
```

<210> SEQ ID NO 6
<211> LENGTH: 1317
<212> TYPE: DNA
<213> ORGANISM: Schizosaccharomyces pombe

<400> SEQUENCE: 6

```
atgggtgaat tgaaagagat tttgaaacaa agatatcatg aattacttga ttggaatgtt     60

aaggcaccac atgtcccttt atcccagaga ttgaagcact ttacttggtc atggtttgct    120

tgtactatgg caaccggtgg tgttggtttg atcattggtt ccttcccatt cagattctac    180

ggtttgaaca ccattggcaa gattgtttac atcttacaaa tctttttgtt ttctcttttt    240

ggctcttgta tgttgtttcg tttcatcaag tatccatcta ccattaagga ctcttggaat    300

catcacttgg aaaagttgtt tatcgcaact tgtttgttat ctatttccac attcatcgac    360

atgttagcta tctatgctta tccagatacc ggtgaatgga tggtctgggt cattagaatc    420

ttatactaca tctatgtcgc tgtctctttc atctactgtg ttatggcctt tttcaccatt    480

ttcaacaatc atgtttacac tattgaaact gcttctccag cttggatttt gccaatcttc    540

cctccaatga tctgtggtgt cattgctggt gctgttaact ccacccaacc tgctcaccaa    600

ttgaaaaaca tggtcatttt cggtatcttg tttcaaggtt taggtttttg ggtttacctt    660

ttacttttcg ccgttaatgt tttgagattc ttcacagtcg gtttagcaaa gccacaagat    720

agaccaggta tgtttatgtt cgttggtcca ccagctttct ctggtttagc attgattaac    780

attgcaagag gtgcaatggg ctcaagacct tacattttcg ttggtgcaaa ctcttccgaa    840

tacttaggtt ttgtctcaac cttcatggcc attttcatct ggggtttagc cgcatggtgt    900

tattgcttag ctatggtttc cttccttgcc ggcttttca ctagagcacc attgaaattc     960

gcttgtggtt ggttcgcttt catctttcca aatgttggtt ttgttaactg tactatcgaa   1020

atcggcaaga tgattgattc taaggctttt caaatgtttg gtcacatcat tggtgttatc   1080

ttgtgtattc aatggatttt gttaatgtac ttaatggtta gagcattcct tgttaatgac   1140

ttgtgctatc ctggtaaaga cgaagatgca cacccaccac caaagccaaa cactggtgtc   1200

ttaaacccaa ctttcccacc agagaaggct ccagcatcat tagagaaggt tgatactcat   1260

gttacatcaa caggtggtga atccgatcct ccatcttccg aacatgaatc cgtttaa      1317
```

<210> SEQ ID NO 7
<211> LENGTH: 6527
<212> TYPE: DNA
<213> ORGANISM: Artificial
<220> FEATURE:
<223> OTHER INFORMATION: PYC gene inserter fragment

<400> SEQUENCE: 7

```
ctaaaagtgt tggtgtatta gatgagtttg tccaaattga aaaaacagag gatcaagagc      60
aaataagaaa aaaggaaaat ggcaatgatg gtaagaaaga agaagaagaa gaagaagaag     120
aagaagaaga agaagaagaa gaagaagaag aagaagaaga agaggagctg gtaagaaaaa     180
gaaacgtcgg tgctgtagaa gttcgtgttt atttataaag ccattacatt aaaggatata     240
gaagtgtata ttgaaattgt aaattattag atttccccca gtttcttttc gttactctca     300
tggatctttt tgatgcacat ccaagaaata taattcagct cattataaat tcttttcatt     360
aagatccaaa ttaggattga acttatcgat attgtccttc aatagttgaa catcttttag     420
acatcgctca tattcccttt gaaaatacag cttctccaat ccgtgtatga ttgtttcacg     480
ttctattttc gatctatctg tgattgaata atcttcacta attgtgtttt caataaactt     540
ttcaacaaat tcagtcacaa atgtgtgatt ctgtactaaa ggacccgtgg accagaactg     600
ctccttttga aaattgtagt cttcctcaga ctgtccctta cgaaatcgta ttaacccact     660
tgctcttttc gtaactgact caccatcatt atagtccagt tgtttaggca tttgtatgtt     720
gttatttttt gtaagggttt gcatgcttgc tttctgtgac atgataaaga aactaagaga     780
acgtgtagat ggcacaccaa ctaaaatcat acacactgga gttttataaa ggcctatccg     840
gtactatagt ttttgctttg cccgagaagt gtacaaaaat aaaggtgtga ccaaaaaaaa     900
atgggccaat aataaagaca atccggaaat ttttcaactg atttcctaat aaagaaggtg     960
caagaggctc aacgcataca ttatggtagc ggccgcgagt ccatcggttc ctgtcagatg    1020
ggatactctt gacgtggaaa attcaaacag aaaaaaaacc ccaataatga aaaataacac    1080
tacgttatat ccgtggtatc ctctatcgta tcgtatcgta gcgtatcgta gcgtaccgta    1140
tcacagtata gtctaatatt ccgtatctta ttgtatccta tcctattcga tcctattgta    1200
tttcagtgca ccattttaat ttctattgct ataatgtcct tattagttgc cactgtgagg    1260
tgaccaatgg acgagggcga gccgttcaga agccgcgaag ggtgttcttc ccatgaattt    1320
cttaaggagg gcggctcagc tccgagagtg aggcgagacg tctcggtcag cgtatccccc    1380
ttcctcggct tttacaaatg atgcgctctt aatagtgtgt cgttatcctt ttggcattga    1440
cgggggaggg aaattgattg agcgcatcca tatttttgcg gactgctgag gacaatggtg    1500
gtttttccgg gtggcgtggg ctacaaatga tacgatggtt tttttctttt cggagaaggc    1560
gtataaaaag gacacggaga acccatttat tctaaaaaca gttgagcttc tttaattatt    1620
ttttgatata atattctatt attatatatt ttcttcccaa taaaacaaaa taaaacaaaa    1680
cacagcaaaa cacaaaaatt ctagataaaa tgtcaactgt ggaagatcac tcctccctac    1740
ataaattgag aaaggaatct gagattcttt ccaatgcaaa caaaatctta gtggctaata    1800
gaggtgaaat tccaattaga attttcaggt cagcccatga attgtcaatg catactgtgg    1860
cgatctattc ccatgaagat cggttgtcca tgcataggtt gaaggccgac gaggcttatg    1920
caatcggtaa gactggtcaa tattcgccag ttcaagctta tctacaaatt gacgaaatta    1980
tcaaaatagc aaaggaacat gatgtttcca tgatccatcc aggttatggt ttcttatctg    2040
aaaactccga attcgcaaag aaggttgaag aatccggtat gatttgggtt gggcctcctg    2100
ctgaagttat tgattctgtt ggtgacaagg tttctgcaag aaatttggca attaaatgtg    2160
acgttcctgt tgttcctggt accgatggtc caattgaaga cattgaacag gctaaacagt    2220
ttgtggaaca atatggttat cctgtcatta taaaggctgc atttggtggt ggtggtagag    2280
gtatgagagt tgttagagaa ggtgatgata tagttgatgc tttccaaaga gcgtcatctg    2340
```

-continued

```
aagcaaagtc tgcctttggt aatggtactt gttttattga aagatttttg gataagccaa   2400
aacatattga ggttcaatta ttggctgata attatggtaa cacaatccat ctctttgaaa   2460
gagattgttc tgttcaaaga agacatcaaa aggttgttga aattgcacct gccaaaactt   2520
tacctgttga agttagaaat gctatattaa aggatgctgt aacgttagct aaaaccgcta   2580
actatagaaa tgctggtact gcagaatttt tagttgattc ccaaaacaga cattatttta   2640
ttgaaattaa tccaagaatt caagttgaac atacaattac tgaagaaatc acgggtgttg   2700
atattgttgc cgctcaaatt caaattgctg caggtgcatc attggaacaa ttgggtctat   2760
tacaaaacaa aattacaact agaggttttg caattcaatg tagaattaca accgaggatc   2820
ctgctaagaa ttttgcccca gatacaggta aaattgaggt ttatagatct gcaggtggta   2880
acggtgtcag attagatggt ggtaatgggt ttgccggtgc tgttatatct cctcattatg   2940
actcgatgtt ggttaaatgt tcaacatctg gttctaacta tgaaattgcc agaagaaaga   3000
tgattagagc tttagttgaa tttagaatca gaggtgtcaa gaccaatatt cctttcttat   3060
tggcattgct aactcatcca gttttcattt cgggtgattg ttggacaact tttattgatg   3120
atacccccttc gttattcgaa atggtttctt caaagaatag agcccaaaaa ttattggcat   3180
atattggtga cttgtgtgtc aatggttctt caattaaagg tcaaattggt ttccctaaat   3240
tgaacaagga agcagaaatc ccagatttgt tggatccaaa tgatgaggtt attgatgttt   3300
ctaaaccttc taccaatggt ctaagaccgt atctattaaa gtatggacca gatgcgtttt   3360
ccaaaaaagt tcgtgaattc gatggttgta tgattatgga taccacctgg agagatgcac   3420
atcaatcatt attggctaca agagttagaa ctattgattt actgagaatt gctccaacga   3480
ctagtcatgc cttacaaaat gcatttgcat tagaatgttg gggtggcgca acatttgatg   3540
ttgcgatgag gttcctctat gaagatcctt gggagagatt aagacaactt agaaaggcag   3600
ttccaaatat tcctttccaa atgttattga gaggtgctaa tggtgttgct tattcgtcat   3660
tacctgataa tgcaattgat cattttgtta agcaagcaaa ggataatggt gttgatattt   3720
tcagagtctt tgatgctttg aacgatttgg aacaattgaa ggttggtgtt gatgctgtca   3780
agaaagccgg aggtgttgtt gaagctacag tttgttactc aggtgatatg ttaattccag   3840
gtaaaaagta taacttggat tattatttag agactgttgg aaagattgtg gaaatgggta   3900
cccatatttt aggtattaag gatatggctg gcacgttaaa gccaaaggct gctaagttgt   3960
tgattggctc gatcagatca aaataccctg acttggttat ccatgtccat acccatgact   4020
ctgctggtac cggtatttca acttatgttg catgcgcatt ggcaggtgcc gacattgtcg   4080
attgtgcaat caattcgatg tctggtttaa cctctcaacc ttcaatgagt gcttttattg   4140
ctgctttaga tggtgatatc gaaactggtg ttccagaaca ttttgcaaga caattagatg   4200
catactgggc agaaatgaga ttgttatact catgtttcga agccgacttg aagggaccag   4260
acccagaagt ttataaacat gaaattccag gtggacagtt gactaaccta atcttccaag   4320
cccaacaagt tggtttgggt gaacaatggg aagaaactaa gaagaagtat gaagatgcta   4380
acatgttgtt gggtgatatt gtcaaggtta ccccaacctc caaggttgtt ggtgatttag   4440
cccaatttat ggtttctaat aaattagaaa aagaagatgt tgaaaaactt gctaatgaat   4500
tagatttccc agattcagtt cttgatttct ttgaaggatt aatgggtaca ccatatggtg   4560
gattcccaga gcctttgaga acaaatgtca tttccggcaa gagaagaaaa ttaaagggta   4620
gaccaggttt agaattagaa cctttcaacc tcgaggaaat cagagaaaat ttggtttcca   4680
gatttggtcc aggtattact gaatgtgatg ttgcatctta taacatgtat ccaaaggttt   4740
```

```
acgagcaata tcgtaaggtg gttgaaaaat atggtgattt atctgtttta ccaacaaaag   4800

cattttttggc tcctccaact attggtgaag aagttcatgt ggaaattgag caaggtaaga   4860

ctttgattat taagttatta gccatttctg acttgtctaa atctcatggt acaagagaag   4920

tatactttga attgaatggt gaaatgagaa aggttacaat tgaagataaa acagctgcaa   4980

ttgagactgt tacaagagca aaggctgacg gacacaatcc aaatgaagtt ggtgcgccaa   5040

tggctggtgt cgttgttgaa gttagagtga agcatggaac agaagttaag aagggtgatc   5100

cattagccgt tttgagtgca atgaaaatgg aaatggttat ttctgctcct gttagtggta   5160

gggtcggtga agtttttgtc aacgaaggcg attccgttga tatgggtgat ttgcttgtga   5220

aaattgccaa agatgaagcg ccagcagctt aattaattct gtctttgatt ttcttatgtt   5280

attcaaaaca tctgccccaa aatctaacga ttatatatat tcctacgtat aactgtatag   5340

ctaattattg atttatttgt acataaaaac cacataaatg taaaagcaag aaaaaaaata   5400

actaaggaga aggatcaata tctcatttat aatgctcgcc aaagcagcgt acgtgaattt   5460

taatcaagac atcaacaaat cttgcaactt ggttatatcg cttcttcacc cactcacccg   5520

cttttctaca ttgttgaaca caaatatata caggggtatg tctcaaggtc aagtgcagtt   5580

tcaacagaga ctacctcaag gtacctcttc agaaatgcag aacttcactc ttgatcagat   5640

tttctccgaa ttaaaggttt aaacatagcc tcatgaaatc agccatttgc ttttgttcaa   5700

cgatcttttg aaattgttgt tgttcttggt agttaagttg atccatcttg gcttatgttg   5760

tgtgtatgtt gtagttattc ttagtatatt cctgtcctga gtttagtgaa acataatatc   5820

gccttgaaat gaaaatgctg aaattcgtcg acatacaatt tttcaaactt ttttttttc   5880

ttggtgcacg gacatgtttt taaaggaagt actctatacc agttattctt cacaaattta   5940

attgctggag aatagatctt caacgcttta ataaagtagt ttgtttgtca aggatggcgt   6000

catacaaaga aagatcagaa tcacacactt cccctgttgc taggagactt ttctccatca   6060

tggaggaaaa gaagtctaac ctttgtgcat cattggatat tactgaaact gaaaagcttc   6120

tctctatttt ggacactatt ggtccttaca tctgtctagt taaaacacac atcgatattg   6180

tttctgattt tacgtatgaa ggaactgtgt tgcctttgaa ggagcttgcc aagaaacata   6240

attttatgat ttttgaagat agaaaatttg ctgatattgg taacactgtt aaaaatcaat   6300

ataaatctgg tgtcttccgt attgccgaat gggctgacat cactaatgca catggtgtaa   6360

cgggtgcagg tattgtttct ggcttgaagg aggcagccca agaaacaacc agtgaaccta   6420

gaggtttgct aatgcttgct gagttatcat caaagggttc tttagcatat ggtgaatata   6480

cagaaaaaac agtagaaatt gctaaatctg ataaagagtt tgttgag                6527
```

```
<210> SEQ ID NO 8
<211> LENGTH: 4760
<212> TYPE: DNA
<213> ORGANISM: Artificial
<220> FEATURE:
<223> OTHER INFORMATION: MAE gene integration fragment

<400> SEQUENCE: 8

aattctttga aggagcttgc caagaaacat aattttatga tttttgaaga tagaaaattt     60

gctgatattg gtaacactgt taaaaatcaa tataaatctg gtgtcttccg tattgccgaa    120

tgggctgaca tcactaatgc acatggtgta acgggtgcag gtattgtttc tggcttgaag    180

gaggcagccc aagaaacaac cagtgaacct agaggtttgc taatgcttgc tgagttatca    240
```

-continued

```
tcaaagggtt ctttagcata tggtgaatat acagaaaaaa cagtagaaat tgctaaatct    300
gataaagagt ttgtcattgg ttttattgcg caacacgata tgggcggtag agaagaaggt    360
tttgactgga tcattatgac tccaggggtt ggtttagatg acaaaggtga tgcacttggt    420
caacaatata gaactgttga tgaagttgta aagactggaa cggatatcat aattgttggt    480
agaggtttgt acggtcaagg aagagatcct atagagcaag ctaaaagata ccaacaagct    540
ggttggaatg cttatttaaa cagatttaaa tgattcttac acaaagattt gatacatgta    600
cactagttta aataagcatg aaaagaatta cacaagcaaa aaaaaaaaaa taaatgaggt    660
actttacgtt cacctacaac caaaaaaact agatagagta aaatcttaag atttagaaaa    720
agttgtttaa caaaggcttt agtatgtgaa tttttaatgt agcaaagcga taactaataa    780
acataaacaa aagtatggtt ttctttatca gtcaaatcat tatcgattga ttgttccgcg    840
tatctgcaga tagcctcatg aaatcagcca tttgcttttg ttcaacgatc ttttgaaatt    900
gttgttgttc ttggtagtta agttgatcca tcttggctta tgttgtgtgt atgttgtagt    960
tattcttagt atattcctgt cctgagttta gtgaaacata atatcgcctt gaaatgaaaa   1020
tgctgaaatt cgtcgacata caatttttca aacttttttt ttttcttggt gcacggacat   1080
gtttttaaag gaagtactct ataccagtta ttcttcacaa atttaattgc tggagaatag   1140
atcttcaacg cgtttaaaca gcaatttgag gaaggaatag gagaaggaga agcaatttct   1200
aggaaagagc aaggtgtgca acagcatgct ctgaatgata ttttcagcaa tagttcagtt   1260
gaagaacctg ttggcgtatc tacatcactt cctacaaaca acaccacgaa ttgcgtccgt   1320
ggtgacgcaa ctacgaatgg cattgtcaat gccaatgcca gtgcacatac acgtgcaagt   1380
cccaccggtt ccctgcccgg ctatggtaga gacaagaagg acgataccgg catcgacatc   1440
aacagtttca acagcaatgc gtttggcgtc gacgcgtcga tggggctgcc gtatttggat   1500
ttggacgggc tagatttcga tatggatatg gatatggata tggatatgga gatgaatttg   1560
aatttagatt tgggtcttga tttggggttg gaattaaaag gggataacaa tgagggtttt   1620
cctgttgatt taaacaatgg acgtgggagg tgattgattt aacctgatcc aaaaggggta   1680
tgtctatttt ttagagtgtg tctttgtgtc aaattatggt agaatgtgta aagtagtata   1740
aactttcctc tcaaatgacg aggtttaaaa caccccccgg gtgagccgag ccgagaatgg   1800
ggcaattgtt caatgtgaaa tagaagtatc gagtgagaaa cttgggtgtt ggccagccaa   1860
gggggaagga aaatggcgcg aatgctcagg tgagattgtt ttggaattgg gtgaagcgag   1920
gaaatgagcg acccggaggt tgtgacttta gtggcggagg aggaacggga ggaaaaggcc   1980
aagagggaaa gtgtatataa gggggagcaa tttgccaacc aggatagaat tggatgagtt   2040
ataattctac tgtatttatt gtataattta tttctccttt tatatcaaac acattacaaa   2100
acacacaaaa catacaaaca tacacagcta gcatgggtga attgaaagag attttgaaac   2160
aaagatatca tgaattactt gattggaatg ttaaggcacc acatgtccct ttatcccaga   2220
gattgaagca ctttacttgg tcatggtttg cttgtactat ggcaaccggt ggtgttggtt   2280
tgatcattgg ttccttccca ttcagattct acggtttgaa caccattggc aagattgttt   2340
acatcttaca aatctttttg ttttctcttt ttggctcttg tatgttgttt cgtttcatca   2400
agtatccatc taccattaag gactcttgga atcatcactt ggaaaagttg tttatcgcaa   2460
cttgtttgtt atctatttcc acattcatcg acatgttagc tatctatgct tatccagata   2520
ccggtgaatg gatggtctgg gtcattagaa tcttatacta catctatgtc gctgtctctt   2580
tcatctactg tgttatggcc tttttcacca ttttcaacaa tcatgtttac actattgaaa   2640
```

```
ctgcttctcc agcttggatt ttgccaatct tccctccaat gatctgtggt gtcattgctg   2700
gtgctgttaa ctccacccaa cctgctcacc aattgaaaaa catggtcatt ttcggtatct   2760
tgtttcaagg tttaggtttt tgggtttacc ttttactttt cgccgttaat gttttgagat   2820
tcttcacagt cggtttagca aagccacaag atagaccagg tatgtttatg ttcgttggtc   2880
caccagcttt ctctggttta gcattgatta acattgcaag aggtgcaatg ggctcaagac   2940
cttacatttt cgttggtgca aactcttccg aatacttagg ttttgtctca accttcatgg   3000
ccattttcat ctggggttta gccgcatggt gttattgctt agctatggtt tccttccttg   3060
ccggcttttt cactagagca ccattgaaat tcgcttgtgg ttggttcgct ttcatctttc   3120
caaatgttgg ttttgttaac tgtactatcg aaatcggcaa gatgattgat tctaaggctt   3180
ttcaaatgtt tggtcacatc attggtgtta tcttgtgtat tcaatggatt ttgttaatgt   3240
acttaatggt tagagcattc cttgttaatg acttgtgcta tcctggtaaa gacgaagatg   3300
cacacccacc accaaagcca aacactggtg tcttaaaccc aactttccca ccagagaagg   3360
ctccagcatc attagagaag gttgatactc atgttacatc aacaggtggt gaatccgatc   3420
ctccatcttc cgaacatgaa tccgtttaag gcgcgccatc taatagttta atcacagctt   3480
atagtctact atagttttct tttttaaaca ttgttgtatt ttgtcccccc cctctaattg   3540
atgatgatta tcctataaga atccaataaa acgatggaaa ctaataccct ctcctttgtc   3600
atgtggtctt tagtatttct tgaacattgg ctctgatttc tcgactttat agtcctatta   3660
aaatcgctgt tagttctcga tcgttgtatc tcgtttcttg tctctttggt ggatgatttt   3720
gcgtgcgaac atgttttttt ccctttctct caccatcatc gtgtagttct tgtcaccatc   3780
ccccccaccc cttccttctc tcattgattc tataagagct tatccacaga ggtgcagtaa   3840
cgaggtagtt taaccttcga gtggatcaaa atgtcacaca ggcctgcggc cgcatttggc   3900
aaggcgtatc tatataggag gatcacaaga aaagagagtt caacttaggg aaccaggctt   3960
gacaaaagat aatattaaaa aaggaagaaa aagagagaaa gaaagtaaag acaagaagaa   4020
tcaactccaa tttgaataaa tggcctgta agaatcttca atctcgatga cggggaaaac   4080
gtcctctttt atagaccaac cccttgtggg gctgtcggga aaagcgggtt tcccgggaaa   4140
ctcatatctg attgggggt tgaagctatt ccgcgttttg gggggtgcgg tttataagaa   4200
gaatgagtaa tgcaaacggc gtttataaag agaaagggtg tggcggtgtt aagcggttga   4260
ggttttaagg tgtgggggac ggggtgtgat tttttcggcg ttacgggcac ggggtatgat   4320
tctcttaatg tcatttccct ttctttctac ttctagggcg cgcagcgtgc gacaatggtg   4380
tttgttgtgc aaataggtgg ttgtgttgtc gttggagttc tcatgaacat atcactctat   4440
tagcaaattt accctaagta tgtaaggttt agtgtgttga ggactaatac agacaatctt   4500
tgtcttatat ataaatggtt ctactcaatt ttataagttt tttttttttt tttttaatct   4560
ctttatgaaa atcaagaatg acattaaaac aatcacaata ttgtatgcaa gaactttgcc   4620
tctaaacctc tttcaaagag atgcataatt ataaaacaaa tctatttgca tattcgcttt   4680
acacaactat tcaagaatat aattacctaa agagtccatc ttgagttcac caacaccact   4740
acttagagct cggtacccgc                                              4760
```

<210> SEQ ID NO 9
<211> LENGTH: 6874
<212> TYPE: DNA
<213> ORGANISM: Artificial
<220> FEATURE:

<223> OTHER INFORMATION: FRD gene integration fragment

<400> SEQUENCE: 9

```
aaacctccgt tatgtatgtt tgtacccaaa aagaatgcgc tatattagtt taatctttta     60
taaacccgga attataaaaa tacagttagg aataaagtaa tagaaagatg aacaacgggc    120
ctaaaaagac taatgtgttg tggatcggaa tgtttcgaat agagtattaa agttatgctt    180
tcttttcttt ttgaacatgc ttggtattac tttgatatgc aaaagatatc gacaaattga    240
aaatggtttt gatgtctata gatgtggcat ggtaaggttc atttcaattt agcaaatatc    300
agacgagctc agcggccgcg gatccctcga ggagtccatc ggttcctgtc agatgggata    360
ctcttgacgt ggaaaattca aacagaaaaa aaaccccaat aatgaaaaat aacactacgt    420
tatatccgtg gtatcctcta tcgtatcgta tcgtagcgta tcgtagcgta ccgtatcaca    480
gtatagtcta atattccgta tcttattgta tcctatccta ttcgatccta ttgtatttca    540
gtgcaccatt ttaatttcta ttgctataat gtccttatta gttgccactg tgaggtgacc    600
aatggacgag ggcgagccgt tcagaagccg cgaagggtgt tcttcccatg aatttcttaa    660
ggagggcggc tcagctccga gagtgaggcg agacgtctcg gtcagcgtat ccccccttcct    720
cggcttttac aaatgatgcg ctcttaatag tgtgtcgtta tccttttggc attgacgggg    780
gagggaaatt gattgagcgc atccatattt ttgcggactg ctgaggacaa tggtggtttt    840
tccgggtggc gtgggctaca aatgatacga tggttttttt cttttcggag aaggcgtata    900
aaaaggacac ggagaaccca tttattctaa aaacagttga gcttctttaa ttattttttg    960
atataatatt ctattattat atattttctt cccaataaaa caaaataaaa caaaacacag   1020
caaaacacaa aaattctaga atggctgatg gcaaaacctc tgcatcagtt gttgctgttg   1080
atgctgaacg tgccgctaag gaaagagatg cagcagctag agctatgttg caaggtggtg   1140
gtgtctctcc tgctggcaag gcacaattgt tgaaaaaggg tttggttcac actgttccat   1200
ataccttaaa ggttgtcgtc gcagatccaa aggaaatgga gaaggcaact gctgacgcag   1260
aagaggtttt acaagctgca tttcaagtcg tcgacaccct tttgaacaac tttaacgaaa   1320
actcagaagt ttcaagagtc aataggttgg cagttggtga ggaacatcaa atgtctgaaa   1380
cattgaaaca cgtcatggcc tgttgtcaaa aggtttatca ttcctccaga ggtgtttttg   1440
acccagcagt tggtccatta gtccgtgaac ttagagaagc tgctcacaag ggtaaaactg   1500
ttccagccga aagagttaat gatttgttat ccaaatgtac ccttaatgca tctttttcaa   1560
ttgatatgtc cagaggtatg attgcaagga agcatccaga cgccatgttg gatttgggtg   1620
gtgtcaacaa gggttatggt atcgactaca ttgttgaaca cttaaactct ttgggttatg   1680
atgatgtctt tttcgaatgg ggtggtgatg ttagagcatc cggcaaaaac cagttatctc   1740
aaccttgggc tgttggtatt gttagaccac ctgccttggc cgacattaga actgttgtcc   1800
cagaggacaa aagatccttt atccgtgtcg tcagattgaa caacgaagct attgctacct   1860
ctggtgatta tgagaatttg gttgaaggtc ctggttctaa ggtttactct tccaccttca   1920
atccaacttc caaaaacttg ttggaaccta ccgaagcagg tatggctcaa gtttctgtca   1980
agtgttgctc atgtatctac gctgatgctt tagcaacagc agctttgttg aaaaacgatc   2040
ctgctgccgt tagaaggatc ttagataact ggagatatgt cagagatact gttactgact   2100
acaccactta cacaagggaa ggtgaaagag ttgctaagat gttggaaatt gctaccgaag   2160
atgctgaaat gagagcaaag agaatcaagg gctctttacc agcaagagtt atcattgttg   2220
gtggtggttt ggccggttgt tccgcagcta tcgaagcagc taactgtggc gcccacgtca   2280
```

```
tcttgttaga aaaggaacca aagttaggtg gtaactctgc aaaggctacc tccggtatca   2340
acgcctgggg tactagagca caagcaaaac aaggtgtcat ggacggcggc aagtttttcg   2400
aaagagatac ccatagatcc ggcaagggtg gtaattgcga tccatgcctt gttaagactt   2460
tgtccgttaa gtcctctgat gcagttaagt ggttatctga attaggtgtt ccattgactg   2520
ttttgtctca attaggtggt gcttcaagga aacgttgtca ccgtgcacca gataagtctg   2580
atggtacacc agtcccagtt ggtttcacca ttatgaaaac ccttgaaaac cacattgtca   2640
acgatttgtc cagacatgtt acagttatga caggtattac cgtcacagct ttagaatcta   2700
catcaagagt cagacctgat ggtgttttag tcaagcatgt tactggtgtt cacttgattc   2760
aggcatctgg tcaatctatg gttttgaatg cagacgctgt tatcttagct actggtggtt   2820
tctccaatga tcatacccca aactcccttt tacaacaata cgccccacag ttgtcatctt   2880
ttccaacaac caatggtgtc tgggcaactg gcgatggtgt taagatggct tccaagttgg   2940
gtgtcgcctt agttgatatg gataaggtcc aattacatcc taccggcttg ttagacccaa   3000
aagatccatc taatagaacc aagtatcttg gtccagaggc cttaagaggt tccggcggtg   3060
tcttgttaaa caaaaacggt gaaagatttg ttaatgaatt agacttaaga tctgttgtct   3120
ctcaagctat catcgcacaa gataatgagt acccaggctc tggtggttcc aagttcgcat   3180
actgtgtttt gaacgaaact gcagcaaagt tattcggcaa aaacttcctt ggtttctact   3240
ggaatagatt aggtcttttc caaaaggttg attccgttgc tggtttagct aagttgattg   3300
gttgtccaga agctaatgtt gttgctacat tgaagcaata tgaggagtta tcttccaaaa   3360
agcttaatcc ttgtccattg actggcaagt ctgtctttcc ttgtgtttta ggcactcaag   3420
gtccatacta tgttgccttg gttaccccat ccattcacta cactatgggt ggttgtttga   3480
tttccccatc tgctgagatg caaaccattg acaactctgg tgttactcct gtcagacgtc   3540
caatcttagg cttattcggt gctggtgaag ttactggcgg tgtccatggt ggtaacagat   3600
taggcggtaa ctctttgtta gaatgtgttg ttttcggcaa gatcgctggt gacagagctg   3660
caaccatctt gcaaaagaaa aacaccggct tatcaatgac agaatggtct actgtcgtct   3720
taagagaagt tagagaaggt ggtgtctatg gtgctggttc cagagttttg aggtttaaca   3780
tgcctggtgc attacagaga actggtttag ctttaggtca attcatcggt atcagaggtg   3840
attgggacgg tcacagattg atcggttact attctccaat cactttacct gatgatgttg   3900
gtgttattgg tatcttagct agagcagaca agggtagatt ggcagaatgg atttctgcat   3960
tgcagccagg tgacgctgtt gagatgaagg cctgcggtgg tcttatcatt gacagaagat   4020
tcgctgaaag acatttcttt ttccgtggtc ataagatcag aaagttggcc cttatcggtg   4080
gtggtactgg tgttgcacca atgttacaaa tcgtcagagc tgctgtcaaa aagccatttg   4140
tcgattcaat tgagtccatt cagttcatct atgctgcaga ggatgtttcc gagcttacat   4200
acagaacctt acttgaatct tacgaagagg aatatggttc agaaaagttt aagtgtcact   4260
tcgttttgaa taacccacca gctcaatgga ctgacggtgt tggtttcgtt gatactgcat   4320
tgttgagatc cgcagttcaa gcaccatcaa atgatttgct tgttgcaatt tgtggtccac   4380
caatcatgca aagagcagtt aagggtgcat tgaaaggttt aggttacaat atgaatcttg   4440
ttagaaccgt tgacgaaact gaaccaccat cataattaat taacatctga atgtaaaatg   4500
aacattaaaa tgaattacta aactttacgt ctactttaca atctataaac tttgtttaat   4560
catataacga aatacactaa tacacaatcc tgtacgtatg taatactttt atccatcaag   4620
```

```
gattgagaaa aaaaagtaat gattccctgg gccattaaaa cttagacccc caagcttgga   4680
taggtcactc tctattttcg tttctccctt ccctgataga agggtgatat gtaattaaga   4740
ataatatata attttataat aaaagaattc atagcctcat gaaatcagcc atttgctttt   4800
gttcaacgat cttttgaaat tgttgttgtt cttggtagtt aagttgatcc atcttggctt   4860
atgttgtgtg tatgttgtag ttattcttag tatattcctg tcctgagttt agtgaaacat   4920
aatatcgcct tgaaatgaaa atgctgaaat tcgtcgacat acaatttttc aaactttttt   4980
tttttcttgg tgcacggaca tgtttttaaa ggaagtactc tataccagtt attcttcaca   5040
aatttaattg ctggagaata gatcttcaac gctttaataa agtagtttgt ttgtcaagga   5100
tggcgtcata caaagaaaga tcagaatcac acacttcccc tgttgctagg agacttttct   5160
ccatcatgga ggaaaagaag tctaaccttt gtgcatcatt ggatattact gaaactgaaa   5220
agcttctctc tattttggac actattggtc cttacatctg tctagttaaa acacacatcg   5280
atattgtttc tgattttacg tatgaaggaa ctgtgttgcc tttgaaggag cttgccaaga   5340
aacataattt tatgattttt gaagatagaa aatttgctga tattggtaac actgttaaaa   5400
atcaatataa atctggtgtc ttccgtattg ccgaatgggc tgacatcact aatgcacatg   5460
gtgtaacggg tgcaggtatt gtttctggct tgaaggaggc agcccaagaa acaaccagtg   5520
aacctagagg tttgctaatg cttgctgagt tatcatcaaa gggttcttta gcatatggtg   5580
aatatacaga aaaaacagta gaaattgcta aatctgataa agagtttgtc attggtttta   5640
ttgcgcaaca cgatatgggc ggtagagaag aaggttttga ctggatcatt atgactccag   5700
ggggttggttt agatgacaaa ggtgatgcac ttggtcaaca atatagaact gttgatgaag   5760
ttgtaaagac tggaacggat atcataattg ttggtagagg tttgtacggt caaggaagag   5820
atcctataga gcaagctaaa agataccaac aagctggttg gaatgcttat ttaaacagat   5880
ttaaatgatt cttacacaaa gatttgatac atgtacacta gtttaaataa gcatgaaaag   5940
aattacacaa gcaaaaaaaa aaaaataaat gaggtacttt acgttcacct acaaccaaaa   6000
aaactagata gagtaaaatc ttaagattta gaaaaagttg tttaacaaag gctttagtat   6060
gtgaattttt aatgtagcaa agcgataact aataaacata aacaaaagta tggttttctt   6120
tatcagtcaa atcattatcg attgattgtt ccgcgtatct gcagatagcc tcatgaaatc   6180
agccatttgc ttttgttcaa cgatcttttg aaattgttgt tgttcttggt agttaagttg   6240
atccatcttg gcttatgttg tgtgtatgtt gtagttattc ttagtatatt cctgtcctga   6300
gtttagtgaa acataatatc gccttgaaat gaaaatgctg aaattcgtcg acatacaatt   6360
tttcaaactt tttttttttc ttggtgcacg gacatgtttt taaaggaagt actctatacc   6420
agttattctt cacaaattta attgctggag aatagatctt caacgccccg ggggatctgg   6480
atccgcggcc gctcatatgt ttgaaggtat tatcactgct gttgatttac gttcttgaaa   6540
actgcacgga taatattcac aatactaaca ataaagaaga ctcattgtgg aaggtgactc   6600
aatcatgcta gaaaagctgg ggaataaagg cacttttata gtagccacat tttggttcaa   6660
aagaatataa aggaaaaaaa aatattttcc agtgaaaaag aaaagactct ttctccgaga   6720
agccgagttt ctacgaggcc ttgttgagtc ataggggacc tctgtggttg actccggctt   6780
attacgtgaa tcatcggggg agccgcaccg tttgtccgcg acaggagaaa acgcaaggag   6840
tcaaacatta aattggtagg cactaccgag gttt                               6874
```

<210> SEQ ID NO 10
<211> LENGTH: 3435

<212> TYPE: DNA
<213> ORGANISM: Leishmania mexicana

<400> SEQUENCE: 10

```
atggctgatg gcaaaacctc tgcatcagtt gttgctgttg atgctgaacg tgccgctaag     60
gaaagagatg cagcagctag agctatgttg caaggtggtg gtgtctctcc tgctggcaag    120
gcacaattgt tgaaaaaggg tttggttcac actgttccat ataccttaaa ggttgtcgtc    180
gcagatccaa aggaaatgga gaaggcaact gctgacgcag aagaggtttt acaagctgca    240
tttcaagtcg tcgacaccct tttgaacaac tttaacgaaa actcagaagt ttcaagagtc    300
aataggttgg cagttggtga ggaacatcaa atgtctgaaa cattgaaaca cgtcatggcc    360
tgttgtcaaa aggtttatca ttcctccaga ggtgtttttg acccagcagt tggtccatta    420
gtccgtgaac ttagagaagc tgctcacaag ggtaaaactg ttccagccga aagagttaat    480
gatttgttat ccaaatgtac ccttaatgca tctttttcaa ttgatatgtc cagaggtatg    540
attgcaagga agcatccaga cgccatgttg gatttgggtg gtgtcaacaa gggttatggt    600
atcgactaca ttgttgaaca cttaaactct ttgggttatg atgatgtctt tttcgaatgg    660
ggtggtgatg ttagagcatc cggcaaaaac cagttatctc aaccttgggc tgttggtatt    720
gttagaccac ctgccttggc cgacattaga actgttgtcc cagaggacaa aagatccttt    780
atccgtgtcg tcagattgaa caacgaagct attgctacct ctggtgatta tgagaatttg    840
gttgaaggtc ctggttctaa ggtttactct tccaccttca atccaacttc caaaaacttg    900
ttggaaccta ccgaagcagg tatggctcaa gtttctgtca agtgttgctc atgtatctac    960
gctgatgctt tagcaacagc agctttgttg aaaaacgatc ctgctgccgt tagaaggatc   1020
ttagataact ggagatatgt cagagatact gttactgact acaccactta cacaagggaa   1080
ggtgaaagag ttgctaagat gttggaaatt gctaccgaag atgctgaaat gagagcaaag   1140
agaatcaagg gctctttacc agcaagagtt atcattgttg gtggtggttt ggccggttgt   1200
tccgcagcta tcgaagcagc taactgtggc gcccacgtca tcttgttaga aaaggaacca   1260
aagttaggtg gtaactctgc aaaggctacc tccggtatca acgcctgggg tactagagca   1320
caagcaaaac aaggtgtcat ggacggcggc aagtttttcg aaagagatac ccatagatcc   1380
ggcaagggtg gtaattgcga tccatgcctt gttaagactt tgtccgttaa gtcctctgat   1440
gcagttaagt ggttatctga attaggtgtt ccattgactg ttttgtctca attaggtggt   1500
gcttcaagga aacgttgtca ccgtgcacca gataagtctg atggtacacc agtcccagtt   1560
ggtttcacca ttatgaaaac ccttgaaaac cacattgtca acgatttgtc cagacatgtt   1620
acagttatga caggtattac cgtcacagct ttagaatcta catcaagagt cagacctgat   1680
ggtgttttag tcaagcatgt tactggtgtt cacttgattc aggcatctgg tcaatctatg   1740
gttttgaatg cagacgctgt tatcttagct actggtggtt tctccaatga tcatacccca   1800
aactcccttt tacaacaata cgccccacag ttgtcatctt ttccaacaac caatggtgtc   1860
tgggcaactg gcgatggtgt taagatggct tccaagttgg gtgtcgcctt agttgatatg   1920
gataaggtcc aattacatcc taccggcttg ttagacccaa aagatccatc taatagaacc   1980
aagtatcttg gtccagaggc cttaagaggt tccggcggtg tcttgttaaa caaaaacggt   2040
gaaagatttg ttaatgaatt agacttaaga tctgttgtct ctcaagctat catcgcacaa   2100
gataatgagt acccaggctc tggtggttcc aagttcgcat actgtgtttt gaacgaaact   2160
gcagcaaagt tattcggcaa aaacttcctt ggtttctact ggaatagatt aggtcttttc   2220
```

```
caaaaggttg attccgttgc tggtttagct aagttgattg gttgtccaga agctaatgtt   2280
gttgctacat tgaagcaata tgaggagtta tcttccaaaa agcttaatcc ttgtccattg   2340
actggcaagt ctgtctttcc ttgtgtttta ggcactcaag gtccatacta tgttgccttg   2400
gttaccccat ccattcacta cactatgggt ggttgtttga tttccccatc tgctgagatg   2460
caaaccattg acaactctgg tgttactcct gtcagacgtc caatcttagg cttattcggt   2520
gctggtgaag ttactggcgg tgtccatggt ggtaacagat taggcggtaa ctctttgtta   2580
gaatgtgttg ttttcggcaa gatcgctggt gacagagctg caaccatctt gcaaaagaaa   2640
aacaccggct tatcaatgac agaatggtct actgtcgtct taagagaagt tagagaaggt   2700
ggtgtctatg gtgctggttc cagagttttg aggtttaaca tgcctggtgc attacagaga   2760
actggtttag ctttaggtca attcatcggt atcagaggtg attgggacgg tcacagattg   2820
atcggttact attctccaat cactttacct gatgatgttg gtgttattgg tatcttagct   2880
agagcagaca agggtagatt ggcagaatgg atttctgcat tgcagccagg tgacgctgtt   2940
gagatgaagg cctgcggtgg tcttatcatt gacagaagat tcgctgaaag acatttcttt   3000
ttccgtggtc ataagatcag aaagttggcc cttatcggtg gtggtactgg tgttgcacca   3060
atgttacaaa tcgtcagagc tgctgtcaaa aagccatttg tcgattcaat tgagtccatt   3120
cagttcatct atgctgcaga ggatgtttcc gagcttacat acagaacctt acttgaatct   3180
tacgaagagg aatatggttc agaaaagttt aagtgtcact tcgttttgaa taacccacca   3240
gctcaatgga ctgacggtgt tggtttcgtt gatactgcat tgttgagatc cgcagttcaa   3300
gcaccatcaa atgatttgct tgttgcaatt tgtggtccac caatcatgca aagagcagtt   3360
aagggtgcat tgaaaggttt aggttacaat atgaatcttg ttagaaccgt tgacgaaact   3420
gaaccaccat cataa                                                    3435
```

<210> SEQ ID NO 11
<211> LENGTH: 6874
<212> TYPE: DNA
<213> ORGANISM: Artificial
<220> FEATURE:
<223> OTHER INFORMATION: FRD gene integration fragment

<400> SEQUENCE: 11

```
aaacctcggt agtgcctacc aatttaatgt ttgactcctt gcgttttctc ctgtcgcgga     60
caaacggtgc ggctccccg atgattcacg taataagccg gagtcaacca cagaggtccc    120
ctatgactca acaaggcctc gtagaaactc ggcttctcgg agaaagagtc ttttcttttt    180
cactggaaaa tattttttt tcctttatat tcttttgaac caaaatgtgg ctactataaa    240
agtgccttta ttccccagct tttctagcat gattgagtca ccttccacaa tgagtcttct    300
ttattgttag tattgtgaat attatccgtg cagttttcaa gaacgtaaat caacagcagt    360
gataatacct tcaaacatat gagcggccgc ggatccctcg aggagtccat cggttcctgt    420
cagatgggat actcttgacg tggaaaattc aaacagaaaa aaaaccccaa taatgaaaaa    480
taacactacg ttatatccgt ggtatcctct atcgtatcgt atcgtagcgt atcgtagcgt    540
accgtatcac agtatagtct aatattccgt atcttattgt atcctatcct attcgatcct    600
attgtatttc agtgcaccat tttaatttct attgctataa tgtccttatt agttgccact    660
gtgaggtgac caatggacga gggcgagccg ttcagaagcc gcgaagggtg ttcttcccat    720
gaatttctta aggagggcgg ctcagctccg agagtgaggc gagacgtctc ggtcagcgta    780
tcccccttcc tcggctttta caaatgatgc gctcttaata gtgtgtcgtt atcctttgg    840
```

```
cattgacggg ggagggaaat tgattgagcg catccatatt tttgcggact gctgaggaca    900
atggtggttt ttccgggtgg cgtgggctac aaatgatacg atggtttttt tcttttcgga    960
gaaggcgtat aaaaaggaca cggagaaccc atttattcta aaaacagttg agcttcttta   1020
attatttttt gatataatat tctattatta tatattttct tcccaataaa acaaaataaa   1080
acaaaacaca gcaaaacaca aaaattctag aatggctgat ggcaaaacct ctgcatcagt   1140
tgttgctgtt gatgctgaac gtgccgctaa ggaaagagat gcagcagcta gagctatgtt   1200
gcaaggtggt ggtgtctctc ctgctggcaa ggcacaattg ttgaaaaagg gtttggttca   1260
cactgttcca tataccttaa aggttgtcgt cgcagatcca aaggaaatgg agaaggcaac   1320
tgctgacgca gaagaggttt tacaagctgc atttcaagtc gtcgacaccc ttttgaacaa   1380
ctttaacgaa aactcagaag tttcaagagt caataggttg gcagttggtg aggaacatca   1440
aatgtctgaa acattgaaac acgtcatggc ctgttgtcaa aaggtttatc attcctccag   1500
aggtgttttt gacccagcag ttggtccatt agtccgtgaa cttagagaag ctgctcacaa   1560
gggtaaaact gttccagccg aaagagttaa tgatttgtta tccaaatgta cccttaatgc   1620
atctttttca attgatatgt ccagaggtat gattgcaagg aagcatccag acgccatgtt   1680
ggatttgggt ggtgtcaaca agggttatgg tatcgactac attgttgaac acttaaactc   1740
tttgggttat gatgatgtct tttcgaatgg gggtggtgat gttagagcat ccggcaaaaa   1800
ccagttatct caaccttggg ctgttggtat tgttagacca cctgccttgg ccgacattag   1860
aactgttgtc ccagaggaca aaagatcctt tatccgtgtc gtcagattga acaacgaagc   1920
tattgctacc tctggtgatt atgagaattt ggttgaaggt cctggttcta aggtttactc   1980
ttccaccttc aatccaactt ccaaaaactt gttggaacct accgaagcag gtatggctca   2040
agtttctgtc aagtgttgct catgtatcta cgctgatgct ttagcaacag cagctttgtt   2100
gaaaaacgat cctgctgccg ttagaaggat cttagataac tggagatatg tcagagatac   2160
tgttactgac tacaccactt acacaaggga aggtgaaaga gttgctaaga tgttggaaat   2220
tgctaccgaa gatgctgaaa tgagagcaaa gagaatcaag ggctctttac cagcaagagt   2280
tatcattgtt ggtggtggtt tggccggttg ttccgcagct atcgaagcag ctaactgtgg   2340
cgcccacgtc atcttgttag aaaaggaacc aaagttaggt ggtaactctg caaaggctac   2400
ctccggtatc aacgcctggg gtactagagc acaagcaaaa caaggtgtca tggacggcgg   2460
caagtttttc gaaagagata cccatagatc cggcaagggt ggtaattgcg atccatgcct   2520
tgttaagact ttgtccgtta agtcctctga tgcagttaag tggttatctg aattaggtgt   2580
tccattgact gttttgtctc aattaggtgg tgcttcaagg aaacgttgtc accgtgcacc   2640
agataagtct gatggtacac cagtcccagt tggtttcacc attatgaaaa cccttgaaaa   2700
ccacattgtc aacgatttgt ccagacatgt tacagttatg acaggtatta ccgtcacagc   2760
tttagaatct acatcaagag tcagacctga tggtgtttta gtcaagcatg ttactggtgt   2820
tcacttgatt caggcatctg gtcaatctat ggttttgaat gcagacgctg ttatcttagc   2880
tactggtggt ttctccaatg atcatacccc aaactccctt ttacaacaat acgccccaca   2940
gttgtcatct tttccaacaa ccaatggtgt ctgggcaact ggcgatggtg ttaagatggc   3000
ttccaagttg ggtgtcgcct tagttgatat ggataaggtc caattacatc ctaccggctt   3060
gttagaccca aaagatccat ctaatagaac caagtatctt ggtccagagg ccttaagagg   3120
ttccggcggt gtcttgttaa acaaaaacgg tgaaagattt gttaatgaat tagacttaag   3180
```

```
atctgttgtc tctcaagcta tcatcgcaca agataatgag tacccaggct ctggtggttc   3240
caagttcgca tactgtgttt tgaacgaaac tgcagcaaag ttattcggca aaaacttcct   3300
tggtttctac tggaatagat taggtctttt ccaaaaggtt gattccgttg ctggtttagc   3360
taagttgatt ggttgtccag aagctaatgt tgttgctaca ttgaagcaat atgaggagtt   3420
atcttccaaa aagcttaatc cttgtccatt gactggcaag tctgtctttc cttgtgtttt   3480
aggcactcaa ggtccatact atgttgcctt ggttacccca tccattcact acactatggg   3540
tggttgtttg atttccccat ctgctgagat gcaaaccatt gacaactctg gtgttactcc   3600
tgtcagacgt ccaatcttag gcttattcgg tgctggtgaa gttactggcg gtgtccatgg   3660
tggtaacaga ttaggcggta actctttgtt agaatgtgtt gttttcggca agatcgctgg   3720
tgacagagct gcaaccatct tgcaaaagaa aaacaccggc ttatcaatga cagaatggtc   3780
tactgtcgtc ttaagagaag ttagagaagg tggtgtctat ggtgctggtt ccagagtttt   3840
gaggtttaac atgcctggtg cattacagag aactggttta gctttaggtc aattcatcgg   3900
tatcagaggt gattgggacg gtcacagatt gatcggttac tattctccaa tcactttacc   3960
tgatgatgtt ggtgttattg gtatcttagc tagagcagac aagggtagat tggcagaatg   4020
gatttctgca ttgcagccag gtgacgctgt tgagatgaag gcctgcggtg gtcttatcat   4080
tgacagaaga ttcgctgaaa gacatttctt tttccgtggt cataagatca gaaagttggc   4140
ccttatcggt ggtggtactg gtgttgcacc aatgttacaa atcgtcagag ctgctgtcaa   4200
aaagccattt gtcgattcaa ttgagtccat tcagttcatc tatgctgcag aggatgtttc   4260
cgagcttaca tacagaacct tacttgaatc ttacgaagag gaatatggtt cagaaaagtt   4320
taagtgtcac ttcgttttga ataacccacc agctcaatgg actgacggtg ttggtttcgt   4380
tgatactgca ttgttgagat ccgcagttca agcaccatca aatgatttgc ttgttgcaat   4440
ttgtggtcca ccaatcatgc aaagagcagt taagggtgca ttgaaaggtt taggttacaa   4500
tatgaatctt gttagaaccg ttgacgaaac tgaaccacca tcataattaa ttaacatctg   4560
aatgtaaaat gaacattaaa atgaattact aaactttacg tctactttac aatctataaa   4620
ctttgtttaa tcatataacg aaatacacta atacacaatc ctgtacgtat gtaatacttt   4680
tatccatcaa ggattgagaa aaaaaagtaa tgattccctg ggccattaaa acttagaccc   4740
ccaagcttgg ataggtcact ctctattttc gtttctccct tccctgatag aagggtgata   4800
tgtaattaag aataatatat aattttataa taaaagaatt catagcctca tgaaatcagc   4860
catttgcttt tgttcaacga tcttttgaaa ttgttgttgt tcttggtagt taagttgatc   4920
catcttggct tatgttgtgt gtatgttgta gttattctta gtatattcct gtcctgagtt   4980
tagtgaaaca taatatcgcc ttgaaatgaa aatgctgaaa ttcgtcgaca tacaattttt   5040
caaacttttt ttttttcttg gtgcacggac atgtttttaa aggaagtact ctataccagt   5100
tattcttcac aaatttaatt gctggagaat agatcttcaa cgctttaata aagtagtttg   5160
tttgtcaagg atggcgtcat acaaagaaag atcagaatca cacacttccc ctgttgctag   5220
gagacttttc tccatcatgg aggaaaagaa gtctaacctt tgtgcatcat tggatattac   5280
tgaaactgaa aagcttctct ctattttgga cactattggt ccttacatct gtctagttaa   5340
aacacacatc gatattgttt ctgattttac gtatgaagga actgtgttgc ctttgaagga   5400
gcttgccaag aaacataatt ttatgatttt tgaagataga aaatttgctg atattggtaa   5460
cactgttaaa aatcaatata aatctggtgt cttccgtatt gccgaatggg ctgacatcac   5520
taatgcacat ggtgtaacgg gtgcaggtat tgtttctggc ttgaaggagg cagcccaaga   5580
```

```
aacaaccagt gaacctagag gtttgctaat gcttgctgag ttatcatcaa agggttcttt   5640
agcatatggt gaatatacag aaaaaacagt agaaattgct aaatctgata aagagtttgt   5700
cattggtttt attgcgcaac acgatatggg cggtagagaa gaaggttttg actggatcat   5760
tatgactcca ggggttggtt tagatgacaa aggtgatgca cttggtcaac aatatagaac   5820
tgttgatgaa gttgtaaaga ctggaacgga tatcataatt gttggtagag gtttgtacgg   5880
tcaaggaaga gatcctatag agcaagctaa aagataccaa caagctggtt ggaatgctta   5940
tttaaacaga tttaaatgat tcttacacaa agatttgata catgtacact agtttaaata   6000
agcatgaaaa gaattacaca agcaaaaaaa aaaaaataaa tgaggtactt tacgttcacc   6060
tacaaccaaa aaaactagat agagtaaaat cttaagattt agaaaaagtt gtttaacaaa   6120
ggctttagta tgtgaatttt taatgtagca aagcgataac taataaacat aaacaaaagt   6180
atggttttct ttatcagtca aatcattatc gattgattgt tccgcgtatc tgcagatagc   6240
ctcatgaaat cagccatttg cttttgttca acgatctttt gaaattgttg ttgttcttgg   6300
tagttaagtt gatccatctt ggcttatgtt gtgtgtatgt tgtagttatt cttagtatat   6360
tcctgtcctg agtttagtga aacataatat cgccttgaaa tgaaaatgct gaaattcgtc   6420
gacatacaat tttcaaact tttttttttt cttggtgcac ggacatgttt ttaaaggaag   6480
tactctatac cagttattct tcacaaattt aattgctgga gaatagatct tcaacgcccc   6540
gggggatctg gatccgcggc cgctgagctc gtctgatatt tgctaaattg aaatgaacct   6600
taccatgcca catctataga catcaaaacc attttcaatt tgtcgatatc ttttgcatat   6660
caaagtaata ccaagcatgt tcaaaaagaa aagaaagcat aactttaata ctctattcga   6720
aacattccga tccacaacac attagtcttt ttaggcccgt tgttcatctt tctattactt   6780
tattcctaac tgtattttta taattccggg tttataaaag attaaactaa tatagcgcat   6840
tctttttggg tacaaacata cataacggag gttt                              6874
```

```
<210> SEQ ID NO 12
<211> LENGTH: 4127
<212> TYPE: DNA
<213> ORGANISM: Artificial
<220> FEATURE:
<223> OTHER INFORMATION: MDH gene integration fragment

<400> SEQUENCE: 12

gttaacccgt ttcgatggga ttcccagaag tggatactat actgtctgca atgcactaca     60
ctctaaaaaa gtattataca ttaccataca ttagcaaatc accaatactc tgcactgttt    120
cagtgtgtgc acattgctac ccaattggga aatcgcaggg aaaatgagac accccctcca    180
ttcgtattac gtaagacaat atcagggctg ccgaattcgg cagaaaagcc gagccggccg    240
agtcctcttg cacggagtgt gtccgaaaag ggcagctctg cagtggggga gaggaggtcg    300
cacgtctatg cggtgttggc atggcctgtg cgtgtacctg tcccctccct gggcatcccc    360
cactgcgcgc cttctccatt gggcgctgcg ggcactccgc gccgttaata caggaggggg    420
gggggaaagc ttaagattag agcgggtaca gtcagtgggt gtattgaccc catttctgtc    480
agtataaacc ccccgttgag ccgccggttt ggttgtttat ggataaaatt tttttttccc    540
cgcatggaga agattgaggg ggggaaggaa tgggaaaaag gccagagcca tctccacagc    600
ggaatccgac cgttaatggg gtgaaacacc cccaccaggt agagcaggaa gaatggggaa    660
acaaggtgga gagatggtca ttgttgggaa tagtgggaaa atgaggggga agagaatgac    720
```

-continued

```
tataaaatgg gaagggggtc caagttatcc aagcagtcca tttagagaag ggagcggccc    780
ctattggtag ttctttcccc ctctcaagct ggcgtgaaat gcaaccttac ggcgtctacg    840
ttactacaag gtccagaaag tgtaggtatt gctactattt ttattttta ttggttctgg     900
agaaatgcag acagtcaatg aacacaactg tctcaatatg catctatgca catgcacaca    960
cacacacatc acaggtaccc ctacaaagag aggtctcttg ataatgtttc attaccacgt   1020
ggcatccccc cccccccccc caataaacaa gtggccgagt tcccctgttg cagaggagga   1080
caaaaaaacc gctggtgttg gtaccattat gcagcaacta gcacaacaaa caaccgaccc   1140
agacatacaa atcaacaaca cttcgccaaa gacacccttt ccagggagga tccactccca   1200
acgtctctcc ataatgtctc tgttggccca tgtctctgtc gttgacaccg taaccacacc   1260
aaccaacccg tccattgtac tgggatggtc gtccatagac acctctccaa cggggaacac   1320
ctcattcgta aaccgccaag gttaccgttc ctcctgactc gccccgttgt tgatgctgcg   1380
cacctgtggt tgcccaacat ggttgtatat cgtgtaacca caccaacaca tgtgcagcac   1440
atgtgtttaa aagagtgtca tggaggtgga tcatgatgga agtggacttt accacttggg   1500
aactgtctcc actcccggga agaaaagacc cggcgtatca cgcggttgcc tcaatggggc   1560
aatttggaag gagaaatata gggaaaatca cgtcgctctc ggacggggaa gagttccaga   1620
ctatgagggg ggggggtggt atataaagac aggagatgtc cacccccaga gagaggaaga   1680
agttggaact ttagaagaga gagataactt tccccagtgt ccatcaatac acaaccaaac   1740
acaaactcta tatttacaca tataaccccc tctctagaat ggttaaagtt acagtttgtg   1800
gtgctgctgg tggtattggt caacccettt ctttactctt gaagcaatcc tctcacatta   1860
ctcacttatc tctttatgat atcgttaata ctcctggtgt tgctgctgat cttagtcata   1920
tcgataccaa atccaaggtc actggtcatg taggtgctgc tcaacttgaa gaagctatca   1980
aggattctga tgttgtcgtt attcccgctg gtgtcccaag aaagccaggt atgacgcgtg   2040
atgatctttt caagattaat gctggtattg tacgtgattt ggctacagct gctgcaaagt   2100
acgctccaaa ggccttcatg tgtatcattt ctaacccagt caactcgact gtcccaatcg   2160
ttactgaagt attcaaacag cacaatgttt atgaccccaa aagaatcttt ggtgtaacaa   2220
cacttgatat tgttcgtgca tccacctttg tatccgaatt gattggaggt gaacctaatt   2280
cacttcgtgt tcccgtcatt ggtggtcaca gcggcgtaac catcttacct ttactctcac   2340
aggtccccgg cattgaaaag ttaaaccaag aacaaattga gaaggtaact catcgtattc   2400
aatttggtgg cgatgaagtt gtcaaggcca aggatggtgc tggttctgcc actctttcca   2460
tggcttatgc tggtgctcgt tttgctacaa acatcattga ggctgctttt gctggaaaga   2520
agggcattgt tgaatgtacc tatgttcaat tggatgctga taaatctggt gcccaatctg   2580
tcaaggattt ggttggtagt gaacttgaat atttctctgt tcccgttgaa ttgggtccta   2640
gtggtgttga aaagatttta cccattggaa acgttaatga atatgaaaag aagttgttga   2700
acgaggcttc tcctgaatta aaaaccaaca ttgataaagg ttgtactttt gttactgaag   2760
gctcaaagtt gtaattaatt aatttatttt actagtttat ttttgctcct gagaatagga   2820
ttacaaacac ttaaagtctt taattacaac tatatataat attctgttgg ttttcttgaa   2880
ttggttcgct gcgattcatg cctcccattc accaaaggtg gagtgggaaa taacggtttt   2940
actgcggtaa ttagcagagg caagaacagg atacactttt tgatgataaa tctgtattat   3000
agtcgagcct atttaggaaa tcaaattttc ttgtgtttac ttttcaaata aataatgttc   3060
gaaaattttt actttactcc ttcatttaac tataccagac gttatatcat caacaccttc   3120
```

```
tgaccatata cagctcaaga tgtttaagag tctgttaaat tttttcaatc catttcatgg   3180
agtaccagga ggtgctacaa aaggaattca tagcctcatg aaatcagcca tttgcttttg   3240
ttcaacgatc ttttgaaatt gttgttgttc ttggtagtta agttgatcca tcttggctta   3300
tgttgtgtgt atgttgtagt tattcttagt atattcctgt cctgagttta gtgaaacata   3360
atatcgcctt gaaatgaaaa tgctgaaatt cgtcgacata caatttttca aacttttttt   3420
ttttcttggt gcacggacat gtttttaaag gaagtactct ataccagtta ttcttcacaa   3480
atttaattgc tggagaatag atcttcaacg ctttaataaa gtagtttgtt tgtcaaggat   3540
ggcgtcatac aaagaaagat cagaatcaca cacttcccct gttgctagga gacttttctc   3600
catcatggag gaaaagaagt ctaacctttg tgcatcattg gatattactg aaactgaaaa   3660
gcttctctct attttggaca ctattggtcc ttacatctgt ctagttaaaa cacacatcga   3720
tattgtttct gattttacgt atgaaggaac tgtgttgcct ttgaaggagc ttgccaagaa   3780
acataatttt atgatttttg aagatagaaa atttgctgat attggtaaca ctgttaaaaa   3840
tcaatataaa tctggtgtct tccgtattgc cgaatgggct gacatcacta atgcacatgg   3900
tgtaacgggt gcaggtattg tttctggctt gaaggaggca gcccaagaaa caaccagtga   3960
acctagaggt ttgctaatgc ttgctgagtt atcatcaaag ggttctttag catatggtga   4020
atatacagaa aaaacagtag aaattgctaa atctgataaa gagtttgtca ttggttttat   4080
tgcgcaacac gatatgggcg gtagagaaga aggttttgac tccgcgg                 4127
```

<210> SEQ ID NO 13
<211> LENGTH: 987
<212> TYPE: DNA
<213> ORGANISM: Rhizopus delemar

<400> SEQUENCE: 13

```
atggttaaag ttacagtttg tggtgctgct ggtggtattg gtcaacccct ttctttactc     60
ttgaagcaat cctctcacat tactcactta tctctttatg atatcgttaa tactcctggt    120
gttgctgctg atcttagtca tatcgatacc aaatccaagg tcactggtca tgtaggtgct    180
gctcaacttg aagaagctat caaggattct gatgttgtcg ttattcccgc tggtgtccca    240
agaaagccag gtatgacgcg tgatgatctt ttcaagatta atgctggtat tgtacgtgat    300
ttggctacag ctgctgcaaa gtacgctcca aaggccttca tgtgtatcat ttctaaccca    360
gtcaactcga ctgtcccaat cgttactgaa gtattcaaac agcacaatgt ttatgacccc    420
aaaagaatct ttggtgttac aacacttgat attgttcgtg catccacctt tgtatccgaa    480
ttgattggag gtgaacctaa ttcacttcgt gttcccgtca ttggtggtca cagcggcgta    540
accatcttac ctttactctc acaggtcccc ggcattgaaa agttaaacca agaacaaatt    600
gagaaggtaa ctcatcgtat tcaatttggt ggcgatgaag ttgtcaaggc caaggatggt    660
gctggttctg ccactctttc catggcttat gctggtgctc gttttgctac aaacatcatt    720
gaggctgctt ttgctggaaa gaagggcatt gttgaatgta cctatgttca attggatgct    780
gataaatctg gtgcccaatc tgtcaaggat ttggttggta gtgaacttga atatttctct    840
gttcccgttg aattgggtcc tagtggtgtt gaaaagattt tacccattgg aaacgttaat    900
gaatatgaaa agaagttgtt gaacgaggct tctcctgaat taaaaaccaa cattgataaa    960
ggttgtactt ttgttactga aggctaa                                        987
```

<210> SEQ ID NO 14

<211> LENGTH: 4112
<212> TYPE: DNA
<213> ORGANISM: Artificial
<220> FEATURE:
<223> OTHER INFORMATION: A. succinogenes FUM gene integration fragment

<400> SEQUENCE: 14

```
aattctttga aggagcttgc caagaaacat aattttatga tttttgaaga tagaaaattt     60
gctgatattg gtaacactgt taaaaatcaa tataaatctg gtgtcttccg tattgccgaa    120
tgggctgaca tcactaatgc acatggtgta acgggtgcag gtattgtttc tggcttgaag    180
gaggcagccc aagaaacaac cagtgaacct agaggtttgc taatgcttgc tgagttatca    240
tcaaagggtt ctttagcata tggtgaatat acagaaaaaa cagtagaaat tgctaaatct    300
gataaagagt ttgtcattgg ttttattgcg caacacgata tgggcggtag agaagaaggt    360
tttgactgga tcattatgac tccaggggtt ggtttagatg acaaaggtga tgcacttggt    420
caacaatata gaactgttga tgaagttgta aagactggaa cggatatcat aattgttggt    480
agaggtttgt acggtcaagg aagagatcct atagagcaag ctaaaagata ccaacaagct    540
ggttggaatg cttatttaaa cagatttaaa tgattcttac acaaagattt gatacatgta    600
cactagttta aataagcatg aaaagaatta cacaagcaaa aaaaaaaaaa taaatgaggt    660
actttacgtt cacctacaac caaaaaaact agatagagta aaatcttaag atttagaaaa    720
agttgtttaa caaaggcttt agtatgtgaa tttttaatgt agcaaagcga taactaataa    780
acataaacaa aagtatggtt ttctttatca gtcaaatcat tatcgattga ttgttccgcg    840
tatctgcaga tagcctcatg aaatcagcca tttgcttttg ttcaacgatc ttttgaaatt    900
gttgttgttc ttggtagtta agttgatcca tcttggctta tgttgtgtgt atgttgtagt    960
tattcttagt atattcctgt cctgagttta gtgaaacata atatcgcctt gaaatgaaaa   1020
tgctgaaatt cgtcgacata caatttttca aactttttttt ttttcttggt gcacggacat   1080
gtttttaaag gaagtactct ataccagtta ttcttcacaa atttaattgc tggagaatag   1140
atcttcaacg cgtttcctcg acatttgctg caacggcaac atcaatgtcc acgtttacac   1200
acctacattt atatctatat ttatatttat atttatttat ttatgctact tagcttctat   1260
agttagttaa tgcactcacg atattcaaaa ttgacaccct tcaactactc cctactattg   1320
tctactactg tctactactc ctctttacta tagctgctcc caataggctc caccaatagg   1380
ctctgtcaat acattttgcg ccgccacctt tcaggttgtg tcactcctga aggaccatat   1440
tgggtaatcg tgcaatttct ggaagagagt ccgcgagaag tgaggccccc actgtaaatc   1500
ctcgaggggg catggagtat ggggcatgga ggatggagga tggggggggg gggggggaaa   1560
ataggtagcg aaaggacccg ctatcacccc acccggagaa ctcgttgccg ggaagtcata   1620
tttcgacact ccggggagtc tataaaaggc gggttttgtc ttttgccagt tgatgttgct   1680
gagaggactt gtttgccgtt tcttccgatt taacagtata gaatcaacca ctgttaatta   1740
tacacgttat actaacacaa caaaaacaaa aacaacgaca acaacaacaa catctagaat   1800
gatcattatg actttccgta ttgagaagga tactatgggt gaagttcaag tcccagctga   1860
taagtattgg gctgcccaga ccgaaagatc tagaaacaac ttcaagattg gtccagctgc   1920
ttctatgcca catgaaatca ttgaagcttt tggttacttg aaaaaggcag ctgcatacgc   1980
taacgctgac ttgggtgttt tgccagctga aaagagagat ttgattgccc aagcttgtga   2040
cgaaatctta gccagaaagc ttgacgatca gttcccattg gttatctggc aaacaggttc   2100
tggtacccaa tccaatatga acttgaatga ggttatcgct aatagagcac atgttatcaa   2160
```

```
tggtggcaag ttgggtgaaa agtctatcat tcaccctaat gacgatgtca acaaatccca   2220

atcttctaat gacacttatc caacagcaat gcatattgcc acttacaaaa aggttgttga   2280

agctaccatc cctgcaattg aaagattaca aaagacctta gcagctaagt cagaagagtt   2340

taaggatgtt gtcaaaatcg gtaggactca tcttatggat gccaccccat taaccttggg   2400

tcaagagttc tctggttatg ctgcacaatt gtccttcggt ttagcagcaa tcaaaaacac   2460

cttgcctcat ttgagacaat tagcattagg tggtactgca gtcggtactg gtcttaacac   2520

tccaaaaggt tatgatgtta aagttgcaga atacattgcc aagtttactg gtttaccatt   2580

catcactgct gaaaacaagt tcgaggcctt agcaactcac gatgctattg tcgaaaccca   2640

cggtgcctta aagcaggttg caatgtcact tttcaagatc gcaaacgaca ttagattgtt   2700

ggcatcaggt ccaagatctg gcattggcga gatccttatc cctgaaaacg aaccaggttc   2760

atccattatg ccaggcaagg ttaaccctac tcaatgtgaa gcaatgacaa tggttgcagc   2820

acaagtctta ggtaatgata caacaatctc cttcgctggc tctcaaggtc acttcgaatt   2880

gaatgtcttt aagccagtta tggctgctaa ctttttgcaa tctgctcaac ttattgctga   2940

tgtttgcatt tcctttgacg aacactgtgc ttccggtatc aagcctaata ccccacgtat   3000

tcaacatttg ttagaatcct ccttaatgtt agtcaccgca ttgaacaccc acattggtta   3060

cgaaaatgca gctaagattg ctaagaccgc tcacaaaaac ggtactacat taagagaaga   3120

ggccattaac ttaggtttag tttctgctga agattttgat aagtgggtta gaccagaaga   3180

tatggttggt tccttgaagt aattaattaa catctgaatg taaaatgaac attaaaatga   3240

attactaaac tttacgtcta ctttacaatc tataaacttt gtttaatcat ataacgaaat   3300

acactaatac acaatcctgt acgtatgtaa tacttttatc catcaaggat tgagaaaaaa   3360

aagtaatgat tccctgggcc attaaaactt agacccccaa gcttggatag gtcactctct   3420

attttcgttt ctcccttccc tgatagaagg gtgatatgta attaagaata atatataatt   3480

ttataataaa agcggccgca ccaggggttt agtgaagtca ccaattaaga ttgttggttt   3540

gagtgagttg ccaaagatct atgaattgat ggagcaaggt aagattttag gcagatatgt   3600

tgttgacact tcgaaatgat gggctgactt gggtgtactg gtgtgacgtt tttatgtgta   3660

tattgatatg catgggggat gtatagtgat gaggagtaga gtatataacg aaatgaaatg   3720

aaataatatg atatgataag ataagatgag atcaatacga taatataaga tgcgacatga   3780

ggagttcaat gtagcatact acacgatgct gcagtacaac tctgatacgc tagactatac   3840

tatacaaaac tgtagtacac tatacgttag tgtagtatcc agaaacaaca ctgctttata   3900

gtacaataca actctataat actatagtat actatgccaa accacgtaat accataatat   3960

gctccacgac atggtacaat gtgctatact tcatactatt ataccatata tactccgata   4020

tattattgat atactatttt atactataat accataccac acaacactac attacaacga   4080

gcaaccttac cataaatgtc agttatggcc gc                                 4112
```

<210> SEQ ID NO 15
<211> LENGTH: 1404
<212> TYPE: DNA
<213> ORGANISM: Actinobacillus succinogenes

<400> SEQUENCE: 15

```
atgatcatta tgactttccg tattgagaag gatactatgg gtgaagttca agtcccagct     60

gataagtatt gggctgccca gaccgaaaga tctagaaaca acttcaagat tggtccagct    120
```

-continued

```
gcttctatgc cacatgaaat cattgaagct tttggttact tgaaaaaggc agctgcatac    180

gctaacgctg acttgggtgt tttgccagct gaaaagagag atttgattgc ccaagcttgt    240

gacgaaatct tagccagaaa gcttgacgat cagttcccat tggttatctg gcaaacaggt    300

tctggtaccc aatccaatat gaacttgaat gaggttatcg ctaatagagc acatgttatc    360

aatggtggca agttgggtga aaagtctatc attcacccta atgacgatgt caacaaatcc    420

caatcttcta atgacactta tccaacagca atgcatattg ccacttacaa aaaggttgtt    480

gaagctacca tccctgcaat tgaaagatta caaaagacct tagcagctaa gtcagaagag    540

tttaaggatg ttgtcaaaat cggtaggact catcttatgg atgccacccc attaaccttg    600

ggtcaagagt tctctggtta tgctgcacaa ttgtccttcg gtttagcagc aatcaaaaac    660

accttgcctc atttgagaca attagcatta ggtggtactg cagtcggtac tggtcttaac    720

actccaaaag gttatgatgt taaagttgca gaatacattg ccaagtttac tggtttacca    780

ttcatcactg ctgaaaacaa gttcgaggcc ttagcaactc acgatgctat tgtcgaaacc    840

cacggtgcct taaagcaggt tgcaatgtca cttttcaaga tcgcaaacga cattagattg    900

ttggcatcag gtccaagatc tggcattggc gagatcctta tccctgaaaa cgaaccaggt    960

tcatccatta tgccaggcaa ggttaaccct actcaatgtg aagcaatgac aatggttgca   1020

gcacaagtct taggtaatga tacaacaatc tccttcgctg gctctcaagg tcacttcgaa   1080

ttgaatgtct ttaagccagt tatggctgct aactttttgc aatctgctca acttattgct   1140

gatgtttgca tttcctttga cgaacactgt gcttccggta tcaagcctaa taccccacgt   1200

attcaacatt tgttagaatc ctccttaatg ttagtcaccg cattgaacac ccacattggt   1260

tacgaaaatg cagctaagat tgctaagacc gctcacaaaa acggtactac attaagagaa   1320

gaggccatta acttaggttt agtttctgct gaagattttg ataagtgggt tagaccagaa   1380

gatatggttg gttccttgaa gtaa                                          1404
```

<210> SEQ ID NO 16
<211> LENGTH: 3983
<212> TYPE: DNA
<213> ORGANISM: Artificial
<220> FEATURE:
<223> OTHER INFORMATION: R. delemar MDH gene integration fragment

<400> SEQUENCE: 16

```
gggccccata actgacattt atggtaaggt tgctcgttgt aatgtagtgt tgtgtggtat     60

ggtattatag tataaaatag tatatcaata atatatcgga gtatatatgg tataatagta    120

tgaagtatag cacattgtac catgtcgtgg agcatattat ggtattacgt ggtttggcat    180

agtatactat agtattatag agttgtattg tactataaag cagtgttgtt tctggatact    240

acactaacgt atagtgtact acagttttgt atagtatagt ctagcgtatc agagttgtac    300

tgcagcatcg tgtagtatgc tacattgaac tcctcatgtc gcatcttata ttatcgtatt    360

gatctcatct tatcttatca tatcatatta tttcatttca tttcgttata tactctactc    420

ctcatcacta tacatccccc atgcatatca atatacacat aaaaacgtca caccagtaca    480

cccaagtcag cccatcattt cgaagtgtca acaacatatc tgcctaaaat cttaccttgc    540

tccatcaatt catagatctt tggcaactca ctcaaaccaa caatcttaat tggtgacttc    600

actaaacccc tggtgcggcc gcggatccct cgagattggt agttctttcc ccctctcaag    660

ctggcgtgaa atgcaacctt acggcgtcta cgttactaca aggtccagaa agtgtaggta    720

ttgctactat ttttattttt tattggttct ggagaaatgc agacagtcaa tgaacacaac    780
```

```
tgtctcaata tgcatctatg cacatgcaca cacacacaca tcacaggtac ccctacaaag    840
agaggtctct tgataatgtt tcattaccac gtggcatccc cccccccccc cccaataaac    900
aagtggccga gttcccctgt tgcagaggag gacaaaaaaa ccgctggtgt tggtaccatt    960
atgcagcaac tagcacaaca aacaaccgac ccagacatac aaatcaacaa cacttcgcca   1020
aagacaccct ttccagggag gatccactcc caacgtctct ccataatgtc tctgttggcc   1080
catgtctctg tcgttgacac cgtaaccaca ccaaccaacc cgtccattgt actgggatgg   1140
tcgtccatag acacctctcc aacggggaac acctcattcg taaaccgcca aggttaccgt   1200
tcctcctgac tcgccccgtt gttgatgctg cgcacctgtg gttgcccaac atggttgtat   1260
atcgtgtaac cacaccaaca catgtgcagc acatgtgttt aaaagagtgt catggaggtg   1320
gatcatgatg gaagtggact ttaccacttg ggaactgtct ccactcccgg gaagaaaaga   1380
cccggcgtat cacgcggttg cctcaatggg gcaatttgga aggagaaata tagggaaaat   1440
cacgtcgctc tcggacgggg aagagttcca gactatgagg ggggggggtg gtatataaag   1500
acaggagatg tccaccccca gagagaggaa gaagttggaa ctttagaaga gagagataac   1560
tttccccagt gtccatcaat acacaaccaa acacaaactc tatatttaca catataaccc   1620
cctctctaga taaaatggtt aaagttacag tttgtggtgc tgctggtggt attggtcaac   1680
ccctttcttt actcttgaag caatcctctc acattactca cttatctctt tatgatatcg   1740
ttaatactcc tggtgttgct gctgatctta gtcatatcga taccaaatcc aaggtcactg   1800
gtcatgtagg tgctgctcaa cttgaagaag ctatcaagga ttctgatgtt gtcgttattc   1860
ccgctggtgt cccaagaaag ccaggtatga cgcgtgatga tcttttcaag attaatgctg   1920
gtattgtacg tgatttggct acagctgctg caaagtacgc tccaaaggcc ttcatgtgta   1980
tcatttctaa cccagtcaac tcgactgtcc caatcgttac tgaagtattc aaacagcaca   2040
atgtttatga ccccaaaaga atctttggtg taacaacact tgatattgtt cgtgcatcca   2100
cctttgtatc cgaattgatt ggaggtgaac ctaattcact tcgtgttccc gtcattggtg   2160
gtcacagcgg cgtaaccatc ttacctttac tctcacaggt ccccggcatt gaaaagttaa   2220
accaagaaca aattgagaag gtaactcatc gtattcaatt tggtggcgat gaagttgtca   2280
aggccaagga tggtgctggt tctgccactc tttccatggc ttatgctggt gctcgttttg   2340
ctacaaacat cattgaggct gcttttgctg gaaagaaggg cattgttgaa tgtacctatg   2400
ttcaattgga tgctgataaa tctggtgccc aatctgtcaa ggatttggtt ggtagtgaac   2460
ttgaatattt ctctgttccc gttgaattgg gtcctagtgg tgttgaaaag attttaccca   2520
ttggaaacgt taatgaatat gaaaagaagt tgttgaacga ggcttctcct gaattaaaaa   2580
ccaacattga taaaggttgt acttttgtta ctgaaggctc aaagttgtaa ttaattaatt   2640
tattttacta gtttattttt gctcctgaga ataggattac aaacacttaa agtctttaat   2700
tacaactata tataatattc tgttggtttt cttgaattgg ttcgctgcga ttcatgcctc   2760
ccattcacca aaggtggagt gggaaataac ggttttactg cggtaattag cagaggcaag   2820
aacaggatac actttttgat gataaatctg tattatagtc gagcctattt aggaaatcaa   2880
atttcttgt gtttactttt caaataaata atgttcgaaa atttttactt tactccttca   2940
tttaactata ccagacgtta tatcatcaac accttctgac catatacagc tcaagatgtt   3000
taagagtctg ttaaattttt tcaatccatt tcatggagta ccaggaggtg ctacaaaagg   3060
aattcatagc ctcatgaaat cagccatttg cttttgttca acgatctttt gaaattgttg   3120
```

```
ttgttcttgg tagttaagtt gatccatctt ggcttatgtt gtgtgtatgt tgtagttatt   3180
cttagtatat tcctgtcctg agtttagtga aacataatat cgccttgaaa tgaaaatgct   3240
gaaattcgtc gacatacaat ttttcaaact tttttttttt cttggtgcac ggacatgttt   3300
ttaaaggaag tactctatac cagttattct tcacaaattt aattgctgga gaatagatct   3360
tcaacgcttt aataaagtag tttgtttgtc aaggatggcg tcatacaaag aaagatcaga   3420
atcacacact tcccctgttg ctaggagact tttctccatc atggaggaaa agaagtctaa   3480
cctttgtgca tcattggata ttactgaaac tgaaaagctt ctctctattt tggacactat   3540
tggtccttac atctgtctag ttaaaacaca catcgatatt gtttctgatt ttacgtatga   3600
aggaactgtg ttgcctttga aggagcttgc caagaaacat aattttatga tttttgaaga   3660
tagaaaattt gctgatattg gtaacactgt taaaaatcaa tataaatctg gtgtcttccg   3720
tattgccgaa tgggctgaca tcactaatgc acatggtgta acgggtgcag gtattgtttc   3780
tggcttgaag gaggcagccc aagaaacaac cagtgaacct agaggtttgc taatgcttgc   3840
tgagttatca tcaaagggtt ctttagcata tggtgaatat acagaaaaaa cagtagaaat   3900
tgctaaatct gataaagagt ttgtcattgg ttttattgcg caacacgata tgggcggtag   3960
agaagaaggt tttgactccg cgg                                           3983
```

```
<210> SEQ ID NO 17
<211> LENGTH: 4060
<212> TYPE: DNA
<213> ORGANISM: Artificial
<220> FEATURE:
<223> OTHER INFORMATION: A. succinogenes FUM gene integration fragment

<400> SEQUENCE: 17

aattctttga aggagcttgc caagaaacat aattttatga tttttgaaga tagaaaattt     60
gctgatattg gtaacactgt taaaaatcaa tataaatctg gtgtcttccg tattgccgaa    120
tgggctgaca tcactaatgc acatggtgta acgggtgcag gtattgtttc tggcttgaag    180
gaggcagccc aagaaacaac cagtgaacct agaggtttgc taatgcttgc tgagttatca    240
tcaaagggtt ctttagcata tggtgaatat acagaaaaaa cagtagaaat tgctaaatct    300
gataaagagt ttgtcattgg ttttattgcg caacacgata tgggcggtag agaagaaggt    360
tttgactgga tcattatgac tccaggggtt ggtttagatg acaaaggtga tgcacttggt    420
caacaatata gaactgttga tgaagttgta aagactggaa cggatatcat aattgttggt    480
agaggtttgt acggtcaagg aagagatcct atagagcaag ctaaaagata ccaacaagct    540
ggttggaatg cttatttaaa cagatttaaa tgattcttac acaaagattt gatacatgta    600
cactagttta aataagcatg aaaagaatta cacaagcaaa aaaaaaaaaa taaatgaggt    660
actttacgtt cacctacaac caaaaaaact agatagagta aaatcttaag atttagaaaa    720
agttgtttaa caaaggcttt agtatgtgaa tttttaatgt agcaaagcga taactaataa    780
acataaacaa aagtatggtt ttctttatca gtcaaatcat tatcgattga ttgttccgcg    840
tatctgcaga tagcctcatg aaatcagcca tttgcttttg ttcaacgatc ttttgaaatt    900
gttgttgttc ttggtagtta agttgatcca tcttggctta tgttgtgtgt atgttgtagt    960
tattcttagt atattcctgt cctgagttta gtgaaacata atatcgcctt gaaatgaaaa   1020
tgctgaaatt cgtcgacata caatttttca aacttttttt ttttcttggt gcacggacat   1080
gtttttaaag gaagtactct ataccagtta ttcttcacaa atttaattgc tggagaatag   1140
atcttcaacg cgtttcctcg acatttgctg caacggcaac atcaatgtcc acgtttacac   1200
```

```
acctacattt atatctatat ttatatttat atttatttat ttatgctact tagcttctat   1260
agttagttaa tgcactcacg atattcaaaa ttgacaccct tcaactactc cctactattg   1320
tctactactg tctactactc ctctttacta tagctgctcc caataggctc caccaatagg   1380
ctctgtcaat acattttgcg ccgccacctt tcaggttgtg tcactcctga aggaccatat   1440
tgggtaatcg tgcaatttct ggaagagagt ccgcgagaag tgaggccccc actgtaaatc   1500
ctcgaggggg catggagtat ggggcatgga ggatggagga tggggggggg ggggggggaaa   1560
ataggtagcg aaaggacccg ctatcacccc acccggagaa ctcgttgccg ggaagtcata   1620
tttcgacact ccggggagtc tataaaaggc gggttttgtc ttttgccagt tgatgttgct   1680
gagaggactt gtttgccgtt tcttccgatt taacagtata gaatcaacca ctgttaatta   1740
tacacgttat actaacacaa caaaaacaaa aacaacgaca acaacaacaa catctagata   1800
aaatgatcat tatgactttc cgtattgaga aggatactat gggtgaagtt caagtcccag   1860
ctgataagta ttgggctgcc cagaccgaaa gatctagaaa caacttcaag attggtccag   1920
ctgcttctat gccacatgaa atcattgaag cttttggtta cttgaaaaag gcagctgcat   1980
acgctaacgc tgacttgggt gttttgccag ctgaaaagag agatttgatt gcccaagctt   2040
gtgacgaaat cttagccaga aagcttgacg atcagttccc attggttatc tggcaaacag   2100
gttctggtac ccaatccaat atgaacttga atgaggttat cgctaataga gcacatgtta   2160
tcaatggtgg caagttgggt gaaaagtcta tcattcaccc taatgacgat gtcaacaaat   2220
cccaatcttc taatgacact tatccaacag caatgcatat tgccacttac aaaaaggttg   2280
ttgaagctac catccctgca attgaaagat tacaaaagac cttagcagct aagtcagaag   2340
agtttaagga tgttgtcaaa atcggtagga ctcatcttat ggatgccacc ccattaacct   2400
tgggtcaaga gttctctggt tatgctgcac aattgtcctt cggtttagca gcaatcaaaa   2460
acaccttgcc tcatttgaga caattagcat taggtggtac tgcagtcggt actggtctta   2520
acactccaaa aggttatgat gttaaagttg cagaatacat tgccaagttt actggtttac   2580
cattcatcac tgctgaaaac aagttcgagg ccttagcaac tcacgatgct attgtcgaaa   2640
cccacggtgc cttaaagcag gttgcaatgt cacttttcaa gatcgcaaac gacattagat   2700
tgttggcatc aggtccaaga tctggcattg gcgagatcct tatccctgaa aacgaaccag   2760
gttcatccat tatgccaggc aaggttaacc ctactcaatg tgaagcaatg acaatggttg   2820
cagcacaagt cttaggtaat gatacaacaa tctccttcgc tggctctcaa ggtcacttcg   2880
aattgaatgt ctttaagcca gttatggctg ctaacttttt gcaatctgct caacttattg   2940
ctgatgtttg catttccttt gacgaacact gtgcttccgg tatcaagcct aataccccac   3000
gtattcaaca tttgttagaa tcctccttaa tgttagtcac cgcattgaac acccacattg   3060
gttacgaaaa tgcagctaag attgctaaga ccgctcacaa aaacggtact acattaagag   3120
aagaggccat taacttaggt ttagtttctg ctgaagattt tgataagtgg gttagaccag   3180
aagatatggt tggttccttg aagtaattaa ttaacatctg aatgtaaaat gaacattaaa   3240
atgaattact aaactttacg tctactttac aatctataaa ctttgtttaa tcatataacg   3300
aaatacacta atacacaatc ctgtacgtat gtaatacttt tatccatcaa ggattgagaa   3360
aaaaaagtaa tgattccctg ggccattaaa acttagaccc ccaagcttgg ataggtcact   3420
ctctattttc gtttctccct tccctgatag aagggtgata tgtaattaag aataatatat   3480
aattttataa taaaagcggc cgcctccctt ctctaaatgg actgcttgga taacttggac   3540
```

```
ccccttccca ttttatagtc attctcttcc ccctcatttt cccactattc ccaacaatga   3600
ccatctctcc accttgtttc cccattcttc ctgctctacc tggtgggggt gtttcacccc   3660
attaacggtc ggattccgct gtggagatgg ctctggcctt tttcccattc cttccccccc   3720
tcaatcttct ccatgcgggg aaaaaaaaat tttatccata aacaaccaaa ccggcggctc   3780
aacgggggt ttatactgac agaaatgggg tcaatacacc cactgactgt acccgctcta   3840
atcttaagct ttcccccccc cctcctgtat taacggcgcg gagtgcccgc agcgcccaat   3900
ggagaaggcg cgcagtgggg gatgcccagg gaggggacag gtacacgcac aggccatgcc   3960
aacaccgcat agacgtgcga cctcctctcc cccactgcag agctgccctt ttcggacaca   4020
ctccgtgcaa gaggactcgg ccggctcggc ttttctgccg                          4060
```

<210> SEQ ID NO 18
<211> LENGTH: 3835
<212> TYPE: DNA
<213> ORGANISM: Artificial
<220> FEATURE:
<223> OTHER INFORMATION: 5' integration fragment

<400> SEQUENCE: 18

```
aactactatg tacactgtat aagtaaaaag acgataccc cctcccactc tgggtgctac      60
ggtgtagatc tctccgtaaa cacaaaaagg cggctcagat gataattggg gtccgggcgc    120
aaccggaagg ggggagagag gggagcgatg gcttctcctc cggggggcta cgggagtttc    180
ctctttggga aggataaaga ggggatggat tgatacaaga ttctgagaac ctattacgat    240
gatgttcagt ggtattttgt cttttgttat ttaaagggag gggactttcc tcaatacctt    300
agttgtaaaa ttacgctatt atctttaacc ctttcttttg agcaataatt aaaaagagcg    360
gccgcgagtc catcggttcc tgtcagatgg gatactcttg acgtggaaaa ttcaaacaga    420
aaaaaaaccc caataatgaa aaataacact acgttatatc cgtggtatcc tctatcgtat    480
cgtatcgtag cgtatcgtag cgtaccgtat cacagtatag tctaatattc cgtatcttat    540
tgtatcctat cctattcgat cctattgtat ttcagtgcac cattttaatt tctattgcta    600
taatgtcctt attagttgcc actgtgaggt gaccaatgga cgagggcgag ccgttcagaa    660
gccgcgaagg gtgttcttcc catgaatttc ttaaggaggg cggctcagct ccgagagtga    720
ggcgagacgt ctcggtcagc gtatccccct tcctcggctt ttacaaatga tgcgctctta    780
atagtgtgtc gttatccttt tggcattgac gggggaggga aattgattga gcgcatccat    840
atttttgcgg actgctgagg acaatggtgg tttttccggg tggcgtgggc tacaaatgat    900
acgatggttt ttttctttc ggagaaggcg tataaaaagg acacggagaa cccatttatt    960
ctaaaaacag ttgagcttct ttaattattt tttgatataa tattctatta ttatatattt   1020
tcttcccaat aaaacaaaat aaaacaaaac acagcaaaac acaaaaagct agcggcgcgc   1080
cttctgtctt tgattttctt atgttattca aaacatctgc cccaaaatct aacgattata   1140
tatattccta cgtataactg tatagctaat tattgattta tttgtacata aaaaccacat   1200
aaatgtaaaa gcaagaaaaa aaataactaa ggagaaggat caatatctca tttataatgc   1260
tcgccaaagc agcgtacgtg aattttaatc aagacatcaa caaatcttgc aacttggtta   1320
tatcgcttct tcacccactc acccgctttt ctacattgtt gaacacaaat atatacaggg   1380
gtatgtctca aggtcaagtg cagtttcaac agagactacc tcaaggtacc tcttcagaaa   1440
tgcagaactt cactcttgat cagattttct ccgaattaaa ggaggcctat tggtagttct   1500
ttcccctct caagctggcg tgaaatgcaa ccttacggcg tctacgttac tacaaggtcc    1560
```

```
agaaagtgta ggtattgcta ctatttttat tttttattgg ttctggagaa atgcagacag   1620
tcaatgaaca caactgtctc aatatgcatc tatgcacatg cacacacaca cacatcacag   1680
gtacccctac aaagagaggt ctcttgataa tgtttcatta ccacgtggca tccccccccc   1740
cccccccaat aaacaagtgg ccgagttccc ctgttgcaga ggaggacaaa aaaaccgctg   1800
gtgttggtac cattatgcag caactagcac aacaaacaac cgacccagac atacaaatca   1860
acaacacttc gccaaagaca ccctttccag ggaggatcca ctcccaacgt ctctccataa   1920
tgtctctgtt ggcccatgtc tctgtcgttg acaccgtaac cacaccaacc aacccgtcca   1980
ttgtactggg atggtcgtcc atagacacct ctccaacggg gaacacctca ttcgtaaacc   2040
gccaaggtta ccgttcctcc tgactcgccc cgttgttgat gctgcgcacc tgtggttgcc   2100
caacatggtt gtatatcgtg taaccacacc aacacatgtg cagcacatgt gtttaaaaga   2160
gtgtcatgga ggtggatcat gatggaagtg gactttacca cttgggaact gtctccactc   2220
ccgggaagaa aagacccggc gtatcacgcg gttgcctcaa tggggcaatt tggaaggaga   2280
aatataggga aaatcacgtc gctctcggac ggggaagagt tccagactat gaggggggggg  2340
ggtggtatat aaagacagga gatgtccacc cccagagaga ggaagaagtt ggaactttag   2400
aagagagaga taactttccc cagtgtccat caatacacaa ccaaacacaa actctatatt   2460
tacacatata accccctctc tagattaatt aatttatttt actagtttat ttttgctcct   2520
gagaatagga ttacaaacac ttaaagtctt taattacaac tatatataat attctgttgg   2580
ttttcttgaa ttggttcgct gcgattcatg cctcccattc accaaaggtg gagtgggaaa   2640
taacggtttt actgcggtaa ttagcagagg caagaacagg atacactttt tgatgataaa   2700
tctgtattat agtcgagcct atttaggaaa tcaaattttc ttgtgtttac ttttcaaata   2760
aataatgttc gaaaattttt actttactcc ttcatttaac tataccagac gttatatcat   2820
caacaccttc tgaccatata cagctcaaga tgtttaagag tctgttaaat tttttcaatc   2880
catttcatgg agtaccagga ggtgctacaa aaggaattca tagcctcatg aaatcagcca   2940
tttgcttttg ttcaacgatc ttttgaaatt gttgttgttc ttggtagtta agttgatcca   3000
tcttggctta tgttgtgtgt atgttgtagt tattcttagt atattcctgt cctgagttta   3060
gtgaaacata atatcgcctt gaaatgaaaa tgctgaaatt cgtcgacata caatttttca   3120
aacttttttt ttttcttggt gcacggacat gtttttaaag gaagtactct ataccagtta   3180
ttcttcacaa atttaattgc tggagaatag atcttcaacg ctttaataaa gtagtttgtt   3240
tgtcaaggat ggcgtcatac aaagaaagat cagaatcaca cacttcccct gttgctagga   3300
gacttttctc catcatggag gaaaagaagt ctaacctttg tgcatcattg gatattactg   3360
aaactgaaaa gcttctctct attttggaca ctattggtcc ttacatctgt ctagttaaaa   3420
cacacatcga tattgtttct gattttacgt atgaaggaac tgtgttgcct ttgaaggagc   3480
ttgccaagaa acataatttt atgatttttg aagatagaaa atttgctgat attggtaaca   3540
ctgttaaaaa tcaatataaa tctggtgtct tccgtattgc cgaatgggct gacatcacta   3600
atgcacatgg tgtaacgggt gcaggtattg tttctggctt gaaggaggca gcccaagaaa   3660
caaccagtga acctagaggt ttgctaatgc ttgctgagtt atcatcaaag ggttctttag   3720
catatggtga atatacagaa aaaacagtag aaattgctaa atctgataaa gagtttgtca   3780
ttggttttat tgcgcaacac gatatgggcg gtagagaaga aggttttgac tccgc        3835
```

<210> SEQ ID NO 19

<211> LENGTH: 3883
<212> TYPE: DNA
<213> ORGANISM: Artificial
<220> FEATURE:
<223> OTHER INFORMATION: Integration fragment targeted to MAE gene

<400> SEQUENCE: 19

```
aattctttga aggagcttgc caagaaacat aattttatga tttttgaaga tagaaaattt     60
gctgatattg gtaacactgt taaaaatcaa tataaatctg gtgtcttccg tattgccgaa    120
tgggctgaca tcactaatgc acatggtgta acgggtgcag gtattgtttc tggcttgaag    180
gaggcagccc aagaaacaac cagtgaacct agaggtttgc taatgcttgc tgagttatca    240
tcaaagggtt ctttagcata tggtgaatat acagaaaaaa cagtagaaat tgctaaatct    300
gataaagagt ttgtcattgg ttttattgcg caacacgata tgggcggtag agaagaaggt    360
tttgactgga tcattatgac tccaggggtt ggtttagatg acaaaggtga tgcacttggt    420
caacaatata gaactgttga tgaagttgta aagactggaa cggatatcat aattgttggt    480
agaggtttgt acggtcaagg aagagatcct atagagcaag ctaaaagata ccaacaagct    540
ggttggaatg cttatttaaa cagatttaaa tgattcttac acaaagattt gatacatgta    600
cactagttta aataagcatg aaaagaatta cacaagcaaa aaaaaaaaaa taaatgaggt    660
actttacgtt cacctacaac caaaaaaact agatagagta aaatcttaag atttagaaaa    720
agttgtttaa caaaggcttt agtatgtgaa tttttaatgt agcaaagcga taactaataa    780
acataaacaa aagtatggtt ttctttatca gtcaaatcat tatcgattga ttgttccgcg    840
tatctgcaga tagcctcatg aaatcagcca tttgcttttg ttcaacgatc ttttgaaatt    900
gttgttgttc ttggtagtta agttgatcca tcttggctta tgttgtgtgt atgttgtagt    960
tattcttagt atattcctgt cctgagttta gtgaaacata atatcgcctt gaaatgaaaa   1020
tgctgaaatt cgtcgacata caatttttca aacttttttt ttttcttggt gcacggacat   1080
gtttttaaag gaagtactct ataccagtta ttcttcacaa atttaattgc tggagaatag   1140
atcttcaacg cgtttaaaca gcaatttgag gaaggaatag gagaaggaga agcaatttct   1200
aggaaagagc aaggtgtgca acagcatgct ctgaatgata ttttcagcaa tagttcagtt   1260
gaagaacctg ttggcgtatc tacatcactt cctacaaaca acaccacgaa ttgcgtccgt   1320
ggtgacgcaa ctacgaatgg cattgtcaat gccaatgcca gtgcacatac acgtgcaagt   1380
cccaccggtt ccctgcccgg ctatggtaga gacaagaagg acgataccgg catcgacatc   1440
aacagtttca acagcaatgc gtttggcgtc gacgcgtcga tggggctgcc gtatttggat   1500
ttggacgggc tagatttcga tatggatatg gatatggata tggatatgga gatgaatttg   1560
aatttagatt tgggtcttga tttggggttg gaattaaaag gggataacaa tgagggtttt   1620
cctgttgatt taaacaatgg acgtgggagg tgattgattt aacctgatcc aaaaggggta   1680
tgtctatttt ttagagtgtg tctttgtgtc aaattatggt agaatgtgta aagtagtata   1740
aactttcctc tcaaatgacg aggtttaaaa caccccccgg gtgagccgag ccgagaatgg   1800
ggcaattgtt caatgtgaaa tagaagtatc gagtgagaaa cttgggtgtt ggccagccaa   1860
gggggaagga aaatggcgcg aatgctcagg tgagattgtt ttggaattgg gtgaagcgag   1920
gaaatgagcg acccggaggt tgtgacttta gtggcggagg aggaacggga ggaaaaggcc   1980
aagagggaaa gtgtatataa gggggagcaa tttgccaacc aggatagaat tggatgagtt   2040
ataattctac tgtatttatt gtataattta tttctccttt tatatcaaac acattacaaa   2100
acacacaaaa catacaaaca tacacagcta gcaaaggcgc gccatctaat agtttaatca   2160
```

```
cagcttatag tctactatag ttttcttttt taaacattgt tgtattttgt cccccccctc   2220

taattgatga tgattatcct ataagaatcc aataaaacga tggaaactaa taccctctcc   2280

tttgtcatgt ggtctttagt atttcttgaa cattggctct gatttctcga ctttatagtc   2340

ctattaaaat cgctgttagt tctcgatcgt tgtatctcgt ttcttgtctc tttggtggat   2400

gattttgcgt gcgaacatgt ttttttccct ttctctcacc atcatcgtgt agttcttgtc   2460

accatccccc ccaccccttc cttctctcat tgattctata agagcttatc cacagaggtg   2520

cagtaacgag gtagtttaac cttcgagtgg atcaaaatgt cacacaggcc tcgacatttg   2580

ctgcaacggc aacatcaatg tccacgttta cacacctaca tttatatcta tatttatatt   2640

tatatttatt tatttatgct acttagcttc tatagttagt taatgcactc acgatattca   2700

aaattgacac ccttcaacta ctccctacta ttgtctacta ctgtctacta ctcctcttta   2760

ctatagctgc tcccaatagg ctccaccaat aggctctgtc aatacatttt gcgccgccac   2820

ctttcaggtt gtgtcactcc tgaaggacca tattgggtaa tcgtgcaatt tctggaagag   2880

agtccgcgag aagtgaggcc cccactgtaa atcctcgagg gggcatggag tatggggcat   2940

ggaggatgga ggatgggggg gggggggggg aaaataggta gcgaaaggac ccgctatcac   3000

cccacccgga gaactcgttg ccgggaagtc atatttcgac actccgggga gtctataaaa   3060

ggcgggtttt gtcttttgcc agttgatgtt gctgagagga cttgtttgcc gtttcttccg   3120

atttaacagt atagaatcaa ccactgttaa ttatacacgt tatactaaca caacaaaaac   3180

aaaaacaacg acaacaacaa caacatctag ataattaatt aacatctgaa tgtaaaatga   3240

acattaaaat gaattactaa actttacgtc tactttacaa tctataaact ttgtttaatc   3300

atataacgaa atacactaat acacaatcct gtacgtatgt aatactttta tccatcaagg   3360

attgagaaaa aaaagtaatg attccctggg ccattaaaac ttagaccccc aagcttggat   3420

aggtcactct ctattttcgt ttctcccttc cctgatagaa gggtgatatg taattaagaa   3480

taatatataa ttttataata aaagcggccg cacacataca cattatcaaa tgcatttatt   3540

cctaatatca cactaaaacg tattatataa ttttaatctt tatagacttc atagcaccaa   3600

ttggatttgc tttctttcag aataccgcac ttaatctcaa tgtacgtaac gtaggcaaaa   3660

tctgtcgata aggatctgta tgccgtaaac ggaaactcca agcgcccaga aaacttacat   3720

tatattcttg ccagtttcat ctcaccagcc agtcacagtt taaaaggttt gattgcgttt   3780

cttgtttcgt cggattcagt gctaattggt aacgcactgt accgccacac caaagcaaaa   3840

atgcagaaac aaacaacaat gagtgtatgt ttaccaactt tgg                     3883
```

<210> SEQ ID NO 20
<211> LENGTH: 5722
<212> TYPE: DNA
<213> ORGANISM: Artificial
<220> FEATURE:
<223> OTHER INFORMATION: E. coli SthA gene integration fragment

<400> SEQUENCE: 20

```
aactactatg tacactgtat aagtaaaaag acgatacccc cctcccactc tgggtgctac     60

ggtgtagatc tctccgtaaa cacaaaaagg cggctcagat gataattggg gtccgggcgc    120

aaccggaagg ggggagagag gggagcgatg gcttctcctc cggggggcta cgggagtttc    180

ctctttggga aggataaaga ggggatggat tgatacaaga ttctgagaac ctattacgat    240

gatgttcagt ggtattttgt cttttgttat ttaaagggag gggactttcc tcaatacctt    300
```

```
agttgtaaaa ttacgctatt atctttaacc ctttcttttg agcaataatt aaaaagagcg    360
gccgcgagtc catcggttcc tgtcagatgg gatactcttg acgtggaaaa ttcaaacaga    420
aaaaaaaccc caataatgaa aaataacact acgttatatc cgtggtatcc tctatcgtat    480
cgtatcgtag cgtatcgtag cgtaccgtat cacagtatag tctaatattc cgtatcttat    540
tgtatcctat cctattcgat cctattgtat ttcagtgcac cattttaatt tctattgcta    600
taatgtcctt attagttgcc actgtgaggt gaccaatgga cgagggcgag ccgttcagaa    660
gccgcgaagg gtgttcttcc catgaatttc ttaaggaggg cggctcagct ccgagagtga    720
ggcgagacgt ctcggtcagc gtatcccccct tcctcggctt ttacaaatga tgcgctctta    780
atagtgtgtc gttatccttt tggcattgac gggggaggga aattgattga gcgcatccat    840
atttttgcgg actgctgagg acaatggtgg tttttccggg tggcgtgggc tacaaatgat    900
acgatggttt ttttctttc ggagaaggcg tataaaaagg acacggagaa cccatttatt    960
ctaaaaacag ttgagcttct ttaattattt tttgatataa tattctatta ttatatattt   1020
tcttcccaat aaaacaaaat aaaacaaaac acagcaaaac acaaaaagct agcctgaaag   1080
ggaaccataa tgggtaagat cgcaccacat tagcgggctc gaagatggat cttgcgaatg   1140
ggtgacacca gtcataaggc ctcgttgtcc cagcatacct cccgcgctat ctaattgctt   1200
cgctctccat tgttcttggt aaacatcact ctggcttgat ggtgtcatct atgcccgcca   1260
agcctatcgg tctatggccc ggagtttgct ccgtcttcca attgcaatcg cacggaatcc   1320
gggatagaaa gaacgatacg cattcatacg attctcacgt tattggttgg tgaatcaaat   1380
gcacaacgaa cccaatcgcc ctggactcag cgtctaggcc ccccgtatgg ccgacgggga   1440
ctcagagcgt caatccacgt tgaagtcgag gttttggcag ttacagccct tgcaataagg   1500
tttttcggac agtctacttt gtcggcgcgc cttctgtctt tgattttctt atgttattca   1560
aaacatctgc cccaaaatct aacgattata tatattccta cgtataactg tatagctaat   1620
tattgattta tttgtacata aaaaccacat aaatgtaaaa gcaagaaaaa aaataactaa   1680
ggagaaggat caatatctca tttataatgc tcgccaaagc agcgtacgtg aattttaatc   1740
aagacatcaa caaatcttgc aacttggtta tatcgcttct tcacccactc acccgctttt   1800
ctacattgtt gaacacaaat atatacaggg gtatgtctca aggtcaagtg cagtttcaac   1860
agagactacc tcaaggtacc tcttcagaaa tgcagaactt cactcttgat cagattttct   1920
ccgaattaaa ggaggcctat tggtagttct ttcccccctct caagctggcg tgaaatgcaa   1980
ccttacggcg tctacgttac tacaaggtcc agaaagtgta ggtattgcta ctatttttat   2040
tttttattgg ttctggagaa atgcagacag tcaatgaaca caactgtctc aatatgcatc   2100
tatgcacatg cacacacaca cacatcacag gtacccctac aaagagaggt ctcttgataa   2160
tgtttcatta ccacgtggca tccccccccc ccccccccaat aaacaagtgg ccgagttccc   2220
ctgttgcaga ggaggacaaa aaaaccgctg gtgttggtac cattatgcag caactagcac   2280
aacaaacaac cgacccagac atacaaatca acaacacttc gccaaagaca ccctttccag   2340
ggaggatcca ctcccaacgt ctctccataa tgtctctgtt ggcccatgtc tctgtcgttg   2400
acaccgtaac cacaccaacc aacccgtcca ttgtactggg atggtcgtcc atagacacct   2460
ctccaacggg gaacacctca ttcgtaaacc gccaaggtta ccgttcctcc tgactcgccc   2520
cgttgttgat gctgcgcacc tgtggttgcc caacatggtt gtatatcgtg taaccacacc   2580
aacacatgtg cagcacatgt gtttaaaaga gtgtcatgga ggtggatcat gatggaagtg   2640
gactttacca cttgggaact gtctccactc ccgggaagaa aagacccggc gtatcacgcg   2700
```

```
gttgcctcaa tggggcaatt tggaaggaga aatataggga aaatcacgtc gctctcggac   2760
ggggaagagt tccagactat gagggggggg ggtggtatat aaagacagga gatgtccacc   2820
cccagagaga ggaagaagtt ggaactttag aagagagaga taactttccc cagtgtccat   2880
caatacacaa ccaaacacaa actctatatt tacacatata accccctctc tagaatgcca   2940
cattcctacg attacgatgc catagtaata ggttccggcc ccggcggcga aggcgctgca   3000
atgggcctgg ttaagcaagg tgcgcgcgtc gcagttatcg agcgttatca aaatgttggc   3060
ggcggttgca cccactgggg caccatcccg tcgaaagctc tccgtcacgc cgtcagccgc   3120
attatagaat tcaatcaaaa cccactttac agcgaccatt cccgactgct ccgctcttct   3180
tttgccgata tccttaacca tgccgataac gtgattaatc aacaaacgcg catgcgtcag   3240
ggatttacg aacgtaatca ctgtgaaata ttgcagggaa acgctcgctt tgttgacgag   3300
catacgttgg cgctggattg cccggacggc agcgttgaaa cactaaccgc tgaaaaattt   3360
gttattgcct gcggctctcg tccatatcat ccaacagatg ttgatttcac ccatccacgc   3420
atttacgaca gcgactcaat tctcagcatg caccacgaac cgcgccatgt acttatctat   3480
ggtgctggag tgatcggctg tgaatatgcg tcgatcttcc gcggtatgga tgtaaaagtg   3540
gatctgatca acacccgcga tcgcctgctg gcatttctcg atcaagagat gtcagattct   3600
ctctcctatc acttctggaa cagtggcgta gtgattcgtc acaacgaaga gtacgagaag   3660
atcgaaggct gtgacgatgg tgtgatcatg catctgaagt cgggtaaaaa actgaaagct   3720
gactgcctgc tctatgccaa cggtcgcacc ggtaataccg attcgctggc gttacagaac   3780
attgggctag aaactgacag ccgcggacag ctgaaggtca acagcatgta tcagaccgca   3840
cagccacacg tttacgcggt gggcgacgtg attggttatc cgagcctggc gtcggcggcc   3900
tatgaccagg ggcgcattgc cgcgcaggcg ctggtaaaag gcgaagccac cgcacatctg   3960
attgaagata tccctaccgg tatttacacc atcccggaaa tcagctctgt gggcaaaacc   4020
gaacagcagc tgaccgcaat gaaagtgcca tatgaagtgg gccgcgccca gtttaaacat   4080
ctggcacgcg cacaaatcgt cggcatgaac gtgggcacgc tgaaaatttt gttccatcgg   4140
gaaacaaaag agattctggg tattcactgc tttggcgagc gcgctgccga aattattcat   4200
atcggtcagg cgattatgga acagaaaggt ggcggcaaca ctattgagta cttcgtcaac   4260
accaccttta actacccgac gatggcggaa gcctatcggg tagctgcgtt aaacggttta   4320
aaccgcctgt tttaaaactt tatcgaaatg gccatccatt cttgcgcgga tttaattaat   4380
ttattttact agtttatttt tgctcctgag aataggatta caaacactta aagtctttaa   4440
ttacaactat atataatatt ctgttggttt tcttgaattg gttcgctgcg attcatgcct   4500
cccattcacc aaaggtggag tgggaaataa cggttttact gcggtaatta gcagaggcaa   4560
gaacaggata cactttttga tgataaatct gtattatagt cgagcctatt taggaaatca   4620
aattttcttg tgtttacttt tcaaataaat aatgttcgaa aatttttact ttactccttc   4680
atttaactat accagacgtt atatcatcaa caccttctga ccatatacag ctcaagatgt   4740
ttaagagtct gttaaatttt ttcaatccat ttcatggagt accaggaggt gctacaaaag   4800
gaattcatag cctcatgaaa tcagccattt gcttttgttc aacgatcttt tgaaattgtt   4860
gttgttcttg gtagttaagt tgatccatct tggcttatgt tgtgtgtatg ttgtagttat   4920
tcttagtata ttcctgtcct gagtttagtg aaacataaata tcgccttgaa atgaaaatgc   4980
tgaaattcgt cgacatacaa tttttcaaac tttttttttt tcttggtgca cggacatgtt   5040
```

```
tttaaaggaa gtactctata ccagttattc ttcacaaatt taattgctgg agaatagatc   5100

ttcaacgctt taataaagta gtttgtttgt caaggatggc gtcatacaaa gaaagatcag   5160

aatcacacac ttcccctgtt gctaggagac ttttctccat catggaggaa aagaagtcta   5220

acctttgtgc atcattggat attactgaaa ctgaaaagct tctctctatt ttggacacta   5280

ttggtcctta catctgtcta gttaaaacac acatcgatat tgtttctgat tttacgtatg   5340

aaggaactgt gttgcctttg aaggagcttg ccaagaaaca taattttatg atttttgaag   5400

atagaaaatt tgctgatatt ggtaacactg ttaaaaatca atataaatct ggtgtcttcc   5460

gtattgccga atgggctgac atcactaatg cacatggtgt aacgggtgca ggtattgttt   5520

ctggcttgaa ggaggcagcc caagaaacaa ccagtgaacc tagaggtttg ctaatgcttg   5580

ctgagttatc atcaaagggt tctttagcat atggtgaata tacagaaaaa acagtagaaa   5640

ttgctaaatc tgataaagag tttgtcattg gttttattgc gcaacacgat atgggcggta   5700

gagaagaagg ttttgactcc gc                                            5722
```

<210> SEQ ID NO 21
<211> LENGTH: 1401
<212> TYPE: DNA
<213> ORGANISM: Escherichia coli

<400> SEQUENCE: 21

```
atgccacatt cctacgatta cgatgccata gtaataggtt ccggccccgg cggcgaaggc     60

gctgcaatgg gcctggttaa gcaaggtgcg cgcgtcgcag ttatcgagcg ttatcaaaat    120

gttggcggcg gttgcaccca ctggggcacc atcccgtcga aagctctccg tcacgccgtc    180

agccgcatta tagaattcaa tcaaaaccca ctttacagcg accattcccg actgctccgc    240

tcttcttttg ccgatatcct taaccatgcc gataacgtga ttaatcaaca aacgcgcatg    300

cgtcagggat tttacgaacg taatcactgt gaaatattgc agggaaacgc tcgctttgtt    360

gacgagcata cgttggcgct ggattgcccg gacggcagcg ttgaaacact aaccgctgaa    420

aaatttgtta ttgcctgcgg ctctcgtcca tatcatccaa cagatgttga tttcacccat    480

ccacgcattt acgacagcga ctcaattctc agcatgcacc acgaaccgcg ccatgtactt    540

atctatggtg ctggagtgat cggctgtgaa tatgcgtcga tcttccgcgg tatggatgta    600

aaagtggatc tgatcaacac ccgcgatcgc ctgctggcat ttctcgatca agagatgtca    660

gattctctct cctatcactt ctggaacagt ggcgtagtga ttcgtcacaa cgaagagtac    720

gagaagatcg aaggctgtga cgatggtgtg atcatgcatc tgaagtcggg taaaaaactg    780

aaagctgact gcctgctcta tgccaacggt cgcaccggta ataccgattc gctggcgtta    840

cagaacattg ggctagaaac tgacagccgc ggacagctga aggtcaacag catgtatcag    900

accgcacagc cacacgttta cgcggtgggc gacgtgattg gttatccgag cctggcgtcg    960

gcggcctatg accaggggcg cattgccgcg caggcgctgg taaaaggcga agccaccgca   1020

catctgattg aagatatccc taccggtatt tacaccatcc cggaaatcag ctctgtgggc   1080

aaaaccgaac agcagctgac cgcaatgaaa gtgccatatg aagtgggccg cgcccagttt   1140

aaacatctgg cacgcgcaca aatcgtcggc atgaacgtgg gcacgctgaa aattttgttc   1200

catcgggaaa caaaagagat tctgggtatt cactgctttg gcgagcgcgc tgccgaaatt   1260

attcatatcg gtcaggcgat tatggaacag aaaggtggcg gcaacactat tgagtacttc   1320

gtcaacacca cctttaacta cccgacgatg gcggaagcct atcgggtagc tgcgttaaac   1380

ggtttaaacc gcctgtttta a                                             1401
```

<210> SEQ ID NO 22
<211> LENGTH: 5335
<212> TYPE: DNA
<213> ORGANISM: Artificial
<220> FEATURE:
<223> OTHER INFORMATION: RH E. coli integration fragment

<400> SEQUENCE: 22
aattctttga aggagcttgc caagaaacat aattttatga tttttgaaga tagaaaattt 60
gctgatattg gtaacactgt taaaaatcaa tataaatctg gtgtcttccg tattgccgaa 120
tgggctgaca tcactaatgc acatggtgta acgggtgcag gtattgtttc tggcttgaag 180
gaggcagccc aagaaacaac cagtgaacct agaggtttgc taatgcttgc tgagttatca 240
tcaaagggtt ctttagcata tggtgaatat acagaaaaaa cagtagaaat tgctaaatct 300
gataaagagt ttgtcattgg ttttattgcg caacacgata tgggcggtag agaagaaggt 360
tttgactgga tcattatgac tccaggggtt ggtttagatg acaaaggtga tgcacttggt 420
caacaatata gaactgttga tgaagttgta aagactggaa cggatatcat aattgttggt 480
agaggtttgt acggtcaagg aagagatcct atagagcaag ctaaaagata ccaacaagct 540
ggttggaatg cttatttaaa cagatttaaa tgattcttac acaaagattt gatacatgta 600
cactagttta aataagcatg aaaagaatta cacaagcaaa aaaaaaaaaa taaatgaggt 660
actttacgtt cacctacaac caaaaaaact agatagagta aaatcttaag atttagaaaa 720
agttgtttaa caaaggcttt agtatgtgaa tttttaatgt agcaaagcga taactaataa 780
acataaacaa aagtatggtt ttctttatca gtcaaatcat tatcgattga ttgttccgcg 840
tatctgcaga tagcctcatg aaatcagcca tttgcttttg ttcaacgatc ttttgaaatt 900
gttgttgttc ttggtagtta agttgatcca tcttggctta tgttgtgtgt atgttgtagt 960
tattcttagt atattcctgt cctgagttta gtgaaacata atatcgcctt gaaatgaaaa 1020
tgctgaaatt cgtcgacata caatttttca aactttttttt ttttcttggt gcacggacat 1080
gtttttaaag gaagtactct ataccagtta ttcttcacaa atttaattgc tggagaatag 1140
atcttcaacg cgtttaaaca gcaatttgag gaaggaatag gagaaggaga agcaatttct 1200
aggaaagagc aaggtgtgca acagcatgct ctgaatgata ttttcagcaa tagttcagtt 1260
gaagaacctg ttggcgtatc tacatcactt cctacaaaca acaccacgaa ttgcgtccgt 1320
ggtgacgcaa ctacgaatgg cattgtcaat gccaatgcca gtgcacatac acgtgcaagt 1380
cccaccggtt ccctgcccgg ctatggtaga gacaagaagg acgataccgg catcgacatc 1440
aacagtttca acagcaatgc gtttggcgtc gacgcgtcga tggggctgcc gtatttggat 1500
ttggacgggc tagatttcga tatggatatg gatatggata tggatatgga gatgaatttg 1560
aatttagatt tgggtcttga tttggggttg gaattaaaag gggataacaa tgagggtttt 1620
cctgttgatt taaacaatgg acgtgggagg tgattgattt aacctgatcc aaaaggggta 1680
tgtctatttt ttagagtgtg tctttgtgtc aaattatggt agaatgtgta aagtagtata 1740
aactttcctc tcaaatgacg aggtttaaaa caccccccgg gtgagccgag ccgagaatgg 1800
ggcaattgtt caatgtgaaa tagaagtatc gagtgagaaa cttgggtgtt ggccagccaa 1860
gggggaagga aaatggcgcg aatgctcagg tgagattgtt ttggaattgg gtgaagcgag 1920
gaaatgagcg acccggaggt tgtgacttta gtggcggagg aggaacggga ggaaaaggcc 1980
aagagggaaa gtgtatataa gggggagcaa tttgccaacc aggatagaat tggatgagtt 2040

```
ataattctac tgtatttatt gtataattta tttctccttt tatatcaaac acattacaaa   2100
acacacaaaa catacaaaca tacacagcta gcaaaggcgc gccatctaat agtttaatca   2160
cagcttatag tctactatag ttttcttttt taaacattgt tgtattttgt cccccccctc   2220
taattgatga tgattatcct ataagaatcc aataaaacga tggaaactaa taccctctcc   2280
tttgtcatgt ggtctttagt atttcttgaa cattggctct gatttctcga ctttatagtc   2340
ctattaaaat cgctgttagt tctcgatcgt tgtatctcgt ttcttgtctc tttggtggat   2400
gattttgcgt gcgaacatgt ttttttccct ttctctcacc atcatcgtgt agttcttgtc   2460
accatccccc ccaccccttc cttctctcat tgattctata agagcttatc cacagaggtg   2520
cagtaacgag gtagtttaac cttcgagtgg atcaaaatgt cacacaggcc tcgacatttg   2580
ctgcaacggc aacatcaatg tccacgttta cacacctaca tttatatcta tatttatatt   2640
tatatttatt tatttatgct acttagcttc tatagttagt taatgcactc acgatattca   2700
aaattgacac ccttcaacta ctccctacta ttgtctacta ctgtctacta ctcctcttta   2760
ctatagctgc tcccaatagg ctccaccaat aggctctgtc aatacatttt gcgccgccac   2820
ctttcaggtt gtgtcactcc tgaaggacca tattgggtaa tcgtgcaatt tctggaagag   2880
agtccgcgag aagtgaggcc cccactgtaa atcctcgagg gggcatggag tatggggcat   2940
ggaggatgga ggatgggggg gggggggggg aaaataggta gcgaaaggac ccgctatcac   3000
cccacccgga gaactcgttg ccgggaagtc atatttcgac actccgggga gtctataaaa   3060
ggcgggtttt gtcttttgcc agttgatgtt gctgagagga cttgtttgcc gtttcttccg   3120
atttaacagt atagaatcaa ccactgttaa ttatacacgt tatactaaca caacaaaaac   3180
aaaaacaacg acaacaacaa caacatctag aatgccacat tcctacgatt acgatgccat   3240
agtaataggt tccggccccg gcggcgaagg cgctgcaatg ggcctggtta agcaaggtgc   3300
gcgcgtcgca gttatcgagc gttatcaaaa tgttggcggc ggttgcaccc actggggcac   3360
catcccgtcg aaagctctcc gtcacgccgt cagccgcatt atagaattca atcaaaaccc   3420
actttacagc gaccattccc gactgctccg ctcttctttt gccgatatcc ttaaccatgc   3480
cgataacgtg attaatcaac aaacgcgcat gcgtcaggga ttttacgaac gtaatcactg   3540
tgaaatattg cagggaaacg ctcgctttgt tgacgagcat acgttggcgc tggattgccc   3600
ggacggcagc gttgaaacac taaccgctga aaaatttgtt attgcctgcg gctctcgtcc   3660
atatcatcca acagatgttg atttcaccca tccacgcatt tacgacagcg actcaattct   3720
cagcatgcac cacgaaccgc gccatgtact tatctatggt gctggagtga tcggctgtga   3780
atatgcgtcg atcttccgcg gtatggatgt aaaagtggat ctgatcaaca cccgcgatcg   3840
cctgctggca tttctcgatc aagagatgtc agattctctc tcctatcact tctggaacag   3900
tggcgtagtg attcgtcaca acgaagagta cgagaagatc gaaggctgtg acgatggtgt   3960
gatcatgcat ctgaagtcgg gtaaaaaact gaaagctgac tgcctgctct atgccaacgg   4020
tcgcaccggt aataccgatt cgctggcgtt acagaacatt gggctagaaa ctgacagccg   4080
cggacagctg aaggtcaaca gcatgtatca gaccgcacag ccacacgttt acgcggtggg   4140
cgacgtgatt ggttatccga gcctggcgtc ggcggcctat gaccaggggc gcattgccgc   4200
gcaggcgctg gtaaaaggcg aagccaccgc acatctgatt gaagatatcc ctaccggtat   4260
ttacaccatc ccggaaatca gctctgtggg caaaaccgaa cagcagctga ccgcaatgaa   4320
agtgccatat gaagtgggcc gcgcccagtt taaacatctg gcacgcgcac aaatcgtcgg   4380
catgaacgtg ggcacgctga aaattttgtt ccatcgggaa acaaaagaga ttctgggtat   4440
```

```
tcactgcttt ggcgagcgcg ctgccgaaat tattcatatc ggtcaggcga ttatggaaca   4500

gaaaggtggc ggcaacacta ttgagtactt cgtcaacacc acctttaact acccgacgat   4560

ggcggaagcc tatcgggtag ctgcgttaaa cggtttaaac cgcctgtttt aaaactttat   4620

cgaaatggcc atccattctt gcgcggattt aattaacatc tgaatgtaaa atgaacatta   4680

aaatgaatta ctaaacttta cgtctacttt acaatctata aactttgttt aatcatataa   4740

cgaaatacac taatacacaa tcctgtacgt atgtaatact tttatccatc aaggattgag   4800

aaaaaaaagt aatgattccc tggccatta aaacttagac cccaagctt ggataggtca   4860

ctctctattt tcgtttctcc cttccctgat agaagggtga tatgtaatta agaataatat   4920

ataattttat aataaaagcg gccgcacaca tacacattat caaatgcatt tattcctaat   4980

atcacactaa aacgtattat ataattttaa tctttataga cttcatagca ccaattggat   5040

ttgctttctt tcagaatacc gcacttaatc tcaatgtacg taacgtaggc aaaatctgtc   5100

gataaggatc tgtatgccgt aaacggaaac tccaagcgcc cagaaaactt acattatatt   5160

cttgccagtt tcatctcacc agccagtcac agtttaaaag gtttgattgc gtttcttgtt   5220

tcgtcggatt cagtgctaat tggtaacgca ctgtaccgcc acaccaaagc aaaaatgcag   5280

aaacaaacaa caatgagtgt atgtttacca actttggttt tgaaagttaa cccgc        5335
```

```
<210> SEQ ID NO 23
<211> LENGTH: 5642
<212> TYPE: DNA
<213> ORGANISM: Artificial
<220> FEATURE:
<223> OTHER INFORMATION: Codon-optimized E. coli Stha gene integration
      fragment

<400> SEQUENCE: 23

aaccccactc tgggtgctac ggtgtagatc tctccgtaaa cacaaaaagg cggctcagat     60

gataattggg gtccgggcgc aaccggaagg ggggagagag gggagcgatg gcttctcctc    120

cggggggcta cgggagtttc ctctttggga aggataaaga ggggatggat tgatacaaga    180

ttctgagaac ctattacgat gatgttcagt ggtattttgt cttttgttat ttaaagggag    240

gggactttcc tcaatacctt agttgtaaaa ttacgctatt atctttaacc ctttcttttg    300

agcaataatt aaaaagagcg gccgcgagtc catcggttcc tgtcagatgg gatactcttg    360

acgtggaaaa ttcaaacaga aaaaaaaccc caataatgaa aaataacact acgttatatc    420

cgtggtatcc tctatcgtat cgtatcgtag cgtatcgtag cgtaccgtat cacagtatag    480

tctaatattc cgtatcttat tgtatcctat cctattcgat cctattgtat ttcagtgcac    540

cattttaatt tctattgcta taatgtcctt attagttgcc actgtgaggt gaccaatgga    600

cgagggcgag ccgttcagaa gccgcgaagg gtgttcttcc catgaatttc ttaaggaggg    660

cggctcagct ccgagagtga ggcgagacgt ctcggtcagc gtatccccct tcctcggctt    720

ttacaaatga tgcgctctta atagtgtgtc gttatccttt tggcattgac gggggaggga    780

aattgattga gcgcatccat atttttgcgg actgctgagg acaatggtgg tttttccggg    840

tggcgtgggc tacaaatgat acgatggttt ttttcttttc ggagaaggcg tataaaaagg    900

acacggagaa cccatttatt ctaaaaacag ttgagcttct ttaattattt tttgatataa    960

tattctatta ttatatattt tcttcccaat aaaacaaaat aaaacaaaac acagcaaaac   1020

acaaaaagct agcctgaaag ggaaccataa tgggtaagat cgcaccacat tagcgggctc   1080

gaagatggat cttgcgaatg ggtgacacca gtcataaggc ctcgttgtcc cagcatacct   1140
```

```
cccgcgctat ctaattgctt cgctctccat tgttcttggt aaacatcact ctggcttgat   1200
ggtgtcatct atgcccgcca agcctatcgg tctatggccc ggagtttgct ccgtcttcca   1260
attgcaatcg cacggaatcc gggatagaaa gaacgatacg cattcatacg attctcacgt   1320
tattggttgg tgaatcaaat gcacaacgaa cccaatcgcc ctggactcag cgtctaggcc   1380
ccccgtatgg ccgacgggga ctcagagcgt caatccacgt tgaagtcgag gttttggcag   1440
ttacagccct tgcaataagg tttttcggac agtctacttt gtcggcgcgc cttctgtctt   1500
tgattttctt atgttattca aaacatctgc cccaaaatct aacgattata tatattccta   1560
cgtataactg tatagctaat tattgattta tttgtacata aaaaccacat aaatgtaaaa   1620
gcaagaaaaa aaataactaa ggagaaggat caatatctca tttataatgc tcgccaaagc   1680
agcgtacgtg aattttaatc aagacatcaa caaatcttgc aacttggtta tatcgcttct   1740
tcacccactc acccgctttt ctacattgtt gaacacaaat atatacaggg gtatgtctca   1800
aggtcaagtg cagtttcaac agagactacc tcaaggtacc tcttcagaaa tgcagaactt   1860
cactcttgat cagattttct ccgaattaaa ggaggcctat tggtagttct ttccccctct   1920
caagctggcg tgaaatgcaa ccttacggcg tctacgttac tacaaggtcc agaaagtgta   1980
ggtattgcta ctatttttat tttttattgg ttctggagaa atgcagacag tcaatgaaca   2040
caactgtctc aatatgcatc tatgcacatg cacacacaca cacatcacag gtacccctac   2100
aaagagaggt ctcttgataa tgtttcatta ccacgtggca tccccccccc cccccccaat   2160
aaacaagtgg ccgagttccc ctgttgcaga ggaggacaaa aaaaccgctg gtgttggtac   2220
cattatgcag caactagcac aacaaacaac cgacccagac atacaaatca acaacacttc   2280
gccaaagaca ccctttccag ggaggatcca ctcccaacgt ctctccataa tgtctctgtt   2340
ggcccatgtc tctgtcgttg acaccgtaac cacaccaacc aacccgtcca ttgtactggg   2400
atggtcgtcc atagacacct ctccaacggg gaacacctca ttcgtaaacc gccaaggtta   2460
ccgttcctcc tgactcgccc cgttgttgat gctgcgcacc tgtggttgcc caacatggtt   2520
gtatatcgtg taaccacacc aacacatgtg cagcacatgt gtttaaaaga gtgtcatgga   2580
ggtggatcat gatggaagtg gactttacca cttgggaact gtctccactc ccgggaagaa   2640
aagacccggc gtatcacgcg gttgcctcaa tggggcaatt tggaaggaga aatataggga   2700
aaatcacgtc gctctcggac ggggaagagt tccagactat gaggggggggg ggtggtatat   2760
aaagacagga gatgtccacc cccagagaga ggaagaagtt ggaactttag aagagagaga   2820
taactttccc cagtgtccat caatacacaa ccaaacacaa actctatatt tacacatata   2880
accccctctc tagaatgcca cattcctatg actacgatgc cattgtcatt ggttccggtc   2940
caggtggtga aggtgctgca atgggcttag ttaagcaggg tgctagagtt gctgtcatcg   3000
aaagatatca aaatgttggt ggtggttgta ctcactgggg tacaattcca tctaaggcat   3060
tgagacatgc agtttccaga attattgagt ttaaccaaaa ccctttatac tctgatcatt   3120
caagattgtt gagatcatct tttgctgata ttttgaacca tgctgacaac gtcatcaacc   3180
aacaaactcg tatgcgtcaa ggcttctatg agagaaatca ttgtgagatt ttacaaggta   3240
acgctagatt tgtcgatgag catactcttg cattagactg tccagacggt tccgttgaga   3300
ctcttaccgc tgaaaaattc gttattgctt gtggttccag accataccac ccaaccgatg   3360
tcgatttcac tcaccctcgt atctacgatt ccgattctat tttgtctatg catcatgaac   3420
caagacatgt tttgatttat ggtgctggtg ttatcggttg tgaatatgct tctattttca   3480
```

```
gaggtatgga tgttaaggtt gacttgatta atacaagaga cagattatta gctttccttg   3540
atcaggaaat gtctgattcc ctttcctacc atttttggaa ctccggtgtc gtcatcagac   3600
acaacgagga atatgaaaag attgaaggtt gtgatgacgg cgttattatg caccttaagt   3660
ctggtaaaaa gttaaaagca gattgcttgt tatatgcaaa tggtagaacc ggtaacacag   3720
actccttggc tttacaaaac attggtttag aaaccgattc aagaggtcaa ttaaaggtca   3780
attcaatgta tcaaactgca caaccacacg tttacgcagt tggtgacgtt attggttacc   3840
cttcattggc atctgccgct tacgatcaag gtagaatcgc cgctcaagca cttgttaagg   3900
gtgaagcaac tgcacactta atcgaagata tccctaccgg tatctacact atcccagaaa   3960
tctcttctgt tggcaagact gaacaacaat taaccgcaat gaaggttcca tacgaagtcg   4020
gtcgtgccca gttcaagcat ttggctagag cacaaattgt tggtatgaat gttggtactt   4080
tgaaaatctt gtttcacaga gaaacaaagg aaatcttggg cattcactgt ttcggcgaaa   4140
gagctgcaga gattattcac atcggtcaag ccattatgga acaaaaaggc ggtggtaata   4200
ccattgaata tttcgttaat accaccttca actacccaac aatggccgaa gcatatagag   4260
tcgctgcttt aaacggttta aacagattgt tttaattaat ttattttact agtttatttt   4320
tgctcctgag aataggatta caaacactta aagtctttaa ttacaactat atataatatt   4380
ctgttggttt tcttgaattg gttcgctgcg attcatgcct cccattcacc aaaggtggag   4440
tgggaaataa cggttttact gcggtaatta gcagaggcaa gaacaggata cactttttga   4500
tgataaatct gtattatagt cgagcctatt taggaaatca aattttcttg tgtttacttt   4560
tcaaataaat aatgttcgaa aatttttact ttactccttc atttaactat accagacgtt   4620
atatcatcaa caccttctga ccatatacag ctcaagatgt ttaagagtct gttaaatttt   4680
ttcaatccat ttcatggagt accaggaggt gctacaaaag gaattcatag cctcatgaaa   4740
tcagccattt gcttttgttc aacgatcttt tgaaattgtt gttgttcttg gtagttaagt   4800
tgatccatct tggcttatgt tgtgtgtatg ttgtagttat tcttagtata ttcctgtcct   4860
gagtttagtg aaacataata tcgccttgaa atgaaaatgc tgaaattcgt cgacatacaa   4920
tttttcaaac tttttttttt tcttggtgca cggacatgtt tttaaaggaa gtactctata   4980
ccagttattc ttcacaaatt taattgctgg agaatagatc ttcaacgctt taataaagta   5040
gtttgtttgt caaggatggc gtcatacaaa gaaagatcag aatcacacac ttcccctgtt   5100
gctaggagac ttttctccat catggaggaa aagaagtcta acctttgtgc atcattggat   5160
attactgaaa ctgaaaagct tctctctatt ttggacacta ttggtcctta catctgtcta   5220
gttaaaacac acatcgatat tgtttctgat tttacgtatg aaggaactgt gttgcctttg   5280
aaggagcttg ccaagaaaca taattttatg atttttgaag atagaaaatt tgctgatatt   5340
ggtaacactg ttaaaaatca atataaatct ggtgtcttcc gtattgccga atgggctgac   5400
atcactaatg cacatggtgt aacgggtgca ggtattgttt ctggcttgaa ggaggcagcc   5460
caagaaacaa ccagtgaacc tagaggtttg ctaatgcttg ctgagttatc atcaaagggt   5520
tctttagcat atggtgaata tacagaaaaa acagtagaaa ttgctaaatc tgataaagag   5580
tttgtcattg gttttattgc gcaacacgat atgggcggta gagaagaagg ttttgactcc   5640
gc                                                                  5642
```

<210> SEQ ID NO 24
<211> LENGTH: 1401
<212> TYPE: DNA
<213> ORGANISM: Artificial
<220> FEATURE:
<223> OTHER INFORMATION: Codon optimized E. coli SthA gene

<400> SEQUENCE: 24

```
atgccacatt cctatgacta cgatgccatt gtcattggtt ccggtccagg tggtgaaggt     60

gctgcaatgg gcttagttaa gcagggtgct agagttgctg tcatcgaaag atatcaaaat    120

gttggtggtg gttgtactca ctggggtaca attccatcta aggcattgag acatgcagtt    180

tccagaatta ttgagtttaa ccaaaaccct ttatactctg atcattcaag attgttgaga    240

tcatcttttg ctgatatttt gaaccatgct gacaacgtca tcaaccaaca aactcgtatg    300

cgtcaaggct tctatgagag aaatcattgt gagattttac aaggtaacgc tagatttgtc    360

gatgagcata ctcttgcatt agactgtcca gacggttccg ttgagactct taccgctgaa    420

aaattcgtta ttgcttgtgg ttccagacca taccacccaa ccgatgtcga tttcactcac    480

cctcgtatct acgattccga ttctattttg tctatgcatc atgaaccaag acatgttttg    540

atttatggtg ctggtgttat cggttgtgaa tatgcttcta ttttcagagg tatggatgtt    600

aaggttgact tgattaatac aagagacaga ttattagctt tccttgatca ggaaatgtct    660

gattcccttt cctaccattt ttggaactcc ggtgtcgtca tcagacacaa cgaggaatat    720

gaaaagattg aaggttgtga tgacggcgtt attatgcacc ttaagtctgg taaaaagtta    780

aaagcagatt gcttgttata tgcaaatggt agaaccggta acacagactc cttggcttta    840

caaaacattg gtttagaaac cgattcaaga ggtcaattaa aggtcaattc aatgtatcaa    900

actgcacaac cacacgttta cgcagttggt gacgttattg gttacccttc attggcatct    960

gccgcttacg atcaaggtag aatcgccgct caagcacttg ttaagggtga agcaactgca   1020

cacttaatcg aagatatccc taccggtatc tacactatcc cagaaatctc ttctgttggc   1080

aagactgaac aacaattaac cgcaatgaag gttccatacg aagtcggtcg tgcccagttc   1140

aagcatttgg ctagagcaca aattgttggt atgaatgttg gtactttgaa aatcttgttt   1200

cacagagaaa caaaggaaat cttgggcatt cactgtttcg gcgaaagagc tgcagagatt   1260

attcacatcg gtcaagccat tatggaacaa aaaggcggtg gtaataccat tgaatatttc   1320

gttaatacca ccttcaacta cccaacaatg gccgaagcat atagagtcgc tgctttaaac   1380

ggtttaaaca gattgtttta a                                             1401
```

<210> SEQ ID NO 25
<211> LENGTH: 5304
<212> TYPE: DNA
<213> ORGANISM: Artificial
<220> FEATURE:
<223> OTHER INFORMATION: Codon-optimized E. coli SthA gene integration fragment

<400> SEQUENCE: 25

```
aattctttga aggagcttgc caagaaacat aattttatga tttttgaaga tagaaaattt     60

gctgatattg gtaacactgt taaaaatcaa tataaatctg gtgtcttccg tattgccgaa    120

tgggctgaca tcactaatgc acatggtgta acgggtgcag gtattgtttc tggcttgaag    180

gaggcagccc aagaaacaac cagtgaacct agaggtttgc taatgcttgc tgagttatca    240

tcaaagggtt ctttagcata tggtgaatat acagaaaaaa cagtagaaat tgctaaatct    300

gataaagagt ttgtcattgg ttttattgcg caacacgata tgggcggtag agaagaaggt    360

tttgactgga tcattatgac tccaggggtt ggtttagatg acaaaggtga tgcacttggt    420

caacaatata gaactgttga tgaagttgta aagactggaa cggatatcat aattgttggt    480
```

```
agaggtttgt acggtcaagg aagagatcct atagagcaag ctaaaagata ccaacaagct    540
ggttggaatg cttatttaaa cagatttaaa tgattcttac acaaagattt gatacatgta    600
cactagttta aataagcatg aaaagaatta cacaagcaaa aaaaaaaaaa taaatgaggt    660
actttacgtt cacctacaac caaaaaaact agatagagta aaatcttaag atttagaaaa    720
agttgtttaa caaaggcttt agtatgtgaa tttttaatgt agcaaagcga taactaataa    780
acataaacaa aagtatggtt ttctttatca gtcaaatcat tatcgattga ttgttccgcg    840
tatctgcaga tagcctcatg aaatcagcca tttgcttttg ttcaacgatc ttttgaaatt    900
gttgttgttc ttggtagtta agttgatcca tcttggctta tgttgtgtgt atgttgtagt    960
tattcttagt atattcctgt cctgagttta gtgaaacata atatcgcctt gaaatgaaaa   1020
tgctgaaatt cgtcgacata caatttttca aacttttttt ttttcttggt gcacggacat   1080
gtttttaaag gaagtactct ataccagtta ttcttcacaa atttaattgc tggagaatag   1140
atcttcaacg cgtttaaaca gcaatttgag gaaggaatag gagaaggaga agcaatttct   1200
aggaaagagc aaggtgtgca acagcatgct ctgaatgata ttttcagcaa tagttcagtt   1260
gaagaacctg ttggcgtatc tacatcactt cctacaaaca acaccacgaa ttgcgtccgt   1320
ggtgacgcaa ctacgaatgg cattgtcaat gccaatgcca gtgcacatac acgtgcaagt   1380
cccaccggtt ccctgcccgg ctatggtaga gacaagaagg acgataccgg catcgacatc   1440
aacagtttca acagcaatgc gtttggcgtc gacgcgtcga tggggctgcc gtatttggat   1500
ttggacgggc tagatttcga tatggatatg gatatggata tggatatgga gatgaatttg   1560
aatttagatt tgggtcttga tttggggttg gaattaaaag gggataacaa tgagggtttt   1620
cctgttgatt taaacaatgg acgtgggagg tgattgattt aacctgatcc aaaaggggta   1680
tgtctatttt ttagagtgtg tctttgtgtc aaattatggt agaatgtgta aagtagtata   1740
aactttcctc tcaaatgacg aggtttaaaa caccccccgg gtgagccgag ccgagaatgg   1800
ggcaattgtt caatgtgaaa tagaagtatc gagtgagaaa cttgggtgtt ggccagccaa   1860
gggggaagga aaatggcgcg aatgctcagg tgagattgtt ttggaattgg gtgaagcgag   1920
gaaatgagcg acccggaggt tgtgacttta gtggcggagg aggaacggga ggaaaaggcc   1980
aagagggaaa gtgtatataa gggggagcaa tttgccaacc aggatagaat tggatgagtt   2040
ataattctac tgtatttatt gtataattta tttctccttt tatatcaaac acattacaaa   2100
acacacaaaa catacaaaca tacacagcta gcaaaggcgc gccatctaat agtttaatca   2160
cagcttatag tctactatag ttttcttttt taaacattgt tgtattttgt cccccccctc   2220
taattgatga tgattatcct ataagaatcc aataaaacga tggaaactaa taccctctcc   2280
tttgtcatgt ggtctttagt atttcttgaa cattggctct gatttctcga ctttatagtc   2340
ctattaaaat cgctgttagt tctcgatcgt tgtatctcgt ttcttgtctc tttggtggat   2400
gattttgcgt gcgaacatgt ttttttccct ttctctcacc atcatcgtgt agttcttgtc   2460
accatccccc ccaccccttc cttctctcat tgattctata agagcttatc cacagaggtg   2520
cagtaacgag gtagtttaac cttcgagtgg atcaaaatgt cacacaggcc tcgacatttg   2580
ctgcaacggc aacatcaatg tccacgttta cacacctaca tttatatcta tatttatatt   2640
tatatttatt tatttatgct acttagcttc tatagttagt taatgcactc acgatattca   2700
aaattgacac ccttcaacta ctccctacta ttgtctacta ctgtctacta ctcctcttta   2760
ctatagctgc tcccaatagg ctccaccaat aggctctgtc aatacatttt gcgccgccac   2820
```

```
ctttcaggtt gtgtcactcc tgaaggacca tattgggtaa tcgtgcaatt tctggaagag   2880
agtccgcgag aagtgaggcc cccactgtaa atcctcgagg gggcatggag tatggggcat   2940
ggaggatgga ggatgggggg gggggggggg aaaataggta gcgaaaggac ccgctatcac   3000
cccacccgga gaactcgttg ccgggaagtc atatttcgac actccgggga gtctataaaa   3060
ggcgggtttt gtcttttgcc agttgatgtt gctgagagga cttgtttgcc gtttcttccg   3120
atttaacagt atagaatcaa ccactgttaa ttatacacgt tatactaaca caacaaaaac   3180
aaaaacaacg acaacaacaa caacatctag aatgccacat tcctatgact acgatgccat   3240
tgtcattggt tccggtccag gtggtgaagg tgctgcaatg ggcttagtta agcagggtgc   3300
tagagttgct gtcatcgaaa gatatcaaaa tgttggtggt ggttgtactc actggggtac   3360
aattccatct aaggcattga gacatgcagt ttccagaatt attgagttta accaaaaccc   3420
tttatactct gatcattcaa gattgttgag atcatctttt gctgatattt tgaaccatgc   3480
tgacaacgtc atcaaccaac aaactcgtat gcgtcaaggc ttctatgaga gaaatcattg   3540
tgagatttta caaggtaacg ctagatttgt cgatgagcat actcttgcat tagactgtcc   3600
agacggttcc gttgagactc ttaccgctga aaaattcgtt attgcttgtg gttccagacc   3660
ataccaccca accgatgtcg atttcactca ccctcgtatc tacgattccg attctatttt   3720
gtctatgcat catgaaccaa gacatgtttt gatttatggt gctggtgtta tcggttgtga   3780
atatgcttct attttcagag gtatggatgt taaggttgac ttgattaata caagagacag   3840
attattagct ttccttgatc aggaaatgtc tgattccctt tcctaccatt tttggaactc   3900
cggtgtcgtc atcagacaca acgaggaata tgaaaagatt gaaggttgtg atgacggcgt   3960
tattatgcac cttaagtctg gtaaaaagtt aaaagcagat tgcttgttat atgcaaatgg   4020
tagaaccggt aacacagact ccttggcttt acaaaacatt ggtttagaaa ccgattcaag   4080
aggtcaatta aaggtcaatt caatgtatca aactgcacaa ccacacgttt acgcagttgg   4140
tgacgttatt ggttaccctt cattggcatc tgccgcttac gatcaaggta gaatcgccgc   4200
tcaagcactt gttaagggtg aagcaactgc acacttaatc gaagatatcc ctaccggtat   4260
ctacactatc ccagaaatct cttctgttgg caagactgaa caacaattaa ccgcaatgaa   4320
ggttccatac gaagtcggtc gtgcccagtt caagcatttg gctagagcac aaattgttgg   4380
tatgaatgtt ggtactttga aaatcttgtt tcacagagaa acaaaggaaa tcttgggcat   4440
tcactgtttc ggcgaaagag ctgcagagat tattcacatc ggtcaagcca ttatggaaca   4500
aaaaggcggt ggtaatacca ttgaatattt cgttaatacc accttcaact acccaacaat   4560
ggccgaagca tatagagtcg ctgctttaaa cggtttaaac agattgtttt aattaacatc   4620
tgaatgtaaa atgaacatta aaatgaatta ctaaacttta cgtctacttt acaatctata   4680
aactttgttt aatcatataa cgaaatacac taatacacaa tcctgtacgt atgtaatact   4740
tttatccatc aaggattgag aaaaaaaagt aatgattccc tgggccatta aaacttagac   4800
ccccaagctt ggataggtca ctctctattt tcgtttctcc cttccctgat agaagggtga   4860
tatgtaatta agaataatat ataattttat aataaaagcg gccgccaagt tagttagagc   4920
tagagttaac acatacacat tatcaaatgc atttattcct aatatcacac taaaacgtat   4980
tatataattt taatctttat agacttcata gcaccaattg gatttgcttt ctttcagaat   5040
accgcactta atctcaatgt acgtaacgta ggcaaaatct gtcgataagg atctgtatgc   5100
cgtaaacgga aactccaagc gcccagaaaa cttacattat attcttgcca gtttcatctc   5160
accagccagt cacagtttaa aaggtttgat tgcgtttctt gtttcgtcgg attcagtgct   5220
```

aattggtaac gcactgtacc gccacaccaa agcaaaaatg cagaaacaaa caacaatgag 5280
tgtatgttta ccaactttgg ccgc 5304

<210> SEQ ID NO 26
<211> LENGTH: 5676
<212> TYPE: DNA
<213> ORGANISM: Artificial
<220> FEATURE:
<223> OTHER INFORMATION: A. vinelandii Stha gene integration fragment

<400> SEQUENCE: 26
aactactatg tacactgtat aagtaaaaag acgatacccc cctcccactc tgggtgctac 60
ggtgtagatc tctccgtaaa cacaaaaagg cggctcagat gataattggg gtccgggcgc 120
aaccggaagg ggggagagag gggagcgatg gcttctcctc cggggggcta cgggagtttc 180
ctctttggga aggataaaga ggggatggat tgatacaaga ttctgagaac ctattacgat 240
gatgttcagt ggtattttgt cttttgttat ttaaagggag gggactttcc tcaatacctt 300
agttgtaaaa ttacgctatt atctttaacc ctttcttttg agcaataatt aaaaagagcg 360
gccgcgagtc catcggttcc tgtcagatgg gatactcttg acgtggaaaa ttcaaacaga 420
aaaaaaaccc caataatgaa aaataacact acgttatatc cgtggtatcc tctatcgtat 480
cgtatcgtag cgtatcgtag cgtaccgtat cacagtatag tctaatattc cgtatcttat 540
tgtatcctat cctattcgat cctattgtat ttcagtgcac cattttaatt tctattgcta 600
taatgtcctt attagttgcc actgtgaggt gaccaatgga cgagggcgag ccgttcagaa 660
gccgcgaagg gtgttcttcc catgaatttc ttaaggaggg cggctcagct ccgagagtga 720
ggcgagacgt ctcggtcagc gtatccccct tcctcggctt ttacaaatga tgcgctctta 780
atagtgtgtc gttatccttt tggcattgac gggggaggga aattgattga gcgcatccat 840
atttttgcgg actgctgagg acaatggtgg tttttccggg tggcgtgggc tacaaatgat 900
acgatggttt ttttcttttc ggagaaggcg tataaaaagg acacggagaa cccatttatt 960
ctaaaaacag ttgagcttct ttaattattt tttgatataa tattctatta ttatatattt 1020
tcttcccaat aaaacaaaat aaaacaaaac acagcaaaac acaaaaagct agcctgaaag 1080
ggaaccataa tgggtaagat cgcaccacat tagcgggctc gaagatggat cttgcgaatg 1140
ggtgacacca gtcataaggc ctcgttgtcc cagcatacct cccgcgctat ctaattgctt 1200
cgctctccat tgttcttggt aaacatcact ctggcttgat ggtgtcatct atgcccgcca 1260
agcctatcgg tctatggccc ggagtttgct ccgtcttcca attgcaatcg cacggaatcc 1320
gggatagaaa gaacgatacg cattcatacg attctcacgt tattggttgg tgaatcaaat 1380
gcacaacgaa cccaatcgcc ctggactcag cgtctaggcc ccccgtatgg ccgacgggga 1440
ctcagagcgt caatccacgt tgaagtcgag gttttggcag ttacagccct tgcaataagg 1500
tttttcggac agtctacttt gtcggcgcgc cttctgtctt tgattttctt atgttattca 1560
aaacatctgc cccaaaatct aacgattata tatattccta cgtataactg tatagctaat 1620
tattgattta tttgtacata aaaaccacat aaatgtaaaa gcaagaaaaa aaataactaa 1680
ggagaaggat caatatctca tttataatgc tcgccaaagc agcgtacgtg aattttaatc 1740
aagacatcaa caaatcttgc aacttggtta tatcgcttct tcacccactc acccgctttt 1800
ctacattgtt gaacacaaat atatacaggg gtatgtctca aggtcaagtg cagtttcaac 1860
agagactacc tcaaggtacc tcttcagaaa tgcagaactt cactcttgat cagattttct 1920

```
ccgaattaaa ggaggcctat tggtagttct ttccccctct caagctggcg tgaaatgcaa   1980
ccttacggcg tctacgttac tacaaggtcc agaaagtgta ggtattgcta ctatttttat   2040
tttttattgg ttctggagaa atgcagacag tcaatgaaca caactgtctc aatatgcatc   2100
tatgcacatg cacacacaca cacatcacag gtacccctac aaagagaggt ctcttgataa   2160
tgtttcatta ccacgtggca tccccccccc cccccccaat aaacaagtgg ccgagttccc   2220
ctgttgcaga ggaggacaaa aaaaccgctg gtgttggtac cattatgcag caactagcac   2280
aacaaacaac cgacccagac atacaaatca acaacacttc gccaaagaca ccctttccag   2340
ggaggatcca ctcccaacgt ctctccataa tgtctctgtt ggcccatgtc tctgtcgttg   2400
acaccgtaac cacaccaacc aacccgtcca ttgtactggg atggtcgtcc atagacacct   2460
ctccaacggg gaacacctca ttcgtaaacc gccaaggtta ccgttcctcc tgactcgccc   2520
cgttgttgat gctgcgcacc tgtggttgcc caacatggtt gtatatcgtg taaccacacc   2580
aacacatgtg cagcacatgt gtttaaaaga gtgtcatgga ggtggatcat gatggaagtg   2640
gactttacca cttgggaact gtctccactc ccgggaagaa aagacccggc gtatcacgcg   2700
gttgcctcaa tggggcaatt tggaaggaga aatataggga aaatcacgtc gctctcggac   2760
ggggaagagt tccagactat gaggggggggg ggtggtatat aaagacagga gatgtccacc   2820
cccagagaga ggaagaagtt ggaactttag aagagagaga taactttccc cagtgtccat   2880
caatacacaa ccaaacacaa actctatatt tacacatata acccccctctc tagaatggca   2940
gtctataact atgatgttgt tgtcattggt actggtccag ctggtgaagg tgctgctatg   3000
aatgctgtca aagctggcag aaaggttgct gtcgttgacg acagacctca agtcggtggt   3060
aactgtactc atcttggtac tatcccatcc aaggcattaa gacattcagt tagacagatc   3120
atgcagtata acaacaaccc attattcaga caaattggtg aacctagatg gttttctttc   3180
gcagacgttc ttaagtccgc tgaacaagtt atcgcaaagc aagtctcttc aagaaccggc   3240
tattacgcaa gaaatcgtat tgatactttc tttggcaccg cctcattctg tgatgaacat   3300
actatcgaag ttgtccactt gaatggtatg gttgaaacct tagttgctaa gcaattcgtt   3360
attgcaacag gttcaagacc atacagacca gctgacgtcg actttaccca cccaagaatc   3420
tacgattccg ataccattct ttccttgggt catacaccaa gacgtttgat tatctacggt   3480
gccggtgtca ttggctgtga gtacgcttca attttctccg gtttaggtgt tttagttgat   3540
ttgattgaca acagagatca gttgttgtcc tttttggatg atgaaatttc tgattctttg   3600
tcctatcact taagaaataa caacgttttg attagacaca acgaagaata cgaaagagtt   3660
gaaggtcttg ataatggtgt tatcttacac ttaaagtctg gtaaaaagat taaggcagat   3720
gcatttttgt ggtctaacgg tagaactggt aacactgata agttaggttt ggaaaacatt   3780
ggtttgaagg ctaatggcag aggtcaaatt caagttgatg agcattatcg tacagaagtc   3840
tccaatatct acgcagccgg tgacgtcatc ggttggccat ccttagcttc agcagcttat   3900
gatcaaggta gatctgctgc tggttctatt accgagaatg actcttggcg tttcgttgat   3960
gatgttccta ccggtatcta caccatccct gaaatttcct ctgttggtaa aaccgaaaga   4020
gagttgacac aagcaaaagt cccatacgag gttggtaaag ccttttttcaa gggcatggct   4080
cgtgcacaaa ttgcagttga aaaagccggt atgttaaaga ttctttttca tagagagact   4140
ttagaaatct tgggtgtcca ctgcttcggt taccaagcat ctgaaattgt tcatattggt   4200
caagcaatta tgaaccaaaa gggcgaagca aatacattaa agtatttcat caacactaca   4260
ttcaattatc caactatggc tgaagcttat agagttgcag cctacgacgg tttaaacaga   4320
```

```
ttgttttaat taatttattt tactagttta tttttgctcc tgagaatagg attacaaaca   4380
cttaaagtct ttaattacaa ctatatataa tattctgttg gttttcttga attggttcgc   4440
tgcgattcat gcctcccatt caccaaaggt ggagtgggaa ataacggttt tactgcggta   4500
attagcagag gcaagaacag gatacacttt ttgatgataa atctgtatta tagtcgagcc   4560
tatttaggaa atcaaatttt cttgtgttta cttttcaaat aaataatgtt cgaaaatttt   4620
tactttactc cttcatttaa ctataccaga cgttatatca tcaacacctt ctgaccatat   4680
acagctcaag atgtttaaga gtctgttaaa ttttttcaat ccatttcatg gagtaccagg   4740
aggtgctaca aaaggaattc atagcctcat gaaatcagcc atttgctttt gttcaacgat   4800
cttttgaaat tgttgttgtt cttggtagtt aagttgatcc atcttggctt atgttgtgtg   4860
tatgttgtag ttattcttag tatattcctg tcctgagttt agtgaaacat aatatcgcct   4920
tgaaatgaaa atgctgaaat tcgtcgacat acaatttttc aaactttttt tttttcttgg   4980
tgcacggaca tgtttttaaa ggaagtactc tataccagtt attcttcaca aatttaattg   5040
ctggagaata gatcttcaac gctttaataa agtagtttgt ttgtcaagga tggcgtcata   5100
caaagaaaga tcagaatcac acacttcccc tgttgctagg agacttttct ccatcatgga   5160
ggaaaagaag tctaaccttt gtgcatcatt ggatattact gaaactgaaa agcttctctc   5220
tattttggac actattggtc cttacatctg tctagttaaa acacacatcg atattgtttc   5280
tgattttacg tatgaaggaa ctgtgttgcc tttgaaggag cttgccaaga aacataattt   5340
tatgattttt gaagatagaa aatttgctga tattggtaac actgttaaaa atcaatataa   5400
atctggtgtc ttccgtattg ccgaatgggc tgacatcact aatgcacatg gtgtaacggg   5460
tgcaggtatt gtttctggct tgaaggaggc agcccaagaa acaaccagtg aacctagagg   5520
tttgctaatg cttgctgagt tatcatcaaa gggttcttta gcatatggtg aatatacaga   5580
aaaaacagta gaaattgcta aatctgataa agagtttgtc attggtttta ttgcgcaaca   5640
cgatatgggc ggtagagaag aaggttttga ctccgc                             5676
```

```
<210> SEQ ID NO 27
<211> LENGTH: 1395
<212> TYPE: DNA
<213> ORGANISM: Azotobacter vinelandii

<400> SEQUENCE: 27

atggcagtct ataactatga tgttgttgtc attggtactg gtccagctgg tgaaggtgct     60
gctatgaatg ctgtcaaagc tggcagaaag gttgctgtcg ttgacgacag acctcaagtc    120
ggtggtaact gtactcatct tggtactatc ccatccaagg cattaagaca ttcagttaga    180
cagatcatgc agtataacaa caacccatta ttcagacaaa ttggtgaacc tagatggttt    240
tctttcgcag acgttcttaa gtccgctgaa caagttatcg caaagcaagt ctcttcaaga    300
accggctatt acgcaagaaa tcgtattgat actttctttg gcaccgcctc attctgtgat    360
gaacatacta tcgaagttgt ccacttgaat ggtatggttg aaaccttagt tgctaagcaa    420
ttcgttattg caacaggttc aagaccatac agaccagctg acgtcgactt tacccaccca    480
agaatctacg attccgatac cattctttcc ttgggtcata caccaagacg tttgattatc    540
tacggtgccg gtgtcattgg ctgtgagtac gcttcaattt tctccggttt aggtgtttta    600
gttgatttga ttgacaacag agatcagttg ttgtcctttt tggatgatga aatttctgat    660
tctttgtcct atcacttaag aaataacaac gttttgatta gacacaacga agaatacgaa    720
```

```
agagttgaag gtcttgataa tggtgttatc ttacacttaa agtctggtaa aaagattaag    780
gcagatgcat ttttgtggtc taacggtaga actggtaaca ctgataagtt aggtttggaa    840
aacattggtt tgaaggctaa tggcagaggt caaattcaag ttgatgagca ttatcgtaca    900
gaagtctcca atatctacgc agccggtgac gtcatcggtt ggccatcctt agcttcagca    960
gcttatgatc aaggtagatc tgctgctggt tctattaccg agaatgactc ttggcgtttc   1020
gttgatgatg ttcctaccgg tatctacacc atccctgaaa tttcctctgt tggtaaaacc   1080
gaaagagagt tgacacaagc aaaagtccca tacgaggttg gtaaagcctt tttcaagggc   1140
atggctcgtg cacaaattgc agttgaaaaa gccggtatgt taaagattct tttcatagaa   1200
gagactttag aaatcttggg tgtccactgc ttcggttacc aagcatctga aattgttcat   1260
attggtcaag caattatgaa ccaaaagggc gaagcaaata cattaaagta tttcatcaac   1320
actacattca attatccaac tatggctgaa gcttatagag ttgcagccta cgacggttta   1380
aacagattgt tttaa                                                    1395
```

<210> SEQ ID NO 28
<211> LENGTH: 5298
<212> TYPE: DNA
<213> ORGANISM: Artificial
<220> FEATURE:
<223> OTHER INFORMATION: A. vinelandii SthA gene integration fragment

<400> SEQUENCE: 28

```
aattctttga aggagcttgc caagaaacat aattttatga tttttgaaga tagaaaattt     60
gctgatattg gtaacactgt taaaaatcaa tataaatctg gtgtcttccg tattgccgaa    120
tgggctgaca tcactaatgc acatggtgta acgggtgcag gtattgtttc tggcttgaag    180
gaggcagccc aagaaacaac cagtgaacct agaggtttgc taatgcttgc tgagttatca    240
tcaaagggtt ctttagcata tggtgaatat acagaaaaaa cagtagaaat tgctaaatct    300
gataaagagt ttgtcattgg ttttattgcg caacacgata tgggcggtag agaagaaggt    360
tttgactgga tcattatgac tccaggggtt ggtttagatg acaaaggtga tgcacttggt    420
caacaatata gaactgttga tgaagttgta aagactggaa cggatatcat aattgttggt    480
agaggtttgt acggtcaagg aagagatcct atagagcaag ctaaaagata ccaacaagct    540
ggttggaatg cttatttaaa cagatttaaa tgattcttac acaaagattt gatacatgta    600
cactagttta aataagcatg aaaagaatta cacaagcaaa aaaaaaaaaa taaatgaggt    660
actttacgtt cacctacaac caaaaaaact agatagagta aaatcttaag atttagaaaa    720
agttgtttaa caaaggcttt agtatgtgaa tttttaatgt agcaaagcga taactaataa    780
acataaacaa aagtatggtt ttctttatca gtcaaatcat tatcgattga ttgttccgcg    840
tatctgcaga tagcctcatg aaatcagcca tttgcttttg ttcaacgatc ttttgaaatt    900
gttgttgttc ttggtagtta agttgatcca tcttggctta tgttgtgtgt atgttgtagt    960
tattcttagt atattcctgt cctgagttta gtgaaacata atatcgcctt gaaatgaaaa   1020
tgctgaaatt cgtcgacata caatttttca aacttttttt ttttcttggt gcacggacat   1080
gtttttaaag gaagtactct ataccagtta ttcttcacaa atttaattgc tggagaatag   1140
atcttcaacg cgtttaaaca gcaatttgag gaaggaatag gagaaggaga agcaatttct   1200
aggaaagagc aaggtgtgca acagcatgct ctgaatgata ttttcagcaa tagttcagtt   1260
gaagaacctg ttggcgtatc tacatcactt cctacaaaca acaccacgaa ttgcgtccgt   1320
ggtgacgcaa ctacgaatgg cattgtcaat gccaatgcca gtgcacatac acgtgcaagt   1380
```

```
cccaccggtt ccctgcccgg ctatggtaga gacaagaagg acgataccgg catcgacatc   1440

aacagtttca acagcaatgc gtttggcgtc gacgcgtcga tggggctgcc gtatttggat   1500

ttggacgggc tagatttcga tatggatatg gatatggata tggatatgga gatgaatttg   1560

aatttagatt tgggtcttga tttggggttg gaattaaaag gggataacaa tgagggtttt   1620

cctgttgatt taaacaatgg acgtgggagg tgattgattt aacctgatcc aaaaggggta   1680

tgtctatttt ttagagtgtg tctttgtgtc aaattatggt agaatgtgta aagtagtata   1740

aactttcctc tcaaatgacg aggtttaaaa caccccccgg gtgagccgag ccgagaatgg   1800

ggcaattgtt caatgtgaaa tagaagtatc gagtgagaaa cttgggtgtt ggccagccaa   1860

gggggaagga aaatggcgcg aatgctcagg tgagattgtt ttggaattgg gtgaagcgag   1920

gaaatgagcg acccggaggt tgtgacttta gtggcggagg aggaacggga ggaaaaggcc   1980

aagagggaaa gtgtatataa gggggagcaa tttgccaacc aggatagaat tggatgagtt   2040

ataattctac tgtatttatt gtataattta tttctccttt tatatcaaac acattacaaa   2100

acacacaaaa catacaaaca tacacagcta gcaaaggcgc gccatctaat agtttaatca   2160

cagcttatag tctactatag ttttcttttt taaacattgt tgtattttgt cccccccctc   2220

taattgatga tgattatcct ataagaatcc aataaaacga tggaaactaa taccctctcc   2280

tttgtcatgt ggtctttagt atttcttgaa cattggctct gatttctcga ctttatagtc   2340

ctattaaaat cgctgttagt tctcgatcgt tgtatctcgt ttcttgtctc tttggtggat   2400

gattttgcgt gcgaacatgt ttttttccct ttctctcacc atcatcgtgt agttcttgtc   2460

accatccccc ccaccccttc cttctctcat tgattctata agagcttatc cacagaggtg   2520

cagtaacgag gtagtttaac cttcgagtgg atcaaaatgt cacacaggcc tcgacatttg   2580

ctgcaacggc aacatcaatg tccacgttta cacacctaca tttatatcta tatttatatt   2640

tatatttatt tatttatgct acttagcttc tatagttagt taatgcactc acgatattca   2700

aaattgacac ccttcaacta ctccctacta ttgtctacta ctgtctacta ctcctcttta   2760

ctatagctgc tcccaatagg ctccaccaat aggctctgtc aatacatttt gcgccgccac   2820

ctttcaggtt gtgtcactcc tgaaggacca tattgggtaa tcgtgcaatt tctggaagag   2880

agtccgcgag aagtgaggcc cccactgtaa atcctcgagg gggcatggag tatggggcat   2940

ggaggatgga ggatgggggg gggggggggg aaaataggta gcgaaaggac ccgctatcac   3000

cccacccgga gaactcgttg ccgggaagtc atatttcgac actccgggga gtctataaaa   3060

ggcgggtttt gtcttttgcc agttgatgtt gctgagagga cttgtttgcc gtttcttccg   3120

atttaacagt atagaatcaa ccactgttaa ttatacacgt tatactaaca caacaaaaac   3180

aaaaacaacg acaacaacaa caacatctag aatggcagtc tataactatg atgttgttgt   3240

cattggtact ggtccagctg gtgaaggtgc tgctatgaat gctgtcaaag ctggcagaaa   3300

ggttgctgtc gttgacgaca gacctcaagt cggtggtaac tgtactcatc ttggtactat   3360

cccatccaag gcattaagac attcagttag acagatcatg cagtataaca acaacccatt   3420

attcagacaa attggtgaac ctagatggtt ttctttcgca gacgttctta agtccgctga   3480

acaagttatc gcaaagcaag tctcttcaag aaccggctat tacgcaagaa atcgtattga   3540

tactttcttt ggcaccgcct cattctgtga tgaacatact atcgaagttg tccacttgaa   3600

tggtatggtt gaaaccttag ttgctaagca attcgttatt gcaacaggtt caagaccata   3660

cagaccagct gacgtcgact ttacccaccc aagaatctac gattccgata ccattctttc   3720
```

```
cttgggtcat acaccaagac gtttgattat ctacggtgcc ggtgtcattg gctgtgagta   3780

cgcttcaatt ttctccggtt taggtgtttt agttgatttg attgacaaca gagatcagtt   3840

gttgtccttt ttggatgatg aaatttctga ttctttgtcc tatcacttaa gaaataacaa   3900

cgttttgatt agacacaacg aagaatacga aagagttgaa ggtcttgata atggtgttat   3960

cttacactta aagtctggta aaaagattaa ggcagatgca tttttgtggt ctaacggtag   4020

aactggtaac actgataagt taggtttgga aaacattggt ttgaaggcta atggcagagg   4080

tcaaattcaa gttgatgagc attatcgtac agaagtctcc aatatctacg cagccggtga   4140

cgtcatcggt tggccatcct tagcttcagc agcttatgat caaggtagat ctgctgctgg   4200

ttctattacc gagaatgact cttggcgttt cgttgatgat gttcctaccg gtatctacac   4260

catccctgaa atttcctctg ttggtaaaac cgaaagagag ttgacacaag caaaagtccc   4320

atacgaggtt ggtaaagcct tttcaaggg catggctcgt gcacaaattg cagttgaaaa   4380

agccggtatg ttaaagattc tttttcatag agagacttta gaaatcttgg gtgtccactg   4440

cttcggttac caagcatctg aaattgttca tattggtcaa gcaattatga accaaaaggg   4500

cgaagcaaat acattaaagt atttcatcaa cactacattc aattatccaa ctatggctga   4560

agcttataga gttgcagcct acgacggttt aaacagattg ttttaattaa catctgaatg   4620

taaaatgaac attaaaatga attactaaac tttacgtcta ctttacaatc tataaacttt   4680

gtttaatcat ataacgaaat acactaatac acaatcctgt acgtatgtaa tacttttatc   4740

catcaaggat tgagaaaaaa aagtaatgat tccctgggcc attaaaactt agacccccaa   4800

gcttggatag gtcactctct attttcgttt ctcccttccc tgatagaagg gtgatatgta   4860

attaagaata atatataatt ttataataaa agcggccgcc aagttagtta gagctagagt   4920

taacacatac acattatcaa atgcatttat tcctaatatc acactaaaac gtattatata   4980

attttaatct ttatagactt catagcacca attggatttg ctttctttca gaataccgca   5040

cttaatctca atgtacgtaa cgtaggcaaa atctgtcgat aaggatctgt atgccgtaaa   5100

cggaaactcc aagcgcccag aaaacttaca ttatattctt gccagtttca tctcaccagc   5160

cagtcacagt ttaaaaggtt tgattgcgtt tcttgtttcg tcggattcag tgctaattgg   5220

taacgcactg taccgccaca ccaaagcaaa aatgcagaaa caaacaacaa tgagtgtatg   5280

tttaccaact ttggccgc                                                 5298
```

```
<210> SEQ ID NO 29
<211> LENGTH: 6139
<212> TYPE: DNA
<213> ORGANISM: Artificial
<220> FEATURE:
<223> OTHER INFORMATION: S. cerevisiae SthA gene integration fragment

<400> SEQUENCE: 29
```

```
aattctttga aggagcttgc caagaaacat aattttatga tttttgaaga tagaaaattt     60

gctgatattg gtaacactgt taaaaatcaa tataaatctg gtgtcttccg tattgccgaa    120

tgggctgaca tcactaatgc acatggtgta acgggtgcag gtattgtttc tggcttgaag    180

gaggcagccc aagaaacaac cagtgaacct agaggtttgc taatgcttgc tgagttatca    240

tcaaagggtt ctttagcata tggtgaatat acagaaaaaa cagtagaaat tgctaaatct    300

gataaagagt ttgtcattgg ttttattgcg caacacgata tgggcggtag agaagaaggt    360

tttgactgga tcattatgac tccaggggtt ggtttagatg acaaaggtga tgcacttggt    420

caacaatata gaactgttga tgaagttgta aagactggaa cggatatcat aattgttggt    480
```

```
agaggtttgt acggtcaagg aagagatcct atagagcaag ctaaaagata ccaacaagct    540
ggttggaatg cttatttaaa cagatttaaa tgattcttac acaaagattt gatacatgta    600
cactagttta aataagcatg aaaagaatta cacaagcaaa aaaaaaaaaa taaatgaggt    660
actttacgtt cacctacaac caaaaaaact agatagagta aaatcttaag atttagaaaa    720
agttgtttaa caaaggcttt agtatgtgaa tttttaatgt agcaaagcga taactaataa    780
acataaacaa aagtatggtt ttctttatca gtcaaatcat tatcgattga ttgttccgcg    840
tatctgcaga tagcctcatg aaatcagcca tttgcttttg ttcaacgatc ttttgaaatt    900
gttgttgttc ttggtagtta agttgatcca tcttggctta tgttgtgtgt atgttgtagt    960
tattcttagt atattcctgt cctgagttta gtgaaacata atatcgcctt gaaatgaaaa   1020
tgctgaaatt cgtcgacata caatttttca aacttttttt ttttcttggt gcacggacat   1080
gtttttaaag gaagtactct ataccagtta ttcttcacaa atttaattgc tggagaatag   1140
atcttcaacg cgtttaaaca gcaatttgag gaaggaatag gagaaggaga agcaatttct   1200
aggaaagagc aaggtgtgca acagcatgct ctgaatgata ttttcagcaa tagttcagtt   1260
gaagaacctg ttggcgtatc tacatcactt cctacaaaca acaccacgaa ttgcgtccgt   1320
ggtgacgcaa ctacgaatgg cattgtcaat gccaatgcca gtgcacatac acgtgcaagt   1380
cccaccggtt ccctgcccgg ctatggtaga gacaagaagg acgataccgg catcgacatc   1440
aacagtttca acagcaatgc gtttggcgtc gacgcgtcga tggggctgcc gtatttggat   1500
ttggacgggc tagatttcga tatggatatg gatatggata tggatatgga gatgaatttg   1560
aatttagatt tgggtcttga tttggggttg gaattaaaag gggataacaa tgagggtttt   1620
cctgttgatt taaacaatgg acgtgggagg tgattgattt aacctgatcc aaaaggggta   1680
tgtctatttt ttagagtgtg tctttgtgtc aaattatggt agaatgtgta aagtagtata   1740
aactttcctc tcaaatgacg aggtttaaaa caccccccgg gtgagccgag ccgagaatgg   1800
ggcaattgtt caatgtgaaa tagaagtatc gagtgagaaa cttgggtgtt ggccagccaa   1860
gggggaagga aaatggcgcg aatgctcagg tgagattgtt ttggaattgg gtgaagcgag   1920
gaaatgagcg acccggaggt tgtgacttta gtggcggagg aggaacggga ggaaaaggcc   1980
aagagggaaa gtgtatataa gggggagcaa tttgccaacc aggatagaat tggatgagtt   2040
ataattctac tgtatttatt gtataattta tttctccttt tatatcaaac acattacaaa   2100
acacacaaaa catacaaaca tacacagcta gcatggatgg tcctaacttc gcccatcaag   2160
gcggtagatc ccaaagaact accgagttgt actcatgtgc acgttgccgt aagcttaaga   2220
agaaatgtgg taaacaaatc ccaacttgtg caaactgtga taagaacggt gcacattgtt   2280
cttatcctgg tagagctcct agacgtacca agaaggagtt ggctgatgca atgcttagag   2340
gtgaatatgt tccagttaaa cgtaacaaga aagtcggcaa atctccttta tctactaagt   2400
ctatgccaaa ctcctcttct ccattatccg ctaacggtgc aatcactcct ggtttttctc   2460
catatgaaaa cgatgacgcc cacaagatga agcagttaaa gccatctgat ccaattaact   2520
tagtcatggg tgcatctcca aattcctccg agggcgtttc ctctttgatt tccgttttaa   2580
cctcattgaa cgacaattcc aatccttctt ctcacttgtc ctctaacgaa aattccatga   2640
tcccttctcg ttcccttcca gcatccgttc aacaatcatc tacaacttct tcctttggtg   2700
gttataacac ccatcacca ttgatttcct ctcacgttcc agccaatgca caagcagtcc   2760
cattacaaaa caacaacaga aacacctcta acggtgacaa tggttctaac gttaatcatg   2820
```

```
acaacaataa tggttccacc aacacaccac aattatcctt gactccatac gctaataact   2880
ctgctcctaa cggcaaattc gattccgtcc ctgtcgatgc ttcttccatc gagtttgaga   2940
caatgtcttg ttgttttaag ggtggcagaa ctacttcttg ggttagagaa gatggttctt   3000
ttaagtctat tgacagatca ttattggaca gattcatcgc agcttacttc aagcacaacc   3060
acagattgtt cccaatgatt gataagattg cattcttgaa tgatgctgct actattaccg   3120
atttcgaaag attgtacgat aacaagaact atccagattc ttttgttttc aaggtttaca   3180
tgattatggc aattggctgt actacattac aaagagctgg catggtttcc caagacgaag   3240
aatgtttgtc tgaacatttg gctttccttg ctatgaagaa gtttagatct gtcattatct   3300
tacaagatat cgaaactgtt agatgcttgt tgttattagg tatctactca ttctttgaac   3360
caaagggttc ttcctcttgg actatttcag gcattatcat gcgtcttact attggtttgg   3420
gtttgaatag agaattgact gctaagaaat tgaagtctat gtcagcctta gaagcagaag   3480
caagatatag agttttctgg tctgcttatt gttttgaaag attggtctgt acatccttgg   3540
gtagaatttc cggtattgac gacgaagata ttactgttcc attaccaaga gcattgtatg   3600
tcgatgagag agatgatttg gaaatgacca agttaatgat ctccttaaga aagatgggtg   3660
gtagaatcta caagcaagtc cattctgttt ccgctggtag acaaaagttg accatcgaac   3720
agaagcagga gattatctct ggtttgagaa aagaacttga cgaaatctac tccagagaat   3780
ccgaaagaag aaagttaaag aagtctcaaa tggaccaagt cgaaagagaa aacaattcaa   3840
caactaatgt tatttccttt cactcatctg agatttggtt agctatgaga tactctcaat   3900
tgcaaatctt gttgtataga ccatccgccc ttatgccaaa accacctatt gattctttgt   3960
caacccttgg tgaattttgt ttacaagcat ggaaacacac ttacacattg tacaagaaaa   4020
gattgttacc attgaattgg attaccttat tcagaacttt aactatttgt aacacaatct   4080
tatactgttt atgccaatgg tccattgact taattgaatc taagattgaa atccaacagt   4140
gtgttgaaat cttgcgtcat tttggtgaaa gatggatttt cgccatgaga tgtgctgatg   4200
ttttccaaaa catttcaaat accattttag acatctccct ttcccatggt aaagttccaa   4260
acatggatca attaaccaga gagttattcg gtgcatctga ctcctaccaa gacatcttag   4320
acgaaaacaa tgttgatgtt tcttgggtcg ataagttggt ctaaggcgcg ccatctaata   4380
gtttaatcac agcttatagt ctactatagt ttttcttttt aaacattgtt gtattttgtc   4440
cccccctct aattgatgat gattatccta taagaatcca ataaaacgat ggaaactaat   4500
accctctcct ttgtcatgtg gtctttagta tttcttgaac attggctctg atttctcgac   4560
tttatagtcc tattaaaatc gctgttagtt ctcgatcgtt gtatctcgtt tcttgtctct   4620
ttggtggatg attttgcgtg cgaacatgtt tttttccctt tctctcacca tcatcgtgta   4680
gttcttgtca ccatcccccc cacccccttcc ttctctcatt gattctataa gagcttatcc   4740
acagaggtgc agtaacgagg tagtttaacc ttcgagtgga tcaaaatgtc acacaggcct   4800
cgacatttgc tgcaacggca acatcaatgt ccacgtttac acacctacat ttatatctat   4860
atttatattt atatttattt atttatgcta cttagcttct atagttagtt aatgcactca   4920
cgatattcaa aattgacacc cttcaactac tccctactat tgtctactac tgtctactac   4980
tcctctttac tatagctgct cccaataggc tccaccaata ggctctgtca atacattttg   5040
cgccgccacc tttcaggttg tgtcactcct gaaggaccat attgggtaat cgtgcaattt   5100
ctggaagaga gtccgcgaga agtgaggccc ccactgtaaa tcctcgaggg ggcatggagt   5160
atggggcatg gaggatggag gatggggggg ggggggggga aaataggtag cgaaaggacc   5220
```

```
cgctatcacc ccacccggag aactcgttgc cgggaagtca tatttcgaca ctccggggag   5280

tctataaaag gcgggttttg tcttttgcca gttgatgttg ctgagaggac ttgtttgccg   5340

tttcttccga tttaacagta tagaatcaac cactgttaat tatacacgtt atactaacac   5400

aacaaaaaca aaaacaacga caacaacaac aacatctaga taattaatta acatctgaat   5460

gtaaaatgaa cattaaaatg aattactaaa ctttacgtct actttacaat ctataaactt   5520

tgtttaatca tataacgaaa tacactaata cacaatcctg tacgtatgta atacttttat   5580

ccatcaagga ttgagaaaaa aaagtaatga ttccctgggc cattaaaact tagacccccca  5640

agcttggata ggtcactctc tattttcgtt tctcccttcc ctgatagaag ggtgatatgt   5700

aattaagaat aatatataat tttataataa aagcggccgc caagttagtt agagctagag   5760

ttaacacata cacattatca aatgcattta ttcctaatat cacactaaaa cgtattatat   5820

aattttaatc tttatagact tcatagcacc aattggattt gctttctttc agaataccgc   5880

acttaatctc aatgtacgta acgtaggcaa aatctgtcga taaggatctg tatgccgtaa   5940

acggaaactc caagcgccca gaaaacttac attatattct tgccagtttc atctcaccag   6000

ccagtcacag tttaaaaggt ttgattgcgt ttcttgtttc gtcggattca gtgctaattg   6060

gtaacgcact gtaccgccac accaaagcaa aaatgcagaa acaaacaaca atgagtgtat   6120

gtttaccaac tttggccgc                                                6139
```

<210> SEQ ID NO 30
<211> LENGTH: 2232
<212> TYPE: DNA
<213> ORGANISM: Saccharomyces cerevisiae

<400> SEQUENCE: 30

```
atggatggtc ctaacttcgc ccatcaaggc ggtagatccc aaagaactac cgagttgtac     60

tcatgtgcac gttgccgtaa gcttaagaag aaatgtggta aacaaatccc aacttgtgca    120

aactgtgata agaacggtgc acattgttct tatcctggta gagctcctag acgtaccaag    180

aaggagttgg ctgatgcaat gcttagaggt gaatatgttc cagttaaacg taacaagaaa    240

gtcggcaaat ctcctttatc tactaagtct atgccaaact cctcttctcc attatccgct    300

aacggtgcaa tcactcctgg tttttctcca tatgaaaacg atgacgccca caagatgaag    360

cagttaaagc catctgatcc aattaactta gtcatgggtg catctccaaa ttcctccgag    420

ggcgtttcct ctttgatttc cgttttaacc tcattgaacg acaattccaa tccttcttct    480

cacttgtcct ctaacgaaaa ttccatgatc ccttctcgtt cccttccagc atccgttcaa    540

caatcatcta caacttcttc ctttggtggt tataacaccc catcaccatt gatttcctct    600

cacgttccag ccaatgcaca agcagtccca ttacaaaaca acaacagaaa cacctctaac    660

ggtgacaatg gttctaacgt taatcatgac aacaataatg gttccaccaa cacaccacaa    720

ttatccttga ctccatacgc taataactct gctcctaacg gcaaattcga ttccgtccct    780

gtcgatgctt cttccatcga gtttgagaca atgtcttgtt gttttaaggg tggcagaact    840

acttcttggg ttagagaaga tggttctttt aagtctattg acagatcatt attggacaga    900

ttcatcgcag cttacttcaa gcacaaccac agattgttcc caatgattga taagattgca    960

ttcttgaatg atgctgctac tattaccgat ttcgaaagat tgtacgataa caagaactat   1020

ccagattctt ttgttttcaa ggtttacatg attatggcaa ttggctgtac tacattacaa   1080

agagctggca tggtttccca agacgaagaa tgtttgtctg aacatttggc tttccttgct   1140
```

```
atgaagaagt ttagatctgt cattatctta caagatatcg aaactgttag atgcttgttg   1200

ttattaggta tctactcatt ctttgaacca aagggttctt cctcttggac tatttcaggc   1260

attatcatgc gtcttactat tggtttgggt ttgaatagag aattgactgc taagaaattg   1320

aagtctatgt cagccttaga agcagaagca agatatagag ttttctggtc tgcttattgt   1380

tttgaaagat tggtctgtac atccttgggt agaatttccg gtattgacga cgaagatatt   1440

actgttccat taccaagagc attgtatgtc gatgagagag atgatttgga aatgaccaag   1500

ttaatgatct ccttaagaaa gatgggtggt agaatctaca agcaagtcca ttctgtttcc   1560

gctggtagac aaaagttgac catcgaacag aagcaggaga ttatctctgg tttgagaaaa   1620

gaacttgacg aaatctactc cagagaatcc gaaagaagaa agttaaagaa gtctcaaatg   1680

gaccaagtcg aaagagaaaa caattcaaca actaatgtta tttcctttca ctcatctgag   1740

atttggttag ctatgagata ctctcaattg caaatcttgt tgtatagacc atccgccctt   1800

atgccaaaac cacctattga ttctttgtca acccttggtg aattttgttt acaagcatgg   1860

aaacacactt acacattgta caagaaaaga ttgttaccat tgaattggat taccttattc   1920

agaactttaa ctatttgtaa cacaatctta tactgtttat gccaatggtc cattgactta   1980

attgaatcta agattgaaat ccaacagtgt gttgaaatct tgcgtcattt tggtgaaaga   2040

tggattttcg ccatgagatg tgctgatgtt ttccaaaaca tttcaaatac cattttagac   2100

atctcccttt cccatggtaa agttccaaac atggatcaat taaccagaga gttattcggt   2160

gcatctgact cctaccaaga catcttagac gaaaacaatg ttgatgtttc ttgggtcgat   2220

aagttggtct aa                                                       2232
```

```
<210> SEQ ID NO 31
<211> LENGTH: 506
<212> TYPE: PRT
<213> ORGANISM: Issatchenkia orientalis

<400> SEQUENCE: 31

Met Gly Val Gln Phe Ile Glu Asn Thr Ile Ile Val Val Phe Gly Ala
1               5                   10                  15

Ser Gly Asp Leu Ala Lys Lys Lys Thr Phe Pro Ala Leu Phe Gly Leu
            20                  25                  30

Phe Arg Glu Gly Gln Leu Ser Glu Thr Thr Lys Ile Ile Gly Phe Ala
        35                  40                  45

Arg Ser Lys Leu Ser Asn Asp Asp Leu Arg Asn Arg Ile Lys Pro Tyr
    50                  55                  60

Leu Lys Leu Asn Lys Arg Thr Asp Ala Glu Arg Gln Ser Leu Glu Lys
65                  70                  75                  80

Phe Leu Gln Ile Leu Glu Tyr His Gln Ser Asn Tyr Asp Asp Ser Glu
                85                  90                  95

Gly Phe Glu Lys Leu Glu Lys Leu Ile Asn Lys Tyr Asp Asp Glu Ala
            100                 105                 110

Asn Val Lys Glu Ser His Arg Leu Tyr Tyr Leu Ala Leu Pro Pro Ser
        115                 120                 125

Val Phe Thr Thr Val Ala Thr Met Leu Lys Lys His Cys His Pro Gly
    130                 135                 140

Asp Ser Gly Ile Ala Arg Leu Ile Val Glu Lys Pro Phe Gly His Asp
145                 150                 155                 160

Leu Ser Ser Ser Arg Glu Leu Gln Lys Ser Leu Ala Pro Leu Trp Asn
                165                 170                 175
```

```
Glu Asp Glu Leu Phe Arg Ile Asp His Tyr Leu Gly Lys Glu Met Val
            180                 185                 190

Lys Asn Leu Ile Pro Leu Arg Phe Ser Asn Thr Phe Leu Ser Ser Ser
        195                 200                 205

Trp Asn Asn Gln Phe Ile Asp Thr Ile Gln Ile Thr Phe Lys Glu Asn
    210                 215                 220

Phe Gly Thr Glu Gly Arg Gly Gly Tyr Phe Asp Ser Ile Gly Ile Ile
225                 230                 235                 240

Arg Asp Val Ile Gln Asn His Leu Leu Gln Val Leu Thr Ile Val Leu
                245                 250                 255

Met Glu Lys Pro Ala Asp Phe Asn Gly Glu Ser Ile Arg Asp Glu Lys
            260                 265                 270

Val Lys Val Leu Lys Ala Ile Glu Gln Ile Asp Phe Asn Asn Val Leu
        275                 280                 285

Val Gly Gln Tyr Asp Lys Ser Glu Asp Gly Ser Lys Pro Gly Tyr Leu
    290                 295                 300

Asp Asp Asp Thr Val Asn Pro Asp Ser Lys Ala Val Thr Tyr Ala Ala
305                 310                 315                 320

Leu Val Leu Asn Val Ala Asn Glu Arg Trp Asn Asn Val Pro Ile Ile
                325                 330                 335

Leu Lys Ala Gly Lys Ala Leu Asn Gln Ser Lys Val Glu Ile Arg Ile
            340                 345                 350

Gln Phe Lys Pro Val Glu Asn Gly Ile Phe Lys Asn Ser Ala Arg Asn
        355                 360                 365

Glu Leu Val Ile Arg Ile Gln Pro Asn Glu Ala Met Tyr Leu Lys Met
    370                 375                 380

Asn Ile Lys Val Pro Gly Val Ser Asn Gln Val Ser Ile Ser Glu Met
385                 390                 395                 400

Asp Leu Thr Tyr Lys Asn Arg Tyr Ser Ser Glu Phe Tyr Ile Pro Glu
                405                 410                 415

Ala Tyr Glu Ser Leu Ile Lys Asp Ala Leu Met Asp Asp His Ser Asn
            420                 425                 430

Phe Val Arg Asp Asp Glu Leu Asp Ile Ser Trp Ala Leu Phe Thr Pro
        435                 440                 445

Leu Leu Glu His Ile Glu Gly Pro Asp Gly Pro Thr Pro Thr Lys Tyr
    450                 455                 460

Pro Tyr Gly Ser Arg Gly Pro Lys Glu Ile Asp Glu Phe Leu Arg Asn
465                 470                 475                 480

His Gly Tyr Val Lys Glu Pro Arg Glu Asn Tyr Gln Trp Pro Leu Thr
                485                 490                 495

Thr Pro Lys Glu Leu Asn Ser Ser Lys Phe
            500                 505
```

<210> SEQ ID NO 32
<211> LENGTH: 3435
<212> TYPE: DNA
<213> ORGANISM: Artificial
<220> FEATURE:
<223> OTHER INFORMATION: Mutated L. mexicana FRD gene

<400> SEQUENCE: 32

```
atggctgatg gcaaaacctc tgcatcagtt gttgctgttg atgctgaacg tgccgctaag      60

gaaagagatg cagcagctag agctatgttg caaggtggtg gtgtctctcc tgctggcaag     120

gcacaattgt tgaaaaaggg tttggttcac actgttccat ataccttaaa ggttgtcgtc     180
```

```
gcagatccaa aggaaatgga gaaggcaact gctgacgcag aagaggtttt acaagctgca    240
tttcaagtcg tcgacaccct tttgaacaac tttaacgaaa actcagaagt ttcaagagtc    300
aataggttgg cagttggtga ggaacatcaa atgtctgaaa cattgaaaca cgtcatggcc    360
tgttgtcaaa aggtttatca ttcctccaga ggtgtttttg acccagcagt tggtccatta    420
gtccgtgaac ttagagaagc tgctcacaag ggtaaaactg ttccagccga aagagttaat    480
gatttgttat ccaaatgtac ccttaatgca tctttttcaa ttgatatgtc cagaggtatg    540
attgcaagga agcatccaga cgccatgttg gatttgggtg gtgtcaacaa gggttatggt    600
atcgactaca ttgttgaaca cttaaactct ttgggttatg atgatgtctt tttcggacgg    660
ggtggtgatg ttagagcatc cggcaaaaac cagttatctc aaccttgggc tgttggtatt    720
gttagaccac ctgccttggc cgacattaga actgttgtcc cagaggacaa aagatccttt    780
atccgtgtcg tcagattgaa caacgaagct attgctacct ctggtgatta tgagaatttg    840
gttgaaggtc ctggttctaa ggtttactct tccaccttca atccaacttc caaaaacttg    900
ttggaaccta ccgaagcagg tatggctcaa gtttctgtca agtgttgctc atgtatctac    960
gctgatgctt tagcaacagc agctttgttg aaaaacgatc ctgctgccgt tagaaggatc   1020
ttagataact ggagatatgt cagagatact gttactgact acaccactta cacaagggaa   1080
ggtgaaagag ttgctaagat gttggaaatt gctaccgaag atgctgaaat gagagcaaag   1140
agaatcaagg gctctttacc agcaagagtt atcattgttg gtggtggttt ggccggttgt   1200
tccgcagcta tcgaagcagc taactgtggc gcccacgtca tcttgttaga aaaggaacca   1260
aagttaggtg gtaactctgc aaaggctacc tccggtatca acgcctgggg tactagagca   1320
caagcaaaac aaggtgtcat ggacggcggc aagtttttcg aaagagatac ccatagatcc   1380
ggcaagggtg gtaattgcga tccatgcctt gttaagactt tgtccgttaa gtcctctgat   1440
gcagttaagt ggttatctga attaggtgtt ccattgactg ttttgtctca attaggtggt   1500
gcttcaagga aacgttgtca ccgtgcacca gataagtctg atggtacacc agtcccagtt   1560
ggtttcacca ttatgaaaac ccttgaaaac cacattgtca acgatttgtc cagacatgtt   1620
acagttatga caggtattac cgtcacagct ttagaatcta catcaagagt cagacctgat   1680
ggtgttttag tcaagcatgt tactggtgtt cacttgattc aggcatctgg tcaatctatg   1740
gttttgaatg cagacgctgt tatcttagct actggtggtt tctccaatga tcatacccca   1800
aactcccttt tacaacaata cgccccacag ttgtcatctt ttccaacaac caatggtgtc   1860
tgggcaactg gcgatggtgt taagatggct tccaagttgg gtgtcgcctt agttgatatg   1920
gataaggtcc aattacatcc taccggcttg ttagacccaa aagatccatc taatagaacc   1980
aagtatcttg gtccagaggc cttaagaggt tccggcggtg tcttgttaaa caaaaacggt   2040
gaaagatttg ttaatgaatt agacttaaga tctgttgtct ctcaagctat catcgcacaa   2100
gataatgagt acccaggctc tggtggttcc aagttcgcat actgtgtttt gaacgaaact   2160
gcagcaaagt tattcggcaa aaacttcctt ggtttctact ggaatagatt aggtcttttc   2220
caaaaggttg attccgttgc tggtttagct aagttgattg gttgtccaga agctaatgtt   2280
gttgctacat tgaagcaata tgaggagtta tcttccaaaa agcttaatcc ttgtccattg   2340
actggcaagt ctgtctttcc ttgtgtttta ggcactcaag gtccatacta tgttgccttg   2400
gttaccccat ccattcacta cactatgggt ggttgtttga tttccccatc tgctgagatg   2460
caaaccattg acaactctgg tgttactcct gtcagacgtc caatcttagg cttattcggt   2520
gctggtgaag ttactggcgg tgtccatggt ggtaacagat taggcggtaa ctctttgtta   2580
```

```
gaatgtgttg ttttcggcaa gatcgctggt gacagagctg caaccatctt gcaaaagaaa   2640

aacaccggct tatcaatgac agaatggtct actgtcgtct taagagaagt tagagaaggt   2700

ggtgtctatg gtgctggttc cagagttttg aggtttaaca tgcctggtgc attacagaga   2760

actggtttag ctttaggtca attcatcggt atcagaggtg attgggacgg tcacagattg   2820

atcggttact attctccaat cactttacct gatgatgttg gtgttattgg tatcttagct   2880

agagcagaca agggtagatt ggcagaatgg atttctgcat tgcagccagg tgacgctgtt   2940

gagatgaagg cctgcggtgg tcttatcatt gacagaagat tcgctgaaag acatttcttt   3000

ttccgtggtc ataagatcag aaagttggcc cttatcggtg gtggtactgg tgttgcacca   3060

atgttacaaa tcgtcagagc tgctgtcaaa aagccatttg tcgattcaat tgagtccatt   3120

cagttcatct atgctgcaga ggatgtttcc gagcttacat acagaacctt acttgaatct   3180

tacgaagagg aatatggttc agaaaagttt aagtgtcact tcgttttgaa taacccacca   3240

gctcaatgga ctgacggtgt tggtttcgtt gatactgcat tgttgagatc cgcagttcaa   3300

gcaccatcaa atgatttgct tgttgcaatt tgtggtccac caatcatgca aagagcagtt   3360

aagggtgcat tgaaaggttt aggttacaat atgaatcttg ttagaaccgt tgacgaaact   3420

gaaccaccat cataa                                                    3435
```

```
<210> SEQ ID NO 33
<211> LENGTH: 3444
<212> TYPE: DNA
<213> ORGANISM: Artificial
<220> FEATURE:
<223> OTHER INFORMATION: Mutated L. mexicana FRD gene

<400> SEQUENCE: 33
```

```
atggctgatg gcaaaacctc tgcatcagtt gttgctgttg atgctgaacg tgccgctaag     60

gaaagagatg cagcagctag agctatgttg caaggtggtg gtgtctctcc tgctggcaag    120

gcacaattgt tgaaaaaggg tttggttcac actgttccat ataccttaaa ggttgtcgtc    180

gcagatccaa aggaaatgga gaaggcaact gctgacgcag aagaggtttt acaagctgca    240

tttcaagtcg tcgacaccct tttgaacaac tttaacgaaa actcagaagt ttcaagagtc    300

aataggttgg cagttggtga ggaacatcaa atgtctgaaa cattgaaaca cgtcatggcc    360

tgttgtcaaa aggtttatca ttcctccaga ggtgtttttg acccagcagt tggtccatta    420

gtccgtgaac ttagagaagc tgctcacaag ggtaaaactg ttccagccga aagagttaat    480

gatttgttat ccaaatgtac ccttaatgca tctttttcaa ttgatatgtc cagaggtatg    540

attgcaagga agcatccaga cgccatgttg gatttgggtg gtgtcaacaa gggttatggt    600

atcgactaca ttgttgaaca cttaaactct ttgggttatg atgatgtctt tttcgaatgg    660

ggtggtgatg ttagagcatc cggcaaaaac cagttatctc aaccttgggc tgttggtatt    720

gttagaccac ctgccttggc cgacattaga actgttgtcc cagaggacaa aagatccttt    780

atccgtgtcg tcagattgaa caacgaagct attgctacct ctggtgatta tgagaatttg    840

gttgaaggtc ctggttctaa ggtttactct tccaccttca atccaacttc caaaaacttg    900

ttggaaccta ccgaagcagg tatggctcaa gtttctgtca agtgttgctc atgtatctac    960

gctgatgctt tagcaacagc agctttgttg aaaaacgatc ctgctgccgt tagaaggatc   1020

ttagataact ggagatatgt cagagatact gttactgact acaccactta cacaagggaa   1080

ggtgaaagag ttgctaagat gttggaaatt gctaccgaag atgctgaaat gagagcaaag   1140
```

-continued

```
agaatcaagg gctctttacc agcaagagtt atcattgttg gtggtggttt ggccggttgt   1200
tccgcagcta tcgaagcagc taactgtggc gcccacgtca tcttgttagg taaggaacca   1260
aagttaggtg gtaactctgc aaaggctacc tccggtatca acgcctgggg tactagagca   1320
caagcaaaac aaggtgtcat ggacggcggc aagtttttcg aaagagatac ccatagatcc   1380
ggcaagggtg gtaattgcga tccatgcctt gttaagactt tgtccgttaa gtcctctgat   1440
gcagttaagt ggttatctga attaggtgtt ccattgactg ttttgtctca attaggtggt   1500
gcttcaagga aacgttgtca ccgtgcacca gataagtctg atggtacacc agtcccagtt   1560
ggtttcacca ttatgaaaac ccttgaaaac cacattgtca acgatttgtc cagacatgtt   1620
acagttatga caggtattac cgtcacagct ttagaatcta catcaagagt cagacctgat   1680
ggtgttttag tcaagcatgt tactggtgtt cacttgattc aggcatctgg tcaatctatg   1740
gttttgaatg cagacgctgt tatcttagct actggtggtt tctccaatga tcatacccca   1800
aactcccttt tacaacaata cgccccacag ttgtcatctt ttccaacaac caatggtgtc   1860
tgggcaactg gcgatggtgt taagatggct tccaagttgg gtgtcgcctt agttgatatg   1920
gataaggtcc aattacatcc taccggcttg ttagacccaa aagatccatc taatagaacc   1980
aagtatcttg gtccagaggc cttaagaggt tccggcggtg tcttgttaaa caaaaacggt   2040
gaaagatttg ttaatgaatt agacttaaga tctgttgtct ctcaagctat catcgcacaa   2100
gataatgagt acccaggctc tggtggttcc aagttcgcat actgtgtttt gaacgaaact   2160
gcagcaaagt tattcggcaa aaacttcctt ggtttctact ggaatagatt aggtcttttc   2220
caaaaggttg attccgttgc tggtttagct aagttgattg gttgtccaga agctaatgtt   2280
gttgctacat tgaagcaata tgaggagtta tcttccaaaa agcttaatcc ttgtccattg   2340
actggcaagt ctgtctttcc ttgtgtttta ggcactcaag gtccatacta tgttgccttg   2400
gttaccccat ccattcacta cactatgggt ggttgtttga tttccccatc tgctgagatg   2460
caaaccattg acaactctgg tgttactcct gtcagacgtc caatcttagg cttattcggt   2520
gctggtgaag ttactggcgg tgtccatggt ggtaacagat taggcggtaa ctctttgtta   2580
gaatgtgttg ttttcggcaa gatcgctggt gacagagctg caaccatctt gcaaaagaaa   2640
aacaccggct tatcaatgac agaatggtct actgtcgtct taagagaagt tagagaaggt   2700
ggtgtctatg gtgctggttc cagagttttg aggtttaaca tgcctggtgc attacagaga   2760
actggtttag ctttaggtca attcatcggt atcagaggtg attgggacgg tcacagattg   2820
atcggttact attctccaat cactttacct gatgatgttg gtgttattgg tatcttagct   2880
agagcagaca agggtagatt ggcagaatgg atttctgcat tgcagccagg tgacgctgtt   2940
gagatgaagg cctgcggtgg tcttatcatt gacagaagat tcgctgaaag acatttcttt   3000
ttccgtggtc ataagatcag aaagttggcc cttatcggtg gtggtactgg tgttgcacca   3060
atgttacaaa tcgtcagagc tgctgtcaaa aagccatttg tcgattcaat tgagtccatt   3120
cagttcatct atgctgcaga ggatgtttcc gagcttacat acagaacctt acttgaatct   3180
tacgaagagg aatatggttc agaaaagttt aagtgtcact tcgttttgaa taacccacca   3240
gctcaatgga ctgacggtgt tggtttcgtt gatactgcat tgttgagatc cgcagttcaa   3300
gcaccatcaa atgatttgct tgttgcaatt tgtggtccac caatcatgca aagagcagtt   3360
aagggtgcat tgaaaggttt aggttacaat atgaatcttg ttagaaccgt tgacgaaact   3420
gaaccaccat cataattaat taac                                          3444
```

<210> SEQ ID NO 34
<211> LENGTH: 3444
<212> TYPE: DNA
<213> ORGANISM: Artificial
<220> FEATURE:
<223> OTHER INFORMATION: Mutated L. mexicana FRD gene

<400> SEQUENCE: 34

```
atggctgatg gcaaaacctc tgcatcagtt gttgctgttg atgctgaacg tgccgctaag     60
gaaagagatg cagcagctag agctatgttg caaggtggtg gtgtctctcc tgctggcaag    120
gcacaattgt tgaaaaaggg tttggttcac actgttccat ataccttaaa ggttgtcgtc    180
gcagatccaa aggaaatgga gaaggcaact gctgacgcag aagaggtttt acaagctgca    240
tttcaagtcg tcgacaccct tttgaacaac tttaacgaaa actcagaagt ttcaagagtc    300
aataggttgg cagttggtga ggaacatcaa atgtctgaaa cattgaaaca cgtcatggcc    360
tgttgtcaaa aggtttatca ttcctccaga ggtgtttttg acccagcagt tggtccatta    420
gtccgtgaac ttagagaagc tgctcacaag ggtaaaactg ttccagccga aagagttaat    480
gatttgttat ccaaatgtac ccttaatgca tctttttcaa ttgatatgtc cagaggtatg    540
attgcaagga agcatccaga cgccatgttg gatttgggtg gtgtcaacaa gggttatggt    600
atcgactaca ttgttgaaca cttaaactct ttgggttatg atgatgtctt tttcgaatgg    660
ggtggtgatg ttagagcatc cggcaaaaac cagttatctc aaccttgggc tgttggtatt    720
gttagaccac ctgccttggc cgacattaga actgttgtcc cagaggacaa aagatccttt    780
atccgtgtcg tcagattgaa caacgaagct attgctacct ctggtgatta tgagaatttg    840
gttgaaggtc ctggttctaa ggtttactct tccaccttca atccaacttc caaaaacttg    900
ttggaaccta ccgaagcagg tatggctcaa gtttctgtca agtgttgctc atgtatctac    960
gctgatgctt tagcaacagc agctttgttg aaaaacgatc ctgctgccgt tagaaggatc   1020
ttagataact ggagatatgt cagagatact gttactgact acaccactta cacaagggaa   1080
ggtgaaagag ttgctaagat gttggaaatt gctaccgaag atgctgaaat gagagcaaag   1140
agaatcaagg gctctttacc agcaagagtt atcattgttg gtggtggttt ggccggttgt   1200
tccgcagcta tcgaagcagc taactgtggc gcccacgtca tcttgttaga aaaggaacca   1260
aagttaggtg gtaactctgc aaaggctacc tccggtatca acgcctgggg tactagagca   1320
caagcaaaac aaggtgtcat ggacggcggc aagtttttcg aaagagatac ccatagatcc   1380
ggcaagggtg gtaattgcga tccatgcctt gttaagactt tgtccgttaa gtcctctgat   1440
gcagttaagt ggttatctga attaggtgtt ccattgactg ttttgtctca attaggtggt   1500
gcttcaagga aacgttgtca ccgtgcacca gataagtctg atggtacacc agtcccagtt   1560
ggtttcacca ttatgaaaac ccttgaaaac cacattgtca acgatttgtc cagacatgtt   1620
acagttatga caggtattac cgtcacagct ttagaatcta catcaagagt cagacctgat   1680
ggtgttttag tcaagcatgt tactggtgtt cacttgattc aggcatctgg tcaatctatg   1740
gttttgaatg cagacgctgt tatcttagct actggtggtt tctccaatga tcatacccca   1800
aactcccttt tacaacaata cgccccacag ttgtcatctt ttccaacaac caatggtgtc   1860
tgggcaactg gcgatggtgt taagatggct tccaagttgg gtgtcgcctt agttgatatg   1920
ggtaaggtcc aattacatcc taccggcttg ttagacccaa aagatccatc taatagaacc   1980
aagtatcttg gtccagaggc cttaagaggt tccggcggtg tcttgttaaa caaaaacggt   2040
gaaagatttg ttaatgaatt agacttaaga tctgttgtct ctcaagctat catcgcacaa   2100
```

```
gataatgagt acccaggctc tggtggttcc aagttcgcat actgtgtttt gaacgaaact   2160

gcagcaaagt tattcggcaa aaacttcctt ggtttctact ggaatagatt aggtcttttc   2220

caaaaggttg attccgttgc tggtttagct aagttgattg gttgtccaga agctaatgtt   2280

gttgctacat tgaagcaata tgaggagtta tcttccaaaa agcttaatcc ttgtccattg   2340

actggcaagt ctgtctttcc ttgtgtttta ggcactcaag gtccatacta tgttgccttg   2400

gttaccccat ccattcacta cactatgggt ggttgtttga tttccccatc tgctgagatg   2460

caaaccattg acaactctgg tgttactcct gtcagacgtc caatcttagg cttattcggt   2520

gctggtgaag ttactggcgg tgtccatggt ggtaacagat taggcggtaa ctctttgtta   2580

gaatgtgttg ttttcggcaa gatcgctggt gacagagctg caaccatctt gcaaaagaaa   2640

aacaccggct tatcaatgac agaatggtct actgtcgtct taagagaagt tagagaaggt   2700

ggtgtctatg gtgctggttc cagagttttg aggtttaaca tgcctggtgc attacagaga   2760

actggtttag ctttaggtca attcatcggt atcagaggtg attgggacgg tcacagattg   2820

atcggttact attctccaat cactttacct gatgatgttg gtgttattgg tatcttagct   2880

agagcagaca agggtagatt ggcagaatgg atttctgcat tgcagccagg tgacgctgtt   2940

gagatgaagg cctgcggtgg tcttatcatt gacagaagat tcgctgaaag acatttcttt   3000

ttccgtggtc ataagatcag aaagttggcc cttatcggtg gtggtactgg tgttgcacca   3060

atgttacaaa tcgtcagagc tgctgtcaaa aagccatttg tcgattcaat tgagtccatt   3120

cagttcatct atgctgcaga ggatgtttcc gagcttacat acagaacctt acttgaatct   3180

tacgaagagg aatatggttc agaaaagttt aagtgtcact tcgttttgaa taacccacca   3240

gctcaatgga ctgacggtgt tggtttcgtt gatactgcat tgttgagatc cgcagttcaa   3300

gcaccatcaa atgatttgct tgttgcaatt tgtggtccac caatcatgca aagagcagtt   3360

aagggtgcat tgaaaggttt aggttacaat atgaatcttg ttagaaccgt tgacgaaact   3420

gaaccaccat cataattaat taac                                           3444
```

```
<210> SEQ ID NO 35
<211> LENGTH: 3435
<212> TYPE: DNA
<213> ORGANISM: Artificial
<220> FEATURE:
<223> OTHER INFORMATION: Mutated L. mexicana FRD gene

<400> SEQUENCE: 35
```

```
atggctgatg gcaaaacctc tgcatcagtt gttgctgttg atgctgaacg tgccgctaag     60

gaaagagatg cagcagctag agctatgttg caaggtggtg gtgtctctcc tgctggcaag    120

gcacaattgt tgaaaaaggg tttggttcac actgttccat ataccttaaa ggttgtcgtc    180

gcagatccaa aggaaatgga gaaggcaact gctgacgcag aagaggtttt acaagctgca    240

tttcaagtcg tcgacaccct tttgaacaac tttaacgaaa actcagaagt ttcaagagtc    300

aataggttgg cagttggtga ggaacatcaa atgtctgaaa cattgaaaca cgtcatggcc    360

tgttgtcaaa aggtttatca ttcctccaga ggtgtttttg acccagcagt tggtccatta    420

gtccgtgaac ttagagaagc tgctcacaag ggtaaaactg ttccagccga aagagttaat    480

gatttgttat ccaaatgtac ccttaatgca tctttttcaa ttgatatgtc cagaggtatg    540

attgcaagga agcatccaga cgccatgttg gatttgggtg gtgtcaacaa gggttatggt    600

atcgactaca ttgttgaaca cttaaactct ttgggttatg atgatgtctt tttcgaatgg    660

ggtggtgatg ttagagcatc cggcaaaaac cagttatctc aaccttgggc tgttggtatt    720
```

```
gttagaccac ctgccttggc cgacattaga actgttgtcc cagaggacaa aagatccttt    780
atccgtgtcg tcagattgaa caacgaagct attgctacct ctggtgatta tgagaatttg    840
gttgaaggtc ctggttctaa ggtttactct tccaccttca atccaacttc caaaaacttg    900
ttggaaccta ccgaagcagg tatggctcaa gtttctgtca agtgttgctc atgtatctac    960
gctgatgctt tagcaacagc agctttgttg aaaaacgatc ctgctgccgt tagaaggatc   1020
ttagataact ggagatatgt cagagatact gttactgact acaccactta cacaagggaa   1080
ggtgaaagag ttgctaagat gttggaaatt gctaccgaag atgctgaaat gagagcaaag   1140
agaatcaagg gctctttacc agcaagagtt atcattgttg gtggtggttt ggccggttgt   1200
tccgcagcta tcgaagcagc taactgtggc gcccacgtca tcttgttaga aaaggaacca   1260
aagttaggtg gtaactctgc aaaggctacc tccggtatca acgcctgggg tactagagca   1320
caagcaaaac aaggtgtcat ggacggcggc aagtttttcg aaagagatac ccatagatcc   1380
ggcaagggtg gtaattgcga tccatgcctt gttaagactt tgtccgttaa gtcctctgat   1440
gcagttaagt ggttatctga attaggtgtt ccattgactg ttttgtctca attaggtggt   1500
gcttcaagga aacgttgtca ccgtgcacca gataagtctg atggtacacc agtcccagtt   1560
ggtttcacca ttatgaaaac ccttgaaaac cacattgtca acgatttgtc cagacatgtt   1620
acagttatga caggtattac cgtcacagct ttagaatcta catcaagagt cagacctgat   1680
ggtgttttag tcaagcatgt tactggtgtt cacttgattc aggcatctgg tcaatctatg   1740
gttttgaatg cagacgctgt tatcttagct actggtggtt tctccaatga tcatacccca   1800
aactcccttt tacaacaata cgccccacag ttgtcatctt ttccaacaac caatggtgtc   1860
tgggcaactg gcgatggtgt taagatggct tccaagttgg gtgtcgcctt agttgatatg   1920
gataaggtcc aattacatcc taccggcttg ttagacccaa aagatccatc taatagaacc   1980
aagtatcttg gtccagaggc cttaagaggt tccggcggtg tcttgttaaa caaaaacggt   2040
gaaagatttg ttaatgaatt agacttaaga tctgttgtct ctcaagctat catcgcacaa   2100
gataatgagt acccaggctc tggtggttcc aagttcgcat actgtgtttt gaacgaaact   2160
gcagcaaagt tattcggcaa aaacttcctt ggtttctact ggaatagatt aggtcttttc   2220
caaaaggttg attccgttgc tggtttagct aagttgattg gttgtccaga agctaatgtt   2280
gttgctacat tgaagcaata tgaggagtta tcttccaaaa agcttaatcc ttgtccattg   2340
actggcaagt ctgtctttcc ttgtgtttta ggcactcaag gtccatacta tgttgccttg   2400
gttaccccat ccattcacta cactatgggt ggttgtttga tttccccatc tgctgagatg   2460
caaaccattg acaactctgg tgttactcct gtcagacgtc caatcttagg cttattcggt   2520
gctggtgaag ttactggcgg tgtccatggt ggtaacagat taggcggtaa ctctttgtta   2580
ggacgtgttg ttttcggcaa gatcgctggt gacagagctg caaccatctt gcaaaagaaa   2640
aacaccggct tatcaatgac agaatggtct actgtcgtct taagagaagt tagagaaggt   2700
ggtgtctatg gtgctggttc cagagttttg aggtttaaca tgcctggtgc attacagaga   2760
actggtttag ctttaggtca attcatcggt atcagaggtg attgggacgg tcacagattg   2820
atcggttact attctccaat cactttacct gatgatgttg gtgttattgg tatcttagct   2880
agagcagaca agggtagatt ggcagaatgg atttctgcat tgcagccagg tgacgctgtt   2940
gagatgaagg cctgcggtgg tcttatcatt gacagaagat tcgctgaaag acatttcttt   3000
ttccgtggtc ataagatcag aaagttggcc cttatcggtg gtggtactgg tgttgcacca   3060
```

```
atgttacaaa tcgtcagagc tgctgtcaaa aagccatttg tcgattcaat tgagtccatt   3120

cagttcatct atgctgcaga ggatgtttcc gagcttacat acagaacctt acttgaatct   3180

tacgaagagg aatatggttc agaaaagttt aagtgtcact tcgttttgaa taacccacca   3240

gctcaatgga ctgacggtgt tggtttcgtt gatactgcat tgttgagatc cgcagttcaa   3300

gcaccatcaa atgatttgct tgttgcaatt tgtggtccac caatcatgca aagagcagtt   3360

aagggtgcat tgaaaggttt aggttacaat atgaatcttg ttagaaccgt tgacgaaact   3420

gaaccaccat cataa                                                    3435
```

<210> SEQ ID NO 36
<211> LENGTH: 3435
<212> TYPE: DNA
<213> ORGANISM: Artificial
<220> FEATURE:
<223> OTHER INFORMATION: Mutated L. mexicana FRD gene

<400> SEQUENCE: 36

```
atggctgatg gcaaaacctc tgcatcagtt gttgctgttg atgctgaacg tgccgctaag     60

gaaagagatg cagcagctag agctatgttg caaggtggtg gtgtctctcc tgctggcaag    120

gcacaattgt tgaaaaaggg tttggttcac actgttccat ataccttaaa ggttgtcgtc    180

gcagatccaa aggaaatgga gaaggcaact gctgacgcag aagaggtttt acaagctgca    240

tttcaagtcg tcgacaccct tttgaacaac tttaacgaaa actcagaagt ttcaagagtc    300

aataggttgg cagttggtga ggaacatcaa atgtctgaaa cattgaaaca cgtcatggcc    360

tgttgtcaaa aggtttatca ttcctccaga ggtgtttttg acccagcagt tggtccatta    420

gtccgtgaac ttagagaagc tgctcacaag ggtaaaactg ttccagccga aagagttaat    480

gatttgttat ccaaatgtac ccttaatgca tctttttcaa ttgatatgtc cagaggtatg    540

attgcaagga agcatccaga cgccatgttg gatttgggtg gtgtcaacaa gggttatggt    600

atcgactaca ttgttgaaca cttaaactct ttgggttatg atgatgtctt tttcgaatgg    660

ggtggtgatg ttagagcatc cggcaaaaac cagttatctc aaccttgggc tgttggtatt    720

gttagaccac ctgccttggc cgacattaga actgttgtcc cagaggacaa aagatccttt    780

atccgtgtcg tcagattgaa caacgaagct attgctacct ctggtgatta tgagaatttg    840

gttgaaggtc ctggttctaa ggtttactct tccaccttca atccaacttc caaaaacttg    900

ttggaaccta ccgaagcagg tatggctcaa gtttctgtca agtgttgctc atgtatctac    960

gctgatgctt tagcaacagc agctttgttg aaaaacgatc ctgctgccgt tagaaggatc   1020

ttagataact ggagatatgt cagagatact gttactgact acaccactta cacaagggaa   1080

ggtgaaagag ttgctaagat gttggaaatt gctaccgaag atgctgaaat gagagcaaag   1140

agaatcaagg gctctttacc agcaagagtt atcattgttg gtggtggttt ggccggttgt   1200

tccgcagcta tcgaagcagc taactgtggc gcccacgtca tcttgttaga aaaggaacca   1260

aagttaggtg gtaactctgc aaaggctacc tccggtatca acgcctgggg tactagagca   1320

caagcaaaac aaggtgtcat ggacggcggc aagtttttcg aaagagatac ccatagatcc   1380

ggcaagggtg gtaattgcga tccatgcctt gttaagactt tgtccgttaa gtcctctgat   1440

gcagttaagt ggttatctga attaggtgtt ccattgactg ttttgtctca attaggtggt   1500

gcttcaagga aacgttgtca ccgtgcacca gataagtctg atggtacacc agtcccagtt   1560

ggtttcacca ttatgaaaac ccttgaaaac cacattgtca acgatttgtc cagacatgtt   1620

acagttatga caggtattac cgtcacagct ttagaatcta catcaagagt cagacctgat   1680
```

```
ggtgttttag tcaagcatgt tactggtgtt cacttgattc aggcatctgg tcaatctatg   1740
gttttgaatg cagacgctgt tatcttagct actggtggtt tctccaatga tcatacccca   1800
aactcccttt tacaacaata cgccccacag ttgtcatctt ttccaacaac caatggtgtc   1860
tgggcaactg gcgatggtgt taagatggct tccaagttgg gtgtcgcctt agttgatatg   1920
gataaggtcc aattacatcc taccggcttg ttagacccaa aagatccatc taatagaacc   1980
aagtatcttg gtccagaggc cttaagaggt tccggcggtg tcttgttaaa caaaaacggt   2040
gaaagatttg ttaatgaatt agacttaaga tctgttgtct ctcaagctat catcgcacaa   2100
gataatgagt acccaggctc tggtggttcc aagttcgcat actgtgtttt gaacgaaact   2160
gcagcaaagt tattcggcaa aaacttcctt ggtttctact ggaatagatt aggtcttttc   2220
caaaaggttg attccgttgc tggtttagct aagttgattg gttgtccaga agctaatgtt   2280
gttgctacat tgaagcaata tgaggagtta tcttccaaaa agcttaatcc ttgtccattg   2340
actggcaagt ctgtctttcc ttgtgtttta ggcactcaag gtccatacta tgttgccttg   2400
gttaccccat ccattcacta cactatgggt ggttgtttga tttccccatc tgctgagatg   2460
caaaccattg acaactctgg tgttactcct gtcagacgtc caatcttagg cttattcggt   2520
gctggtgaag ttactggcgg tgtccatggt ggtaacagat taggcggtaa ctctttgtta   2580
gaatgtgttg ttttcggcaa gatcgctggt gacagagctg caaccatctt gcaaaagaaa   2640
aacaccggct tatcaatgac agaatggtct actgtcgtct taagagaagt tagagaaggt   2700
ggtgtctatg gtgctggttc cagagttttg aggtttaaca tgcctggtgc attacagaga   2760
actggtttag ctttaggtca attcatcggt atcagaggtg attgggacgg tcacagattg   2820
atcggttact attctccaat cactttacct gatgatgttg gtgttattgg tatcttagct   2880
agagcagaca agggtagatt ggcagaatgg atttctgcat tgcagccagg tgacgctgtt   2940
gagatgaagg cctgcggtgg tcttatcatt gacagaagat tcgctgaaag acatttcttt   3000
ttccgtggtc ataagatcag aaagttggcc cttatcggtg gtggtactgg tgttgcacca   3060
atgttacaaa tcgtcagagc tgctgtcaaa aagccattgg tcggtcgaat tgagtccatt   3120
cagttcatct atgctgcaga ggatgtttcc gagcttacat acagaacctt acttgaatct   3180
tacgaagagg aatatggttc agaaaagttt aagtgtcact tcgttttgaa taacccacca   3240
gctcaatgga ctgacggtgt tggtttcgtt gatactgcat tgttgagatc cgcagttcaa   3300
gcaccatcaa atgatttgct tgttgcaatt tgtggtccac caatcatgca aagagcagtt   3360
aagggtgcat tgaaaggttt aggttacaat atgaatcttg ttagaaccgt tgacgaaact   3420
gaaccaccat cataa                                                    3435
```

<210> SEQ ID NO 37
<211> LENGTH: 3420
<212> TYPE: DNA
<213> ORGANISM: Artificial
<220> FEATURE:
<223> OTHER INFORMATION: Mutated T.brucei FRD gene

<400> SEQUENCE: 37

```
atggttgatg gtagatcttc agcttctatt gttgcagttg atccagaaag agcagcaaga     60
gaaagagatg ctgcagctag agctttgtta caagattctc cattgcacac taccatgcaa    120
tatgctacct ccggtttaga attgaccgtc ccttatgcat tgaaagttgt tgcatctgcc    180
gacaccttcg atagagctaa ggaagttgca gatgaagtcc ttagatgtgc ctggcaattg    240
```

-continued

```
gctgatacag tccttaactc ctttaaccca aactctgaag tctctcttgt tggtagactt    300
ccagtcggtc agaagcatca aatgtccgcc ccacttaaga gagttatggc ttgttgtcaa    360
agagtttaca attcctctgc tggttgtttc gacccatcca ccgccccagt tgcaaaggct    420
ttgcgtgaaa tcgctttagg caaggagaga aacaatgcct gtttggaggc tttaacacaa    480
gcatgcactt tgccaaactc tttcgtcatt gactttgaag caggtactat ctcacgtaaa    540
catgaacatg cttcacttga cttaggtggt gtttcaaagg gttacatcgt tgactatgtt    600
attgataaca ttaacgcagc tggtttccaa aatgtctttt tcgattgggg tggtgattgt    660
agagcctccg gtatgaatgc tagaaatacc ccttgggttg ttggtattac tagaccacca    720
tcattagata tgttaccaaa cccaccaaag gaagcatcct atatctctgt tatctcattg    780
gacaacgaag ctttggcaac ctccggtgat tacgagaatt tgatctacac agctgatgac    840
aagcctttaa cttgtactta cgattggaag ggcaaggaac ttatgaagcc atctcaatca    900
aacattgccc aagtttcagt taagtgctat tcagcaatgt acgctgacgc tttagccacc    960
gcttgtttca tcaaaagaga tccagccaag gttagacaat tgttagatgg ttggagatac   1020
gttagagata ctgtcagaga ttacagagtt tatgttagag aaaatgagag agtcgctaag   1080
atgtttgaaa ttgcaaccga agatgctgaa atgagaaaaa gacgtatctc taatactttg   1140
cctgcaagag tcatcgttgt cggtggcggt ttagcaggtt tatctgcagc aattgaagct   1200
gcaggctgcg gtgcacaagt cgttttgatg ggaaaggaag ctaagttagg tggtaactct   1260
gcaaaggcaa cctctggtat caatggttgg ggtactagag cccaagcaaa ggcttccatt   1320
gttgacggtg gcaagtattt cgaaagagat acttacaaat ctggtattgg tggtaatacc   1380
gacccagctt tagttaagac tctttccatg aagtctgctg acgctattgg ttggttaaca   1440
tcattaggtg ttcctttaac agtcttatca caattgggtg gtcattccag aaagagaact   1500
cacagagcac cagacaaaaa ggatggcacc ccattaccta ttggttttac cattatgaaa   1560
accttagaag atcacgtcag aggtaatctt tctggtagaa ttactatcat ggaaaactgt   1620
tccgttacct ctttactttc tgaaactaag gaaagaccag atggtactaa acaaatcaga   1680
gttaccggtg ttgagttcac tcaagcaggc tctggcaaaa ctaccatttt ggccgacgca   1740
gtcatcttgg ccactggtgg tttctctaac gacaagaccg cagactcttt gttgagagaa   1800
catgcccctc acttagttaa ctttcctaca actaacggtc cttgggcaac tggtgacggt   1860
gttaagcttg ctcaaagatt aggtgcacaa ttggtcgaca tggataaggt tcaattgcat   1920
ccaactggtt tgattaaccc aaaagatcca gctaatccaa caaagttttt gggtccagaa   1980
gctttaagag gttccggtgg tgtcttgtta aacaaacagg gtaaaagatt tgttaacgaa   2040
ttagatttgc gttctgttgt ttccaaggcc attatggaac aaggtgctga atacccaggc   2100
tctggtggtt ctatgttcgc atattgtgtc cttaatgcag ctgcacaaaa gttgtttggt   2160
gtctcttccc acgagttcta ctggaaaaag atgggtttgt tcgttaaggc tgatactatg   2220
agagatttgg cagcattgat tggttgtcca gtcgagtctg ttcaacaaac tttagaggaa   2280
tatgaaagat tatctatttc tcagagatcc tgtccaatca ctagaaaatc tgtttaccca   2340
tgtgttttgg gcactaaggg tccatactac gttgctttcg tcaccccatc tattcactat   2400
acaatgggtg gttgtttgat ttccccatca gcagaaattc agatgaaaaa cacctcctcc   2460
cgtgctccat tgtcccattc caaccctatc ttgggtttgt tcggtgctgg tgaagttact   2520
ggtggtgtcc acggtggcaa tagattaggt ggtaactcat tgttagaatg tgttgtcttt   2580
ggtagaattg ctggtgatag agcttctacc attttgcaga gaaagtcctc cgcattatct   2640
```

ttcaaggtct ggactaccgt tgttttgaga gaagttagag aaggtggcgt ctatggtgcc 2700
ggttcaagag ttttgagatt caacttgcct ggtgctttac aaagatccgg tttgtccttg 2760
ggtcaattca tcgcaatcag aggtgactgg gatggtcaac aattgattgg ttactattcc 2820
ccaattacat tgccagatga cttgggtatg attgacattt tggctagatc cgataaaggt 2880
actttaagag aatggatttc tgctttagaa ccaggcgacg ctgttgagat gaaagcatgc 2940
ggtggtttag tcatcgagag aagattgtca gataagcact ttgtctttat gggtcacatc 3000
attaacaagt tatgtttgat cgctggtggt acaggcgttg cacctatgtt acaaatcatt 3060
aaggcagcat tcatgaaacc ttttatcgat accttagaat ctgtccatct tatctatgct 3120
gcagaagatg ttaccgagtt aacttataga gaagttttag aggagcgtag aagagagtct 3180
cgtggcaagt tcaaaaagac ctttgttttg aacagacctc caccactttg gactgatggt 3240
gttggtttca tcgatagagg tatcttaact aatcatgtcc aaccaccatc cgataacctt 3300
ttggttgcaa tctgtggtcc acctgtcatg cagcgtattg ttaaggccac cttaaagact 3360
ttgggttaca atatgaatct tgttagaaca gttgacgaaa cagaaccatc cggttcctaa 3420

<210> SEQ ID NO 38
<211> LENGTH: 3889
<212> TYPE: DNA
<213> ORGANISM: Artificial
<220> FEATURE:
<223> OTHER INFORMATION: GPD gene deletion fragment

<400> SEQUENCE: 38
ccttcattta cgaaataaag tgccgcggtt acgcagcaca caccagcaat cacgtgcagt 60
gtctttttct tttttttttc ttttttttcc tctttttctt ttgttttgtt tcgtttcttt 120
tccgccagtt cccgttttcc atttccggaa caacaatggg actccactgt tttctttccc 180
cccttccgtt ttcggctcgc agtctgtaca tgcacgttta tccgacacct gtcttgtttg 240
gcgcgtaatt aatacagttt ctccggagtc caggtctcgg acgggtaatt tacacgtcat 300
cattcatttc tgtgtcaaga gaggtagcgc aaaaagtaga aatggtgaac cacgggaatg 360
acttgctgga aatcgacgcc agagtccatt tgaaaaccta cctctacaag agaggaaaca 420
cactacaggg tgtccctggt ccgtaaaatg gcgtaatatg atgacttccc tctatagacg 480
ttgtatttcc agctccaaca tggttaaact attgctatgg tgatggtatt acagatagta 540
aaagaaggaa ggggggtgg caatctcacc ctaacagtta ctaagaacgt ctacttcatc 600
tactgtcaat atacattggc cacatgccga gaaattacgt cgacgccaaa gaagggctca 660
gccgaaaaaa gaaatggaaa acttggccga aaagggaaac aaacaaaaag gtgatgtaaa 720
attagcggaa aggggaattg gcaaattgag ggagaaaaaa aaaaggcaga aaaggaggcg 780
gaaagtcagt acgttttgaa ggcgtcattg gttttccctt ttgcagagtg tttcatttct 840
tttgtttcat gacgtagtgg cgtttctttt cctgcacttt agaaatctat cttttcctta 900
tcaagtaaca agcggttggc aaaggtgtat ataaatcaag gaattcccac tttgaaccct 960
ttgaattttg atatcgttta ttttaaattt atttgcggcc gcggatccct cgaggcctta 1020
attaacatct gaatgtaaaa tgaacattaa aatgaattac taaactttac gtctacttta 1080
caatctataa actttgttta atcatataac gaaatacact aatacacaat cctgtacgta 1140
tgtaatactt ttatccatca aggattgaga aaaaaaagta atgattccct gggccattaa 1200
aacttagacc cccaagcttg gataggtcac tctctatttt cgtttctccc ttccctgata 1260

```
gaagggtgat atgtaattaa gaataatata taattttata ataaaagaat tcatagcctc   1320
atgaaatcag ccatttgctt ttgttcaacg atcttttgaa attgttgttg ttcttggtag   1380
ttaagttgat ccatcttggc ttatgttgtg tgtatgttgt agttattctt agtatattcc   1440
tgtcctgagt ttagtgaaac ataatatcgc cttgaaatga aaatgctgaa attcgtcgac   1500
atacaatttt tcaaactttt tttttttctt ggtgcacgga catgttttta aaggaagtac   1560
tctataccag ttattcttca caaatttaat tgctggagaa tagatcttca acgctttaat   1620
aaagtagttt gtttgtcaag gatggcgtca tacaaagaaa gatcagaatc acacacttcc   1680
cctgttgcta ggagactttt ctccatcatg gaggaaaaga agtctaacct ttgtgcatca   1740
ttggatatta ctgaaactga aaagcttctc tctattttgg acactattgg tccttacatc   1800
tgtctagtta aaacacacat cgatattgtt tctgatttta cgtatgaagg aactgtgttg   1860
cctttgaagg agcttgccaa gaaacataat tttatgattt ttgaagatag aaaatttgct   1920
gatattggta acactgttaa aaatcaatat aaatctggtg tcttccgtat tgccgaatgg   1980
gctgacatca ctaatgcaca tggtgtaacg ggtgcaggta ttgtttctgg cttgaaggag   2040
gcagcccaag aaacaaccag tgaacctaga ggtttgctaa tgcttgctga gttatcatca   2100
aagggttctt tagcatatgg tgaatataca gaaaaaacag tagaaattgc taaatctgat   2160
aaagagtttg tcattggttt tattgcgcaa cacgatatgg gcggtagaga agaaggtttt   2220
gactggatca ttatgactcc aggggttggt ttagatgaca aaggtgatgc acttggtcaa   2280
caatatagaa ctgttgatga agttgtaaag actggaacgg atatcataat tgttggtaga   2340
ggtttgtacg gtcaaggaag agatcctata gagcaagcta aaagatacca acaagctggt   2400
tggaatgctt atttaaacag atttaaatga ttcttacaca aagatttgat acatgtacac   2460
tagtttaaat aagcatgaaa agaattacac aagcaaaaaa aaaaaaataa atgaggtact   2520
ttacgttcac ctacaaccaa aaaaaactaga tagagtaaaa tcttaagatt tagaaaaagt   2580
tgtttaacaa aggctttagt atgtgaattt ttaatgtagc aaagcgataa ctaataaaca   2640
taaacaaaag tatggttttc tttatcagtc aaatcattat cgattgattg ttccgcgtat   2700
ctgcagatag cctcatgaaa tcagccattt gcttttgttc aacgatcttt tgaaattgtt   2760
gttgttcttg gtagttaagt tgatccatct tggcttatgt tgtgtgtatg ttgtagttat   2820
tcttagtata ttcctgtcct gagtttagtg aaacataata tcgccttgaa atgaaaatgc   2880
tgaaattcgt cgacatacaa tttttcaaac tttttttttt tcttggtgca cggacatgtt   2940
tttaaaggaa gtactctata ccagttattc ttcacaaatt taattgctgg agaatagatc   3000
ttcaacgccc cgggggatct ggatccgcgg ccgcaataac ctcagggaga actttggcat   3060
tgtactctcc attgacgagt ccgccaaccc attcttgtta aacctaacct tgcattatca   3120
cattcccttt gacccccttt agctgcattt ccacttgtct acattaagat tcattacaca   3180
ttctttttcg tatttctctt acctccctcc cccctccatg gatcttatat ataaatcttt   3240
tctataacaa taatatctac tagagttaaa caacaattcc acttggcatg gctgtctcag   3300
caaatctgct tctacctact gcacgggttt gcatgtcatt gtttctagca gggaatcgtc   3360
catgtacgtt gtcctccatg atggtcttcc cgctgccact ttctttagta tcttaaatag   3420
agcagatctt acgtccactg tgcatccgtg caccccgaaa atcgtatggt tttccttgcc   3480
acctctcaca attttgaata tgctcaacgc gaaagagagg ggaagaggaa tcgcattcgt   3540
agagtggcta cattcaaccc tgacaaagga actagcgttt gtgcaggaga gagtggtttg   3600
catagatttc ctttcctttg caagcatatt atatagagta gccaatacag taacagctac   3660
```

```
agcacaaaaa agagaacgag aacgagaacg agaacaagaa caagaactag cactactgtc   3720

actgccagca tcaacattac taccattatt ccaacatgtt tgcaactaga aatataacca   3780

ttggtgtcag aacactcaga ccaaccagtt tcttgaaaac aaggtctttt ctgcaacaga   3840

ggctacaatc aacgctaaag aagagctatg aaccaaccaa atccgagct              3889
```

<210> SEQ ID NO 39
<211> LENGTH: 3889
<212> TYPE: DNA
<213> ORGANISM: Artificial
<220> FEATURE:
<223> OTHER INFORMATION: GPD gene deletion fragment

<400> SEQUENCE: 39

```
ccttcattta cgaaataaag tgccgcggtt acgcagcaca caccagcaat cacgtgcagt     60

gtctttttct tttttttttc ttttttttcc tctttttctt ttgttttgtt tcgtttcttt    120

tccgccagtt cccgttttcc atttccggaa caacaatggg actccactgt tttctttccc    180

cccttccgtt ttcggctcgc agtctgtaca tgcacgttta tccgacacct gtcttgtttg    240

gcgcgtaatt aatacagttt ctccggagtc caggtctcgg acgggtaatt tacacgtcat    300

cattcatttc tgtgtcaaga gaggtagcgc aaaaagtaga aatggtgaac cacgggaatg    360

acttgctgga aatcgacgcc agagtccatt tgaaaaccta cctctacaag agaggaaaca    420

cactacaggg tgtccctggt ccgtaaaatg gcgtaatatg atgacttccc tctatagacg    480

ttgtatttcc agctccaaca tggttaaact attgctatgg tgatggtatt acagatagta    540

aaagaaggaa ggggggtgg caatctcacc ctaacagtta ctaagaacgt ctacttcatc    600

tactgtcaat atacattggc cacatgccga gaaattacgt cgacgccaaa gaagggctca    660

gccgaaaaaa gaaatggaaa acttggccga aaagggaaac aaacaaaaag gtgatgtaaa    720

attagcggaa aggggaattg gcaaattgag ggagaaaaaa aaaaggcaga aaaggaggcg    780

gaaagtcagt acgttttgaa ggcgtcattg gttttccctt ttgcagagtg tttcatttct    840

tttgtttcat gacgtagtgg cgtttctttt cctgcacttt agaaatctat cttttcctta    900

tcaagtaaca agcggttggc aaaggtgtat ataaatcaag gaattcccac tttgaaccct    960

ttgaattttg atatcgttta ttttaaattt atttgcggcc gcggatccag atcccccggg   1020

gcgttgaaga tctattctcc agcaattaaa tttgtgaaga ataactggta tagagtactt   1080

cctttaaaaa catgtccgtg caccaagaaa aaaaaaaagt ttgaaaaatt gtatgtcgac   1140

gaatttcagc attttcattt caaggcgata ttatgtttca ctaaactcag gacaggaata   1200

tactaagaat aactacaaca tacacacaac ataagccaag atggatcaac ttaactacca   1260

agaacaacaa caatttcaaa agatcgttga acaaaagcaa atggctgatt tcatgaggct   1320

atctgcagat acgcggaaca atcaatcgat aatgatttga ctgataaaga aaaccatact   1380

tttgtttatg tttattagtt atcgctttgc tacattaaaa attcacatac taaagccttt   1440

gttaaacaac tttttctaaa tcttaagatt ttactctatc tagttttttt ggttgtaggt   1500

gaacgtaaag tacctcattt attttttttt ttttgcttgt gtaattcttt tcatgcttat   1560

ttaaactagt gtacatgtat caaatctttg tgtaagaatc atttaaatct gtttaaataa   1620

gcattccaac cagcttgttg gtatctttta gcttgctcta taggatctct tccttgaccg   1680

tacaaacctc taccaacaat tatgatatcc gttccagtct ttacaacttc atcaacagtt   1740

ctatattgtt gaccaagtgc atcacctttg tcatctaaac caacccctgg agtcataatg   1800
```

```
atccagtcaa aaccttcttc tctaccgccc atatcgtgtt gcgcaataaa accaatgaca   1860
aactctttat cagatttagc aatttctact gtttttctg tatattcacc atatgctaaa    1920
gaaccctttg atgataactc agcaagcatt agcaaacctc taggttcact ggttgtttct   1980
tgggctgcct ccttcaagcc agaaacaata cctgcacccg ttacaccatg tgcattagtg   2040
atgtcagccc attcggcaat acggaagaca ccagatttat attgattttt aacagtgtta   2100
ccaatatcag caaattttct atcttcaaaa atcataaaat tatgtttctt ggcaagctcc   2160
ttcaaaggca acacagttcc ttcatacgta aaatcagaaa caatatcgat gtgtgtttta   2220
actagacaga tgtaaggacc aatagtgtcc aaaatagaga gaagcttttc agtttcagta   2280
atatccaatg atgcacaaag gttagacttc ttttcctcca tgatggagaa aagtctccta   2340
gcaacagggg aagtgtgtga ttctgatctt tctttgtatg acgccatcct tgacaaacaa   2400
actactttat taaagcgttg aagatctatt ctccagcaat taaatttgtg aagaataact   2460
ggtatagagt acttccttta aaaacatgtc cgtgcaccaa gaaaaaaaaa aagtttgaaa   2520
aattgtatgt cgacgaattt cagcattttc atttcaaggc gatattatgt ttcactaaac   2580
tcaggacagg aatatactaa gaataactac aacatacaca caacataagc caagatggat   2640
caacttaact accaagaaca acaacaattt caaaagatcg ttgaacaaaa gcaaatggct   2700
gatttcatga ggctatgaat tcttttatta taaaattata tattattctt aattacatat   2760
caccccttcta tcagggaagg gagaaacgaa aatagagagt gacctatcca agcttggggg  2820
tctaagtttt aatggcccag ggaatcatta cttttttttc tcaatccttg atggataaaa   2880
gtattacata cgtacaggat tgtgtattag tgtatttcgt tatatgatta aacaaagttt   2940
atagattgta aagtagacgt aaagtttagt aattcatttt aatgttcatt ttacattcag   3000
atgttaatta aggcctcgag ggatccgcgg ccgcaataac ctcagggaga actttggcat   3060
tgtactctcc attgacgagt ccgccaaccc attcttgtta aacctaacct tgcattatca   3120
cattcccttt gaccccccttt agctgcattt ccacttgtct acattaagat tcattacaca  3180
ttctttttcg tatttctctt acctccctcc cccctccatg gatcttatat ataaatcttt   3240
tctataacaa taatatctac tagagttaaa caacaattcc acttggcatg gctgtctcag   3300
caaatctgct tctacctact gcacgggttt gcatgtcatt gtttctagca gggaatcgtc   3360
catgtacgtt gtcctccatg atggtcttcc cgctgccact ttctttagta tcttaaatag   3420
agcagatctt acgtccactg tgcatccgtg caccccgaaa atcgtatggt tttccttgcc   3480
acctctcaca attttgaata tgctcaacgc gaaagagagg ggaagaggaa tcgcattcgt   3540
agagtggcta cattcaaccc tgacaaagga actagcgttt gtgcaggaga gagtggtttg   3600
catagatttc ctttcctttg caagcatatt atatagagta gccaatacag taacagctac   3660
agcacaaaaa agagaacgag aacgagaacg agaacaagaa caagaactag cactactgtc   3720
actgccagca tcaacattac taccattatt ccaacatgtt tgcaactaga aatataacca   3780
ttggtgtcag aacactcaga ccaaccagtt tcttgaaaac aaggtctttt ctgcaacaga   3840
ggctacaatc aacgctaaag aagagctatg aaccaaccaa atccgagct               3889
```

```
<210> SEQ ID NO 40
<211> LENGTH: 3175
<212> TYPE: DNA
<213> ORGANISM: Artificial
<220> FEATURE:
<223> OTHER INFORMATION: PGI gene deletion construct

<400> SEQUENCE: 40
```

```
cttcgctcgc catctatatc ttcaacgaac aacggaatta caaacatggg cagtagttca     60
aacaatctcc agactctcaa ctctctctcg ctatcgttga aacatccaca gttccaaggc    120
ctattctccc cactggatgt ccacagtccg tacgaacaga acgtttcttc cccactggcc    180
cccaccgttc cggctgttcc gggaaccgca ccttcattcg agtcggacga tctctacaat    240
gcaacggctg cccgcaaaag agactctctc aagatgaaga gaagatagac gctacatcat    300
tgtctgtgca gtacctaata tatagtactt ggtataaggt ataataaagc tataaaatta    360
taataatctt aataataata accatattaa tggaaggatg aggcccgatg tcctttttt     420
tgcctttcta ctatagtgct tacattgtgt ataaattctc gcggccgcgg atccctcgag    480
gccttaatta acatctgaat gtaaaatgaa cattaaaatg aattactaaa ctttacgtct    540
actttacaat ctataaactt tgtttaatca tataacgaaa tacactaata cacaatcctg    600
tacgtatgta atacttttat ccatcaagga ttgagaaaaa aaagtaatga ttccctgggc    660
cattaaaact tagaccccca agcttggata ggtcactctc tattttcgtt tctcccttcc    720
ctgatagaag ggtgatatgt aattaagaat aatatataat tttataataa aagaattcat    780
agcctcatga aatcagccat ttgcttttgt tcaacgatct tttgaaattg ttgttgttct    840
tggtagttaa gttgatccat cttggcttat gttgtgtgta tgttgtagtt attcttagta    900
tattcctgtc ctgagtttag tgaaacataa tatcgccttg aaatgaaaat gctgaaattc    960
gtcgacatac aatttttcaa actttttttt tttcttggtg cacggacatg tttttaaagg   1020
aagtactcta taccagttat tcttcacaaa tttaattgct ggagaataga tcttcaacgc   1080
tttaataaag tagtttgttt gtcaaggatg gcgtcataca aagaaagatc agaatcacac   1140
acttcccctg ttgctaggag acttttctcc atcatggagg aaaagaagtc taacctttgt   1200
gcatcattgg atattactga aactgaaaag cttctctcta ttttggacac tattggtcct   1260
tacatctgtc tagttaaaac acacatcgat attgtttctg attttacgta tgaaggaact   1320
gtgttgcctt tgaaggagct tgccaagaaa cataatttta tgatttttga agatagaaaa   1380
tttgctgata ttggtaacac tgttaaaaat caatataaat ctggtgtctt ccgtattgcc   1440
gaatgggctg acatcactaa tgcacatggt gtaacgggtg caggtattgt ttctggcttg   1500
aaggaggcag cccaagaaac aaccagtgaa cctagaggtt tgctaatgct tgctgagtta   1560
tcatcaaagg gttctttagc atatggtgaa tatacagaaa aaacagtaga aattgctaaa   1620
tctgataaag agtttgtcat tggttttatt gcgcaacacg atatgggcgg tagagaagaa   1680
ggttttgact ggatcattat gactccaggg gttggtttag atgacaaagg tgatgcactt   1740
ggtcaacaat atagaactgt tgatgaagtt gtaaagactg gaacggatat cataattgtt   1800
ggtagaggtt tgtacggtca aggaagagat cctatagagc aagctaaaag ataccaacaa   1860
gctggttgga atgcttattt aaacagattt aaatgattct tacacaaaga tttgatacat   1920
gtacactagt ttaaataagc atgaaaagaa ttacacaagc aaaaaaaaaa aaataaatga   1980
ggtactttac gttcacctac aaccaaaaaa actagataga gtaaaatctt aagatttaga   2040
aaaagttgtt taacaaaggc tttagtatgt gaatttttaa tgtagcaaag cgataactaa   2100
taaacataaa caaaagtatg gttttcttta tcagtcaaat cattatcgat tgattgttcc   2160
gcgtatctgc agatagcctc atgaaatcag ccatttgctt ttgttcaacg atcttttgaa   2220
attgttgttg ttcttggtag ttaagttgat ccatcttggc ttatgttgtg tgtatgttgt   2280
agttattctt agtatattcc tgtcctgagt ttagtgaaac ataatatcgc cttgaaatga   2340
```

```
aaatgctgaa attcgtcgac atacaatttt tcaaactttt ttttttttctt ggtgcacgga   2400
catgttttta aaggaagtac tctataccag ttattcttca caaatttaat tgctggagaa   2460
tagatcttca acgccccggg ggatctggat ccgcggccgc gttaacgaaa gttccaaact   2520
ttatttataa tgtgtttatg tttgtatttt aatcactctt tatgacctat atatgaagct   2580
tttagcatta tcgcagcaag tataaatgga tgcatgtaaa ttccatagtt catatagtgc   2640
gatttggtga atttttgaaa tttttgctaa tggataatat actctatatt tttacactgt   2700
gtttactgat gcctcttccg aatttctttc tttcaccact caacccatga aaggcaagga   2760
acacatacat catgattaca ataatataga tatcggggta acaataacag ttcccagaag   2820
aaggaaacaa aaacgtacag gatctacaaa tagtcaaagc actgggtgga agaaattgtt   2880
atggctcaaa caaccttatg acgataacta cacagattcg agcttcttat cacaactgaa   2940
acgaaattca acggttgtaa agtactcgta tgtaaagcta gtcaatgatt tttccatcat   3000
tgtattgcat ctgtcgtcca ttatgtttgt tgttgttgta ttttatggga tctatcagtt   3060
aaattggaac ccgattaaac caacagtgat aagtacgatt tgtacactca ttggattcat   3120
tttttatgtt gtaacattga agataataag aaataaagaa ttgattgaac gagct        3175
```

<210> SEQ ID NO 41
<211> LENGTH: 3175
<212> TYPE: DNA
<213> ORGANISM: Artificial
<220> FEATURE:
<223> OTHER INFORMATION: PGI gene deletion construct

<400> SEQUENCE: 41

```
cgttcaatca attctttatt tcttattatc ttcaatgtta caacataaaa aatgaatcca     60
atgagtgtac aaatcgtact tatcactgtt ggtttaatcg ggttccaatt taactgatag    120
atcccataaa atacaacaac aacaaacata atggacgaca gatgcaatac aatgatggaa    180
aaatcattga ctagctttac atacgagtac tttacaaccg ttgaatttcg tttcagttgt    240
gataagaagc tcgaatctgt gtagttatcg tcataaggtt gtttgagcca taacaatttc    300
ttccacccag tgctttgact atttgtagat cctgtacgtt tttgtttcct tcttctggga    360
actgttattg ttaccccgat atctatatta ttgtaatcat gatgtatgtg ttccttgcct    420
ttcatgggtt gagtggtgaa agaaagaaat tcggaagagg catcagtaaa cacagtgtaa    480
aaatatagag tatattatcc attagcaaaa atttcaaaaa ttcaccaaat cgcactatat    540
gaactatgga atttacatgc atccatttat acttgctgcg ataatgctaa aagcttcata    600
tataggtcat aaagagtgat taaaatacaa acataaacac attataaata aagtttggaa    660
ctttcgttaa cgcggccgcg gatccctcga ggccttaatt aacatctgaa tgtaaaatga    720
acattaaaat gaattactaa actttacgtc tactttacaa tctataaact ttgtttaatc    780
atataacgaa atacactaat acacaatcct gtacgtatgt aatactttta tccatcaagg    840
attgagaaaa aaaagtaatg attccctggg ccattaaaac ttagaccccc aagcttggat    900
aggtcactct ctattttcgt ttctcccttc cctgatagaa gggtgatatg taattaagaa    960
taatatataa ttttataata aaagaattca tagcctcatg aaatcagcca tttgcttttg   1020
ttcaacgatc ttttgaaatt gttgttgttc ttggtagtta agttgatcca tcttggctta   1080
tgttgtgtgt atgttgtagt tattcttagt atattcctgt cctgagttta gtgaaacata   1140
atatcgcctt gaaatgaaaa tgctgaaatt cgtcgacata caatttttca aacttttttt   1200
ttttcttggt gcacggacat gtttttaaag gaagtactct ataccagtta ttcttcacaa   1260
```

```
atttaattgc tggagaatag atcttcaacg ctttaataaa gtagtttgtt tgtcaaggat   1320
ggcgtcatac aaagaaagat cagaatcaca cacttcccct gttgctagga gacttttctc   1380
catcatggag gaaaagaagt ctaacctttg tgcatcattg gatattactg aaactgaaaa   1440
gcttctctct attttggaca ctattggtcc ttacatctgt ctagttaaaa cacacatcga   1500
tattgtttct gattttacgt atgaaggaac tgtgttgcct ttgaaggagc ttgccaagaa   1560
acataatttt atgatttttg aagatagaaa atttgctgat attggtaaca ctgttaaaaa   1620
tcaatataaa tctggtgtct tccgtattgc cgaatgggct gacatcacta atgcacatgg   1680
tgtaacgggt gcaggtattg tttctggctt gaaggaggca gcccaagaaa caaccagtga   1740
acctagaggt ttgctaatgc ttgctgagtt atcatcaaag ggttctttag catatggtga   1800
atatacagaa aaaacagtag aaattgctaa atctgataaa gagtttgtca ttggttttat   1860
tgcgcaacac gatatgggcg gtagagaaga aggttttgac tggatcatta tgactccagg   1920
ggttggttta gatgacaaag gtgatgcact tggtcaacaa tatagaactg ttgatgaagt   1980
tgtaaagact ggaacggata tcataattgt tggtagaggt ttgtacggtc aaggaagaga   2040
tcctatagag caagctaaaa gataccaaca agctggttgg aatgcttatt taaacagatt   2100
taaatgattc ttacacaaag atttgataca tgtacactag tttaaataag catgaaaaga   2160
attacacaag caaaaaaaaa aaaataaatg aggtacttta cgttcaccta caaccaaaaa   2220
aactagatag agtaaaatct taagatttag aaaaagttgt ttaacaaagg ctttagtatg   2280
tgaattttta atgtagcaaa gcgataacta ataaacataa acaaaagtat ggttttcttt   2340
atcagtcaaa tcattatcga ttgattgttc cgcgtatctg cagatagcct catgaaatca   2400
gccatttgct tttgttcaac gatcttttga aattgttgtt gttcttggta gttaagttga   2460
tccatcttgg cttatgttgt gtgtatgttg tagttattct tagtatattc ctgtcctgag   2520
tttagtgaaa cataatatcg ccttgaaatg aaaatgctga aattcgtcga catacaattt   2580
ttcaaacttt tttttttct tggtgcacgg acatgttttt aaaggaagta ctctatacca   2640
gttattcttc acaaatttaa ttgctggaga atagatcttc aacgccccgg gggatctgga   2700
tccgcggccg cgagaattta tacacaatgt aagcactata gtagaaaggc aaaaaaaagg   2760
acatcgggcc tcatccttcc attaatatgg ttattattat taagattatt ataattttat   2820
agctttatta taccttatac caagtactat atattaggta ctgcacagac aatgatgtag   2880
cgtctatctt ctcttcatct tgagagagtc tcttttgcgg gcagccgttg cattgtagag   2940
atcgtccgac tcgaatgaag gtgcggttcc cggaacagcc ggaacggtgg gggccagtgg   3000
ggaagaaacg ttctgttcgt acggactgtg gacatccagt ggggagaata ggccttggaa   3060
ctgtggatgt ttcaacgata gcgagagaga gttgagagtc tggagattgt ttgaactact   3120
gcccatgttt gtaattccgt tgttcgttga agatatagat ggcgagcgaa gggcc        3175
```

<210> SEQ ID NO 42
<211> LENGTH: 3420
<212> TYPE: DNA
<213> ORGANISM: Trypanosoma brucei

<400> SEQUENCE: 42

```
atggttgatg gtagatcttc agcttctatt gttgcagttg atccagaaag agcagcaaga     60
gaaagagatg ctgcagctag agctttgtta caagattctc cattgcacac taccatgcaa    120
tatgctacct ccggtttaga attgaccgtc ccttatgcat tgaaagttgt tgcatctgcc    180
```

```
gacaccttcg atagagctaa ggaagttgca gatgaagtcc ttagatgtgc ctggcaattg    240
gctgatacag tccttaactc ctttaaccca aactctgaag tctctcttgt tggtagactt    300
ccagtcggtc agaagcatca aatgtccgcc ccacttaaga gagttatggc ttgttgtcaa    360
agagtttaca attcctctgc tggttgtttc gacccatcca ccgcccccagt tgcaaaggct   420
ttgcgtgaaa tcgctttagg caaggagaga aacaatgcct gtttggaggc tttaacacaa    480
gcatgcactt tgccaaactc tttcgtcatt gactttgaag caggtactat ctcacgtaaa    540
catgaacatg cttcacttga cttaggtggt gtttcaaagg gttacatcgt tgactatgtt    600
attgataaca ttaacgcagc tggtttccaa aatgtctttt tcgattgggg tggtgattgt    660
agagcctccg gtatgaatgc tagaaatacc ccttgggttg ttggtattac tagaccacca    720
tcattagata tgttaccaaa cccaccaaag gaagcatcct atatctctgt tatctcattg    780
gacaacgaag ctttggcaac ctccggtgat tacgagaatt tgatctacac agctgatgac    840
aagcctttaa cttgtactta cgattggaag ggcaaggaac ttatgaagcc atctcaatca    900
aacattgccc aagtttcagt taagtgctat tcagcaatgt acgctgacgc tttagccacc    960
gcttgtttca tcaaaagaga tccagccaag gttagacaat tgttagatgg ttggagatac   1020
gttagagata ctgtcagaga ttacagagtt tatgttagag aaaatgagag agtcgctaag   1080
atgtttgaaa ttgcaaccga agatgctgaa atgagaaaaa gacgtatctc taatactttg   1140
cctgcaagag tcatcgttgt cggtggcggt ttagcaggtt tatctgcagc aattgaagct   1200
gcaggctgcg gtgcacaagt cgttttgatg gaaaaggaag ctaagttagg tggtaactct   1260
gcaaaggcaa cctctggtat caatggttgg ggtactagag cccaagcaaa ggcttccatt   1320
gttgacggtg gcaagtattt cgaaagagat acttacaaat ctggtattgg tggtaatacc   1380
gacccagctt tagttaagac tctttccatg aagtctgctg acgctattgg ttggttaaca   1440
tcattaggtg ttcctttaac agtcttatca caattgggtg gtcattccag aaagagaact   1500
cacagagcac cagacaaaaa ggatggcacc ccattaccta ttggttttac cattatgaaa   1560
accttagaag atcacgtcag aggtaatctt tctggtagaa ttactatcat ggaaaactgt   1620
tccgttacct ctttactttc tgaaactaag gaaagaccag atggtactaa acaaatcaga   1680
gttaccggtg ttgagttcac tcaagcaggc tctggcaaaa ctaccatttt ggccgacgca   1740
gtcatcttgg ccactggtgg tttctctaac gacaagaccg cagactcttt gttgagagaa   1800
catgcccctc acttagttaa ctttcctaca actaacggtc cttgggcaac tggtgacggt   1860
gttaagcttg ctcaaagatt aggtgcacaa ttggtcgaca tggataaggt tcaattgcat   1920
ccaactggtt tgattaaccc aaaagatcca gctaatccaa caaagttttt gggtccagaa   1980
gctttaagag gttccggtgg tgtcttgtta aacaaacagg gtaaaagatt tgttaacgaa   2040
ttagatttgc gttctgttgt ttccaaggcc attatggaac aaggtgctga atacccaggc   2100
tctggtggtt ctatgttcgc atattgtgtc cttaatgcag ctgcacaaaa gttgtttggt   2160
gtctcttccc acgagttcta ctggaaaaag atgggtttgt tcgttaaggc tgatactatg   2220
agagatttgg cagcattgat tggttgtcca gtcgagtctg ttcaacaaac tttagaggaa   2280
tatgaaagat tatctatttc tcagagatcc tgtccaatca ctagaaaatc tgtttaccca   2340
tgtgttttgg gcactaaggg tccatactac gttgctttcg tcaccccatc tattcactat   2400
acaatgggtg gttgtttgat ttccccatca gcagaaattc agatgaaaaa cacctcctcc   2460
cgtgctccat tgtcccattc caaccctatc ttgggtttgt tcggtgctgg tgaagttact   2520
ggtggtgtcc acggtggcaa tagattaggt ggtaactcat tgttagaatg tgttgtcttt   2580
```

```
ggtagaattg ctggtgatag agcttctacc attttgcaga gaaagtcctc cgcattatct   2640

ttcaaggtct ggactaccgt tgttttgaga gaagttagag aaggtggcgt ctatggtgcc   2700

ggttcaagag ttttgagatt caacttgcct ggtgctttac aaagatccgg tttgtccttg   2760

ggtcaattca tcgcaatcag aggtgactgg gatggtcaac aattgattgg ttactattcc   2820

ccaattacat tgccagatga cttgggtatg attgacattt tggctagatc cgataaaggt   2880

actttaagag aatggatttc tgctttagaa ccaggcgacg ctgttgagat gaaagcatgc   2940

ggtggtttag tcatcgagag aagattgtca gataagcact ttgtctttat gggtcacatc   3000

attaacaagt tatgtttgat cgctggtggt acaggcgttg cacctatgtt acaaatcatt   3060

aaggcagcat tcatgaaacc ttttatcgat accttagaat ctgtccatct tatctatgct   3120

gcagaagatg ttaccgagtt aacttataga gaagttttag aggagcgtag aagagagtct   3180

cgtggcaagt tcaaaaagac ctttgttttg aacagacctc caccactttg gactgatggt   3240

gttggtttca tcgatagagg tatcttaact aatcatgtcc aaccaccatc cgataacctt   3300

ttggttgcaa tctgtggtcc acctgtcatg cagcgtattg ttaaggccac cttaaagact   3360

ttgggttaca atatgaatct tgttagaaca gttgacgaaa cagaaccatc cggttcctaa   3420
```

<210> SEQ ID NO 43
<211> LENGTH: 3420
<212> TYPE: DNA
<213> ORGANISM: Trypanosoma cruzi

<400> SEQUENCE: 43

```
atggctgacg gtagatcctc tgcatctgtt gttgcagttg atccagaaaa ggctgcaaga     60

gaaagagatg aagcagctcg tgctttgtta agagactctc cattacaaac tcatcttcag    120

tacatgacta atggtttaga gttgactgtc ccattcacct taaaggttgt cgctgaagca    180

gttgcatttt ccagagcaaa ggaagttgct gacgaagttt tgaggtcagc ctggcatctt    240

gcagacaccg tcttgaacaa ctttaaccct aactccgaga tttctatgat tggtagatta    300

ccagttggtc aaaaacatac aatgtccgct acattgaagt ctgttatcac atgctgtcag    360

catgttttca attcatccag aggtgttttt gatccagcta ctggtcctat cattgaagct    420

ttaagagcta aggttgctga gaaagcctct gtttctgatg aacagatgga gaagttgttt    480

cgtgtttgta acttctcttc ctcattcatc gttgatttgg aaatgggtac tattgccaga    540

aaacacgaag atgcaagatt tgacttaggt ggtgtttcca agggttacat cgttgactac    600

gttgttgaaa gattgaacgc tgctggtatt gtcgatgtct acttcgaatg ggtggtgac    660

tgtagagctt ccggtactaa cgcaagacgt accccatgga tggttggtat cattagacct    720

ccatctttag aacaattgag aaacccacca aaagatccat cctacattag ggttttacca    780

cttaacgatg aagcactttg tacctctggt gactatgaga atttgaccga aggctctaac    840

aaaaagttgt atacatccat tttcgattgg aaaaagagat ccttgttgga accagttgaa    900

tcagaattgg cccaagtttc cattagatgt tattctgcca tgtatgcaga cgcattagca    960

acagcttctc ttatcaagag agatatcaaa aaggttagac aaatgttgga agattggaga   1020

cacgtccgta atagggttac taactatgtt acctatacca gacaaggtga aagagtcgca   1080

cgtatgtttg aaattgctac tgataacgct gagattagga aaaagagaat tgcaggctct   1140

ttacctgcta gggttattgt tgtcggtggt ggtttagctg gtttgtctgc agcaattgaa   1200

gcaactgcat gtggtgccca agttatcctt ttagaaaagg aacctaaagt tggtggtaat   1260
```

tccgcaaagg ctacatctgg tatcaacggt tggggtacta gagcacaagc tgaacaagat 1320
gtctacgact ctggcaagta cttcgaaaga gatacacaca aatctggttt aggtggttct 1380
accgatccag gcttagttcg tactttatca gtcaagtctg gtgacgctat ttcatggtta 1440
tcttctcttg gtgttccatt aactgtcttg tcacaattag gcggtcattc cagaaaaagg 1500
actcacagag cccctgataa ggcagatggt actccagttc caattggttt caccattatg 1560
caaaccttag aacagcatgt tagaaccaag ttagcagaca gagttactat catggagaat 1620
accaccgtta cctccttgct ttctaagtcc agagttagac atgatggtgc aaagcaagtt 1680
agagtctacg gtgttgaagt cttacaagac gaaggtgtcg tttctcgtat cttggccgat 1740
gctgtcattt tggcaacagg tggtttctcc aatgacaaaa ccccaaactc cttattgcaa 1800
gagttcgctc cacaattgtc aggttttcca acaaccaacg gtccatgggc tactggcgat 1860
ggtgttaagt tagcaagaga acttggtgtc aagttggttg atatggataa ggtccaactt 1920
catccaactg gtttgattga ccctaaggac ccagcaaatc caaccaaata cttaggtcca 1980
gaagcattga gaggttctgg tggtgtcttg ttaaacaaaa agggtgaaag atttgtcaat 2040
gagttggact tgcgttccgt cgtttcaaat gctatcattg aacaaggtga tgaatatcca 2100
gatgccggtg gttccaagtt cgccttctgt gttttgaatg atgcagcagt taagttattc 2160
ggtgtcaact cccacggttt ctactggaag agacttggtt tgtttgttaa ggctgatacc 2220
gttgaaaagt tagccgcatt gatcggttgc ccagtcgaaa atgttagaaa cacattaggt 2280
gattatgagc aattgtccaa ggaaaacaga caatgtccaa agactagaaa agttgtctat 2340
ccatgtgttg ttggtccaca aggtccattc tatgttgctt ttgttacccc atctattcac 2400
tataccatgg gtggttgttt gatctcacca tctgctgaga tgcaattgga agagaacact 2460
acctccccat ttggtcacag aaggcctatc ttcggtcttt tcggtgccgg tgaagttact 2520
ggtggtgtcc atggtggtaa cagattaggt ggcaactctt tgttggagtg tgttgttttt 2580
ggtagaatcg ctggtgatag agctgcaacc attttgcaaa agaaaccagt tccactttcc 2640
tttaagactt ggaccaccgt cattttgaga gaggtccgtg aaggtggcat gtacggtact 2700
ggttcaagag tcttaagatt caatttgcca ggtgctttac aaagatctgg tttgcaattg 2760
ggtcaattca tcgctattag aggcgaatgg gatggtcaac aattgattgg ctactattcc 2820
ccaatcactt tgccagacga tttgggtgtc atcggcattt tggctagatc cgataagggt 2880
actttgaagg aatggatttc tgctttggaa cctggtgatg cagttgagat gaagggttgt 2940
ggcggtttag ttattgaaag gagattctct gaaagatact tgtacttttc tggtcacgct 3000
ttgaaaaagt tatgccttat tgctggtggt actggtgtcg caccaatgtt acaaatcatt 3060
agagcagcat tgaaaaagcc attccttgag aatatcgaat caattagact tatctatgct 3120
gctgaggacg tttctgagtt gacatacagg gaattgttag aacatcacca aagagattct 3180
aagggcaagt ttagatccat cttcgttttg aatagaccac ctccaatttg gactgatggt 3240
gttggcttta tcgacaaaaa gttgttatct tcatccgttc agccacctgc taaggatttg 3300
ttagtcgcca tttgtggtcc tcctatcatg caacgtgttg tcaagacttg tcttaagtca 3360
ttaggttatg atatgcagtt agtcagaaca gttgatgaag tcgaaactca aaactcctaa 3420

<210> SEQ ID NO 44
<211> LENGTH: 3435
<212> TYPE: DNA
<213> ORGANISM: Leishmania braziliensis

<400> SEQUENCE: 44

```
atggctgatg gtaaaacctc tgcttccgtt gttgctgtcg acccagagcg tgcagcaaag     60

gagagagatg cagcagcaag agcaatgtta caagacggtg gtgtttctcc agttggtaaa    120

gctcagttgt tgaaaaaggg tttggcatat gctgtccctt acacccttaa gattgttgtt    180

gcagatccta aagctatgga aaagaccacc gcagacgttg agaaggtcct tcaaaccgca    240

ttccaagtcg ttgacacttt gttaaacaat ttcaacgaaa actccgaggt ttctcgtatc    300

aacagaatgc cagtcggtga ggaacaccaa atgtctgctg cattgaagag agttatgggt    360

tgctgtcagc gtgtttacaa ttcatctcgt ggtgcttttg acccagctgt tggtccattg    420

gtcagagaat tgagggaagc tgcaagagaa ggcagaactt taccagcaga aaggattaac    480

gctttgttat ccaagtgtac cttgaatatc tccttttcca ttgatttgaa cagaggtact    540

attgccagaa aacacgcaga tgcaatgttg gatttgggtg gtgtcaataa gggttatggt    600

gttgattatg ttgtcgaaca tttgaacaat ttgggttatg atgatgtctt tttcgaatgg    660

ggtggtgatg ttagagcatc tggcaaaaac ccatcaaacc aacattgggt tgttggtatt    720

gctagaccac cagcacttgc tgatatcaga accgttgttc cacaagacaa gcaatccttc    780

atcagagttg tttgtcttaa tgatgaagca attgccacct ctggtgatta cgaaaatctt    840

gtcgaaggtc ctggttctaa ggtttactcc tctaccttca acgcaacctc taagtcctta    900

ttggaaccaa ccgaaaccaa tatcgcacaa gtctctgtta agtgttactc atgcatgtat    960

gcagacgcat tggctaccgc tgccttattg aaaaacaatc caactgctgt tcgtagaatg   1020

ttagataact ggagatatgt tcgtgatact gttaccgact atacaaccta ttccagagaa   1080

ggtgaaagag ttgcaaagat gtttgagatt gcaaccgaag ataaggaaat gagagctaag   1140

agaatttccg gttccttgcc agcaagagtc attatcgtcg gtggtggttt agctggttgt   1200

tctgcagcta ttgaagcagt caactgtggt gctcaagtca ttttgttaga aaaggaagcc   1260

aagattggtg gcaactccgc aaaggctacc tctggtatca acgcctgggg tactagagcc   1320

caggctaaac aaggtgttat ggatggtggc aagtttttcg agagagacac ccatagatcc   1380

ggtaaaggtg gtcactgtga tccttgtttg gttaagacac tttccgttaa gtcatcagac   1440

gcagttaagt ggttgtctga attgggtgtt ccattaaccg tcttatccca attaggtggt   1500

gcatccagaa agaggtgtca tagagcccca gataagtctg atggtactcc tgttccaatt   1560

ggttttacaa tcatgaaaac attagaaaat cacatcatta acgatctttc tcaccaagtt   1620

actgttatga ctggtatcaa ggttactggt ttggagtcca cttctcacgc tcgtccagat   1680

ggtgttttag ttaagcacgt tactggtgtt agattgattc aaggtgatgg ccaatccaga   1740

gttttgaatg ctgatgccgt tatcttagca actggtggtt tctccaatga ccatactgct   1800

aactctttac ttcaacaata cgctccacaa ctttcatcct ttccaaccac taatggtgtt   1860

tgggccactg gtgacggtgt caaggcagct agagaattag gtgttgagtt ggttgacatg   1920

gataaggtcc aattgcatcc aacaggtttg ttagatccaa aggacccatc caacaggact   1980

aagtacttgg gtccagaagc tttaaggggt tcaggcggtg tcttgttaaa caaaaacggt   2040

gaacgtttcg tcaacgaact tgatttgaga tctgtcgttt ctcaagccat tatcgaacaa   2100

aacaacgttt accctggttc tggtggttcc aagtttgctt actgcgtttt gaacgaagca   2160

gcagctaagt tgttcggcaa aaactttttg ggtttctatt ggcatagatt aggtcttttt   2220

gaaaaggttg aagatgttgc tggtttagcc aaattgatcg gttgtccaga ggaaaatgtt   2280

accgctacat tgaaggaata caaggaattg tcctccaaaa agcttcatgc ctgtccttta   2340
```

```
accaacaaaa acgtctttcc ttgcacttta ggtactgaag gcccttacta tgttgctttc   2400
gtcacacctt caattcacta cacaatgggt ggttgtttga tctccccttc agcagaaatg   2460
cagaccattg ataacactgg tgtcacacca gttcgtagac caatcttggg cttattcggt   2520
gctggtgaag ttactggtgg tgtccatggt ggtaacagat tgggtggtaa ttccttattg   2580
gaatgtgttg tctttggtag aattgctggt gatagagccg ctaccatttt gcaaaagaag   2640
aatgctggtt tatcaatgac tgagtggtct acagttgtct taagagaagt cagagaaggc   2700
ggtgtttacg gtactggttc tcgtgtcctt agattcaata tgccaggtgc cttacaaaag   2760
actggcttag cattgggtca attcatcgca atgagaggtg attgggatgg tcaacagtta   2820
ttgggttact attctccaat tacattacca gacgacattg gtgttattgg tatcttagct   2880
agagctgaca aaggtagatt agctgaatgg atttctgcat tacaaccagg tgatgctgtt   2940
gagatgaagg catgtggcgg tttgattatc catagaagat tcgctgctag acacttgttt   3000
ttccgttctc acaagattag aaagcttgct cttattggtg gtggtactgg tgttgcacca   3060
atgttgcaaa ttgtcagggc tgcagtcaaa aagccatttg ttgactctat tgagtctatt   3120
cagttcatct atgcagctga agatgtctcc gaacttactt atagaacttt gttggaatca   3180
tatgaaaagg aatacggttc tggcaaattc aagtgtcatt tcgtcttgaa taacccacca   3240
tcacaatgga ccgagggcgt tggtttcgtt gatactgctt tgttgcgttc tgccgttcaa   3300
gcaccttcta acgacttgtt agtcgctatt tgtggcccac caatcatgca aagagcagtc   3360
aaatcagcct taaagggttt aggttacaat atgaatttgg ttagaacagt tgatgaacca   3420
gaaccattgt cttaa                                                    3435
```

<210> SEQ ID NO 45
<211> LENGTH: 3537
<212> TYPE: DNA
<213> ORGANISM: Saccharomyces cerevisiae

<400> SEQUENCE: 45

```
atgtcgcaaa gaaaattcgc cggcttgaga gataacttca atctcttggg tgaaaagaac     60
aaaatattgg tggctaatag aggagaaatt ccaatcagaa tttttcgtac cgctcatgaa    120
ctgtctatgc agacggtagc tatatattct catgaagatc gtctttcaac gcacaaacaa    180
aaggctgacg aagcatacgt cataggtgaa gtaggccaat ataccccccgt cggcgcttat    240
ttggccattg acgaaatcat ttccattgcc caaaaacacc aggtagattt catccatcca    300
ggttatgggt tcttgtctga aaattcggaa tttgccgaca aagtagtgaa ggccggtatc    360
acttggattg gccctccagc tgaagttatt gactccgtgg gtgataaggt ctcagctaga    420
aacctggcag caaaagctaa tgtgcccacc gttcctggta caccaggtcc tatagaaact    480
gtagaggaag cacttgactt cgtcaatgaa tacggctacc cggtgatcat taaggccgcc    540
tttggtggtg gtggtagagg tatgagagtc gttagagaag gtgacgacgt ggcagatgcc    600
tttcaacgtg ctacctccga agcccgtact gccttcggta atggtacctg ctttgtggaa    660
agattcttgg acaagccaaa gcatattgaa gttcaattgt tggccgataa ccacggaaac    720
gtggttcatc ttttcgaaag agactgttcc gtgcagagaa gacaccaaaa ggttgtcgaa    780
gtggccccag caaagacttt accccgtgaa gtccgtgacg ccattttgac agatgcagtt    840
aaattggcca aagagtgtgg ctacagaaat gcgggtactg ctgaattctt ggttgataac    900
caaaatagac actatttcat tgaaattaat ccaagaatcc aagtggaaca taccatcaca    960
gaagaaatta ccggtataga tattgtggcg gctcagatcc aaattgcggc aggtgcctct   1020
```

```
ctaccccagc tgggcctatt ccaggacaaa attacgactc gtggctttgc cattcagtgc   1080
cgtattacca cggaagaccc tgctaagaac ttccaaccag ataccggtag aatagaagtg   1140
taccgttctg caggtggtaa tggtgttaga ctggatggtg gtaacgccta tgcaggaaca   1200
ataatctcac ctcattacga ctcaatgctg gtcaaatgct catgctccgg ttccacctac   1260
gaaatcgttc gtagaaaaat gattcgtgca ttaatcgagt tcagaattag aggtgtcaag   1320
accaacattc ccttcctatt gactcttttg accaatccag tatttattga gggtacatac   1380
tggacgactt ttattgacga caccccacaa ctgttccaaa tggtttcatc acaaaacaga   1440
gcccaaaaac ttttacatta cctcgccgac gtggcagtca atggttcatc tatcaagggt   1500
caaattggct tgccaaaatt aaaatcaaat ccaagtgtcc cccatttgca cgatgctcag   1560
ggcaatgtca tcaacgttac aaagtctgca ccaccatccg gatggaggca agtgctacta   1620
gaaaaggggc cagctgaatt tgccagacaa gttagacagt tcaatggtac tttattgatg   1680
gacaccacct ggagagacgc tcatcaatct ctacttgcaa caagagtcag aacccacgat   1740
ttggctacaa tcgctccaac aaccgcacat gcccttgcag gtcgtttcgc cttagaatgt   1800
tggggtggtg ccacattcga tgttgcaatg agatttttgc atgaggatcc atgggaacgt   1860
ttgagaaaat taagatctct ggtgcctaat attccattcc aaatgttatt gcgtggtgcc   1920
aatggtgtgg cttattcttc attgcctgac aatgctattg accatttcgt caagcaagcc   1980
aaggataatg gtgttgatat atttagagtc tttgatgcct taaatgactt ggaacaattg   2040
aaggtcggtg tagatgctgt gaagaaggca ggtggtgttg tagaagccac tgtttgtttc   2100
tctggggata tgcttcagcc aggcaagaaa tacaatttgg attactactt ggaaattgct   2160
gaaaaaattg tccaaatggg cactcatatc ctgggtatca aagatatggc aggtaccatg   2220
aagccagcag ctgccaaact actgattgga tctttgaggg ctaagtaccc tgatctccca   2280
atacatgttc acactcacga ttctgcaggt actgctgttg catcaatgac tgcgtgtgct   2340
ctggcgggcg ccgatgtcgt tgatgttgcc atcaactcaa tgtctggttt aacttcacaa   2400
ccatcaatca atgctctgtt ggcttcatta gaaggtaata ttgacactgg tattaacgtt   2460
gagcatgtcc gtgaactaga tgcatattgg gcagagatga gattgttata ctcttgtttc   2520
gaggctgact tgaagggccc agatccagaa gtttatcaac atgaaatccc aggtggtcaa   2580
ttgacaaact tgttgtttca agcccaacaa ttgggtcttg gagaacaatg ggccgaaaca   2640
aaaagagctt acagagaagc caattattta ttgggtgata ttgtcaaagt taccccaact   2700
tcgaaggtcg ttggtgatct ggcacaattt atggtctcca ataaattaac ttccgatgat   2760
gtgagacgcc tggctaattc tttggatttc cctgactctg ttatggattt cttcgaaggc   2820
ttaatcggcc aaccatacgg tgggttccca gaaccattta gatcagacgt tttaaggaac   2880
aagagaagaa agttgacttg tcgtccaggc ctggaactag agccatttga tctcgaaaaa   2940
attagagaag acttgcagaa tagatttggt gatgttgatg agtgcgacgt tgcttcttat   3000
aacatgtacc caagagttta tgaagacttc caaaagatga gagaaacgta tggtgattta   3060
tctgtattgc caacaagaag ctttttgtct ccactagaga ctgacgaaga aattgaagtt   3120
gtaatcgaac aaggtaaaac gctaattatc aagctacagg ctgtgggtga tttgaacaaa   3180
aagaccggtg aaagagaagt ttactttgat ttgaatggtg aaatgagaaa aattcgtgtt   3240
gctgacagat cacaaaaagt ggaaactgtt actaaatcca aagcagacat gcatgatcca   3300
ttacacattg gtgcaccaat ggcaggtgtc attgttgaag ttaaagttca taaaggatca   3360
```

```
ctaataaaga agggccaacc tgtagccgta ttaagcgcca tgaaaatgga aatgattata   3420

tcttctccat ccgatggaca agttaaagaa gtgtttgtct ctgatggtga aaatgtggac   3480

tcttctgatt tattagttct attagaagac caagttcctg ttgaaactaa ggcataa      3537
```

<210> SEQ ID NO 46
<211> LENGTH: 3528
<212> TYPE: DNA
<213> ORGANISM: Kluyveromyces marxianus

<400> SEQUENCE: 46

```
atgtctaccc aaaacgatct ggccgggttg cgtgataact cgaacctatt aggtgaaaag     60

aacaagattc ttgttgccaa ccgtggtgaa attccaatta gaatctttag aacggctcat    120

gaactttcga tgaagactgt tgcgatctat tcgcacgagg atagactatc tatgcacaga    180

ttgaaggcag acgaagctta cgttattggt gagccaggaa aatacactcc agttggtgcg    240

tatttggcga tcgatgagat tatcaagatt gctcaattgc acggagtgag cttcatccac    300

cctggttatg ggttcttatc ggaaaactct gagtttgcca agaaggtggc cgactctggt    360

atcacgtggg ttggtcctcc agccgatgtg atcgatgctg ttggtgacaa ggtttctgcc    420

agaaacttgg ccgagagagc ggatgttcca gtggttccag gtacgcctgg tccaatagag    480

acagttgaag aagcagttga atttgtggag aagtacggat acccagtcat catcaaggct    540

gccttcggtg gtggtggtcg tggtatgaga gttgttcgtg aaggtgatga tatcgccgat    600

gctttccaaa gagccaagtc cgaagctgtt actgctttcg gtaacggtac ttgtttcgtt    660

gaaagattct tggacaagcc aaagcacatc gaagttcagt tgttggctga tcactacggt    720

aatgtcatcc atctattcga aagagactgt tctgtgcaaa gaagacatca aaaggtcgtt    780

gaagtagcgc cagccaagac tttgccagag agcgtgcgta atgcaatctt gactgacgct    840

gtcaagttgg ctaaggaggc aggatacaga aatgctggta ccgctgaatt tttggtcgac    900

aaccaaaaca gacactactt tattgaaatc aacccaagaa ttcaagtcga acataccatc    960

accgaagaaa ttaccggtat cgacattgtc gccgcacaaa ttcaaatcgc agcaggtgct   1020

tccttggaac aattgggact attgcaagat agaatcacca cccgtggttt cgctattcaa   1080

tgtcgtatca ctactgaaga tccttccaag aacttccagc cagatactgg tcgtatcgat   1140

gtttaccgtt ccgctggtgg taacggtgtc agattggatg gtggtaacgc attcgctggt   1200

tcggtcattt cacctcatta tgattccatg ttggtcaaat gttcttgttc cggttccact   1260

tacgaaatcg ttcgtcgtaa gatgttgcgt gccttgatcg aattcagaat cagaggtgtg   1320

aagacaaaca ttccattctt gctaacgttg ttgactcatc ctgtgttcaa gtccggtgac   1380

tactggacta ccttcatcga tgacactcca caattgttcg aaatggtttc ttctcaaaac   1440

agagcacaaa aactattgca ctacttggcc gatcttgccg ttaacggttc atcgatcaag   1500

ggtcaaattg gtctaccaaa gttaaagact catcctacta tcccacattt gcataaggcc   1560

gatggctcca ttctagatgt gtctgccaag cctcctgccg ggtggagaga tgttctattg   1620

caacacggcc cagaagaatt tgcaaagcaa gttagaaagt tcaagggtac tttgctaatg   1680

gacaccacct ggagagatgc tcatcaatct ctattggcca ctagagtcag aacttacgat   1740

ttggctgcca tcgctccaac tactgctcat gctttgagcg gtgctttcgc tttggaatgt   1800

tggggtggtg ccactttcga tgtctccatg agattcttgc acgaagatcc atgggaacgt   1860

ttgagaactt tgagaaagtt ggttcctaac attccattcc aaatgttgct acgtggtgcc   1920

aacggtgttg catactcttc tctaccagat aacgctatcg accactttgt caagcaagca   1980
```

```
aaggataacg gtgttgacat tttcagagtc ttcgatgctc taaacgattt ggagcaattg   2040
actgtcggtg ttgacgctgt caagaaggct ggtggtgttg tcgaagctac catttgttac   2100
tccggtgaca tgctagcacc aggtaagaag tacaaccttg actactactt ggacattgtt   2160
gaacaagtgg ttaagagagg tacccatatt cttggtatca aggatatggc aggtactttg   2220
aagccatctg ctgctaagct cttgatcggt tctatcagaa caaagtaccc tgacttgcca   2280
attcacgtcc atacccatga ctccgccggt accggtgttg cttccatggc tgcatgtgct   2340
ttcgctggtg ctgatgttgt tgatgttgca accaactcta tgtctggtat gacttctcaa   2400
ccatctgtca atgcactatt ggctgctctt gatggtgaaa tcgactgtaa tgtcaacgtc   2460
agctacatca gtcagctaga tgcttactgg gctgaaatga gactattgta ctcatgtttc   2520
gaagccgact tgaagggtcc tgatccagaa gtttacgtcc atgaaattcc aggtggtcaa   2580
ttgaccaact tgctcttcca agcccaacaa ttgggtcttg gtgagcaatg ggctgaaacc   2640
aagagagctt accgtgaagc aaacctgttg ttgggtgatg ttgttaaggt cactccaaca   2700
tccaaggttg tcggtgattt ggctcaattc atggtcacta acaagttgac ctcggatgat   2760
gttaagagat tagcttcatc tttggatttc ccagactccg tcatggactt ctttgaaggt   2820
ttaatcggtc aaccatacgg tggtttccca gaacctctaa gatctgatgt tttgaagaac   2880
aagagaagaa agttgaccaa gagaccaggt ttggaattgg ctccattcga tttggaaggc   2940
attaaggaag atttgactaa cagatttggt gacattgacg actgtgatgt tgcttcttac   3000
aacatgtatc caaaggtcta cgaagatttc cgtaagatca gagaaaagta cggtgatcta   3060
tctgttttgc caaccaagaa cttcttgtct ccaccttcaa tcggtgaaga aatcgtcgtt   3120
acaattgaac aaggtaagac tttgatcatt aagccacaag ctattggtga tttgaacaag   3180
gagactggta tcagagaagt ttacttcgaa ttgaacggtg aattgagaaa ggtctctgtt   3240
gctgacagat ctcaaaaggt tgaaacgatc tccaagccaa aggctgacgc ccacgatcca   3300
ttccaagttg gttctccaat ggcaggtgtt gttgtcgaag tcaaggtaca caagggttct   3360
ttgatctcca agggccaacc agtcgctgtc ctaagtgcca tgaagatgga aatggttatc   3420
tcctccccat ctgatggtca agtcaaggaa gtgcttgtca aggatggtga aaacgttgac   3480
gcttctgact tgctcgttgt tttggaagaa gctccagcta aagaataa                3528
```

<210> SEQ ID NO 47
<211> LENGTH: 22
<212> TYPE: DNA
<213> ORGANISM: Artificial
<220> FEATURE:
<223> OTHER INFORMATION: Primer

<400> SEQUENCE: 47

```
gcaactgatg ttcacgaatg cg                                              22
```

<210> SEQ ID NO 48
<211> LENGTH: 20
<212> TYPE: DNA
<213> ORGANISM: Artificial
<220> FEATURE:
<223> OTHER INFORMATION: Primer

<400> SEQUENCE: 48

```
ttgccgttgc agcaaatctc                                                 20
```

<210> SEQ ID NO 49

```
<211> LENGTH: 2652
<212> TYPE: DNA
<213> ORGANISM: Escherichia coli

<400> SEQUENCE: 49

atgaacgaac aatattccgc attgcgtagt aatgtcagta tgctcggcaa agtgctggga      60
gaaaccatca aggatgcgtt gggagaacac attcttgaac gcgtagaaac tatccgtaag     120
ttgtcgaaat cttcacgcgc tggcaatgat gctaaccgcc aggagttgct caccacctta     180
caaaatttgt cgaacgacga gctgctgccc gttgcgcgtg cgtttagtca gttcctgaac     240
ctggccaaca ccgccgagca ataccacagc atttcgccga aaggcgaagc tgccagcaac     300
ccggaagtga tcgcccgcac cctgcgtaaa ctgaaaaacc agccggaact gagcgaagac     360
accatcaaaa aagcagtgga atcgctgtcg ctggaactgg tcctcacggc tcacccaacc     420
gaaattaccc gtcgtacact gatccacaaa atggtggaag tgaacgcctg tttaaaacag     480
ctcgataaca aagatatcgc tgactacgaa cacaaccagc tgatgcgtcg cctgcgccag     540
ttgatcgccc agtcatggca taccgatgaa atccgtaagc tgcgtccaag cccggtagat     600
gaagccaaat ggggctttgc cgtagtggaa aacagcctgt ggcaaggcgt accaaattac     660
ctgcgcgaac tgaacgaaca actggaagag aacctcggct acaaactgcc cgtcgaattt     720
gttccggtcc gttttacttc gtggatgggc ggcgaccgcg acggcaaccc gaacgtcact     780
gccgatatca cccgccacgt cctgctactc agccgctgga aagccaccga tttgttcctg     840
aaagatattc aggtgctggt ttctgaactg tcgatggttg aagcgacccc tgaactgctg     900
gcgctggttg gcgaagaagg tgccgcagaa ccgtatcgct atctgatgaa aaacctgcgt     960
tctcgcctga tggcgacaca ggcatggctg gaagcgcgcc tgaaaggcga agaactgcca    1020
aaaccagaag gcctgctgac acaaaacgaa gaactgtggg aaccgctcta cgcttgctac    1080
cagtcacttc aggcgtgtgg catgggtatt atcgccaacg gcgatctgct cgacaccctg    1140
cgccgcgtga aatgtttcgg cgtaccgctg gtccgtattg atatccgtca ggagagcacg    1200
cgtcataccg aagcgctggg cgagctgacc cgctacctcg gtatcggcga ctacgaaagc    1260
tggtcagagg ccgacaaaca ggcgttcctg atccgcgaac tgaactccaa acgtccgctt    1320
ctgccgcgca actggcaacc aagcgccgaa acgcgcgaag tgctcgatac ctgccaggtg    1380
attgccgaag caccgcaagg ctccattgcc gcctacgtga tctcgatggc gaaaacgccg    1440
tccgacgtac tggctgtcca cctgctgctg aaagaagcgg gtatcgggtt tgcgatgccg    1500
gttgctccgc tgtttgaaac cctcgatgat ctgaacaacg ccaacgatgt catgacccag    1560
ctgctcaata ttgactggta tcgtggcctg attcagggca aacagatggt gatgattggc    1620
tattccgact cagcaaaaga tgcgggagtg atggcagctt cctgggcgca atatcaggca    1680
caggatgcat taatcaaaac ctgcgaaaaa gcgggtattg agctgacgtt gttccacggt    1740
cgcggcggtt ccattggtcg cggcggcgca cctgctcatg cggcgctgct gtcacaaccg    1800
ccaggaagcc tgaaaggcgg cctgcgcgta accgaacagg gcgagatgat ccgctttaaa    1860
tatggtctgc cagaaatcac cgtcagcagc ctgtcgcttt ataccggggc gattctggaa    1920
gccaacctgc tgccaccgcc ggagccgaaa gagagctggc gtcgcattat ggatgaactg    1980
tcagtcatct cctgcgatgt ctaccgcggc tacgtacgtg aaaacaaaga ttttgtgcct    2040
tacttccgct ccgctacgcc ggaacaagaa ctgggcaaac tgccgttggg ttcacgtccg    2100
gcgaaacgtc gcccaaccgg cggcgtcgag tcactacgcg ccattccgtg gatcttcgcc    2160
tggacgcaaa accgtctgat gctccccgcc tggctgggtg caggtacggc gctgcaaaaa    2220
```

```
gtggtcgaag acggcaaaca gagcgagctg gaggctatgt gccgcgattg gccattcttc   2280

tcgacgcgtc tcggcatgct ggagatggtc ttcgccaaag cagacctgtg gctggcggaa   2340

tactatgacc aacgcctggt agacaaagca ctgtggccgt taggtaaaga gttacgcaac   2400

ctgcaagaag aagacatcaa agtggtgctg gcgattgcca acgattccca tctgatggcc   2460

gatctgccgt ggattgcaga gtctattcag ctacggaata tttacaccga cccgctgaac   2520

gtattgcagg ccgagttgct gcaccgctcc cgccaggcag aaaaagaagg ccaggaaccg   2580

gatcctcgcg tcgaacaagc gttaatggtc actattgccg ggattgcggc aggtatgcgt   2640

aataccggct aa                                                       2652
```

<210> SEQ ID NO 50
<211> LENGTH: 2643
<212> TYPE: DNA
<213> ORGANISM: Mannheimia succiniproducens

<400> SEQUENCE: 50

```
atgacagaag aatatttaat gatgcgtaat aacatcaata tgctggggcg ctttttgggc     60

gaaactattc aggaggcgca aggtgacgat attctcgaac tgattgaaaa tatccgcgta    120

ctgtcccgca attcccgtag cggcgatgac aaagcccggg cggcattatt agacaccctt    180

tccactattt cggcggataa tattattccg gttgcccgcg ctttcagcca gtttctgaac    240

ctgacaaatg tggcggaaca atatcaaacc atgtctcgct cccatgaaga taaggtttct    300

gcggaacgtt ccactgctgc gctgttcgcc cgcctgaaag aacaacatgt ttctcaggaa    360

gaaatcatta aaaccgtaca gaaactgttg attgaaatcg tccttaccgc tcacccgacg    420

gaagttaccc gccgttcatt aatgcacaaa caggttgaaa tcaacaaatg tctggctcag    480

ctggatcata cggatttaac cgccgaagaa caaaaaaata ttgagtataa attacttcgt    540

cttatcgccg aagcctggca taccaatgaa atccgtacca atcggccgac acctctggaa    600

gaagccaaat ggggttttgc cgttatcgaa aacagtttat gggaaggttt gcccgccttt    660

atccgcaaac ttaacgatgc cgccgtcgaa catttaaatt atgctttgcc ggtagacctc    720

acaccggtac gcttctcttc ctggatgggc ggtgaccgtg acggcaaccc cttcgttacc    780

gcaaaaatta cccgggaagc gctgcaactt gcgcgctgga aagcggcgga tttatttta    840

accgatattc aggaactctg cgacgagttg tcaatgacac aatgcactgc ggaattccga    900

gaaaaatacg gtgatcattt agaaccctat cgtgtagttg tgaaggattt acgcagcaaa    960

ttaaaaaata cgctggatta ttacaacgat atacttgcgg gtcgcattcc gccgtttaaa   1020

caagatgaaa tcatcagtga agaccaacaa ctctggcaac cgctttatga ctgttatcaa   1080

tccctaaccg cctgcggtat gcgtattatt gccaatggat tattgctgga taccttacgc   1140

cgcgttcgtt gtttcggcgt cacattactg cgtttagata tccgtcagga aagcacccgc   1200

catagcgacg ccatcggcga aattacccgc tacatcggtt taggcgatta cagccaatgg   1260

acagaagatg acaaacaagc cttcctgatc cgggaattaa gttcccgtcg tccgctaatt   1320

ccccataact ggacgccttc ggaacacact cgggaaattt tagacacctg taaagtcatt   1380

gcaaaacagc cggaaggcgt tatttcctgc tatatcattt ccatggcgcg caccgcttcc   1440

gatgttttgg cggtgcattt attattgaaa gaagcgggca tttcatacca tctgccggta   1500

gttcctctat ttgaaacatt ggacgacctg gacgcttcta aagaagtgat gacgcaactg   1560

tttaacgtag gctggtatcg cggcgtaatc aaaaaccgcc aaatgatcat gatcggctat   1620
```

tccgatagcg ccaaagatgc gggcatgatg gcggcctcat gggcgcaata ccgggcgcag 1680
gacgctttag tcaaactttg cgaacaaacc ggcatcgaac ttaccctctt ccacggccgc 1740
ggcggcaccg taggacgtgg cggtgcaccg gctcacgccg cattattatc ccaaccgcca 1800
cgttctctga aaaacggctt acgggtaacc gaacaagggg aaatgatccg cttcaaactg 1860
ggattaccgg ctatcgccgc agaaagtctg gatctctacg ccagcgccat tcttgaggcc 1920
aacctcctgc cgccgccgga accgaaagcc agctggtgcc gggtaatgga cgaacttgcc 1980
gtcgcttctt gcgaaatcta tcgcaatgtg gtgcgcggcg ataaagattt tgtgccttac 2040
ttccgcagcg ccacaccgga acaggaactg gcaaaactgc ctttaggttc ccgaccggca 2100
aaacgcaatc cgaacggcgg cgttgaaagc ctgcgtgcca ttccctggat cttcgcctgg 2160
atgcaaaacc gcctgatgct gcccgcctgg ctcggtgccg gcgcctcaat ccgtcaggcg 2220
atggaaagcg gcaaagcggc ggtgattgaa gaaatgtgca accattggcc gtttttcaat 2280
acccgaatcg gcatgcttga aatggtattc agtaaaaccg atagctggct gtccgaatat 2340
tacgaccagc gtttagtgaa aaaagagctt tggtatttag gcgaatcgct gcgcaaacag 2400
ttaagcgaag atatcgctac cgtgttacgg ctttccggca aaggcgatca attaatgtcg 2460
gatttgcctt gggtggcgga atctattgca ctgcgtaacg tttacaccga cccgttaaac 2520
ttattgcaag tggaattatt gcgtcgtttg cgagcggatc ccgaacatcc gaatccggat 2580
atcgagcaag cgctgatgat caccattacc ggtatcgccg cgggtatgcg taatacgggt 2640
tag 2643

<210> SEQ ID NO 51
<211> LENGTH: 21
<212> TYPE: DNA
<213> ORGANISM: Artificial
<220> FEATURE:
<223> OTHER INFORMATION: Primer

<400> SEQUENCE: 51
acggcagtat accctatcag g 21

<210> SEQ ID NO 52
<211> LENGTH: 20
<212> TYPE: DNA
<213> ORGANISM: Artificial
<220> FEATURE:
<223> OTHER INFORMATION: Primer

<400> SEQUENCE: 52
aatgatccat ggtccgagag 20

<210> SEQ ID NO 53
<211> LENGTH: 22
<212> TYPE: DNA
<213> ORGANISM: Artificial
<220> FEATURE:
<223> OTHER INFORMATION: Primer

<400> SEQUENCE: 53
gaagagacgt acaagatccg cc 22

<210> SEQ ID NO 54
<211> LENGTH: 47
<212> TYPE: DNA
<213> ORGANISM: Artificial
<220> FEATURE:
<223> OTHER INFORMATION: Primer

<400> SEQUENCE: 54
ggataaaagt attacatacg tacaggattg tgtattagtg tatttcg 47

<210> SEQ ID NO 55
<211> LENGTH: 22
<212> TYPE: DNA
<213> ORGANISM: Artificial
<220> FEATURE:
<223> OTHER INFORMATION: Primer

<400> SEQUENCE: 55
taggaatggt gcatcatcca ac 22

<210> SEQ ID NO 56
<211> LENGTH: 44
<212> TYPE: DNA
<213> ORGANISM: Artificial
<220> FEATURE:
<223> OTHER INFORMATION: Primer

<400> SEQUENCE: 56
ccaaccaaac acgcgtacaa tgaacgaaca atattccgca ttgc 44

<210> SEQ ID NO 57
<211> LENGTH: 23
<212> TYPE: DNA
<213> ORGANISM: Artificial
<220> FEATURE:
<223> OTHER INFORMATION: Primer

<400> SEQUENCE: 57
ggacacggag aacccattta ttc 23

<210> SEQ ID NO 58
<211> LENGTH: 1029
<212> TYPE: DNA
<213> ORGANISM: Issatchenkia orientalis

<400> SEQUENCE: 58
atgtccaatg ttaaagtagc tctactaggt gccgctggtg gtatcggcca accacttgct 60
ctattactta agcttaatcc aaacataacc catttggcac tctatgacgt tgtgcatgtt 120
cctggagtgg ctgccgacct acaccatata gacacagatg tagtgattac ccaccatttg 180
aaagatgaag acggtacggc cttggcaaac gccctcaagg acgctacgtt tgttattgtc 240
cccgccggtg ttccgagaaa gcccggcatg actagaggtg atttgttcac aattaatgcc 300
ggtatatgtg ccgaattggc taatgctatt agtttgaacg ctcctaatgc attcaccctt 360
gtcattacca atccggtcaa ctcgaccgtt cctatattta aggaaatatt tgctaaaaat 420
gaagccttca atccaaggag actgtttggt gtaactgctc tagatcatgt tagatcaaat 480
acttttctct cggaattaat tgacggtaaa aatccccaac attttgatgt cactgttgtt 540
ggcggacact ctggtaactc aattgtcccc ctattctccc ttgttaaggc tgccgaaaat 600
ttagacgatg aaattataga tgccttgatt catagagttc aatacggtgg agatgaagtt 660
gtggaagcaa agagcggtgc gggctcggca actctttcaa tggcttatgc cgctaacaag 720
ttcttcaata tattgcttaa tggatacttg ggtttgaaga agacaatgat ttcaagttat 780
gtctttttag acgattcaat caacggcgtc cctcaattaa aggaaaattt gtctaaactt 840
ttgaaaggtt ccgaggttga gttaccaagt tatttggctg ttccaatgac ctatggtaaa 900

```
gaaggtattg aacaagtctt ttacgattgg gtgtttgaaa tgtcaccaaa ggaaaaggaa    960

aacttcatta cagcgattga atacattgat caaaatattg aaaaaggtct gaattttatg   1020

gtacgttaa                                                           1029
```

<210> SEQ ID NO 59
<211> LENGTH: 1011
<212> TYPE: DNA
<213> ORGANISM: Issatchenkia orientalis

<400> SEQUENCE: 59

```
atggtcaagg tgactatttt aggcgctgcc ggtggaattg gacaaccact ctcattgtta     60

ttgagactta atccatggat tgacgaattg gccttgtttg atattgtcaa tacccccggc    120

gtgagttgtg atttgtcgca tattcctgca tcacaggttg ttaatggcta tgctccgaaa    180

tcgaaatcag atacagagac aatcaagact gccttgaaag gtgctgatat tgttgttatt    240

cctgcaggaa ttccacgtaa acctggtatg acaagaaacg atctctttaa aatcaatgcc    300

ggaatcgtta agagtttgat tcatagtgca ggaaccactt gccctgatgc atttatttgt    360

gtcatttcga accctgtcaa ctcgacagtt ccaattgccg ttgaagaact aaagcgtttg    420

aatgttttta atccacataa agttttcggt attaccacat tggacaattt cagattagaa    480

gaatttctga gtggagaact tggtggaatt gtcaaaccaa atgatttata tggtgatgta    540

gttgctatag gtggccattc gggcgactct atagtaccga tcttgaattc gtggaatttg    600

aatttcatca atgatggaga ttcttataac aatttggtca agagggtcca gtttggaggc    660

gatgaggttg tcaaggcaaa ggacgggaaa ggttcggcta cattgtcaat ggctacagct    720

gcatacaggt ttgtcaacaa cctcttggac gccattgtca ataacaagaa agtcaaggaa    780

gtggcctttg tgaaaatcga ccaattgcca actacaaggg ttccttattt tgttgttgat    840

gaaactcagt attttagtct acccattatt ctcggtagac aggggattga gagggtcacg    900

ttcccagaat ctctgacaga gcaagaggtg agaatgacaa agcacgctgt tgctaaagtt    960

aaagttgacg ttaataaagg cttcaatttt gtccatggcc caaaactgta a            1011
```

<210> SEQ ID NO 60
<211> LENGTH: 1005
<212> TYPE: DNA
<213> ORGANISM: Issatchenkia orientalis

<400> SEQUENCE: 60

```
atgttctcca gaatctctgc tagacaattc tcctcctctg ctgcttccgc ttacaaggtc     60

accgttttag gtgctgcagg tggtattggc caaccactat ctcttttgat gaagttgaac    120

cacaaggtca ccaacttatc cttgtacgac ttgagattgg gtgctggtgt tgccactgac    180

ttgtcccaca ttccaaccaa ctccgttgtc aagggctatg gtccagaaaa caatggtttg    240

aaggacgcct tgaccggctc cgatgttgtt cttattccag ctggtgttcc aagaaaacca    300

ggtatgacta gagacgatct cttcaacacc aatgcatcga ttgtcagaga cttggcaaag    360

gctgctgcag accactgtcc aaacgccgtc ttgttgatca tttcaaaccc tgtcaactca    420

actgtcccaa ttgttgctga ggttttgaaa tcaaagggcg tctacaaccc aaagaagttg    480

tttggtgtca ccactttgga cgttttgaga tcctcgagat tcttgagtga agtcgtcaac    540

accgacccaa ccaccgaaac cgtcactgtt gttggtggcc actctggtgt caccattgtt    600

cctttaatct cccaaaccaa acacaaggac ttgccaaagg aaacctacga agcattggtc    660

cacagaatcc aattcggtgg tgatgaggtt gtcaaggcca aggacggtgc aggttccgct    720
```

```
accttgtcca tggcccaagc cggtgcaaga atggcctcct ccgtcttgaa gggtttggct    780

ggtgaagttg acattgtcga accaaccttt attgactctc cattgttcaa gtccgaaggt    840

gtcgaattct tctcctccag agtcaccctt ggtccagaag gtgtccaaga agtccaccca    900

ttgggcgtct tatctactgc tgaagaagaa atggttgcta ctgctaagga aaccttgaag    960

aagaacatcc aaaagggtgt cgactttgtc aaggctaacc cataa                   1005
```

<210> SEQ ID NO 61
<211> LENGTH: 1071
<212> TYPE: DNA
<213> ORGANISM: Zygosaccharomyces rouxii

<400> SEQUENCE: 61

```
atgcctcatt ctatcaacgg tgatgttaaa atcgcagtat tgggagctgc aggtggtatt     60

ggacaatcac tttcgctact tttgaagacc cagttaacta gagaattgcc aaatcatcgt    120

catgctcagt tagccctata cgacgtcaat gctgacgcag ttcggggtgt cgcagccgac    180

ttatctcata ttgatacagg tgttactgta acaggatatg aaggtgatag gatcggcgaa    240

gcgttagaag gtacggatat cgtcctgatc cctgcaggtg ttcctagaaa acctggtatg    300

acaagagaag atctattggt tgttaatgca aagattgtca agagtatagg gtcatcgatt    360

gcgcagcatt gcgatttaaa caaagtgttc attctactaa tctcaaaccc aataaattcc    420

cttgttccag tactcgttaa ggaactggaa tctaaatctc aaggcactca agttgagaga    480

cgtgtgcttg gtctcactaa gttggattcc gttagagcaa gtgcattttt gcacgaggtt    540

acgattaaac atggtctaaa acctaaatct aatactcttg atgatgttcc agtagttggt    600

ggtcattctg gtgaaactat tgtaccttta ttctcccaag cccctaatgg taaccgttta    660

tcacaggacg ccttggaagc tcttgttcag cgtgtacaat tcggaggcga tgaagtcgtt    720

agagctaaaa atggtgctgg tagtgccact ctgtgtatgg cccatgccgc ttatactgtt    780

gctgcatctt ttattccact tatcactggt caaaagcgtt ccatctctgg tacattctat    840

gttgccttaa aggatgctca aggtcagcct atcaacagta gcgctaagcg tcttttgggc    900

tcaatcaacg atttaccata ttttgcagtg ccattggaga ttacttctca gggtgtggat    960

gaattagata ccagcgtttt ggaaagaatg accaagtatg agagagaaag actcttagct   1020

ccttgtctgg gtaaattgga aggtggtatc agaaacggtt tgagtttgta a            1071
```

<210> SEQ ID NO 62
<211> LENGTH: 1017
<212> TYPE: DNA
<213> ORGANISM: Kluyveromyces marxianus

<400> SEQUENCE: 62

```
atgcttagag ccctaactcg ccgtcaattt tcctccactg ccttcaaccc atacaaggtc     60

accgttctag gtgctggtgg tggtattggt caaccattgt ccttgttgtt gaagctaaac    120

cacaaggtca ctgacttgag actatacgac ttgaagggtg ccaagggtgt cgctgctgac    180

ttgtctcaca tcccaaccaa ctctaccgtt actggttaca ctccagaatc caaggactct    240

caagaagaat tggctgctgc tttgaaggac actgaggttg ttttgatccc agctggtgtg    300

ccaagaaagc caggtatgac ccgtgacgat ttgttcgcca tcaatgccgg tattgtcaga    360

gatttggcca cttccatcgc caagaacgct ccaaacgccg ccatcttggt catctccaac    420

ccagtcaact ctactgtccc aatcgtcgcc gaggtcttga agcaaaacgg cgtctacaac    480
```

```
ccaaagaagt tgttcggtgt caccactttg gacgttatcc gtgcctccag attcatctcc    540

gaggttagag gtaccgaccc aaccactgag cacgtgaccg tcgtcggtgg tcactccggt    600

atcaccatct tgccgctagt gtcccagacc aagcacaagt ccgtcatcaa gggcgaggaa    660

ttggacaact tgatccacag aatccaattc ggtggtgacg aagtcgtcca ggcaaagaac    720

ggtgctggtt ctgccacttt gtccatggcc caagccggtg cccgtttcgc taacagcgtt    780

ctaagcggtt tcgaaggtga aagagacgtc attgagccaa ctttcgtcga ctccccattg    840

ttcaaggacg aaggtatcga attcttcgct tccccagtca ctttgggccc agaaggtgtc    900

gaaaagatcc acggtttggg tgtcttgtcc gacaaggaag aacaaatgtt ggccacttgt    960

aaggaaacct tgaagaagaa catcgaaaag ggtcaaaact ttgtcaagca aaactaa      1017
```

<210> SEQ ID NO 63
<211> LENGTH: 1017
<212> TYPE: DNA
<213> ORGANISM: Kluyveromyces marxianus

<400> SEQUENCE: 63

```
atggttagcg ttgcagtatt aggatcatcc ggaggcattg gccaaccact ctcactcttg     60

ttgaagctgg accctcgcgt gtccagcttg agattgtacg acttgaagat gtcccacggg    120

atcgccaccg atttgtcgca catggactcc aactccatct gcgagggctt caacaccgac    180

gagatcgcgc tcgcgctcaa gggcgcccag atcgtcgtca tccccgcggg tgtcccaaga    240

aagcccggga tgtcacgtga cgaccttttc aagatcaacg ccaagatcat caagtcgttg    300

gcgttgcaaa tagccgagca cgcgcccgag gcgcgcgtcc tcgtgatctc gaacccggtc    360

aactccttgg tgcccattgt gtacgagact ttgaagagcg tcggcaagtt cgagccgggt    420

aaagtgatgg gaattaccac attggacatt atccgctcac acacgttcct ggtggacgtc    480

ttgggccgca aggcgtacag cgtcgagaag ttgcgcagcg cggttactgt ggtgggcggc    540

cactcgggcg agaccattgt tccgattttc accgaccaga agttctacag gcgtctcaga    600

gacagagagc tctatgacgc gtacgtgcat agggtccaat tcggcggaga cgaggtcgtg    660

aaggccaagg acggcagcgg tagtgctact ttgtctatgg cctgggcggg ttacagtttt    720

gtgaagcagt tgctcaacag cttgcaccta gaaacaggcg aagacgtgca tccgatccca    780

acgtttgtgt acttgccggg tttaccgggc gggaaggagc tccagcagaa gttgggcacc    840

tctgttgagt tttttgccgc gcccgtgaag ctttccaagg gtattgtggt tgaagttgag    900

cacgactggg tcgacaagtt gaacgatgcc gagaagaagt tgattgcaaa gtgtcttcca    960

atccttgaca agaacatcaa gaagggtctc gccttttcgc agcagacaaa gttgtga      1017
```

<210> SEQ ID NO 64
<211> LENGTH: 1125
<212> TYPE: DNA
<213> ORGANISM: Kluyveromyces marxianus

<400> SEQUENCE: 64

```
atgccagcag tatcatatga tgtccagcaa cgggatatcc tcaagatcgc agttctaggg     60

gcggcaggcg gtattggcca atccttgtcg ctcttgttga agtcgaacgc ttcttttttg    120

ttaccacgtg actcgtcaag acacataagc ctagcgctat acgacgtgaa caaagatgcc    180

atcgtgggca cagcagcaga cttgtcacac atagacaccc ctatcaccac cactccacac    240

tacccaaatg atgggaatgg cggtatcgca cggtgcttgc aagatgcaga catggtcatc    300

atcccagcag gtgtgcccag aaaacccggt atgtcacgtg atgacctaat cggtgtcaac    360
```

```
gccaagatca tcaagtcgct aggaaacgac atcgcagagt actgtgactt gtctaaagtg    420

catgtattgg ttatttcgaa cccagtgaac tcgttggtcc cactgatggt gtcgactttg    480

gcaaacagcc cacacagtgc gaacacaaac atcgaggcta gagtgtacgg gatcacccat    540

ttggacctag tgagagcttc cacctttgtg caacagctaa actctttcaa atcaaataac    600

gcacctgaca ttccggtcat tggtggtcat tccggagata ccatcatccc cgtttttttcc   660

gtcttgaatc accgcgcttc taactccgga tacgctaatt tgctagataa tggcgttagg    720

caaaagttgg tccacagagt tcaatatggt ggggacgaaa tcgtccaagc aaagaacggt    780

aacgggagcg cgacattatc catggcatac gcgggcttca aatcgcagc acaattcatc     840

gaccttttgg tcggaaatat ccgcactatc gaaaatattt gcatgtatgt tccgctcact    900

aacaggtata ataccgagat cgccccaggc tctgacgaat taagatcaaa gtacatcaac    960

ggaacccttt atttctcgat tccactttcc atcggaataa acggtatcga aagagtccac   1020

tacgagatca tggaacatct agacagctac gagcgtgaga cgctactacc gatctgcttg   1080

gaaactctaa agggtaatat tgacaagggt ctaagcttgg tataa                  1125
```

<210> SEQ ID NO 65
<211> LENGTH: 22
<212> TYPE: DNA
<213> ORGANISM: Artificial
<220> FEATURE:
<223> OTHER INFORMATION: Primer

<400> SEQUENCE: 65

```
ggaggaatgg aacagtgatg ac                                              22
```

<210> SEQ ID NO 66
<211> LENGTH: 939
<212> TYPE: DNA
<213> ORGANISM: Escherichia coli

<400> SEQUENCE: 66

```
atgaaagtcg cagtcctcgg cgctgctggc ggtattggcc aggcgcttgc actactgtta     60

aaaacccaac tgccttcagg ttcagaactc tctctgtatg atatcgctcc agtgactccc    120

ggtgtggctg tcgatctgag ccatatccct actgctgtga aaatcaaagg tttttctggt    180

gaagatgcga ctccggcgct ggaaggcgca gatgtcgttc ttatctctgc aggcgtagcg    240

cgtaaaccgg gtatggatcg ttccgacctg tttaacgtta acgccggcat cgtgaaaaac    300

ctggtacagc aagttgcgaa aacctgcccg aaagcgtgca ttggtattat cactaacccg    360

gttaacacca cagttgcaat tgctgctgaa gtgctgaaaa aagccggtgt ttatgacaaa    420

aacaaactgt tcggcgttac cacgctggat atcattcgtt ccaacacctt tgttgcggaa    480

ctgaaaggca aacagccagg cgaagttgaa gtgccggtta ttggcggtca ctctggtgtt    540

accattctgc cgctgctgtc acaggttcct ggcgttagtt ttaccgagca ggaagtggct    600

gatctgacca aacgcatcca gaacgcgggt actgaagtgg ttgaagcgaa ggccggtggc    660

gggtctgcaa ccctgtctat gggccaggca gctgcacgtt ttggtctgtc tctggttcgt    720

gcactgcagg gcgaacaagg cgttgtcgaa tgtgcctacg ttgaaggcga cggtcagtac    780

gcccgtttct tctctcaacc gctgctgctg ggtaaaaacg gcgtggaaga gcgtaaatct    840

atcggtaccc tgagcgcatt tgaacagaac gcgctggaag gtatgctgga tacgctgaag    900

aaagatatcg ccctgggcga agagttcgtt aataagtaa                          939
```

<210> SEQ ID NO 67
<211> LENGTH: 20
<212> TYPE: DNA
<213> ORGANISM: Artificial
<220> FEATURE:
<223> OTHER INFORMATION: Primer

<400> SEQUENCE: 67
cacagaggtg cagtaacgag 20

<210> SEQ ID NO 68
<211> LENGTH: 1014
<212> TYPE: DNA
<213> ORGANISM: Rhizopus delemar

<400> SEQUENCE: 68
atgtttgccg cctctcgtgt tttctctatt gctgccaagc gttctttctc tacttctgct 60
gctaatcttt ccaaggttgc cgttcttggc gctgctggtg gtattggtca acccttgtct 120
ttgttgttga aggaaaaccc tcacgtcacc cacctttctc tttatgatat tgtcaacact 180
cctggtgtcg ctgccgatct tagccacatc aacaccaact ccaaggtcac tggccacacc 240
cctgaaaacg atggtttgaa gactgctctt gaaggtgctc acgttgttgt tattcctgct 300
ggcgttcctc gtaagcctgg tatgacccgt gatgatttat tcaacaccaa tgcttccatt 360
gttcgtgacc ttgctgaagc tgctgccaag cactgtcccg acgctcattt ccttatcatc 420
tccaaccctg tcaactccac tgttcccatc tttgccgaaa ccttaaagaa ggctggtgtc 480
ttcaacccta agcgtttgta tggtgtcacc actcttgatg tcgtccgtgc ctctcgcttc 540
gttgccgaag tcaagaactt ggaccccaac gatgtcaagg ttaccgttgt cggtggtcac 600
tctggtgtga ctattgtccc tctcctctct caaaccggtc tcgaattcag caaggaagaa 660
ctcgatgcct tgacccaccg tatccaattc ggtggtgatg aagtcgttca agccaagaat 720
ggtactggtt ctgtcactct ctccatggcc tttgccggtg ctcgtttcgc caactctgtc 780
ttggaagcca ctgttggtgg taagaagggt gttgttgaac cctcctttgt caagtctgat 840
gtctttgcca aggatggtgt tgaatatttc tctaccaaca ttgaacttgg tcctgaaggt 900
gttgaaaaga tcaacgaact cggtcaaatc tctgactatg aaaaggaact tattgctaag 960
gccgttcctg aattaaagaa gaacattgcc aagggtaaca gctttgttca ataa 1014

<210> SEQ ID NO 69
<211> LENGTH: 31
<212> TYPE: DNA
<213> ORGANISM: Artificial
<220> FEATURE:
<223> OTHER INFORMATION: Primer

<400> SEQUENCE: 69
caagagtatc ccatctgaca ggaaccgatg g 31

<210> SEQ ID NO 70
<211> LENGTH: 1458
<212> TYPE: DNA
<213> ORGANISM: Issatchenkia orientalis

<400> SEQUENCE: 70
atgttagctg ctagatcatt aaaggcaaga atgtcaacaa gagctttctc aactacctca 60
attgcaaaaa gaatcgaaaa agatgcattt ggtgacattg aagtcccaaa tgagaaatat 120
tggggtgctc aaactcaaag atctttacaa aatttcaaaa ttggtggtaa gagagaagtt 180
atgccagaac caatcatcaa atcttttggt attttaaaga aggctactgc taagatcaat 240
gctgagtctg gtgctttaga cccaaagtta tctgaagcca tccaacaagc tgcaaccgaa 300
gtttatgaag gtaaactaat ggaccatttc ccattagttg tctttcaaac cggttctggt 360
actcaatcta acatgaatgc caatgaagtc atctctaata gagcaattga aatcttgggt 420
ggtgaattag gctctaaaac tccagtccat cctaatgatc atgttaatat gtcccaatct 480
tctaatgata ctttccctac tgtcatgcat attgcagcag ttacagaagt ttcatcccat 540
ttattaccag aattaactgc actaagagat gcattgcaaa agaaatccga tgaatttaag 600
aatattatca aaatcggtag aacccattta caagatgcaa ctcctttaac tttaggtcaa 660
gaattttctg gttatgttca acaatgtact aatggtatca aaagaatcga aattgctctt 720
gaacatttga gatacttagc tcaaggtggt actgccgttg gtactggtct taacaccaag 780
aaaggttttg ctgaaaaggt tgcaaatgaa gtcactaaat tgactggttt acaattctat 840
accgctccaa ataaattcga agcccttgca gctcacgatg ctgttgttga aatgtctggt 900
gctttgaata ccgttgcagt ctcattattc aaaatcgctc aagatatcag atatttgggt 960
tccggcccaa gatgtggtta tggtgaattg gctttaccag aaaatgaacc aggttcttcc 1020
atcatgccgg gtaaagttaa cccaactcaa aacgaagctt tgactatgct ttgtacccaa 1080
gtctttggta accactcttg tattaccttt gcaggtgctt caggtcaatt cgaattgaat 1140
gtctttaagc cagttatgat ctccaacttg ttatcttcta ttaggttatt aggtgatggt 1200
tgtaattctt ttagaatcca ctgtgttgaa ggtatcattg caaataccga caagattgat 1260
aaattactac atgaatctct catgttagtt actgctttga acccacacat tggttacgat 1320
aaggcttcca agattgcaaa gaatgcacac aagaagggct tgacattgaa acaatctgca 1380
ttggaattag gttacttgac cgaagaacaa ttcaatgaat gggttagacc agaaaacatg 1440
attggtccaa aggattaa 1458

<210> SEQ ID NO 71
<211> LENGTH: 27
<212> TYPE: DNA
<213> ORGANISM: Artificial
<220> FEATURE:
<223> OTHER INFORMATION: Primer

<400> SEQUENCE: 71
catcactgtt aaaggaatgg gtaaatc 27

<210> SEQ ID NO 72
<211> LENGTH: 27
<212> TYPE: DNA
<213> ORGANISM: Artificial
<220> FEATURE:
<223> OTHER INFORMATION: Primer

<400> SEQUENCE: 72
gctggagaat agatcttcaa cgccccg 27

<210> SEQ ID NO 73
<211> LENGTH: 30
<212> TYPE: DNA
<213> ORGANISM: Artificial
<220> FEATURE:
<223> OTHER INFORMATION: Primer

<400> SEQUENCE: 73

```
gagaacttat acgcaccaga acgccttttg                                    30


<210> SEQ ID NO 74
<211> LENGTH: 31
<212> TYPE: DNA
<213> ORGANISM: Artificial
<220> FEATURE:
<223> OTHER INFORMATION: Primer

<400> SEQUENCE: 74

caagagtatc ccatctgaca ggaaccgatg g                                  31


<210> SEQ ID NO 75
<211> LENGTH: 1413
<212> TYPE: DNA
<213> ORGANISM: Saccharomyces cerevisiae

<400> SEQUENCE: 75

atgtctctct ctcccgttgt tgttattgga accggtttgg ccgggctggc tgctgccaac      60

gaattggtta acaagtataa catccctgta accatcctcg aaaaggcttc ctcgatcggt     120

gggaactcta tcaaggcctc cagtggtatt aacggtgctt gcaccgagac tcaacgtcac     180

ttccacatcg aggactcccc acgcttattt gaagatgaca ccatcaagtc tgctaaaggt     240

aaaggtgtcc aagagttaat ggctaagttg gccaatgatt ctcccctggc tattgaatgg     300

ttgaaaaacg aatttgattt gaaattggac ctattggctc aattgggtgg ccactctgtg     360

gcaagaactc acagatcgtc tgggaagttg cctccaggtt tcgaaattgt ttctgcctta     420

tctaacaatt tgaagaaatt agctgagact aaaccagagt tagttaagat taacttagac     480

agtaaagtcg tagacatcca tgaaaaggat ggctccattt ctgctgtagt gtacgaggat     540

aagaatggcg aaaagcacat ggtgagtgct aacgatgtcg ttttttgttc tggagggttt     600

ggcttttcta aggaaatgct taaagaatat gcacccgaac tggtgaactt gccaacgaca     660

aacgggcaac aaacaactgg tgatggtcaa aggcttctgc agaagttagg cgctgatctg     720

attgacatgg accaaattca agttcatcca actgggttca ttgatccaaa tgaccgtagc     780

tcaagctgga aattcttggc tgccgaatcc ttaagaggtc ttggtggtat cctattaaac     840

cctattaccg gtagaagatt tgtcaacgaa ttgaccacaa gagatgtagt cactgcagct     900

attcaaaagg tttgtcctca agaggataac agagcactat tggttatggg cgaaaaaatg     960

tacacagatt tgaagaataa tttagatttt tacatgttca agaaacttgt acagaaattg    1020

acattatctc aagttgtgtc tgaatataat ttaccaatca ctgtcaccca attatgcgag    1080

gaattgcaaa catactcttc gttcactacc aaggctgatc cgttgggacg taccgttatt    1140

ctcaacgaat ttggctctga cgttactcca gaaaccgtgg tttttattgg tgaagtaaca    1200

ccggttgtcc atttcaccat gggtggtgct agaatcaatg tcaaggctca agtcattggc    1260

aagaacgacg aaaggctact aaaaggcctg tacgcggccg gtgaagtttc tggcggtgtt    1320

catggcgcca ataggttggg tggttcaagt ttgttagaat gcgttgtctt tgggagaact    1380

gcagctgaat ctattgccaa tgaccgcaag taa                                1413


<210> SEQ ID NO 76
<211> LENGTH: 1413
<212> TYPE: DNA
<213> ORGANISM: Saccharomyces mikatae

<400> SEQUENCE: 76

atgtcatctt ctccagttgt cgttattggt acaggcttgg caggtttggc aactgctaat      60
```

```
gagttagtca ataagtacaa cattcctgtt accattttgg aaaaggcatc ctctatcggt    120

ggcaattcca ttaaggcatc ttctggtatc aatggtgcat gtacagaaac ccaacgtcat    180

tttcacattg aagatactcc tagacttttt gaagatgata ctgttcaatc cgccaagggc    240

aaaggtgttc aagagttaat gggtaaactt gctaatgatt ctccacttgc tattgaatgg    300

ttaaagactg aattcgactt aaagttagac cttttggctc agttaggtgg tcactctgtt    360

gctagaactc atagatcttc cggtaaactt ccaccaggtt tcgaaatcgt ttccgcctta    420

tccaataact tgaaaaagtt ggcagaaacc aagccagagt tagttaagat taacttagac    480

tcaaaggtcg ttgacatcca caaaaaggac ggctctattt ccgcaattgt ctatgatgac    540

aaaaacggtg aaagacatac cttatccact tcaaatgttg ttttctgctc tggtggtttc    600

ggtttttcta aggaaatgtt aaacgagtat gctccacaat tggtcaactt gccaaccact    660

aacggtcagc aaacaacagg tgacggccaa agattgttac aaaagcttgg tgcagatttg    720

attgatatgg atcaaattca agtccatcct actggtttca tcgacccaaa cgatagaaac    780

tcctcttgga agtttttggc tgctgaatct ttaagaggtt tgggtggtat cttattgaat    840

ccaattactg gtcgtagatt tgtcaacgaa ttgaccacta gagatgtcgt tactgaagca    900

atccagaagc actgtccaca agatgataac agagctttgt tagttatgtc cgaaaagatg    960

tatacagatt tgaaaaacaa tttggacttc tacatgttca aaaagttagt tcaaaagtta   1020

tctttgtccc aagttgtttc cgagtataag ttaccaatta ctgtttccca attgtgtcag   1080

gaattacaaa cctactcatc ttttacttca aaagccgatc ctcttggtag aaccgttgtc   1140

ttaaacgaat tcggtgctga catcacccca gaaacaatgg ttttcatcgg cgaagttacc   1200

ccagtcgttc actttaccat gggtggtgct agaatcaatg ttaaggctca agttatcggc   1260

aaaaacgatg agcctttgtt aaacggtttg tacgcagcag gtgaagtttc tggtggtgtc   1320

catggtgcca atagattagg tggttcatct ttgcttgaat gtgtcgtttt tggtagaact   1380

gcagcagaat caattgccaa taaccacaag taa                                1413
```

```
<210> SEQ ID NO 77
<211> LENGTH: 1413
<212> TYPE: DNA
<213> ORGANISM: Kluyveromyces polysporus

<400> SEQUENCE: 77

atgtcaacca aaaagccagt cgtcatcatt ggtactggtt tagccggttt gtctgctggt     60

aatcaattgg tcaatatgca taaagttcct atcattatgt tggacaaggc atcctccatt    120

ggtggtaatt ctacaaaggc ttcctctggt atcaacggtg cttctactat tactcaacag    180

caacttaatg ttaaagactc tcctgactta ttccttcaag atactgttaa gtctgctaag    240

ggtagaggta ttgagtccct tatgaaaaag ttatcacaag actccaactc tgctatccat    300

tggttgcaac aggattttga tttgaagttg gatttgttag ctcaattggg tggtcattcc    360

gttcctagaa cacaccgttc ctcaggcaag ttacctccag gcttcgaaat tgtccaagct    420

ttatctaaca agttaaaggc tatttctgag tccgatccag aattcgttag aatcttactt    480

aactccaagg ttgttgatgt ttccgttaac aatgagggca aggtcgaatc tattgactat    540

gttgatgcag aaggtaaaca tcacaaaatc gctactgata acgttgtctt ttgttccggt    600

ggtttcggtc actcagcaga aatgttgaac aagtatgcac cagaattagc taacttgcca    660

actactaacg gtcaacaaac cactggcgat ggtcagagaa tcttggagaa attgggtgca    720
```

```
gacttgattg atatgtccca aattcaagtt cacccaacag gtttcatcga tccagcaaac    780
agagattcta agtggaagtt tttggctgcc gaagcattaa gaggtttagg tggtatctta    840
cttaatccat ctaccggcaa gagattcgtt aatgagttaa ccaccagaga tttggtcaca    900
gaagctatcc aatcacaatg tccaagagat gacaataagg cattccttgt tatgtctgaa    960
aaggtctatg agaattacaa aaacaacatg gacttttact tattcaaaaa gttagtttcc   1020
aagatgacca ttaaggaatt tgtcgaaact tacaagttgc caatttctgc cgacgccgtt   1080
acccaagact taatcgacta ttcagttgat aagaccgata agtttggtag accattggtt   1140
atcaacgttt ttgatgaaaa gttgaccgaa gattccgaaa tctatgttgg tgaagttaca   1200
ccagttgtcc atttcactat gggtggtgca aagatcaata ctgaatctca agttatcaac   1260
aaaaacggtc aagttttggc aaagggtatc tacgcagcag gtgaagtctc cggtggtgtt   1320
cacggttcta atagattagg tggttcatct ttgttagaat gcgtcgttta cggtagatct   1380
gctgcagata acattgccaa aaacattgaa taa                                1413
```

<210> SEQ ID NO 78
<211> LENGTH: 1464
<212> TYPE: DNA
<213> ORGANISM: Kluyveromyces marxianus

<400> SEQUENCE: 78

```
atgttgcaca gatacatccg tttgttctcc ttctgcgtca tcttgtactt agtctatttg     60
ttacttacta aggagtcaaa cgtcatgtct aagcctgttg ttgttattgg ttctggttta    120
gcaggcttaa caacatcttc acaattagca aagtttaaca ttccaatcgt ccttttagaa    180
aagacatctt ccattggtgg taattccatt aaggcatctt ctggtatcaa tggcgcaggc    240
accgaaactc aatctcgttt acacgttgaa gatcacccag aattgtttgc tgatgatacc    300
attaagtctg caaaaggtaa aggtgttgtc gctttgatgg aaaagttatc taaagactcc    360
tctgatgcta tttcctggtt acaaaaacgac ttcaagattc ctttggataa gttagctcaa    420
ttaggcggtc attccgttcc tagaacccat agatcatccg gcaagcttcc accaggtttc    480
caaattgtcg ataccttgaa aaaggccttg gagtcttatg actctaaagc agttaagatc    540
caattgaatt ctaaggtcgt tgatgttaag cttgattcca ataacagagt ttcatctgtt    600
gttttcgaag atcaagatgg tactcacacc attgaaacca acaacgtcgt tttctgtact    660
ggtggtttcg gtttcaacaa aaagttattg gagaagtatg caccacactt ggtcgacttg    720
ccaactacca acggtgagca aaccttaggt gaaggtcagg tcttattgga aaaacttggt    780
gctaagttga ttgatatgga ccaaattcaa gttcatccaa ctggctttat cgatccagcc    840
aatccagatt ctaattggaa gtttttggct gccgaggcct taagaggttt aggtggtgtc    900
ttgatcaatc cacacactgg tcagagattt gttaacgaat tgacaactag agacatggtc    960
accgaagcta tccagtctaa gtccgaatcc aagactgctt acttggttat gtccgagtcc   1020
ttatacgaga actacaagcc aaacatggac ttctatatgt tcaaaaagct tgtttccaaa   1080
aagaccgttg ctgaatttgc tgaagatttg ccagtttctg ttgaccaact tattgcagaa   1140
ctttcaactt attccgactt gtctaaggat gatcatttgg gtagaaagtt tagagaaaac   1200
acttttggtt cctcattatc atcagactca accattttcg ttggcaagat tactcctgtt   1260
gttcacttca caatgggtgg tgcaaagatt gatgaacaag ctagagtctt gaatgcagaa   1320
ggtaaaccat tagctactgg tatctacgcc gctggtgaag tttctggtgg tgtccatggt   1380
gctaatagat taggtggttc ctctttgtta gaatgtgttg tctttggtag acaagcagca   1440
```

aaatccatta gagcaaactt gtaa 1464

<210> SEQ ID NO 79
<211> LENGTH: 29
<212> TYPE: DNA
<213> ORGANISM: Artificial
<220> FEATURE:
<223> OTHER INFORMATION: Primer

<400> SEQUENCE: 79
gaggaagttc aaagtatgaa agacgtcag 29

<210> SEQ ID NO 80
<211> LENGTH: 33
<212> TYPE: DNA
<213> ORGANISM: Artificial
<220> FEATURE:
<223> OTHER INFORMATION: Primer

<400> SEQUENCE: 80
gatcgggccc gtcttggaag acgcactagt ctc 33

<210> SEQ ID NO 81
<211> LENGTH: 20
<212> TYPE: DNA
<213> ORGANISM: Artificial
<220> FEATURE:
<223> OTHER INFORMATION: Primer

<400> SEQUENCE: 81
tgacaggaac cgatggactc 20

<210> SEQ ID NO 82
<211> LENGTH: 1144
<212> TYPE: PRT
<213> ORGANISM: Leishmania mexicana

<400> SEQUENCE: 82

Met Ala Asp Gly Lys Thr Ser Ala Ser Val Val Ala Val Asp Ala Glu
1 5 10 15

Arg Ala Ala Lys Glu Arg Asp Ala Ala Ala Arg Ala Met Leu Gln Gly
20 25 30

Gly Gly Val Ser Pro Ala Gly Lys Ala Gln Leu Leu Lys Lys Gly Leu
35 40 45

Val His Thr Val Pro Tyr Thr Leu Lys Val Val Val Ala Asp Pro Lys
50 55 60

Glu Met Glu Lys Ala Thr Ala Asp Ala Glu Glu Val Leu Gln Ala Ala
65 70 75 80

Phe Gln Val Val Asp Thr Leu Leu Asn Asn Phe Asn Glu Asn Ser Glu
85 90 95

Val Ser Arg Val Asn Arg Leu Ala Val Gly Glu Glu His Gln Met Ser
100 105 110

Glu Thr Leu Lys His Val Met Ala Cys Cys Gln Lys Val Tyr His Ser
115 120 125

Ser Arg Gly Val Phe Asp Pro Ala Val Gly Pro Leu Val Arg Glu Leu
130 135 140

Arg Glu Ala Ala His Lys Gly Lys Thr Val Pro Ala Glu Arg Val Asn
145 150 155 160

Asp Leu Leu Ser Lys Cys Thr Leu Asn Ala Ser Phe Ser Ile Asp Met
165 170 175

```
Ser Arg Gly Met Ile Ala Arg Lys His Pro Asp Ala Met Leu Asp Leu
            180                 185                 190

Gly Gly Val Asn Lys Gly Tyr Gly Ile Asp Tyr Ile Val Glu His Leu
        195                 200                 205

Asn Ser Leu Gly Tyr Asp Asp Val Phe Phe Glu Trp Gly Gly Asp Val
    210                 215                 220

Arg Ala Ser Gly Lys Asn Gln Leu Ser Gln Pro Trp Ala Val Gly Ile
225                 230                 235                 240

Val Arg Pro Pro Ala Leu Ala Asp Ile Arg Thr Val Val Pro Glu Asp
                245                 250                 255

Lys Arg Ser Phe Ile Arg Val Val Arg Leu Asn Asn Glu Ala Ile Ala
            260                 265                 270

Thr Ser Gly Asp Tyr Glu Asn Leu Val Glu Gly Pro Gly Ser Lys Val
        275                 280                 285

Tyr Ser Ser Thr Phe Asn Pro Thr Ser Lys Asn Leu Leu Glu Pro Thr
    290                 295                 300

Glu Ala Gly Met Ala Gln Val Ser Val Lys Cys Cys Ser Cys Ile Tyr
305                 310                 315                 320

Ala Asp Ala Leu Ala Thr Ala Ala Leu Leu Lys Asn Asp Pro Ala Ala
                325                 330                 335

Val Arg Arg Ile Leu Asp Asn Trp Arg Tyr Val Arg Asp Thr Val Thr
            340                 345                 350

Asp Tyr Thr Thr Tyr Thr Arg Glu Gly Glu Arg Val Ala Lys Met Leu
        355                 360                 365

Glu Ile Ala Thr Glu Asp Ala Glu Met Arg Ala Lys Arg Ile Lys Gly
    370                 375                 380

Ser Leu Pro Ala Arg Val Ile Ile Val Gly Gly Gly Leu Ala Gly Cys
385                 390                 395                 400

Ser Ala Ala Ile Glu Ala Ala Asn Cys Gly Ala His Val Ile Leu Leu
                405                 410                 415

Glu Lys Glu Pro Lys Leu Gly Gly Asn Ser Ala Lys Ala Thr Ser Gly
            420                 425                 430

Ile Asn Ala Trp Gly Thr Arg Ala Gln Ala Lys Gln Gly Val Met Asp
        435                 440                 445

Gly Gly Lys Phe Phe Glu Arg Asp Thr His Arg Ser Gly Lys Gly Gly
    450                 455                 460

Asn Cys Asp Pro Cys Leu Val Lys Thr Leu Ser Val Lys Ser Ser Asp
465                 470                 475                 480

Ala Val Lys Trp Leu Ser Glu Leu Gly Val Pro Leu Thr Val Leu Ser
                485                 490                 495

Gln Leu Gly Gly Ala Ser Arg Lys Arg Cys His Arg Ala Pro Asp Lys
            500                 505                 510

Ser Asp Gly Thr Pro Val Pro Val Gly Phe Thr Ile Met Lys Thr Leu
        515                 520                 525

Glu Asn His Ile Val Asn Asp Leu Ser Arg His Val Thr Val Met Thr
    530                 535                 540

Gly Ile Thr Val Thr Ala Leu Glu Ser Thr Ser Arg Val Arg Pro Asp
545                 550                 555                 560

Gly Val Leu Val Lys His Val Thr Gly Val His Leu Ile Gln Ala Ser
                565                 570                 575

Gly Gln Ser Met Val Leu Asn Ala Asp Ala Val Ile Leu Ala Thr Gly
            580                 585                 590
```

```
Gly Phe Ser Asn Asp His Thr Pro Asn Ser Leu Leu Gln Gln Tyr Ala
        595                 600                 605

Pro Gln Leu Ser Ser Phe Pro Thr Thr Asn Gly Val Trp Ala Thr Gly
    610                 615                 620

Asp Gly Val Lys Met Ala Ser Lys Leu Gly Val Ala Leu Val Asp Met
625                 630                 635                 640

Asp Lys Val Gln Leu His Pro Thr Gly Leu Leu Asp Pro Lys Asp Pro
                645                 650                 655

Ser Asn Arg Thr Lys Tyr Leu Gly Pro Glu Ala Leu Arg Gly Ser Gly
            660                 665                 670

Gly Val Leu Leu Asn Lys Asn Gly Glu Arg Phe Val Asn Glu Leu Asp
        675                 680                 685

Leu Arg Ser Val Val Ser Gln Ala Ile Ile Ala Gln Asp Asn Glu Tyr
    690                 695                 700

Pro Gly Ser Gly Gly Ser Lys Phe Ala Tyr Cys Val Leu Asn Glu Thr
705                 710                 715                 720

Ala Ala Lys Leu Phe Gly Lys Asn Phe Leu Gly Phe Tyr Trp Asn Arg
                725                 730                 735

Leu Gly Leu Phe Gln Lys Val Asp Ser Val Ala Gly Leu Ala Lys Leu
            740                 745                 750

Ile Gly Cys Pro Glu Ala Asn Val Val Ala Thr Leu Lys Gln Tyr Glu
        755                 760                 765

Glu Leu Ser Ser Lys Lys Leu Asn Pro Cys Pro Leu Thr Gly Lys Ser
    770                 775                 780

Val Phe Pro Cys Val Leu Gly Thr Gln Gly Pro Tyr Tyr Val Ala Leu
785                 790                 795                 800

Val Thr Pro Ser Ile His Tyr Thr Met Gly Gly Cys Leu Ile Ser Pro
                805                 810                 815

Ser Ala Glu Met Gln Thr Ile Asp Asn Ser Gly Val Thr Pro Val Arg
            820                 825                 830

Arg Pro Ile Leu Gly Leu Phe Gly Ala Gly Glu Val Thr Gly Gly Val
        835                 840                 845

His Gly Gly Asn Arg Leu Gly Gly Asn Ser Leu Leu Glu Cys Val Val
    850                 855                 860

Phe Gly Lys Ile Ala Gly Asp Arg Ala Ala Thr Ile Leu Gln Lys Lys
865                 870                 875                 880

Asn Thr Gly Leu Ser Met Thr Glu Trp Ser Thr Val Val Leu Arg Glu
                885                 890                 895

Val Arg Glu Gly Gly Val Tyr Gly Ala Gly Ser Arg Val Leu Arg Phe
            900                 905                 910

Asn Met Pro Gly Ala Leu Gln Arg Thr Gly Leu Ala Leu Gly Gln Phe
        915                 920                 925

Ile Gly Ile Arg Gly Asp Trp Asp Gly His Arg Leu Ile Gly Tyr Tyr
    930                 935                 940

Ser Pro Ile Thr Leu Pro Asp Asp Val Gly Val Ile Gly Ile Leu Ala
945                 950                 955                 960

Arg Ala Asp Lys Gly Arg Leu Ala Glu Trp Ile Ser Ala Leu Gln Pro
                965                 970                 975

Gly Asp Ala Val Glu Met Lys Ala Cys Gly Gly Leu Ile Ile Asp Arg
            980                 985                 990

Arg Phe Ala Glu Arg His Phe Phe  Phe Arg Gly His Lys  Ile Arg Lys
        995                 1000                1005

Leu Ala  Leu Ile Gly Gly Gly  Thr Gly Val Ala Pro  Met Leu Gln
```

```
    1010                1015                1020

Ile Val  Arg Ala Ala Val Lys  Lys Pro Phe Val Asp  Ser Ile Glu
    1025                1030                1035

Ser Ile  Gln Phe Ile Tyr Ala  Ala Glu Asp Val Ser  Glu Leu Thr
    1040                1045                1050

Tyr Arg  Thr Leu Leu Glu Ser  Tyr Glu Glu Glu Tyr  Gly Ser Glu
    1055                1060                1065

Lys Phe  Lys Cys His Phe Val  Leu Asn Asn Pro Pro  Ala Gln Trp
    1070                1075                1080

Thr Asp  Gly Val Gly Phe Val  Asp Thr Ala Leu Leu  Arg Ser Ala
    1085                1090                1095

Val Gln  Ala Pro Ser Asn Asp  Leu Leu Val Ala Ile  Cys Gly Pro
    1100                1105                1110

Pro Ile  Met Gln Arg Ala Val  Lys Gly Ala Leu Lys  Gly Leu Gly
    1115                1120                1125

Tyr Asn  Met Asn Leu Val Arg  Thr Val Asp Glu Thr  Glu Pro Pro
    1130                1135                1140

Ser


<210> SEQ ID NO 83
<211> LENGTH: 743
<212> TYPE: PRT
<213> ORGANISM: Saccharomyces cerevisiae

<400> SEQUENCE: 83

Met Asp Gly Pro Asn Phe Ala His Gln Gly Gly Arg Ser Gln Arg Thr
1               5                   10                  15

Thr Glu Leu Tyr Ser Cys Ala Arg Cys Arg Lys Leu Lys Lys Lys Cys
            20                  25                  30

Gly Lys Gln Ile Pro Thr Cys Ala Asn Cys Asp Lys Asn Gly Ala His
        35                  40                  45

Cys Ser Tyr Pro Gly Arg Ala Pro Arg Arg Thr Lys Lys Glu Leu Ala
    50                  55                  60

Asp Ala Met Leu Arg Gly Glu Tyr Val Pro Val Lys Arg Asn Lys Lys
65                  70                  75                  80

Val Gly Lys Ser Pro Leu Ser Thr Lys Ser Met Pro Asn Ser Ser Ser
                85                  90                  95

Pro Leu Ser Ala Asn Gly Ala Ile Thr Pro Gly Phe Ser Pro Tyr Glu
            100                 105                 110

Asn Asp Asp Ala His Lys Met Lys Gln Leu Lys Pro Ser Asp Pro Ile
        115                 120                 125

Asn Leu Val Met Gly Ala Ser Pro Asn Ser Ser Glu Gly Val Ser Ser
    130                 135                 140

Leu Ile Ser Val Leu Thr Ser Leu Asn Asp Asn Ser Asn Pro Ser Ser
145                 150                 155                 160

His Leu Ser Ser Asn Glu Asn Ser Met Ile Pro Ser Arg Ser Leu Pro
                165                 170                 175

Ala Ser Val Gln Gln Ser Ser Thr Thr Ser Ser Phe Gly Gly Tyr Asn
            180                 185                 190

Thr Pro Ser Pro Leu Ile Ser Ser His Val Pro Ala Asn Ala Gln Ala
        195                 200                 205

Val Pro Leu Gln Asn Asn Asn Arg Asn Thr Ser Asn Gly Asp Asn Gly
    210                 215                 220

Ser Asn Val Asn His Asp Asn Asn Asn Gly Ser Thr Asn Thr Pro Gln
```

```
225                 230                 235                 240

Leu Ser Leu Thr Pro Tyr Ala Asn Asn Ser Ala Pro Asn Gly Lys Phe
                245                 250                 255

Asp Ser Val Pro Val Asp Ala Ser Ser Ile Glu Phe Glu Thr Met Ser
            260                 265                 270

Cys Cys Phe Lys Gly Gly Arg Thr Thr Ser Trp Val Arg Glu Asp Gly
        275                 280                 285

Ser Phe Lys Ser Ile Asp Arg Ser Leu Leu Asp Arg Phe Ile Ala Ala
    290                 295                 300

Tyr Phe Lys His Asn His Arg Leu Phe Pro Met Ile Asp Lys Ile Ala
305                 310                 315                 320

Phe Leu Asn Asp Ala Ala Thr Ile Thr Asp Phe Glu Arg Leu Tyr Asp
                325                 330                 335

Asn Lys Asn Tyr Pro Asp Ser Phe Val Phe Lys Val Tyr Met Ile Met
            340                 345                 350

Ala Ile Gly Cys Thr Thr Leu Gln Arg Ala Gly Met Val Ser Gln Asp
        355                 360                 365

Glu Glu Cys Leu Ser Glu His Leu Ala Phe Leu Ala Met Lys Lys Phe
    370                 375                 380

Arg Ser Val Ile Ile Leu Gln Asp Ile Glu Thr Val Arg Cys Leu Leu
385                 390                 395                 400

Leu Leu Gly Ile Tyr Ser Phe Phe Glu Pro Lys Gly Ser Ser Ser Trp
                405                 410                 415

Thr Ile Ser Gly Ile Ile Met Arg Leu Thr Ile Gly Leu Gly Leu Asn
            420                 425                 430

Arg Glu Leu Thr Ala Lys Lys Leu Lys Ser Met Ser Ala Leu Glu Ala
        435                 440                 445

Glu Ala Arg Tyr Arg Val Phe Trp Ser Ala Tyr Cys Phe Glu Arg Leu
    450                 455                 460

Val Cys Thr Ser Leu Gly Arg Ile Ser Gly Ile Asp Asp Glu Asp Ile
465                 470                 475                 480

Thr Val Pro Leu Pro Arg Ala Leu Tyr Val Asp Glu Arg Asp Asp Leu
                485                 490                 495

Glu Met Thr Lys Leu Met Ile Ser Leu Arg Lys Met Gly Gly Arg Ile
            500                 505                 510

Tyr Lys Gln Val His Ser Val Ser Ala Gly Arg Gln Lys Leu Thr Ile
        515                 520                 525

Glu Gln Lys Gln Glu Ile Ile Ser Gly Leu Arg Lys Glu Leu Asp Glu
    530                 535                 540

Ile Tyr Ser Arg Glu Ser Glu Arg Arg Lys Leu Lys Lys Ser Gln Met
545                 550                 555                 560

Asp Gln Val Glu Arg Glu Asn Asn Ser Thr Thr Asn Val Ile Ser Phe
                565                 570                 575

His Ser Ser Glu Ile Trp Leu Ala Met Arg Tyr Ser Gln Leu Gln Ile
            580                 585                 590

Leu Leu Tyr Arg Pro Ser Ala Leu Met Pro Lys Pro Pro Ile Asp Ser
        595                 600                 605

Leu Ser Thr Leu Gly Glu Phe Cys Leu Gln Ala Trp Lys His Thr Tyr
    610                 615                 620

Thr Leu Tyr Lys Lys Arg Leu Leu Pro Leu Asn Trp Ile Thr Leu Phe
625                 630                 635                 640

Arg Thr Leu Thr Ile Cys Asn Thr Ile Leu Tyr Cys Leu Cys Gln Trp
                645                 650                 655
```

```
Ser Ile Asp Leu Ile Glu Ser Lys Ile Glu Ile Gln Gln Cys Val Glu
            660                 665                 670

Ile Leu Arg His Phe Gly Glu Arg Trp Ile Phe Ala Met Arg Cys Ala
        675                 680                 685

Asp Val Phe Gln Asn Ile Ser Asn Thr Ile Leu Asp Ile Ser Leu Ser
    690                 695                 700

His Gly Lys Val Pro Asn Met Asp Gln Leu Thr Arg Glu Leu Phe Gly
705                 710                 715                 720

Ala Ser Asp Ser Tyr Gln Asp Ile Leu Asp Glu Asn Asn Val Asp Val
                725                 730                 735

Ser Trp Val Asp Lys Leu Val
            740


<210> SEQ ID NO 84
<211> LENGTH: 17
<212> TYPE: DNA
<213> ORGANISM: Artificial
<220> FEATURE:
<223> OTHER INFORMATION: Primer

<400> SEQUENCE: 84

caatccaacc gccaccg                                                    17


<210> SEQ ID NO 85
<211> LENGTH: 47
<212> TYPE: DNA
<213> ORGANISM: Artificial
<220> FEATURE:
<223> OTHER INFORMATION: Primer

<400> SEQUENCE: 85

ggataaaagt attacatacg tacaggattg tgtattagtg tatttcg                   47


<210> SEQ ID NO 86
<211> LENGTH: 21
<212> TYPE: DNA
<213> ORGANISM: Artificial
<220> FEATURE:
<223> OTHER INFORMATION: Primer

<400> SEQUENCE: 86

ctttcattag gttggttgaa g                                               21


<210> SEQ ID NO 87
<211> LENGTH: 1521
<212> TYPE: DNA
<213> ORGANISM: Issatchenkia orientalis

<400> SEQUENCE: 87

atgggtgtcc agtttatcga aaataccatt atcgttgtct ttggtgcgtc tggagattta      60

gccaagaaga agactttccc cgccctgttt ggactattca gggagggcca gctctcagaa     120

acaaccaaaa tcattgggtt tgctcgatca aaactatcaa atgatgactt gaggaacaga     180

ataaagccgt acttgaaatt gaacaagaga acagatgctg aaaggcagtc tctggagaag     240

tttctgcaga ttctcgagta tcaccagtca aactacgacg acagtgaagg ttttgaaaaa     300

ttggagaagc taatcaataa gtacgacgat gaggcaaacg tgaaagagtc tcacaggttg     360

tactatttgg ctttaccacc gtctgtcttt acaaccgttg caacaatgtt gaaaaaacat     420

tgtcatccag gtgattctgg tattgctagg ctaattgtcg agaaaccctt tggccatgac     480
```

```
ttgagctcgt cccgtgagct acaaaagtct ttagctccac tttggaatga agatgaattg    540

tttagaattg atcattattt gggcaaagaa atggttaaga atttaattcc tttgaggttt    600

tcaaatacgt ttttgagcag ttcttggaac aatcaattta ttgacaccat ccaaatcact    660

tttaaggaga actttggaac tgaaggacgt ggtggttact ttgattccat tggtataata    720

agagatgtta tccaaaatca tttgttacaa gtcttgacta ttgttttgat ggaaaaacca    780

gcggatttta atggagaatc tatcagagat gaaaaggtta aagtgttaaa ggcaattgaa    840

caaattgatt tcaataatgt gttggtaggt caatatgata aatctgaaga tggtagtaaa    900

cctggttact tggatgatga taccgtcaat ccagattcta aagctgtcac ttatgctgcc    960

ttagttttaa atgtggcaaa cgaaagatgg aataatgttc cgatcattct aaaggcaggc   1020

aaggccttga atcaatccaa ggtggaaatt agaatccagt tcaaaccagt agaaaatgga   1080

atcttcaaaa actctgctag gaatgagttg gttattagga tccaaccaaa cgaggcaatg   1140

tatttgaaaa tgaacatcaa agtacctggt gtttccaatc aagtgtcgat ttcagaaatg   1200

gatttgactt acaagaatag gtattcctcc gaattttaca ttccagaagc ttatgaatct   1260

ttgattaaag atgccttaat ggatgatcat tcaaattttg ttagagacga tgaattggac   1320

atttcatggg ctttgttcac tccattacta gaacatatcg aaggccccga tggtccaact   1380

ccaaccaagt atccttacgg ttccagaggt ccaaaggaga ttgacgaatt tttgagaaac   1440

catggttatg taaaggaacc aagagaaaat taccaatggc cattaactac tcctaaagaa   1500

ttgaacagtt caaagtttta a                                             1521
```

<210> SEQ ID NO 88
<211> LENGTH: 477
<212> TYPE: PRT
<213> ORGANISM: Issatchenkia orientalis

<400> SEQUENCE: 88

```
Met Gly Gln Asn Leu Ile Leu Asn Ala Ala Asp His Gly Phe Thr Val
1               5                   10                  15

Val Ala Tyr Asn Arg Thr Val Ser Lys Val Asp His Phe Leu Gln Asn
            20                  25                  30

Glu Ala Lys Gly Lys Ser Ile Ile Gly Ala His Ser Ile Glu Glu Leu
        35                  40                  45

Cys Ala Lys Leu Lys Lys Pro Arg Arg Ile Met Leu Leu Val Lys Ala
    50                  55                  60

Gly Asn Pro Val Asp Gln Phe Ile Glu Gln Leu Leu Pro His Leu Asp
65                  70                  75                  80

Glu Gly Asp Ile Ile Ile Asp Gly Gly Asn Ser His Phe Pro Asp Ser
                85                  90                  95

Asn Arg Arg Tyr Glu Glu Leu Lys Lys Lys Gly Ile Leu Phe Val Gly
            100                 105                 110

Ser Gly Val Ser Gly Gly Glu Glu Gly Ala Arg Tyr Gly Pro Ser Leu
        115                 120                 125

Met Pro Gly Gly Ala Lys Glu Ala Trp Pro His Ile Lys Asp Ile Phe
    130                 135                 140

Gln Ser Ile Ser Ala Lys Ala Asp Gly Glu Pro Cys Cys Asp Trp Val
145                 150                 155                 160

Gly Asp Ala Gly Ala Gly His Tyr Val Lys Met Val His Asn Gly Ile
                165                 170                 175

Glu Tyr Gly Asp Met Gln Leu Ile Cys Glu Ala Tyr Asp Leu Met Lys
            180                 185                 190
```

```
Arg Val Gly Gly Leu Thr Asp Lys Glu Ile Ser Asp Val Phe Gly Glu
        195                 200                 205

Trp Asn Glu Gly Val Leu Asp Ser Phe Leu Val Glu Ile Thr Arg Asp
    210                 215                 220

Ile Leu Ala Phe Asn Asp Lys Asp Gly Thr Pro Leu Val Glu Lys Ile
225                 230                 235                 240

Leu Asp Thr Ala Gly Gln Lys Gly Thr Gly Lys Trp Thr Ala Ile Asn
                245                 250                 255

Ala Leu Asp Leu Gly Met Pro Val Thr Leu Ile Gly Glu Ala Val Phe
            260                 265                 270

Ala Arg Cys Leu Ser Ala Leu Lys Pro Glu Arg Glu Arg Ala Ser Glu
        275                 280                 285

Ile Leu Asn Gly Pro Glu Val Glu Gln Val Ser Ala Glu Gly Arg Ala
    290                 295                 300

Gln Phe Ile Ala Asp Leu Met Gln Ala Leu Tyr Ala Ser Lys Ile Ile
305                 310                 315                 320

Ser Tyr Ala Gln Gly Phe Met Leu Ile Arg Glu Ala Ala Lys Glu Tyr
                325                 330                 335

Asn Trp Lys Leu Asn Phe Pro Ser Ile Ala Leu Met Trp Arg Gly Gly
            340                 345                 350

Cys Ile Ile Arg Ser Val Phe Leu Ala Glu Ile Thr Ala Ala Tyr Arg
        355                 360                 365

Glu Asn Pro Asp Leu Glu Asn Leu Leu Phe Asn Lys Phe Phe Gln Asp
    370                 375                 380

Ala Ile His Lys Ala Gln Ser Gly Trp Arg Lys Thr Val Ala Leu Ala
385                 390                 395                 400

Val Thr Gln Gly Ile Pro Thr Pro Ala Phe Ser Thr Ala Leu Ser Phe
                405                 410                 415

Tyr Asp Gly Tyr Arg Ser Lys Lys Leu Pro Ala Asn Leu Leu Gln Ala
            420                 425                 430

Gln Arg Asp Tyr Phe Gly Ala His Thr Phe Gln Ile Leu Pro Glu Cys
        435                 440                 445

Ala Asp Asp Glu Lys Lys Val Gly Asp Tyr Ile His Val Asn Trp Thr
    450                 455                 460

Gly Lys Gly Gly Asn Val Ser Ala Ser Thr Tyr Asp Ala
465                 470                 475
```

<210> SEQ ID NO 89
<211> LENGTH: 1434
<212> TYPE: DNA
<213> ORGANISM: Issatchenkia orientalis

<400> SEQUENCE: 89

```
atgggtcaaa acttgattct taatgcagca gatcatggtt ttactgttgt tgcatacaac      60

agaactgtct ctaaagttga ccatttcctt caaaatgaag caaagggtaa atccattatt     120

ggtgcacact ccattgaaga attatgtgct aagttgaaga aaccaagaag aattatgttg     180

ttagtcaagg caggtaatcc agttgatcaa ttcattgaac aattgttacc tcatttagat     240

gaaggcgata tcattattga cggtggtaac tctcacttcc ctgactccaa cagaagatac     300

gaggaattaa agaagaaggg tattctcttt gtcggttctg gtgtttctgg tggtgaagaa     360

ggtgcaagat atggtccttc tttgatgcct ggtggtgcaa aggaagcatg gcctcatatt     420

aaggacatct tccaatctat ctctgcaaag gccgatggtg agccatgttg tgattgggtt     480
```

```
ggtgatgcag gtgcaggtca ttacgttaag atggtccaca atggtatcga gtatggtgat    540

atgcagttga tctgtgaagc ttacgatttg atgaagagag ttggtggttt aactgacaag    600

gaaatatctg atgttttcgg tgaatggaac gagggtgttc tcgattcttt cttagttgaa    660

attaccagag atatcttagc tttcaacgat aaggatggta ccccattagt tgaaaagatc    720

ttagatactg ccggacagaa gggtactggt aaatggactg caataaatgc tttagacttg    780

ggtatgccag tcactttaat tggtgaagct gtttttgcga gatgtttatc cgctttgaag    840

ccagaaagag agagagcttc tgaaatctta aacggtccgg aagttgaaca agtttctgct    900

gaaggtagag cacaatttat tgcagatttg atgcaagctt tatatgcatc aaagattatt    960

tcttacgcac aaggtttcat gttaatcaga gaagcagcaa aggaatacaa ctggaaatta   1020

aacttccctt ctattgcact tatgtggaga ggtggttgta ttatcaggtc tgttttcttg   1080

gctgaaatta ctgcagctta tagggaaaac cctgacttag agaacttact attcaacaag   1140

ttcttccaag atgctattca taaggcacag tctggttgga gaaagactgt tgcattagct   1200

gttacccaag gtattccaac tccagcattc tctactgcat tgtctttcta cgatggttac   1260

agatccaaga agttaccagc taacttgttg caagcacaaa gagattactt cggtgctcac   1320

actttccaaa ttttacctga atgtgcagat gacgaaaaga aggttggtga ttacatccat   1380

gtcaactgga ctggtaaggg tggtaatgtt tctgctagta cttacgatgc ttaa         1434
```

<210> SEQ ID NO 90
<211> LENGTH: 438
<212> TYPE: PRT
<213> ORGANISM: Schizosaccharomyces pombe

<400> SEQUENCE: 90

```
Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45

Gly Leu Ile Ile Gly Ser Phe Pro Phe Arg Phe Tyr Gly Leu Asn Thr
    50                  55                  60

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
        115                 120                 125

Asp Thr Gly Glu Trp Met Val Trp Val Ile Arg Ile Leu Tyr Tyr Ile
    130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
        195                 200                 205
```

```
Ile Leu Phe Gln Gly Leu Gly Phe Trp Val Tyr Leu Leu Leu Phe Ala
    210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
            260                 265                 270

Phe Val Gly Ala Asn Ser Ser Glu Tyr Leu Gly Phe Val Ser Thr Phe
        275                 280                 285

Met Ala Ile Phe Ile Trp Gly Leu Ala Ala Trp Cys Tyr Cys Leu Ala
    290                 295                 300

Met Val Ser Phe Leu Ala Gly Phe Phe Thr Arg Ala Pro Leu Lys Phe
305                 310                 315                 320

Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
            340                 345                 350

Phe Gly His Ile Ile Gly Val Ile Leu Cys Ile Gln Trp Ile Leu Leu
        355                 360                 365

Met Tyr Leu Met Val Arg Ala Phe Leu Val Asn Asp Leu Cys Tyr Pro
    370                 375                 380

Gly Lys Asp Glu Asp Ala His Pro Pro Pro Lys Pro Asn Thr Gly Val
385                 390                 395                 400

Leu Asn Pro Thr Phe Pro Pro Glu Lys Ala Pro Ala Ser Leu Glu Lys
                405                 410                 415

Val Asp Thr His Val Thr Ser Thr Gly Gly Glu Ser Asp Pro Pro Ser
            420                 425                 430

Ser Glu His Glu Ser Val
        435
```

<210> SEQ ID NO 91
<211> LENGTH: 398
<212> TYPE: PRT
<213> ORGANISM: Aspergillus oryzae

<400> SEQUENCE: 91

```
Met Phe Asn Asn Glu His His Ile Pro Pro Gly Ser Ser His Ser Asp
1               5                   10                  15

Ile Glu Met Leu Thr Pro Pro Lys Phe Glu Asp Glu Lys Gln Leu Gly
            20                  25                  30

Pro Val Gly Ile Arg Glu Arg Leu Arg His Phe Thr Trp Ala Trp Tyr
        35                  40                  45

Thr Leu Thr Met Ser Gly Gly Gly Leu Ala Val Leu Ile Ile Ser Gln
    50                  55                  60

Pro Phe Gly Phe Arg Gly Leu Arg Glu Ile Gly Ile Ala Val Tyr Ile
65                  70                  75                  80

Leu Asn Leu Ile Leu Phe Ala Leu Val Cys Ser Thr Met Ala Ile Arg
                85                  90                  95

Phe Ile Leu His Gly Asn Leu Leu Glu Ser Leu Arg His Asp Arg Glu
            100                 105                 110

Gly Leu Phe Phe Pro Thr Phe Trp Leu Ser Val Ala Thr Ile Ile Cys
        115                 120                 125

Gly Leu Ser Arg Tyr Phe Gly Glu Glu Ser Asn Glu Ser Phe Gln Leu
    130                 135                 140
```

```
Ala Leu Glu Ala Leu Phe Trp Ile Tyr Cys Val Cys Thr Leu Leu Val
145                 150                 155                 160

Ala Ile Ile Gln Tyr Ser Phe Val Phe Ser Ser His Lys Tyr Gly Leu
                165                 170                 175

Gln Thr Met Met Pro Ser Trp Ile Leu Pro Ala Phe Pro Ile Met Leu
            180                 185                 190

Ser Gly Thr Ile Ala Ser Val Ile Gly Glu Gln Gln Pro Ala Arg Ala
        195                 200                 205

Ala Leu Pro Ile Ile Gly Ala Gly Val Thr Phe Gln Gly Leu Gly Phe
    210                 215                 220

Ser Ile Ser Phe Met Met Tyr Ala His Tyr Ile Gly Arg Leu Met Glu
225                 230                 235                 240

Ser Gly Leu Pro His Ser Asp His Arg Pro Gly Met Phe Ile Cys Val
                245                 250                 255

Gly Pro Pro Ala Phe Thr Ala Leu Ala Leu Val Gly Met Ser Lys Gly
            260                 265                 270

Leu Pro Glu Asp Phe Lys Leu Leu His Asp Ala His Ala Leu Glu Asp
        275                 280                 285

Gly Arg Ile Ile Glu Leu Leu Ala Ile Ser Ala Gly Val Phe Leu Trp
    290                 295                 300

Ala Leu Ser Leu Trp Phe Phe Cys Ile Ala Ile Val Ala Val Ile Arg
305                 310                 315                 320

Ser Pro Pro Glu Ala Phe His Leu Asn Trp Trp Ala Met Val Phe Pro
                325                 330                 335

Asn Thr Gly Phe Thr Leu Ala Thr Ile Thr Leu Gly Lys Ala Leu Asn
            340                 345                 350

Ser Asn Gly Val Lys Gly Val Gly Ser Ala Met Ser Ile Cys Ile Val
        355                 360                 365

Cys Met Tyr Ile Phe Val Phe Val Asn Asn Val Arg Ala Val Ile Arg
    370                 375                 380

Lys Asp Ile Met Tyr Pro Gly Lys Asp Glu Asp Val Ser Asp
385                 390                 395
```

<210> SEQ ID NO 92
<211> LENGTH: 1317
<212> TYPE: DNA
<213> ORGANISM: Schizosaccharomyces pombe

<400> SEQUENCE: 92

```
atgggtgaat tgaaagagat tttgaaacaa agatatcatg aattacttga ttggaatgtt      60

aaggcaccac atgtcccttt atcccagaga ttgaagcact ttacttggtc atggtttgct     120

tgtactatgg caaccggtgg tgttggtttg atcattggtt ccttcccatt cagattctac     180

ggtttgaaca ccattggcaa gattgtttac atcttacaaa tctttttgtt ttctcttttt     240

ggctcttgta tgttgtttcg tttcatcaag tatccatcta ccattaagga ctcttggaat     300

catcacttgg aaaagttgtt tatcgcaact tgtttgttat ctatttccac attcatcgac     360

atgttagcta tctatgctta tccagatacc ggtgaatgga tggtctgggt cattagaatc     420

ttatactaca tctatgtcgc tgtctctttc atctactgtg ttatggcctt tttcaccatt     480

ttcaacaatc atgtttacac tattgaaact gcttctccag cttggatttt gccaatcttc     540

cctccaatga tctgtggtgt cattgctggt gctgttaact ccacccaacc tgctcaccaa     600

ttgaaaaaca tggtcatttt cggtatcttg tttcaaggtt taggtttttg ggtttacctt     660
```

```
ttacttttcg ccgttaatgt tttgagattc ttcacagtcg gtttagcaaa gccacaagat    720

agaccaggta tgtttatgtt cgttggtcca ccagctttct ctggtttagc attgattaac    780

attgcaagag gtgcaatggg ctcaagacct tacattttcg ttggtgcaaa ctcttccgaa    840

tacttaggtt ttgtctcaac cttcatggcc attttcatct ggggtttagc cgcatggtgt    900

tattgcttag ctatggtttc cttccttgcc ggctttttca ctagagcacc attgaaattc    960

gcttgtggtt ggttcgcttt catctttcca aatgttggtt ttgttaactg tactatcgaa   1020

atcggcaaga tgattgattc taaggctttt caaatgtttg gtcacatcat tggtgttatc   1080

ttgtgtattc aatggatttt gttaatgtac ttaatggtta gagcattcct tgttaatgac   1140

ttgtgctatc ctggtaaaga cgaagatgca cacccaccac caaagccaaa cactggtgtc   1200

ttaaacccaa ctttcccacc agagaaggct ccagcatcat tagagaaggt tgatactcat   1260

gttacatcaa caggtggtga atccgatcct ccatcttccg aacatgaatc cgtttaa      1317
```

<210> SEQ ID NO 93
<211> LENGTH: 1205
<212> TYPE: DNA
<213> ORGANISM: Aspergillus oryzae

<400> SEQUENCE: 93

```
atgtttaaca atgagcacca tattcctcct ggttcctctc actctgatat cgaaatgtta     60

acaccaccaa agtttgagga tgaaaaacag ttaggtccag tcggtattag agaaagattg    120

agacatttca cttgggcttg gtataccta accatgtccg gtggtggttt ggcagttttg    180

attatctctc agccattcgg ttttagaggt ttaagagaaa ttggtattgc agtttacatt    240

ttgaacttaa tcttattcgc tttggtttgt tctaccatgg ctattcgttt catcttgcac    300

ggtaaccttt tggaatccct tagacatgac agagaaggtt tgtttttccc tactttctgg    360

ttgtctgttg ctaccatcat ttgtggtttg tcaagatact ttggtgagga atccaacgaa    420

tccttccaat tggcattaga agccttgttc tggatctatt gcgtttgtac cttgttggtt    480

gcaatcattc aatactcttt tgttttctca tcccacaagt acggtttaca aacaatgatg    540

ccatcttgga ttttgccagc ctttcctatc atgttgtcag gcacaattgc atctgttatc    600

ggtgaacaac aaccagccag agctgcatta ccaatcattg gtgccggtgt caccttccaa    660

ggtttaggtt tttctatttc cttcatgatg tatgctcatt acattggcag acttatggaa    720

tccggtttac ctcactccga ccatagacca ggcatgttca tctgtgttgg cccaccagcc    780

tttactgctt tggctttagt cggtatgtcc aagggtttac cagaagattt caagctttta    840

catgacgctc atgcattaga ggatggtaga atcattgaat tgttagcaat ttcagcaggt    900

gttttccttt gggcattatc cctttggttt ttctgtattg ctattgtcgc tgtcattaga    960

tctccaccag aagctttcca cttgaactgg tgggctatgg ttttcccaaa tactggtttc   1020

accttagcta ctatcacttt gggtaaagct ttgaactcaa atggtgtcaa gggtgtcggt   1080

tctgcaatgt ccatttgtat tgtctgcatg tacatctttg ttttcgttaa caatgttaga   1140

gctgttattc gtaaggatat catgtatcca ggcaaagatg aggatgtttc tgattaacct   1200

gcagg                                                               1205
```

<210> SEQ ID NO 94
<211> LENGTH: 1180
<212> TYPE: PRT
<213> ORGANISM: Issatchenkia orientalis

<400> SEQUENCE: 94

```
Met Ser Thr Val Glu Asp His Ser Ser Leu His Lys Leu Arg Lys Glu
1               5                   10                  15

Ser Glu Ile Leu Ser Asn Ala Asn Lys Ile Leu Val Ala Asn Arg Gly
            20                  25                  30

Glu Ile Pro Ile Arg Ile Phe Arg Ser Ala His Glu Leu Ser Met His
        35                  40                  45

Thr Val Ala Ile Tyr Ser His Glu Asp Arg Leu Ser Met His Arg Leu
    50                  55                  60

Lys Ala Asp Glu Ala Tyr Ala Ile Gly Lys Thr Gly Gln Tyr Ser Pro
65                  70                  75                  80

Val Gln Ala Tyr Leu Gln Ile Asp Glu Ile Ile Lys Ile Ala Lys Glu
                85                  90                  95

His Asp Val Ser Met Ile His Pro Gly Tyr Gly Phe Leu Ser Glu Asn
            100                 105                 110

Ser Glu Phe Ala Lys Lys Val Glu Glu Ser Gly Met Ile Trp Val Gly
        115                 120                 125

Pro Pro Ala Glu Val Ile Asp Ser Val Gly Asp Lys Val Ser Ala Arg
    130                 135                 140

Asn Leu Ala Ile Lys Cys Asp Val Pro Val Val Pro Gly Thr Asp Gly
145                 150                 155                 160

Pro Ile Glu Asp Ile Glu Gln Ala Lys Gln Phe Val Glu Gln Tyr Gly
                165                 170                 175

Tyr Pro Val Ile Ile Lys Ala Ala Phe Gly Gly Gly Gly Arg Gly Met
            180                 185                 190

Arg Val Val Arg Glu Gly Asp Asp Ile Val Asp Ala Phe Gln Arg Ala
        195                 200                 205

Ser Ser Glu Ala Lys Ser Ala Phe Gly Asn Gly Thr Cys Phe Ile Glu
    210                 215                 220

Arg Phe Leu Asp Lys Pro Lys His Ile Glu Val Gln Leu Leu Ala Asp
225                 230                 235                 240

Asn Tyr Gly Asn Thr Ile His Leu Phe Glu Arg Asp Cys Ser Val Gln
                245                 250                 255

Arg Arg His Gln Lys Val Val Glu Ile Ala Pro Ala Lys Thr Leu Pro
            260                 265                 270

Val Glu Val Arg Asn Ala Ile Leu Lys Asp Ala Val Thr Leu Ala Lys
        275                 280                 285

Thr Ala Asn Tyr Arg Asn Ala Gly Thr Ala Glu Phe Leu Val Asp Ser
    290                 295                 300

Gln Asn Arg His Tyr Phe Ile Glu Ile Asn Pro Arg Ile Gln Val Glu
305                 310                 315                 320

His Thr Ile Thr Glu Glu Ile Thr Gly Val Asp Ile Val Ala Ala Gln
                325                 330                 335

Ile Gln Ile Ala Ala Gly Ala Ser Leu Glu Gln Leu Gly Leu Leu Gln
            340                 345                 350

Asn Lys Ile Thr Thr Arg Gly Phe Ala Ile Gln Cys Arg Ile Thr Thr
        355                 360                 365

Glu Asp Pro Ala Lys Asn Phe Ala Pro Asp Thr Gly Lys Ile Glu Val
    370                 375                 380

Tyr Arg Ser Ala Gly Gly Asn Gly Val Arg Leu Asp Gly Gly Asn Gly
385                 390                 395                 400

Phe Ala Gly Ala Val Ile Ser Pro His Tyr Asp Ser Met Leu Val Lys
                405                 410                 415
```

```
Cys Ser Thr Ser Gly Ser Asn Tyr Glu Ile Ala Arg Arg Lys Met Ile
            420                 425                 430

Arg Ala Leu Val Glu Phe Arg Ile Arg Gly Val Lys Thr Asn Ile Pro
        435                 440                 445

Phe Leu Leu Ala Leu Leu Thr His Pro Val Phe Ile Ser Gly Asp Cys
    450                 455                 460

Trp Thr Thr Phe Ile Asp Asp Thr Pro Ser Leu Phe Glu Met Val Ser
465                 470                 475                 480

Ser Lys Asn Arg Ala Gln Lys Leu Leu Ala Tyr Ile Gly Asp Leu Cys
                485                 490                 495

Val Asn Gly Ser Ser Ile Lys Gly Gln Ile Gly Phe Pro Lys Leu Asn
            500                 505                 510

Lys Glu Ala Glu Ile Pro Asp Leu Leu Asp Pro Asn Asp Glu Val Ile
        515                 520                 525

Asp Val Ser Lys Pro Ser Thr Asn Gly Leu Arg Pro Tyr Leu Leu Lys
    530                 535                 540

Tyr Gly Pro Asp Ala Phe Ser Lys Lys Val Arg Glu Phe Asp Gly Cys
545                 550                 555                 560

Met Ile Met Asp Thr Thr Trp Arg Asp Ala His Gln Ser Leu Leu Ala
                565                 570                 575

Thr Arg Val Arg Thr Ile Asp Leu Leu Arg Ile Ala Pro Thr Thr Ser
            580                 585                 590

His Ala Leu Gln Asn Ala Phe Ala Leu Glu Cys Trp Gly Gly Ala Thr
        595                 600                 605

Phe Asp Val Ala Met Arg Phe Leu Tyr Glu Asp Pro Trp Glu Arg Leu
    610                 615                 620

Arg Gln Leu Arg Lys Ala Val Pro Asn Ile Pro Phe Gln Met Leu Leu
625                 630                 635                 640

Arg Gly Ala Asn Gly Val Ala Tyr Ser Ser Leu Pro Asp Asn Ala Ile
                645                 650                 655

Asp His Phe Val Lys Gln Ala Lys Asp Asn Gly Val Asp Ile Phe Arg
            660                 665                 670

Val Phe Asp Ala Leu Asn Asp Leu Glu Gln Leu Lys Val Gly Val Asp
        675                 680                 685

Ala Val Lys Lys Ala Gly Gly Val Val Glu Ala Thr Val Cys Tyr Ser
    690                 695                 700

Gly Asp Met Leu Ile Pro Gly Lys Lys Tyr Asn Leu Asp Tyr Tyr Leu
705                 710                 715                 720

Glu Thr Val Gly Lys Ile Val Glu Met Gly Thr His Ile Leu Gly Ile
                725                 730                 735

Lys Asp Met Ala Gly Thr Leu Lys Pro Lys Ala Ala Lys Leu Leu Ile
            740                 745                 750

Gly Ser Ile Arg Ser Lys Tyr Pro Asp Leu Val Ile His Val His Thr
        755                 760                 765

His Asp Ser Ala Gly Thr Gly Ile Ser Thr Tyr Val Ala Cys Ala Leu
    770                 775                 780

Ala Gly Ala Asp Ile Val Asp Cys Ala Ile Asn Ser Met Ser Gly Leu
785                 790                 795                 800

Thr Ser Gln Pro Ser Met Ser Ala Phe Ile Ala Ala Leu Asp Gly Asp
                805                 810                 815

Ile Glu Thr Gly Val Pro Glu His Phe Ala Arg Gln Leu Asp Ala Tyr
            820                 825                 830

Trp Ala Glu Met Arg Leu Leu Tyr Ser Cys Phe Glu Ala Asp Leu Lys
```

```
        835                 840                 845

Gly Pro Asp Pro Glu Val Tyr Lys His Glu Ile Pro Gly Gly Gln Leu
    850                 855                 860

Thr Asn Leu Ile Phe Gln Ala Gln Gln Val Gly Leu Gly Glu Gln Trp
865                 870                 875                 880

Glu Glu Thr Lys Lys Lys Tyr Glu Asp Ala Asn Met Leu Leu Gly Asp
                885                 890                 895

Ile Val Lys Val Thr Pro Thr Ser Lys Val Val Gly Asp Leu Ala Gln
            900                 905                 910

Phe Met Val Ser Asn Lys Leu Glu Lys Glu Asp Val Glu Lys Leu Ala
        915                 920                 925

Asn Glu Leu Asp Phe Pro Asp Ser Val Leu Asp Phe Phe Glu Gly Leu
    930                 935                 940

Met Gly Thr Pro Tyr Gly Gly Phe Pro Glu Pro Leu Arg Thr Asn Val
945                 950                 955                 960

Ile Ser Gly Lys Arg Arg Lys Leu Lys Gly Arg Pro Gly Leu Glu Leu
                965                 970                 975

Glu Pro Phe Asn Leu Glu Glu Ile Arg Glu Asn Leu Val Ser Arg Phe
            980                 985                 990

Gly Pro Gly Ile Thr Glu Cys Asp  Val Ala Ser Tyr Asn  Met Tyr Pro
        995                 1000                1005

Lys Val  Tyr Glu Gln Tyr Arg  Lys Val Val Glu Lys  Tyr Gly Asp
    1010                1015                1020

Leu Ser  Val Leu Pro Thr Lys  Ala Phe Leu Ala Pro  Pro Thr Ile
    1025                1030                1035

Gly Glu  Glu Val His Val Glu  Ile Glu Gln Gly Lys  Thr Leu Ile
    1040                1045                1050

Ile Lys  Leu Leu Ala Ile Ser  Asp Leu Ser Lys Ser  His Gly Thr
    1055                1060                1065

Arg Glu  Val Tyr Phe Glu Leu  Asn Gly Glu Met Arg  Lys Val Thr
    1070                1075                1080

Ile Glu  Asp Lys Thr Ala Ala  Ile Glu Thr Val Thr  Arg Ala Lys
    1085                1090                1095

Ala Asp  Gly His Asn Pro Asn  Glu Val Gly Ala Pro  Met Ala Gly
    1100                1105                1110

Val Val  Val Glu Val Arg Val  Lys His Gly Thr Glu  Val Lys Lys
    1115                1120                1125

Gly Asp  Pro Leu Ala Val Leu  Ser Ala Met Lys Met  Glu Met Val
    1130                1135                1140

Ile Ser  Ala Pro Val Ser Gly  Arg Val Gly Glu Val  Phe Val Asn
    1145                1150                1155

Glu Gly  Asp Ser Val Asp Met  Gly Asp Leu Leu Val  Lys Ile Ala
    1160                1165                1170

Lys Asp  Glu Ala Pro Ala Ala
    1175                1180


<210> SEQ ID NO 95
<211> LENGTH: 1178
<212> TYPE: PRT
<213> ORGANISM: Saccharomyces cerevisiae

<400> SEQUENCE: 95

Met Ser Gln Arg Lys Phe Ala Gly Leu Arg Asp Asn Phe Asn Leu Leu
1               5                   10                  15
```

```
Gly Glu Lys Asn Lys Ile Leu Val Ala Asn Arg Gly Glu Ile Pro Ile
            20                  25                  30

Arg Ile Phe Arg Thr Ala His Glu Leu Ser Met Gln Thr Val Ala Ile
        35                  40                  45

Tyr Ser His Glu Asp Arg Leu Ser Thr His Lys Gln Lys Ala Asp Glu
    50                  55                  60

Ala Tyr Val Ile Gly Glu Val Gly Gln Tyr Thr Pro Val Gly Ala Tyr
65                  70                  75                  80

Leu Ala Ile Asp Glu Ile Ile Ser Ile Ala Gln Lys His Gln Val Asp
                85                  90                  95

Phe Ile His Pro Gly Tyr Gly Phe Leu Ser Glu Asn Ser Glu Phe Ala
            100                 105                 110

Asp Lys Val Val Lys Ala Gly Ile Thr Trp Ile Gly Pro Pro Ala Glu
        115                 120                 125

Val Ile Asp Ser Val Gly Asp Lys Val Ser Ala Arg Asn Leu Ala Ala
    130                 135                 140

Lys Ala Asn Val Pro Thr Val Pro Gly Thr Pro Gly Pro Ile Glu Thr
145                 150                 155                 160

Val Glu Glu Ala Leu Asp Phe Val Asn Glu Tyr Gly Tyr Pro Val Ile
                165                 170                 175

Ile Lys Ala Ala Phe Gly Gly Gly Gly Arg Gly Met Arg Val Val Arg
            180                 185                 190

Glu Gly Asp Asp Val Ala Asp Ala Phe Gln Arg Ala Thr Ser Glu Ala
        195                 200                 205

Arg Thr Ala Phe Gly Asn Gly Thr Cys Phe Val Glu Arg Phe Leu Asp
    210                 215                 220

Lys Pro Lys His Ile Glu Val Gln Leu Leu Ala Asp Asn His Gly Asn
225                 230                 235                 240

Val Val His Leu Phe Glu Arg Asp Cys Ser Val Gln Arg Arg His Gln
                245                 250                 255

Lys Val Val Glu Val Ala Pro Ala Lys Thr Leu Pro Arg Glu Val Arg
            260                 265                 270

Asp Ala Ile Leu Thr Asp Ala Val Lys Leu Ala Lys Glu Cys Gly Tyr
        275                 280                 285

Arg Asn Ala Gly Thr Ala Glu Phe Leu Val Asp Asn Gln Asn Arg His
    290                 295                 300

Tyr Phe Ile Glu Ile Asn Pro Arg Ile Gln Val Glu His Thr Ile Thr
305                 310                 315                 320

Glu Glu Ile Thr Gly Ile Asp Ile Val Ala Ala Gln Ile Gln Ile Ala
                325                 330                 335

Ala Gly Ala Ser Leu Pro Gln Leu Gly Leu Phe Gln Asp Lys Ile Thr
            340                 345                 350

Thr Arg Gly Phe Ala Ile Gln Cys Arg Ile Thr Thr Glu Asp Pro Ala
        355                 360                 365

Lys Asn Phe Gln Pro Asp Thr Gly Arg Ile Glu Val Tyr Arg Ser Ala
    370                 375                 380

Gly Gly Asn Gly Val Arg Leu Asp Gly Gly Asn Ala Tyr Ala Gly Thr
385                 390                 395                 400

Ile Ile Ser Pro His Tyr Asp Ser Met Leu Val Lys Cys Ser Cys Ser
                405                 410                 415

Gly Ser Thr Tyr Glu Ile Val Arg Arg Lys Met Ile Arg Ala Leu Ile
            420                 425                 430

Glu Phe Arg Ile Arg Gly Val Lys Thr Asn Ile Pro Phe Leu Leu Thr
```

```
        435                 440                 445

Leu Leu Thr Asn Pro Val Phe Ile Glu Gly Thr Tyr Trp Thr Thr Phe
    450                 455                 460

Ile Asp Asp Thr Pro Gln Leu Phe Gln Met Val Ser Ser Gln Asn Arg
465                 470                 475                 480

Ala Gln Lys Leu Leu His Tyr Leu Ala Asp Val Ala Val Asn Gly Ser
                485                 490                 495

Ser Ile Lys Gly Gln Ile Gly Leu Pro Lys Leu Lys Ser Asn Pro Ser
            500                 505                 510

Val Pro His Leu His Asp Ala Gln Gly Asn Val Ile Asn Val Thr Lys
        515                 520                 525

Ser Ala Pro Pro Ser Gly Trp Arg Gln Val Leu Leu Glu Lys Gly Pro
    530                 535                 540

Ala Glu Phe Ala Arg Gln Val Arg Gln Phe Asn Gly Thr Leu Leu Met
545                 550                 555                 560

Asp Thr Thr Trp Arg Asp Ala His Gln Ser Leu Leu Ala Thr Arg Val
                565                 570                 575

Arg Thr His Asp Leu Ala Thr Ile Ala Pro Thr Thr Ala His Ala Leu
            580                 585                 590

Ala Gly Arg Phe Ala Leu Glu Cys Trp Gly Gly Ala Thr Phe Asp Val
        595                 600                 605

Ala Met Arg Phe Leu His Glu Asp Pro Trp Glu Arg Leu Arg Lys Leu
    610                 615                 620

Arg Ser Leu Val Pro Asn Ile Pro Phe Gln Met Leu Leu Arg Gly Ala
625                 630                 635                 640

Asn Gly Val Ala Tyr Ser Ser Leu Pro Asp Asn Ala Ile Asp His Phe
                645                 650                 655

Val Lys Gln Ala Lys Asp Asn Gly Val Asp Ile Phe Arg Val Phe Asp
            660                 665                 670

Ala Leu Asn Asp Leu Glu Gln Leu Lys Val Gly Val Asp Ala Val Lys
        675                 680                 685

Lys Ala Gly Gly Val Val Glu Ala Thr Val Cys Phe Ser Gly Asp Met
    690                 695                 700

Leu Gln Pro Gly Lys Lys Tyr Asn Leu Asp Tyr Tyr Leu Glu Ile Ala
705                 710                 715                 720

Glu Lys Ile Val Gln Met Gly Thr His Ile Leu Gly Ile Lys Asp Met
                725                 730                 735

Ala Gly Thr Met Lys Pro Ala Ala Ala Lys Leu Leu Ile Gly Ser Leu
            740                 745                 750

Arg Ala Lys Tyr Pro Asp Leu Pro Ile His Val His Thr His Asp Ser
        755                 760                 765

Ala Gly Thr Ala Val Ala Ser Met Thr Ala Cys Ala Leu Ala Gly Ala
    770                 775                 780

Asp Val Val Asp Val Ala Ile Asn Ser Met Ser Gly Leu Thr Ser Gln
785                 790                 795                 800

Pro Ser Ile Asn Ala Leu Leu Ala Ser Leu Glu Gly Asn Ile Asp Thr
                805                 810                 815

Gly Ile Asn Val Glu His Val Arg Glu Leu Asp Ala Tyr Trp Ala Glu
            820                 825                 830

Met Arg Leu Leu Tyr Ser Cys Phe Glu Ala Asp Leu Lys Gly Pro Asp
        835                 840                 845

Pro Glu Val Tyr Gln His Glu Ile Pro Gly Gly Gln Leu Thr Asn Leu
    850                 855                 860
```

Leu Phe Gln Ala Gln Gln Leu Gly Leu Gly Glu Gln Trp Ala Glu Thr
865 870 875 880

Lys Arg Ala Tyr Arg Glu Ala Asn Tyr Leu Leu Gly Asp Ile Val Lys
885 890 895

Val Thr Pro Thr Ser Lys Val Val Gly Asp Leu Ala Gln Phe Met Val
900 905 910

Ser Asn Lys Leu Thr Ser Asp Asp Val Arg Arg Leu Ala Asn Ser Leu
915 920 925

Asp Phe Pro Asp Ser Val Met Asp Phe Phe Glu Gly Leu Ile Gly Gln
930 935 940

Pro Tyr Gly Gly Phe Pro Glu Pro Phe Arg Ser Asp Val Leu Arg Asn
945 950 955 960

Lys Arg Arg Lys Leu Thr Cys Arg Pro Gly Leu Glu Leu Glu Pro Phe
965 970 975

Asp Leu Glu Lys Ile Arg Glu Asp Leu Gln Asn Arg Phe Gly Asp Val
980 985 990

Asp Glu Cys Asp Val Ala Ser Tyr Asn Met Tyr Pro Arg Val Tyr Glu
995 1000 1005

Asp Phe Gln Lys Met Arg Glu Thr Tyr Gly Asp Leu Ser Val Leu
1010 1015 1020

Pro Thr Arg Ser Phe Leu Ser Pro Leu Glu Thr Asp Glu Glu Ile
1025 1030 1035

Glu Val Val Ile Glu Gln Gly Lys Thr Leu Ile Ile Lys Leu Gln
1040 1045 1050

Ala Val Gly Asp Leu Asn Lys Lys Thr Gly Glu Arg Glu Val Tyr
1055 1060 1065

Phe Asp Leu Asn Gly Glu Met Arg Lys Ile Arg Val Ala Asp Arg
1070 1075 1080

Ser Gln Lys Val Glu Thr Val Thr Lys Ser Lys Ala Asp Met His
1085 1090 1095

Asp Pro Leu His Ile Gly Ala Pro Met Ala Gly Val Ile Val Glu
1100 1105 1110

Val Lys Val His Lys Gly Ser Leu Ile Lys Lys Gly Gln Pro Val
1115 1120 1125

Ala Val Leu Ser Ala Met Lys Met Glu Met Ile Ile Ser Ser Pro
1130 1135 1140

Ser Asp Gly Gln Val Lys Glu Val Phe Val Ser Asp Gly Glu Asn
1145 1150 1155

Val Asp Ser Ser Asp Leu Leu Val Leu Leu Glu Asp Gln Val Pro
1160 1165 1170

Val Glu Thr Lys Ala
1175

<210> SEQ ID NO 96
<211> LENGTH: 1175
<212> TYPE: PRT
<213> ORGANISM: Kluyvermyces marxianus

<400> SEQUENCE: 96

Met Ser Thr Gln Asn Asp Leu Ala Gly Leu Arg Asp Asn Ser Asn Leu
1 5 10 15

Leu Gly Glu Lys Asn Lys Ile Leu Val Ala Asn Arg Gly Glu Ile Pro
20 25 30

Ile Arg Ile Phe Arg Thr Ala His Glu Leu Ser Met Lys Thr Val Ala

```
        35                  40                  45

Ile Tyr Ser His Glu Asp Arg Leu Ser Met His Arg Leu Lys Ala Asp
    50                  55                  60

Glu Ala Tyr Val Ile Gly Glu Pro Gly Lys Tyr Thr Pro Val Gly Ala
65                  70                  75                  80

Tyr Leu Ala Ile Asp Glu Ile Ile Lys Ile Ala Gln Leu His Gly Val
                85                  90                  95

Ser Phe Ile His Pro Gly Tyr Gly Phe Leu Ser Glu Asn Ser Glu Phe
            100                 105                 110

Ala Lys Lys Val Ala Asp Ser Gly Ile Thr Trp Val Gly Pro Pro Ala
        115                 120                 125

Asp Val Ile Asp Ala Val Gly Asp Lys Val Ser Ala Arg Asn Leu Ala
    130                 135                 140

Glu Arg Ala Asp Val Pro Val Val Pro Gly Thr Pro Gly Pro Ile Glu
145                 150                 155                 160

Thr Val Glu Glu Ala Val Glu Phe Val Glu Lys Tyr Gly Tyr Pro Val
                165                 170                 175

Ile Ile Lys Ala Ala Phe Gly Gly Gly Gly Arg Gly Met Arg Val Val
            180                 185                 190

Arg Glu Gly Asp Asp Ile Ala Asp Ala Phe Gln Arg Ala Lys Ser Glu
        195                 200                 205

Ala Val Thr Ala Phe Gly Asn Gly Thr Cys Phe Val Glu Arg Phe Leu
    210                 215                 220

Asp Lys Pro Lys His Ile Glu Val Gln Leu Leu Ala Asp His Tyr Gly
225                 230                 235                 240

Asn Val Ile His Leu Phe Glu Arg Asp Cys Ser Val Gln Arg Arg His
                245                 250                 255

Gln Lys Val Val Glu Val Ala Pro Ala Lys Thr Leu Pro Glu Ser Val
            260                 265                 270

Arg Asn Ala Ile Leu Thr Asp Ala Val Lys Leu Ala Lys Glu Ala Gly
        275                 280                 285

Tyr Arg Asn Ala Gly Thr Ala Glu Phe Leu Val Asp Asn Gln Asn Arg
    290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ala Ala Gln Ile Gln Ile
                325                 330                 335

Ala Ala Gly Ala Ser Leu Glu Gln Leu Gly Leu Leu Gln Asp Arg Ile
            340                 345                 350

Thr Thr Arg Gly Phe Ala Ile Gln Cys Arg Ile Thr Thr Glu Asp Pro
        355                 360                 365

Ser Lys Asn Phe Gln Pro Asp Thr Gly Arg Ile Asp Val Tyr Arg Ser
    370                 375                 380

Ala Gly Gly Asn Gly Val Arg Leu Asp Gly Gly Asn Ala Phe Ala Gly
385                 390                 395                 400

Ser Val Ile Ser Pro His Tyr Asp Ser Met Leu Val Lys Cys Ser Cys
                405                 410                 415

Ser Gly Ser Thr Tyr Glu Ile Val Arg Arg Lys Met Leu Arg Ala Leu
            420                 425                 430

Ile Glu Phe Arg Ile Arg Gly Val Lys Thr Asn Ile Pro Phe Leu Leu
        435                 440                 445

Thr Leu Leu Thr His Pro Val Phe Lys Ser Gly Asp Tyr Trp Thr Thr
    450                 455                 460
```

```
Phe Ile Asp Asp Thr Pro Gln Leu Phe Glu Met Val Ser Ser Gln Asn
465                 470                 475                 480

Arg Ala Gln Lys Leu Leu His Tyr Leu Ala Asp Leu Ala Val Asn Gly
                485                 490                 495

Ser Ser Ile Lys Gly Gln Ile Gly Leu Pro Lys Leu Lys Thr His Pro
            500                 505                 510

Thr Ile Pro His Leu His Lys Ala Asp Gly Ser Ile Leu Asp Val Ser
        515                 520                 525

Ala Lys Pro Pro Ala Gly Trp Arg Asp Val Leu Leu Gln His Gly Pro
    530                 535                 540

Glu Glu Phe Ala Lys Gln Val Arg Lys Phe Lys Gly Thr Leu Leu Met
545                 550                 555                 560

Asp Thr Thr Trp Arg Asp Ala His Gln Ser Leu Leu Ala Thr Arg Val
                565                 570                 575

Arg Thr Tyr Asp Leu Ala Ala Ile Ala Pro Thr Thr Ala His Ala Leu
            580                 585                 590

Ser Gly Ala Phe Ala Leu Glu Cys Trp Gly Gly Ala Thr Phe Asp Val
        595                 600                 605

Ser Met Arg Phe Leu His Glu Asp Pro Trp Glu Arg Leu Arg Thr Leu
    610                 615                 620

Arg Lys Leu Val Pro Asn Ile Pro Phe Gln Met Leu Leu Arg Gly Ala
625                 630                 635                 640

Asn Gly Val Ala Tyr Ser Ser Leu Pro Asp Asn Ala Ile Asp His Phe
                645                 650                 655

Val Lys Gln Ala Lys Asp Asn Gly Val Asp Ile Phe Arg Val Phe Asp
            660                 665                 670

Ala Leu Asn Asp Leu Glu Gln Leu Thr Val Gly Val Asp Ala Val Lys
        675                 680                 685

Lys Ala Gly Gly Val Val Glu Ala Thr Ile Cys Tyr Ser Gly Asp Met
    690                 695                 700

Leu Ala Pro Gly Lys Lys Tyr Asn Leu Asp Tyr Tyr Leu Asp Ile Val
705                 710                 715                 720

Glu Gln Val Val Lys Arg Gly Thr His Ile Leu Gly Ile Lys Asp Met
                725                 730                 735

Ala Gly Thr Leu Lys Pro Ser Ala Ala Lys Leu Leu Ile Gly Ser Ile
            740                 745                 750

Arg Thr Lys Tyr Pro Asp Leu Pro Ile His Val His Thr His Asp Ser
        755                 760                 765

Ala Gly Thr Gly Val Ala Ser Met Ala Ala Cys Ala Phe Ala Gly Ala
    770                 775                 780

Asp Val Val Asp Val Ala Thr Asn Ser Met Ser Gly Met Thr Ser Gln
785                 790                 795                 800

Pro Ser Val Asn Ala Leu Leu Ala Ala Leu Asp Gly Glu Ile Asp Cys
                805                 810                 815

Asn Val Asn Val Ser Tyr Ile Ser Gln Leu Asp Ala Tyr Trp Ala Glu
            820                 825                 830

Met Arg Leu Leu Tyr Ser Cys Phe Glu Ala Asp Leu Lys Gly Pro Asp
        835                 840                 845

Pro Glu Val Tyr Val His Glu Ile Pro Gly Gly Gln Leu Thr Asn Leu
    850                 855                 860

Leu Phe Gln Ala Gln Gln Leu Gly Leu Gly Glu Gln Trp Ala Glu Thr
865                 870                 875                 880
```

```
Lys Arg Ala Tyr Arg Glu Ala Asn Leu Leu Leu Gly Asp Val Val Lys
            885                 890                 895

Val Thr Pro Thr Ser Lys Val Val Gly Asp Leu Ala Gln Phe Met Val
            900                 905                 910

Thr Asn Lys Leu Thr Ser Asp Asp Val Lys Arg Leu Ala Ser Ser Leu
        915                 920                 925

Asp Phe Pro Asp Ser Val Met Asp Phe Phe Glu Gly Leu Ile Gly Gln
    930                 935                 940

Pro Tyr Gly Gly Phe Pro Glu Pro Leu Arg Ser Asp Val Leu Lys Asn
945                 950                 955                 960

Lys Arg Arg Lys Leu Thr Lys Arg Pro Gly Leu Glu Leu Ala Pro Phe
            965                 970                 975

Asp Leu Glu Gly Ile Lys Glu Asp Leu Thr Asn Arg Phe Gly Asp Ile
            980                 985                 990

Asp Asp Cys Asp Val Ala Ser Tyr  Asn Met Tyr Pro Lys  Val Tyr Glu
        995                 1000                1005

Asp Phe  Arg Lys Ile Arg Glu  Lys Tyr Gly Asp Leu  Ser Val Leu
    1010                1015                1020

Pro Thr  Lys Asn Phe Leu Ser  Pro Pro Ser Ile Gly  Glu Glu Ile
    1025                1030                1035

Val Val  Thr Ile Glu Gln Gly  Lys Thr Leu Ile Ile  Lys Pro Gln
    1040                1045                1050

Ala Ile  Gly Asp Leu Asn Lys  Glu Thr Gly Ile Arg  Glu Val Tyr
    1055                1060                1065

Phe Glu  Leu Asn Gly Glu Leu  Arg Lys Val Ser Val  Ala Asp Arg
    1070                1075                1080

Ser Gln  Lys Val Glu Thr Ile  Ser Lys Pro Lys Ala  Asp Ala His
    1085                1090                1095

Asp Pro  Phe Gln Val Gly Ser  Pro Met Ala Gly Val  Val Val Glu
    1100                1105                1110

Val Lys  Val His Lys Gly Ser  Leu Ile Ser Lys Gly  Gln Pro Val
    1115                1120                1125

Ala Val  Leu Ser Ala Met Lys  Met Glu Met Val Ile  Ser Ser Pro
    1130                1135                1140

Ser Asp  Gly Gln Val Lys Glu  Val Leu Val Lys Asp  Gly Glu Asn
    1145                1150                1155

Val Asp  Ala Ser Asp Leu Leu  Val Val Leu Glu Glu  Ala Pro Ala
    1160                1165                1170

Lys Glu
    1175
```

<210> SEQ ID NO 97
<211> LENGTH: 883
<212> TYPE: PRT
<213> ORGANISM: Escherichia coli

<400> SEQUENCE: 97

```
Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60
```

```
Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
    370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
    450                 455                 460

Pro Gln Gly Ser Ile Ala Ala Tyr Val Ile Ser Met Ala Lys Thr Pro
465                 470                 475                 480
```

```
Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
            500                 505                 510

Asn Ala Asn Asp Val Met Thr Gln Leu Leu Asn Ile Asp Trp Tyr Arg
        515                 520                 525

Gly Leu Ile Gln Gly Lys Gln Met Val Met Ile Gly Tyr Ser Asp Ser
    530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
        595                 600                 605

Arg Val Thr Glu Gln Gly Glu Met Ile Arg Phe Lys Tyr Gly Leu Pro
    610                 615                 620

Glu Ile Thr Val Ser Ser Leu Ser Leu Tyr Thr Gly Ala Ile Leu Glu
625                 630                 635                 640

Ala Asn Leu Leu Pro Pro Pro Glu Pro Lys Glu Ser Trp Arg Arg Ile
                645                 650                 655

Met Asp Glu Leu Ser Val Ile Ser Cys Asp Val Tyr Arg Gly Tyr Val
            660                 665                 670

Arg Glu Asn Lys Asp Phe Val Pro Tyr Phe Arg Ser Ala Thr Pro Glu
        675                 680                 685

Gln Glu Leu Gly Lys Leu Pro Leu Gly Ser Arg Pro Ala Lys Arg Arg
    690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
        755                 760                 765

Met Val Phe Ala Lys Ala Asp Leu Trp Leu Ala Glu Tyr Tyr Asp Gln
    770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
        835                 840                 845

Arg Ser Arg Gln Ala Glu Lys Glu Gly Gln Glu Pro Asp Pro Arg Val
    850                 855                 860

Glu Gln Ala Leu Met Val Thr Ile Ala Gly Ile Ala Ala Gly Met Arg
865                 870                 875                 880

Asn Thr Gly
```

<210> SEQ ID NO 98

<211> LENGTH: 342
<212> TYPE: PRT
<213> ORGANISM: Issatchenkia orinetalis

<400> SEQUENCE: 98

```
Met Ser Asn Val Lys Val Ala Leu Leu Gly Ala Ala Gly Gly Ile Gly
1               5                   10                  15

Gln Pro Leu Ala Leu Leu Leu Lys Leu Asn Pro Asn Ile Thr His Leu
            20                  25                  30

Ala Leu Tyr Asp Val Val His Val Pro Gly Val Ala Ala Asp Leu His
        35                  40                  45

His Ile Asp Thr Asp Val Val Ile Thr His His Leu Lys Asp Glu Asp
    50                  55                  60

Gly Thr Ala Leu Ala Asn Ala Leu Lys Asp Ala Thr Phe Val Ile Val
65                  70                  75                  80

Pro Ala Gly Val Pro Arg Lys Pro Gly Met Thr Arg Gly Asp Leu Phe
                85                  90                  95

Thr Ile Asn Ala Gly Ile Cys Ala Glu Leu Ala Asn Ala Ile Ser Leu
            100                 105                 110

Asn Ala Pro Asn Ala Phe Thr Leu Val Ile Thr Asn Pro Val Asn Ser
        115                 120                 125

Thr Val Pro Ile Phe Lys Glu Ile Phe Ala Lys Asn Glu Ala Phe Asn
    130                 135                 140

Pro Arg Arg Leu Phe Gly Val Thr Ala Leu Asp His Val Arg Ser Asn
145                 150                 155                 160

Thr Phe Leu Ser Glu Leu Ile Asp Gly Lys Asn Pro Gln His Phe Asp
                165                 170                 175

Val Thr Val Val Gly Gly His Ser Gly Asn Ser Ile Val Pro Leu Phe
            180                 185                 190

Ser Leu Val Lys Ala Ala Glu Asn Leu Asp Asp Glu Ile Ile Asp Ala
        195                 200                 205

Leu Ile His Arg Val Gln Tyr Gly Gly Asp Glu Val Val Glu Ala Lys
    210                 215                 220

Ser Gly Ala Gly Ser Ala Thr Leu Ser Met Ala Tyr Ala Ala Asn Lys
225                 230                 235                 240

Phe Phe Asn Ile Leu Leu Asn Gly Tyr Trp Gly Leu Lys Lys Thr Met
                245                 250                 255

Ile Ser Ser Tyr Val Phe Leu Asp Asp Ser Ile Asn Gly Val Pro Gln
            260                 265                 270

Leu Lys Glu Asn Leu Ser Lys Leu Leu Lys Gly Ser Glu Val Glu Leu
        275                 280                 285

Pro Ser Tyr Leu Ala Val Pro Met Thr Tyr Gly Lys Glu Gly Ile Glu
    290                 295                 300

Gln Val Phe Tyr Asp Trp Val Phe Glu Met Ser Pro Lys Glu Lys Glu
305                 310                 315                 320

Asn Phe Ile Thr Ala Ile Glu Tyr Ile Asp Gln Asn Ile Glu Lys Gly
                325                 330                 335

Leu Asn Phe Met Val Arg
            340
```

<210> SEQ ID NO 99
<211> LENGTH: 333
<212> TYPE: PRT
<213> ORGANISM: Issatchenkia orientalis

<400> SEQUENCE: 99

```
Met Val Lys Val Thr Ile Leu Gly Ala Ala Gly Gly Ile Gly Gln Pro
1               5                   10                  15

Leu Ser Leu Leu Leu Arg Leu Asn Pro Trp Ile Asp Glu Leu Ala Leu
            20                  25                  30

Phe Asp Ile Val Asn Thr Pro Gly Val Ser Cys Asp Leu Ser His Ile
        35                  40                  45

Pro Ala Ser Gln Val Val Asn Gly Tyr Ala Pro Lys Ser Lys Ser Asp
    50                  55                  60

Thr Glu Thr Ile Lys Thr Ala Leu Lys Gly Ala Asp Ile Val Val Ile
65                  70                  75                  80

Pro Ala Gly Ile Pro Arg Lys Pro Gly Met Thr Arg Asn Asp Leu Phe
                85                  90                  95

Lys Ile Asn Ala Gly Ile Val Lys Ser Leu Ile His Ser Ala Gly Thr
            100                 105                 110

Thr Cys Pro Asp Ala Phe Ile Cys Val Ile Ser Asn Pro Val Asn Ser
        115                 120                 125

Thr Val Pro Ile Ala Val Glu Glu Leu Lys Arg Leu Asn Val Phe Asn
    130                 135                 140

Pro His Lys Val Phe Gly Ile Thr Thr Leu Asp Asn Phe Arg Leu Glu
145                 150                 155                 160

Glu Phe Leu Ser Gly Glu Leu Gly Gly Ile Val Lys Pro Asn Asp Leu
                165                 170                 175

Tyr Gly Asp Val Val Ala Ile Gly Gly His Ser Gly Asp Ser Ile Val
            180                 185                 190

Pro Ile Leu Asn Ser Trp Asn Leu Asn Phe Ile Asn Asp Gly Asp Ser
        195                 200                 205

Tyr Asn Asn Leu Val Lys Arg Val Gln Phe Gly Gly Asp Glu Val Val
    210                 215                 220

Lys Ala Lys Asp Gly Lys Gly Ser Ala Thr Leu Ser Met Ala Thr Ala
225                 230                 235                 240

Ala Tyr Arg Phe Val Asn Asn Leu Leu Asp Ala Ile Val Asn Asn Lys
                245                 250                 255

Lys Val Lys Glu Val Ala Phe Val Lys Ile Asp Gln Leu Pro Thr Thr
            260                 265                 270

Arg Val Pro Tyr Phe Val Val Asp Glu Thr Gln Tyr Phe Ser Leu Pro
        275                 280                 285

Ile Ile Leu Gly Arg Gln Gly Ile Glu Arg Val Thr Phe Pro Glu Ser
    290                 295                 300

Leu Thr Glu Gln Glu Val Arg Met Thr Lys His Ala Val Ala Lys Val
305                 310                 315                 320

Lys Val Asp Val Asn Lys Gly Phe Asn Phe Val His Gly
                325                 330
```

<210> SEQ ID NO 100
<211> LENGTH: 334
<212> TYPE: PRT
<213> ORGANISM: Issatchenkia orientalis

<400> SEQUENCE: 100

```
Met Phe Ser Arg Ile Ser Ala Arg Gln Phe Ser Ser Ser Ala Ala Ser
1               5                   10                  15

Ala Tyr Lys Val Thr Val Leu Gly Ala Ala Gly Gly Ile Gly Gln Pro
            20                  25                  30

Leu Ser Leu Leu Met Lys Leu Asn His Lys Val Thr Asn Leu Ser Leu
```

```
        35                  40                  45

Tyr Asp Leu Arg Leu Gly Ala Gly Val Ala Thr Asp Leu Ser His Ile
    50                  55                  60

Pro Thr Asn Ser Val Val Lys Gly Tyr Gly Pro Glu Asn Asn Gly Leu
65                  70                  75                  80

Lys Asp Ala Leu Thr Gly Ser Asp Val Val Leu Ile Pro Ala Gly Val
                85                  90                  95

Pro Arg Lys Pro Gly Met Thr Arg Asp Asp Leu Phe Asn Thr Asn Ala
            100                 105                 110

Ser Ile Val Arg Asp Leu Ala Lys Ala Ala Ala Asp His Cys Pro Asn
        115                 120                 125

Ala Val Leu Leu Ile Ile Ser Asn Pro Val Asn Ser Thr Val Pro Ile
    130                 135                 140

Val Ala Glu Val Leu Lys Ser Lys Gly Val Tyr Asn Pro Lys Lys Leu
145                 150                 155                 160

Phe Gly Val Thr Thr Leu Asp Val Leu Arg Ser Ser Arg Phe Leu Ser
                165                 170                 175

Glu Val Val Asn Thr Asp Pro Thr Thr Glu Thr Val Thr Val Val Gly
            180                 185                 190

Gly His Ser Gly Val Thr Ile Val Pro Leu Ile Ser Gln Thr Lys His
        195                 200                 205

Lys Asp Leu Pro Lys Glu Thr Tyr Glu Ala Leu Val His Arg Ile Gln
    210                 215                 220

Phe Gly Gly Asp Glu Val Val Lys Ala Lys Asp Gly Ala Gly Ser Ala
225                 230                 235                 240

Thr Leu Ser Met Ala Gln Ala Gly Ala Arg Met Ala Ser Ser Val Leu
                245                 250                 255

Lys Gly Leu Ala Gly Glu Val Asp Ile Val Glu Pro Thr Phe Ile Asp
            260                 265                 270

Ser Pro Leu Phe Lys Ser Glu Gly Val Glu Phe Phe Ser Ser Arg Val
        275                 280                 285

Thr Leu Gly Pro Glu Gly Val Gln Glu Val His Pro Leu Gly Val Leu
    290                 295                 300

Ser Thr Ala Glu Glu Glu Met Val Ala Thr Ala Lys Glu Thr Leu Lys
305                 310                 315                 320

Lys Asn Ile Gln Lys Gly Val Asp Phe Val Lys Ala Asn Pro
                325                 330


<210> SEQ ID NO 101
<211> LENGTH: 356
<212> TYPE: PRT
<213> ORGANISM: Zygosaccharomyces rouxii

<400> SEQUENCE: 101

Met Pro His Ser Ile Asn Gly Asp Val Lys Ile Ala Val Leu Gly Ala
1               5                   10                  15

Ala Gly Gly Ile Gly Gln Ser Leu Ser Leu Leu Leu Lys Thr Gln Leu
            20                  25                  30

Thr Arg Glu Leu Pro Asn His Arg His Ala Gln Leu Ala Leu Tyr Asp
        35                  40                  45

Val Asn Ala Asp Ala Val Arg Gly Val Ala Ala Asp Leu Ser His Ile
    50                  55                  60

Asp Thr Gly Val Thr Val Thr Gly Tyr Glu Gly Asp Arg Ile Gly Glu
65                  70                  75                  80
```

```
Ala Leu Glu Gly Thr Asp Ile Val Leu Ile Pro Ala Gly Val Pro Arg
                85                  90                  95

Lys Pro Gly Met Thr Arg Glu Asp Leu Leu Val Val Asn Ala Lys Ile
            100                 105                 110

Val Lys Ser Ile Gly Ser Ser Ile Ala Gln His Cys Asp Leu Asn Lys
        115                 120                 125

Val Phe Ile Leu Leu Ile Ser Asn Pro Ile Asn Ser Leu Val Pro Val
    130                 135                 140

Leu Val Lys Glu Leu Glu Ser Lys Ser Gln Gly Thr Gln Val Glu Arg
145                 150                 155                 160

Arg Val Leu Gly Leu Thr Lys Leu Asp Ser Val Arg Ala Ser Ala Phe
                165                 170                 175

Leu His Glu Val Thr Ile Lys His Gly Leu Lys Pro Lys Ser Asn Thr
            180                 185                 190

Leu Asp Asp Val Pro Val Val Gly Gly His Ser Gly Glu Thr Ile Val
        195                 200                 205

Pro Leu Phe Ser Gln Ala Pro Asn Gly Asn Arg Leu Ser Gln Asp Ala
    210                 215                 220

Leu Glu Ala Leu Val Gln Arg Val Gln Phe Gly Gly Asp Glu Val Val
225                 230                 235                 240

Arg Ala Lys Asn Gly Ala Gly Ser Ala Thr Leu Cys Met Ala His Ala
                245                 250                 255

Ala Tyr Thr Val Ala Ala Ser Phe Ile Pro Leu Ile Thr Gly Gln Lys
            260                 265                 270

Arg Ser Ile Ser Gly Thr Phe Tyr Val Ala Leu Lys Asp Ala Gln Gly
        275                 280                 285

Gln Pro Ile Asn Ser Ser Ala Lys Arg Leu Leu Gly Ser Ile Asn Asp
    290                 295                 300

Leu Pro Tyr Phe Ala Val Pro Leu Glu Ile Thr Ser Gln Gly Val Asp
305                 310                 315                 320

Glu Leu Asp Thr Ser Val Leu Glu Arg Met Thr Lys Tyr Glu Arg Glu
                325                 330                 335

Arg Leu Leu Ala Pro Cys Leu Gly Lys Leu Glu Gly Gly Ile Arg Asn
            340                 345                 350

Gly Leu Ser Leu
        355


<210> SEQ ID NO 102
<211> LENGTH: 338
<212> TYPE: PRT
<213> ORGANISM: Kluyveromyces marxianus

<400> SEQUENCE: 102

Met Leu Arg Ala Leu Thr Arg Arg Gln Phe Ser Ser Thr Ala Phe Asn
1               5                   10                  15

Pro Tyr Lys Val Thr Val Leu Gly Ala Gly Gly Gly Ile Gly Gln Pro
            20                  25                  30

Leu Ser Leu Leu Leu Lys Leu Asn His Lys Val Thr Asp Leu Arg Leu
        35                  40                  45

Tyr Asp Leu Lys Gly Ala Lys Gly Val Ala Ala Asp Leu Ser His Ile
    50                  55                  60

Pro Thr Asn Ser Thr Val Thr Gly Tyr Thr Pro Glu Ser Lys Asp Ser
65                  70                  75                  80

Gln Glu Glu Leu Ala Ala Ala Leu Lys Asp Thr Glu Val Val Leu Ile
                85                  90                  95
```

```
Pro Ala Gly Val Pro Arg Lys Pro Gly Met Thr Arg Asp Asp Leu Phe
            100                 105                 110

Ala Ile Asn Ala Gly Ile Val Arg Asp Leu Ala Thr Ser Ile Ala Lys
        115                 120                 125

Asn Ala Pro Asn Ala Ala Ile Leu Val Ile Ser Asn Pro Val Asn Ser
    130                 135                 140

Thr Val Pro Ile Val Ala Glu Val Leu Lys Gln Asn Gly Val Tyr Asn
145                 150                 155                 160

Pro Lys Lys Leu Phe Gly Val Thr Thr Leu Asp Val Ile Arg Ala Ser
                165                 170                 175

Arg Phe Ile Ser Glu Val Arg Gly Thr Asp Pro Thr Thr Glu His Val
            180                 185                 190

Thr Val Val Gly Gly His Ser Gly Ile Thr Ile Leu Pro Leu Val Ser
        195                 200                 205

Gln Thr Lys His Lys Ser Val Ile Lys Gly Glu Glu Leu Asp Asn Leu
    210                 215                 220

Ile His Arg Ile Gln Phe Gly Gly Asp Glu Val Val Gln Ala Lys Asn
225                 230                 235                 240

Gly Ala Gly Ser Ala Thr Leu Ser Met Ala Gln Ala Gly Ala Arg Phe
                245                 250                 255

Ala Asn Ser Val Leu Ser Gly Phe Glu Gly Glu Arg Asp Val Ile Glu
            260                 265                 270

Pro Thr Phe Val Asp Ser Pro Leu Phe Lys Asp Glu Gly Ile Glu Phe
        275                 280                 285

Phe Ala Ser Pro Val Thr Leu Gly Pro Glu Gly Val Glu Lys Ile His
    290                 295                 300

Gly Leu Gly Val Leu Ser Asp Lys Glu Glu Gln Met Leu Ala Thr Cys
305                 310                 315                 320

Lys Glu Thr Leu Lys Lys Asn Ile Glu Lys Gly Gln Asn Phe Val Lys
                325                 330                 335

Gln Asn


<210> SEQ ID NO 103
<211> LENGTH: 335
<212> TYPE: PRT
<213> ORGANISM: Kluyveromyces marxianus

<400> SEQUENCE: 103

Met Val Ser Val Ala Val Leu Gly Ser Ser Gly Gly Ile Gly Gln Pro
1               5                   10                  15

Leu Ser Leu Leu Leu Lys Leu Asp Pro Arg Val Ser Ser Leu Arg Leu
            20                  25                  30

Tyr Asp Leu Lys Met Ser His Gly Ile Ala Thr Asp Leu Ser His Met
        35                  40                  45

Asp Ser Asn Ser Ile Cys Glu Gly Phe Asn Thr Asp Glu Ile Ala Leu
    50                  55                  60

Ala Leu Lys Gly Ala Gln Ile Val Val Ile Pro Ala Gly Val Pro Arg
65                  70                  75                  80

Lys Pro Gly Met Ser Arg Asp Asp Leu Phe Lys Ile Asn Ala Lys Ile
                85                  90                  95

Ile Lys Ser Leu Ala Leu Gln Ile Ala Glu His Ala Pro Glu Ala Arg
            100                 105                 110

Val Leu Val Ile Ser Asn Pro Val Asn Ser Leu Val Pro Ile Val Tyr
        115                 120                 125
```

```
Glu Thr Leu Lys Ser Val Gly Lys Phe Glu Pro Gly Lys Val Met Gly
    130                 135                 140

Ile Thr Thr Leu Asp Ile Ile Arg Ser His Thr Phe Leu Val Asp Val
145                 150                 155                 160

Leu Gly Arg Lys Ala Tyr Ser Val Glu Lys Leu Arg Ser Ala Val Thr
                165                 170                 175

Val Val Gly Gly His Ser Gly Glu Thr Ile Val Pro Ile Phe Thr Asp
            180                 185                 190

Gln Lys Phe Tyr Arg Arg Leu Arg Asp Arg Glu Leu Tyr Asp Ala Tyr
        195                 200                 205

Val His Arg Val Gln Phe Gly Gly Asp Glu Val Val Lys Ala Lys Asp
    210                 215                 220

Gly Ser Gly Ser Ala Thr Leu Ser Met Ala Trp Ala Gly Tyr Ser Phe
225                 230                 235                 240

Val Lys Gln Leu Leu Asn Ser Leu His Leu Glu Thr Gly Glu Asp Val
                245                 250                 255

His Pro Ile Pro Thr Phe Val Tyr Leu Pro Gly Leu Pro Gly Gly Lys
            260                 265                 270

Glu Leu Gln Gln Lys Leu Gly Thr Ser Val Glu Phe Phe Ala Ala Pro
        275                 280                 285

Val Lys Leu Ser Lys Gly Ile Val Val Glu Val Glu His Asp Trp Val
    290                 295                 300

Asp Lys Leu Asn Asp Ala Glu Lys Lys Leu Ile Ala Lys Cys Leu Pro
305                 310                 315                 320

Ile Leu Asp Lys Asn Ile Lys Lys Gly Leu Ala Phe Ser Gln Gln
                325                 330                 335


<210> SEQ ID NO 104
<211> LENGTH: 374
<212> TYPE: PRT
<213> ORGANISM: Kluyveromyces marxianus

<400> SEQUENCE: 104

Met Pro Ala Val Ser Tyr Asp Val Gln Gln Arg Asp Ile Leu Lys Ile
1               5                   10                  15

Ala Val Leu Gly Ala Ala Gly Gly Ile Gly Gln Ser Leu Ser Leu Leu
            20                  25                  30

Leu Lys Ser Asn Ala Ser Phe Leu Leu Pro Arg Asp Ser Ser Arg His
        35                  40                  45

Ile Ser Leu Ala Leu Tyr Asp Val Asn Lys Asp Ala Ile Val Gly Thr
    50                  55                  60

Ala Ala Asp Leu Ser His Ile Asp Thr Pro Ile Thr Thr Thr Pro His
65                  70                  75                  80

Tyr Pro Asn Asp Gly Asn Gly Gly Ile Ala Arg Cys Leu Gln Asp Ala
                85                  90                  95

Asp Met Val Ile Ile Pro Ala Gly Val Pro Arg Lys Pro Gly Met Ser
            100                 105                 110

Arg Asp Asp Leu Ile Gly Val Asn Ala Lys Ile Ile Lys Ser Leu Gly
        115                 120                 125

Asn Asp Ile Ala Glu Tyr Cys Asp Leu Ser Lys Val His Val Leu Val
    130                 135                 140

Ile Ser Asn Pro Val Asn Ser Leu Val Pro Leu Met Val Ser Thr Leu
145                 150                 155                 160

Ala Asn Ser Pro His Ser Ala Asn Thr Asn Ile Glu Ala Arg Val Tyr
```

```
                165                 170                 175

Gly Ile Thr His Leu Asp Leu Val Arg Ala Ser Thr Phe Val Gln Gln
            180                 185                 190

Leu Asn Ser Phe Lys Ser Asn Asn Ala Pro Asp Ile Pro Val Ile Gly
        195                 200                 205

Gly His Ser Gly Asp Thr Ile Ile Pro Val Phe Ser Val Leu Asn His
    210                 215                 220

Arg Ala Ser Asn Ser Gly Tyr Ala Asn Leu Leu Asp Asn Gly Val Arg
225                 230                 235                 240

Gln Lys Leu Val His Arg Val Gln Tyr Gly Gly Asp Glu Ile Val Gln
                245                 250                 255

Ala Lys Asn Gly Asn Gly Ser Ala Thr Leu Ser Met Ala Tyr Ala Gly
            260                 265                 270

Phe Lys Ile Ala Ala Gln Phe Ile Asp Leu Leu Val Gly Asn Ile Arg
        275                 280                 285

Thr Ile Glu Asn Ile Cys Met Tyr Val Pro Leu Thr Asn Arg Tyr Asn
    290                 295                 300

Thr Glu Ile Ala Pro Gly Ser Asp Glu Leu Arg Ser Lys Tyr Ile Asn
305                 310                 315                 320

Gly Thr Leu Tyr Phe Ser Ile Pro Leu Ser Ile Gly Ile Asn Gly Ile
                325                 330                 335

Glu Arg Val His Tyr Glu Ile Met Glu His Leu Asp Ser Tyr Glu Arg
            340                 345                 350

Glu Thr Leu Leu Pro Ile Cys Leu Glu Thr Leu Lys Gly Asn Ile Asp
        355                 360                 365

Lys Gly Leu Ser Leu Val
    370


<210> SEQ ID NO 105
<211> LENGTH: 312
<212> TYPE: PRT
<213> ORGANISM: Escherichia coli

<400> SEQUENCE: 105

Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Arg Lys Pro Gly Met Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160
```

```
Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
        275                 280                 285

Gln Asn Ala Leu Glu Gly Met Leu Asp Thr Leu Lys Lys Asp Ile Ala
    290                 295                 300

Leu Gly Glu Glu Phe Val Asn Lys
305                 310


<210> SEQ ID NO 106
<211> LENGTH: 337
<212> TYPE: PRT
<213> ORGANISM: Rhizopus oryzae

<400> SEQUENCE: 106

Met Phe Ala Ala Ser Arg Val Phe Ser Ile Ala Ala Lys Arg Ser Phe
1               5                   10                  15

Ser Thr Ser Ala Ala Asn Leu Ser Lys Val Ala Val Leu Gly Ala Ala
            20                  25                  30

Gly Gly Ile Gly Gln Pro Leu Ser Leu Leu Leu Lys Glu Asn Pro His
        35                  40                  45

Val Thr His Leu Ser Leu Tyr Asp Ile Val Asn Thr Pro Gly Val Ala
    50                  55                  60

Ala Asp Leu Ser His Ile Asn Thr Asn Ser Lys Val Thr Gly His Thr
65                  70                  75                  80

Pro Glu Asn Asp Gly Leu Lys Thr Ala Leu Glu Gly Ala His Val Val
                85                  90                  95

Val Ile Pro Ala Gly Val Pro Arg Lys Pro Gly Met Thr Arg Asp Asp
            100                 105                 110

Leu Phe Asn Thr Asn Ala Ser Ile Val Arg Asp Leu Ala Glu Ala Ala
        115                 120                 125

Ala Lys His Cys Pro Asp Ala His Phe Leu Ile Ile Ser Asn Pro Val
    130                 135                 140

Asn Ser Thr Val Pro Ile Phe Ala Glu Thr Leu Lys Lys Ala Gly Val
145                 150                 155                 160

Phe Asn Pro Lys Arg Leu Tyr Gly Val Thr Thr Leu Asp Val Val Arg
                165                 170                 175

Ala Ser Arg Phe Val Ala Glu Val Lys Asn Leu Asp Pro Asn Asp Val
            180                 185                 190

Lys Val Thr Val Val Gly Gly His Ser Gly Val Thr Ile Val Pro Leu
        195                 200                 205

Leu Ser Gln Thr Gly Leu Glu Phe Ser Lys Glu Glu Leu Asp Ala Leu
    210                 215                 220
```

```
Thr His Arg Ile Gln Phe Gly Gly Asp Glu Val Val Gln Ala Lys Asn
225                 230                 235                 240

Gly Thr Gly Ser Val Thr Leu Ser Met Ala Phe Ala Gly Ala Arg Phe
                245                 250                 255

Ala Asn Ser Val Leu Glu Ala Thr Val Gly Gly Lys Lys Gly Val Val
            260                 265                 270

Glu Pro Ser Phe Val Lys Ser Asp Val Phe Ala Lys Asp Gly Val Glu
        275                 280                 285

Tyr Phe Ser Thr Asn Ile Glu Leu Gly Pro Glu Gly Val Glu Lys Ile
    290                 295                 300

Asn Glu Leu Gly Gln Ile Ser Asp Tyr Glu Lys Glu Leu Ile Ala Lys
305                 310                 315                 320

Ala Val Pro Glu Leu Lys Lys Asn Ile Ala Lys Gly Asn Ser Phe Val
                325                 330                 335

Gln
```

```
<210> SEQ ID NO 107
<211> LENGTH: 485
<212> TYPE: PRT
<213> ORGANISM: Issatchenkia orientalis

<400> SEQUENCE: 107

Met Leu Ala Ala Arg Ser Leu Lys Ala Arg Met Ser Thr Arg Ala Phe
1               5                   10                  15

Ser Thr Thr Ser Ile Ala Lys Arg Ile Glu Lys Asp Ala Phe Gly Asp
            20                  25                  30

Ile Glu Val Pro Asn Glu Lys Tyr Trp Gly Ala Gln Thr Gln Arg Ser
        35                  40                  45

Leu Gln Asn Phe Lys Ile Gly Gly Lys Arg Glu Val Met Pro Glu Pro
    50                  55                  60

Ile Ile Lys Ser Phe Gly Ile Leu Lys Lys Ala Thr Ala Lys Ile Asn
65                  70                  75                  80

Ala Glu Ser Gly Ala Leu Asp Pro Lys Leu Ser Glu Ala Ile Gln Gln
                85                  90                  95

Ala Ala Thr Glu Val Tyr Glu Gly Lys Leu Met Asp His Phe Pro Leu
            100                 105                 110

Val Val Phe Gln Thr Gly Ser Gly Thr Gln Ser Asn Met Asn Ala Asn
        115                 120                 125

Glu Val Ile Ser Asn Arg Ala Ile Glu Ile Leu Gly Gly Glu Leu Gly
    130                 135                 140

Ser Lys Thr Pro Val His Pro Asn Asp His Val Asn Met Ser Gln Ser
145                 150                 155                 160

Ser Asn Asp Thr Phe Pro Thr Val Met His Ile Ala Ala Val Thr Glu
                165                 170                 175

Val Ser Ser His Leu Leu Pro Glu Leu Thr Ala Leu Arg Asp Ala Leu
            180                 185                 190

Gln Lys Lys Ser Asp Glu Phe Lys Asn Ile Ile Lys Ile Gly Arg Thr
        195                 200                 205

His Leu Gln Asp Ala Thr Pro Leu Thr Leu Gly Gln Glu Phe Ser Gly
    210                 215                 220

Tyr Val Gln Gln Cys Thr Asn Gly Ile Lys Arg Ile Glu Ile Ala Leu
225                 230                 235                 240

Glu His Leu Arg Tyr Leu Ala Gln Gly Gly Thr Ala Val Gly Thr Gly
                245                 250                 255
```

```
Leu Asn Thr Lys Lys Gly Phe Ala Glu Lys Val Ala Asn Glu Val Thr
            260                 265                 270

Lys Leu Thr Gly Leu Gln Phe Tyr Thr Ala Pro Asn Lys Phe Glu Ala
        275                 280                 285

Leu Ala Ala His Asp Ala Val Val Glu Met Ser Gly Ala Leu Asn Thr
    290                 295                 300

Val Ala Val Ser Leu Phe Lys Ile Ala Gln Asp Ile Arg Tyr Leu Gly
305                 310                 315                 320

Ser Gly Pro Arg Cys Gly Tyr Gly Glu Leu Ala Leu Pro Glu Asn Glu
                325                 330                 335

Pro Gly Ser Ser Ile Met Pro Gly Lys Val Asn Pro Thr Gln Asn Glu
            340                 345                 350

Ala Leu Thr Met Leu Cys Thr Gln Val Phe Gly Asn His Ser Cys Ile
        355                 360                 365

Thr Phe Ala Gly Ala Ser Gly Gln Phe Glu Leu Asn Val Phe Lys Pro
    370                 375                 380

Val Met Ile Ser Asn Leu Leu Ser Ser Ile Arg Leu Leu Gly Asp Gly
385                 390                 395                 400

Cys Asn Ser Phe Arg Ile His Cys Val Glu Gly Ile Ile Ala Asn Thr
                405                 410                 415

Asp Lys Ile Asp Lys Leu Leu His Glu Ser Leu Met Leu Val Thr Ala
            420                 425                 430

Leu Asn Pro His Ile Gly Tyr Asp Lys Ala Ser Lys Ile Ala Lys Asn
        435                 440                 445

Ala His Lys Lys Gly Leu Thr Leu Lys Gln Ser Ala Leu Glu Leu Gly
    450                 455                 460

Tyr Leu Thr Glu Glu Gln Phe Asn Glu Trp Val Arg Pro Glu Asn Met
465                 470                 475                 480

Ile Gly Pro Lys Asp
                485


<210> SEQ ID NO 108
<211> LENGTH: 470
<212> TYPE: PRT
<213> ORGANISM: Saccharomyces cerevisiae

<400> SEQUENCE: 108

Met Ser Leu Ser Pro Val Val Val Ile Gly Thr Gly Leu Ala Gly Leu
1               5                   10                  15

Ala Ala Ala Asn Glu Leu Val Asn Lys Tyr Asn Ile Pro Val Thr Ile
            20                  25                  30

Leu Glu Lys Ala Ser Ser Ile Gly Gly Asn Ser Ile Lys Ala Ser Ser
        35                  40                  45

Gly Ile Asn Gly Ala Cys Thr Glu Thr Gln Arg His Phe His Ile Glu
    50                  55                  60

Asp Ser Pro Arg Leu Phe Glu Asp Asp Thr Ile Lys Ser Ala Lys Gly
65                  70                  75                  80

Lys Gly Val Gln Glu Leu Met Ala Lys Leu Ala Asn Asp Ser Pro Leu
                85                  90                  95

Ala Ile Glu Trp Leu Lys Asn Glu Phe Asp Leu Lys Leu Asp Leu Leu
            100                 105                 110

Ala Gln Leu Gly Gly His Ser Val Ala Arg Thr His Arg Ser Ser Gly
        115                 120                 125

Lys Leu Pro Pro Gly Phe Glu Ile Val Ser Ala Leu Ser Asn Asn Leu
```

```
    130                 135                 140

Lys Lys Leu Ala Glu Thr Lys Pro Glu Leu Val Lys Ile Asn Leu Asp
145                 150                 155                 160

Ser Lys Val Val Asp Ile His Glu Lys Asp Gly Ser Ile Ser Ala Val
                165                 170                 175

Val Tyr Glu Asp Lys Asn Gly Glu Lys His Met Val Ser Ala Asn Asp
            180                 185                 190

Val Val Phe Cys Ser Gly Gly Phe Gly Phe Ser Lys Glu Met Leu Lys
        195                 200                 205

Glu Tyr Ala Pro Glu Leu Val Asn Leu Pro Thr Thr Asn Gly Gln Gln
    210                 215                 220

Thr Thr Gly Asp Gly Gln Arg Leu Leu Gln Lys Leu Gly Ala Asp Leu
225                 230                 235                 240

Ile Asp Met Asp Gln Ile Gln Val His Pro Thr Gly Phe Ile Asp Pro
                245                 250                 255

Asn Asp Arg Ser Ser Ser Trp Lys Phe Leu Ala Ala Glu Ser Leu Arg
            260                 265                 270

Gly Leu Gly Gly Ile Leu Leu Asn Pro Ile Thr Gly Arg Arg Phe Val
        275                 280                 285

Asn Glu Leu Thr Thr Arg Asp Val Val Thr Ala Ala Ile Gln Lys Val
    290                 295                 300

Cys Pro Gln Glu Asp Asn Arg Ala Leu Leu Val Met Gly Glu Lys Met
305                 310                 315                 320

Tyr Thr Asp Leu Lys Asn Asn Leu Asp Phe Tyr Met Phe Lys Lys Leu
                325                 330                 335

Val Gln Lys Leu Thr Leu Ser Gln Val Val Ser Glu Tyr Asn Leu Pro
            340                 345                 350

Ile Thr Val Ala Gln Leu Cys Glu Glu Leu Gln Thr Tyr Ser Ser Phe
        355                 360                 365

Thr Thr Lys Ala Asp Pro Leu Gly Arg Thr Val Ile Leu Asn Glu Phe
    370                 375                 380

Gly Ser Asp Val Thr Pro Glu Thr Val Val Phe Ile Gly Glu Val Thr
385                 390                 395                 400

Pro Val Val His Phe Thr Met Gly Gly Ala Arg Ile Asn Val Lys Ala
                405                 410                 415

Gln Val Ile Gly Lys Asn Asp Glu Arg Leu Leu Lys Gly Leu Tyr Ala
            420                 425                 430

Ala Gly Glu Val Ser Gly Gly Val His Gly Ala Asn Arg Leu Gly Gly
        435                 440                 445

Ser Ser Leu Leu Glu Cys Val Val Phe Gly Arg Thr Ala Ala Glu Ser
    450                 455                 460

Ile Ala Asn Asp Arg Lys
465                 470


<210> SEQ ID NO 109
<211> LENGTH: 470
<212> TYPE: PRT
<213> ORGANISM: Saccharomyces mitakae

<400> SEQUENCE: 109

Met Ser Ser Ser Pro Val Val Val Ile Gly Thr Gly Leu Ala Gly Leu
1               5                   10                  15

Ala Thr Ala Asn Glu Leu Val Asn Lys Tyr Asn Ile Pro Val Thr Ile
            20                  25                  30
```

```
Leu Glu Lys Ala Ser Ser Ile Gly Gly Asn Ser Ile Lys Ala Ser Ser
        35                  40                  45

Gly Ile Asn Gly Ala Cys Thr Glu Thr Gln Arg His Phe His Ile Glu
    50                  55                  60

Asp Thr Pro Arg Leu Phe Glu Asp Asp Thr Val Gln Ser Ala Lys Gly
65                  70                  75                  80

Lys Gly Val Gln Glu Leu Met Gly Lys Leu Ala Asn Asp Ser Pro Leu
                85                  90                  95

Ala Ile Glu Trp Leu Lys Thr Glu Phe Asp Leu Lys Leu Asp Leu Leu
            100                 105                 110

Ala Gln Leu Gly Gly His Ser Val Ala Arg Thr His Arg Ser Ser Gly
        115                 120                 125

Lys Leu Pro Pro Gly Phe Glu Ile Val Ser Ala Leu Ser Asn Asn Leu
    130                 135                 140

Lys Lys Leu Ala Glu Thr Lys Pro Glu Leu Val Lys Ile Asn Leu Asp
145                 150                 155                 160

Ser Lys Val Val Asp Ile His Lys Lys Asp Gly Ser Ile Ser Ala Ile
                165                 170                 175

Val Tyr Asp Asp Lys Asn Gly Glu Arg His Thr Leu Ser Thr Ser Asn
            180                 185                 190

Val Val Phe Cys Ser Gly Gly Phe Gly Phe Ser Lys Glu Met Leu Asn
        195                 200                 205

Glu Tyr Ala Pro Gln Leu Val Asn Leu Pro Thr Thr Asn Gly Gln Gln
    210                 215                 220

Thr Thr Gly Asp Gly Gln Arg Leu Leu Gln Lys Leu Gly Ala Asp Leu
225                 230                 235                 240

Ile Asp Met Asp Gln Ile Gln Val His Pro Thr Gly Phe Ile Asp Pro
                245                 250                 255

Asn Asp Arg Asn Ser Ser Trp Lys Phe Leu Ala Ala Glu Ser Leu Arg
            260                 265                 270

Gly Leu Gly Gly Ile Leu Leu Asn Pro Ile Thr Gly Arg Arg Phe Val
        275                 280                 285

Asn Glu Leu Thr Thr Arg Asp Val Val Thr Glu Ala Ile Gln Lys His
    290                 295                 300

Cys Pro Gln Asp Asp Asn Arg Ala Leu Leu Val Met Ser Glu Lys Met
305                 310                 315                 320

Tyr Thr Asp Leu Lys Asn Asn Leu Asp Phe Tyr Met Phe Lys Lys Leu
                325                 330                 335

Val Gln Lys Leu Ser Leu Ser Gln Val Val Ser Glu Tyr Lys Leu Pro
            340                 345                 350

Ile Thr Val Ser Gln Leu Cys Gln Glu Leu Gln Thr Tyr Ser Ser Phe
        355                 360                 365

Thr Ser Lys Ala Asp Pro Leu Gly Arg Thr Val Val Leu Asn Glu Phe
    370                 375                 380

Gly Ala Asp Ile Thr Pro Glu Thr Met Val Phe Ile Gly Glu Val Thr
385                 390                 395                 400

Pro Val Val His Phe Thr Met Gly Gly Ala Arg Ile Asn Val Lys Ala
                405                 410                 415

Gln Val Ile Gly Lys Asn Asp Glu Pro Leu Leu Asn Gly Leu Tyr Ala
            420                 425                 430

Ala Gly Glu Val Ser Gly Gly Val His Gly Ala Asn Arg Leu Gly Gly
        435                 440                 445

Ser Ser Leu Leu Glu Cys Val Val Phe Gly Arg Thr Ala Ala Glu Ser
```

```
    450                 455                 460

Ile Ala Asn Asn His Lys
465                 470


<210> SEQ ID NO 110
<211> LENGTH: 470
<212> TYPE: PRT
<213> ORGANISM: Kluyvermyces polysporus

<400> SEQUENCE: 110

Met Ser Thr Lys Lys Pro Val Val Ile Ile Gly Thr Gly Leu Ala Gly
1               5                   10                  15

Leu Ser Ala Gly Asn Gln Leu Val Asn Met His Lys Val Pro Ile Ile
            20                  25                  30

Met Leu Asp Lys Ala Ser Ser Ile Gly Gly Asn Ser Thr Lys Ala Ser
        35                  40                  45

Ser Gly Ile Asn Gly Ala Ser Thr Ile Thr Gln Gln Gln Leu Asn Val
    50                  55                  60

Lys Asp Ser Pro Asp Leu Phe Leu Gln Asp Thr Val Lys Ser Ala Lys
65                  70                  75                  80

Gly Arg Gly Ile Glu Ser Leu Met Lys Lys Leu Ser Gln Asp Ser Asn
                85                  90                  95

Ser Ala Ile His Trp Leu Gln Gln Asp Phe Asp Leu Lys Leu Asp Leu
            100                 105                 110

Leu Ala Gln Leu Gly Gly His Ser Val Pro Arg Thr His Arg Ser Ser
        115                 120                 125

Gly Lys Leu Pro Pro Gly Phe Glu Ile Val Gln Ala Leu Ser Asn Lys
    130                 135                 140

Leu Lys Ala Ile Ser Glu Ser Asp Pro Glu Phe Val Arg Ile Leu Leu
145                 150                 155                 160

Asn Ser Lys Val Val Asp Val Ser Val Asn Asn Glu Gly Lys Val Glu
                165                 170                 175

Ser Ile Asp Tyr Val Asp Ala Glu Gly Lys His His Lys Ile Ala Thr
            180                 185                 190

Asp Asn Val Val Phe Cys Ser Gly Gly Phe Gly His Ser Ala Glu Met
        195                 200                 205

Leu Asn Lys Tyr Ala Pro Glu Leu Ala Asn Leu Pro Thr Thr Asn Gly
    210                 215                 220

Gln Gln Thr Thr Gly Asp Gly Gln Arg Ile Leu Glu Lys Leu Gly Ala
225                 230                 235                 240

Asp Leu Ile Asp Met Ser Gln Ile Gln Val His Pro Thr Gly Phe Ile
                245                 250                 255

Asp Pro Ala Asn Arg Asp Ser Lys Trp Lys Phe Leu Ala Ala Glu Ala
            260                 265                 270

Leu Arg Gly Leu Gly Gly Ile Leu Leu Asn Pro Ser Thr Gly Lys Arg
        275                 280                 285

Phe Val Asn Glu Leu Thr Thr Arg Asp Leu Val Thr Glu Ala Ile Gln
    290                 295                 300

Ser Gln Cys Pro Arg Asp Asp Asn Lys Ala Phe Leu Val Met Ser Glu
305                 310                 315                 320

Lys Val Tyr Glu Asn Tyr Lys Asn Asn Met Asp Phe Tyr Leu Phe Lys
                325                 330                 335

Lys Leu Val Ser Lys Met Thr Ile Lys Glu Phe Val Glu Thr Tyr Lys
            340                 345                 350
```

```
Leu Pro Ile Ser Ala Asp Ala Val Thr Gln Asp Leu Ile Asp Tyr Ser
        355                 360                 365

Val Asp Lys Thr Asp Lys Phe Gly Arg Pro Leu Val Ile Asn Val Phe
    370                 375                 380

Asp Glu Lys Leu Thr Glu Asp Ser Glu Ile Tyr Val Gly Glu Val Thr
385                 390                 395                 400

Pro Val Val His Phe Thr Met Gly Gly Ala Lys Ile Asn Thr Glu Ser
                405                 410                 415

Gln Val Ile Asn Lys Asn Gly Gln Val Leu Ala Lys Gly Ile Tyr Ala
            420                 425                 430

Ala Gly Glu Val Ser Gly Gly Val His Gly Ser Asn Arg Leu Gly Gly
        435                 440                 445

Ser Ser Leu Leu Glu Cys Val Val Tyr Gly Arg Ser Ala Ala Asp Asn
    450                 455                 460

Ile Ala Lys Asn Ile Glu
465                 470


<210> SEQ ID NO 111
<211> LENGTH: 487
<212> TYPE: PRT
<213> ORGANISM: Kluyveromyces marxianus

<400> SEQUENCE: 111

Met Leu His Arg Tyr Ile Arg Leu Phe Ser Phe Cys Val Ile Leu Tyr
1               5                   10                  15

Leu Val Tyr Leu Leu Leu Thr Lys Glu Ser Asn Val Met Ser Lys Pro
            20                  25                  30

Val Val Val Ile Gly Ser Gly Leu Ala Gly Leu Thr Thr Ser Ser Gln
        35                  40                  45

Leu Ala Lys Phe Asn Ile Pro Ile Val Leu Leu Glu Lys Thr Ser Ser
    50                  55                  60

Ile Gly Gly Asn Ser Ile Lys Ala Ser Ser Gly Ile Asn Gly Ala Gly
65                  70                  75                  80

Thr Glu Thr Gln Ser Arg Leu His Val Glu Asp His Pro Glu Leu Phe
                85                  90                  95

Ala Asp Asp Thr Ile Lys Ser Ala Lys Gly Lys Gly Val Val Ala Leu
            100                 105                 110

Met Glu Lys Leu Ser Lys Asp Ser Ser Asp Ala Ile Ser Trp Leu Gln
        115                 120                 125

Asn Asp Phe Lys Ile Pro Leu Asp Lys Leu Ala Gln Leu Gly Gly His
    130                 135                 140

Ser Val Pro Arg Thr His Arg Ser Ser Gly Lys Leu Pro Pro Gly Phe
145                 150                 155                 160

Gln Ile Val Asp Thr Leu Lys Lys Ala Leu Glu Ser Tyr Asp Ser Lys
                165                 170                 175

Ala Val Lys Ile Gln Leu Asn Ser Lys Val Val Asp Val Lys Leu Asp
            180                 185                 190

Ser Asn Asn Arg Val Ser Ser Val Val Phe Glu Asp Gln Asp Gly Thr
        195                 200                 205

His Thr Ile Glu Thr Asn Asn Val Val Phe Cys Thr Gly Gly Phe Gly
    210                 215                 220

Phe Asn Lys Lys Leu Leu Glu Lys Tyr Ala Pro His Leu Val Asp Leu
225                 230                 235                 240

Pro Thr Thr Asn Gly Glu Gln Thr Leu Gly Glu Gly Gln Val Leu Leu
                245                 250                 255
```

```
Glu Lys Leu Gly Ala Lys Leu Ile Asp Met Asp Gln Ile Gln Val His
            260                 265                 270

Pro Thr Gly Phe Ile Asp Pro Ala Asn Pro Asp Ser Asn Trp Lys Phe
        275                 280                 285

Leu Ala Ala Glu Ala Leu Arg Gly Leu Gly Gly Val Leu Ile Asn Pro
    290                 295                 300

His Thr Gly Gln Arg Phe Val Asn Glu Leu Thr Thr Arg Asp Met Val
305                 310                 315                 320

Thr Glu Ala Ile Gln Ser Lys Ser Glu Ser Lys Thr Ala Tyr Leu Val
                325                 330                 335

Met Ser Glu Ser Leu Tyr Glu Asn Tyr Lys Pro Asn Met Asp Phe Tyr
            340                 345                 350

Met Phe Lys Lys Leu Val Ser Lys Lys Thr Val Ala Glu Phe Ala Glu
        355                 360                 365

Asp Leu Pro Val Ser Val Asp Gln Leu Ile Ala Glu Leu Ser Thr Tyr
    370                 375                 380

Ser Asp Leu Ser Lys Asp Asp His Leu Gly Arg Lys Phe Arg Glu Asn
385                 390                 395                 400

Thr Phe Gly Ser Ser Leu Ser Ser Asp Ser Thr Ile Phe Val Gly Lys
                405                 410                 415

Ile Thr Pro Val Val His Phe Thr Met Gly Gly Ala Lys Ile Asp Glu
            420                 425                 430

Gln Ala Arg Val Leu Asn Ala Glu Gly Lys Pro Leu Ala Thr Gly Ile
        435                 440                 445

Tyr Ala Ala Gly Glu Val Ser Gly Gly Val His Gly Ala Asn Arg Leu
    450                 455                 460

Gly Gly Ser Ser Leu Leu Glu Cys Val Val Phe Gly Arg Gln Ala Ala
465                 470                 475                 480

Lys Ser Ile Arg Ala Asn Leu
                485


<210> SEQ ID NO 112
<211> LENGTH: 1139
<212> TYPE: PRT
<213> ORGANISM: Trypanosoma brucei

<400> SEQUENCE: 112

Met Val Asp Gly Arg Ser Ser Ala Ser Ile Val Ala Val Asp Pro Glu
1               5                   10                  15

Arg Ala Ala Arg Glu Arg Asp Ala Ala Ala Arg Ala Leu Leu Gln Asp
            20                  25                  30

Ser Pro Leu His Thr Thr Met Gln Tyr Ala Thr Ser Gly Leu Glu Leu
        35                  40                  45

Thr Val Pro Tyr Ala Leu Lys Val Val Ala Ser Ala Asp Thr Phe Asp
    50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
        115                 120                 125

Cys Phe Asp Pro Ser Thr Ala Pro Val Ala Lys Ala Leu Arg Glu Ile
```

```
    130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
        195                 200                 205

Phe Gln Asn Val Phe Phe Asp Trp Gly Gly Asp Cys Arg Ala Ser Gly
    210                 215                 220

Met Asn Ala Arg Asn Thr Pro Trp Val Val Gly Ile Thr Arg Pro Pro
225                 230                 235                 240

Ser Leu Asp Met Leu Pro Asn Pro Pro Lys Glu Ala Ser Tyr Ile Ser
                245                 250                 255

Val Ile Ser Leu Asp Asn Glu Ala Leu Ala Thr Ser Gly Asp Tyr Glu
            260                 265                 270

Asn Leu Ile Tyr Thr Ala Asp Asp Lys Pro Leu Thr Cys Thr Tyr Asp
        275                 280                 285

Trp Lys Gly Lys Glu Leu Met Lys Pro Ser Gln Ser Asn Ile Ala Gln
    290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
                325                 330                 335

Gly Trp Arg Tyr Val Arg Asp Thr Val Arg Asp Tyr Arg Val Tyr Val
            340                 345                 350

Arg Glu Asn Glu Arg Val Ala Lys Met Phe Glu Ile Ala Thr Glu Asp
        355                 360                 365

Ala Glu Met Arg Lys Arg Arg Ile Ser Asn Thr Leu Pro Ala Arg Val
    370                 375                 380

Ile Val Val Gly Gly Gly Leu Ala Gly Leu Ser Ala Ala Ile Glu Ala
385                 390                 395                 400

Ala Gly Cys Gly Ala Gln Val Val Leu Met Glu Lys Glu Ala Lys Leu
                405                 410                 415

Gly Gly Asn Ser Ala Lys Ala Thr Ser Gly Ile Asn Gly Trp Gly Thr
            420                 425                 430

Arg Ala Gln Ala Lys Ala Ser Ile Val Asp Gly Gly Lys Tyr Phe Glu
        435                 440                 445

Arg Asp Thr Tyr Lys Ser Gly Ile Gly Gly Asn Thr Asp Pro Ala Leu
    450                 455                 460

Val Lys Thr Leu Ser Met Lys Ser Ala Asp Ala Ile Gly Trp Leu Thr
465                 470                 475                 480

Ser Leu Gly Val Pro Leu Thr Val Leu Ser Gln Leu Gly Gly His Ser
                485                 490                 495

Arg Lys Arg Thr His Arg Ala Pro Asp Lys Lys Asp Gly Thr Pro Leu
            500                 505                 510

Pro Ile Gly Phe Thr Ile Met Lys Thr Leu Glu Asp His Val Arg Gly
        515                 520                 525

Asn Leu Ser Gly Arg Ile Thr Ile Met Glu Asn Cys Ser Val Thr Ser
    530                 535                 540

Leu Leu Ser Glu Thr Lys Glu Arg Pro Asp Gly Thr Lys Gln Ile Arg
545                 550                 555                 560
```

-continued

```
Val Thr Gly Val Glu Phe Thr Gln Ala Gly Ser Gly Lys Thr Thr Ile
                565                 570                 575

Leu Ala Asp Ala Val Ile Leu Ala Thr Gly Gly Phe Ser Asn Asp Lys
            580                 585                 590

Thr Ala Asp Ser Leu Leu Arg Glu His Ala Pro His Leu Val Asn Phe
        595                 600                 605

Pro Thr Thr Asn Gly Pro Trp Ala Thr Gly Asp Gly Val Lys Leu Ala
    610                 615                 620

Gln Arg Leu Gly Ala Gln Leu Val Asp Met Asp Lys Val Gln Leu His
625                 630                 635                 640

Pro Thr Gly Leu Ile Asn Pro Lys Asp Pro Ala Asn Pro Thr Lys Phe
                645                 650                 655

Leu Gly Pro Glu Ala Leu Arg Gly Ser Gly Gly Val Leu Leu Asn Lys
            660                 665                 670

Gln Gly Lys Arg Phe Val Asn Glu Leu Asp Leu Arg Ser Val Val Ser
        675                 680                 685

Lys Ala Ile Met Glu Gln Gly Ala Glu Tyr Pro Gly Ser Gly Gly Ser
    690                 695                 700

Met Phe Ala Tyr Cys Val Leu Asn Ala Ala Ala Gln Lys Leu Phe Gly
705                 710                 715                 720

Val Ser Ser His Glu Phe Tyr Trp Lys Lys Met Gly Leu Phe Val Lys
                725                 730                 735

Ala Asp Thr Met Arg Asp Leu Ala Ala Leu Ile Gly Cys Pro Val Glu
            740                 745                 750

Ser Val Gln Gln Thr Leu Glu Glu Tyr Glu Arg Leu Ser Ile Ser Gln
        755                 760                 765

Arg Ser Cys Pro Ile Thr Arg Lys Ser Val Tyr Pro Cys Val Leu Gly
    770                 775                 780

Thr Lys Gly Pro Tyr Tyr Val Ala Phe Val Thr Pro Ser Ile His Tyr
785                 790                 795                 800

Thr Met Gly Gly Cys Leu Ile Ser Pro Ser Ala Glu Ile Gln Met Lys
                805                 810                 815

Asn Thr Ser Ser Arg Ala Pro Leu Ser His Ser Asn Pro Ile Leu Gly
            820                 825                 830

Leu Phe Gly Ala Gly Glu Val Thr Gly Gly Val His Gly Gly Asn Arg
        835                 840                 845

Leu Gly Gly Asn Ser Leu Leu Glu Cys Val Val Phe Gly Arg Ile Ala
    850                 855                 860

Gly Asp Arg Ala Ser Thr Ile Leu Gln Arg Lys Ser Ser Ala Leu Ser
865                 870                 875                 880

Phe Lys Val Trp Thr Thr Val Val Leu Arg Glu Val Arg Glu Gly Gly
                885                 890                 895

Val Tyr Gly Ala Gly Ser Arg Val Leu Arg Phe Asn Leu Pro Gly Ala
            900                 905                 910

Leu Gln Arg Ser Gly Leu Ser Leu Gly Gln Phe Ile Ala Ile Arg Gly
        915                 920                 925

Asp Trp Asp Gly Gln Gln Leu Ile Gly Tyr Tyr Ser Pro Ile Thr Leu
    930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
                965                 970                 975
```

```
Met Lys Ala Cys Gly Gly Leu Val Ile Glu Arg Arg Leu Ser Asp Lys
            980                 985                 990

His Phe Val Phe Met Gly His Ile  Ile Asn Lys Leu Cys  Leu Ile Ala
        995                 1000                 1005

Gly Gly  Thr Gly Val Ala Pro  Met Leu Gln Ile Ile  Lys Ala Ala
    1010                 1015                 1020

Phe Met  Lys Pro Phe Ile Asp  Thr Leu Glu Ser Val  His Leu Ile
    1025                 1030                 1035

Tyr Ala  Ala Glu Asp Val Thr  Glu Leu Thr Tyr Arg  Glu Val Leu
    1040                 1045                 1050

Glu Glu  Arg Arg Arg Glu Ser  Arg Gly Lys Phe Lys  Lys Thr Phe
    1055                 1060                 1065

Val Leu  Asn Arg Pro Pro Pro  Leu Trp Thr Asp Gly  Val Gly Phe
    1070                 1075                 1080

Ile Asp  Arg Gly Ile Leu Thr  Asn His Val Gln Pro  Pro Ser Asp
    1085                 1090                 1095

Asn Leu  Leu Val Ala Ile Cys  Gly Pro Pro Val Met  Gln Arg Ile
    1100                 1105                 1110

Val Lys  Ala Thr Leu Lys Thr  Leu Gly Tyr Asn Met  Asn Leu Val
    1115                 1120                 1125

Arg Thr  Val Asp Glu Thr Glu  Pro Ser Gly Ser
    1130                 1135
```

<210> SEQ ID NO 113
<211> LENGTH: 1139
<212> TYPE: PRT
<213> ORGANISM: Trypanosoma cruzi

<400> SEQUENCE: 113

```
Met Ala Asp Gly Arg Ser Ser Ala Ser Val Val Ala Val Asp Pro Glu
1               5                   10                  15

Lys Ala Ala Arg Glu Arg Asp Glu Ala Ala Arg Ala Leu Leu Arg Asp
            20                  25                  30

Ser Pro Leu Gln Thr His Leu Gln Tyr Met Thr Asn Gly Leu Glu Leu
        35                  40                  45

Thr Val Pro Phe Thr Leu Lys Val Val Ala Glu Ala Val Ala Phe Ser
    50                  55                  60

Arg Ala Lys Glu Val Ala Asp Glu Val Leu Arg Ser Ala Trp His Leu
65                  70                  75                  80

Ala Asp Thr Val Leu Asn Asn Phe Asn Pro Asn Ser Glu Ile Ser Met
                85                  90                  95

Ile Gly Arg Leu Pro Val Gly Gln Lys His Thr Met Ser Ala Thr Leu
            100                 105                 110

Lys Ser Val Ile Thr Cys Cys Gln His Val Phe Asn Ser Ser Arg Gly
        115                 120                 125

Val Phe Asp Pro Ala Thr Gly Pro Ile Ile Glu Ala Leu Arg Ala Lys
    130                 135                 140

Val Ala Glu Lys Ala Ser Val Ser Asp Glu Gln Met Glu Lys Leu Phe
145                 150                 155                 160

Arg Val Cys Asn Phe Ser Ser Ser Phe Ile Val Asp Leu Glu Met Gly
                165                 170                 175

Thr Ile Ala Arg Lys His Glu Asp Ala Arg Phe Asp Leu Gly Gly Val
            180                 185                 190

Ser Lys Gly Tyr Ile Val Asp Tyr Val Val Glu Arg Leu Asn Ala Ala
        195                 200                 205
```

```
Gly Ile Val Asp Val Tyr Phe Glu Trp Gly Gly Asp Cys Arg Ala Ser
    210                 215                 220

Gly Thr Asn Ala Arg Arg Thr Pro Trp Met Val Gly Ile Ile Arg Pro
225                 230                 235                 240

Pro Ser Leu Glu Gln Leu Arg Asn Pro Pro Lys Asp Pro Ser Tyr Ile
                245                 250                 255

Arg Val Leu Pro Leu Asn Asp Glu Ala Leu Cys Thr Ser Gly Asp Tyr
            260                 265                 270

Glu Asn Leu Thr Glu Gly Ser Asn Lys Lys Leu Tyr Thr Ser Ile Phe
        275                 280                 285

Asp Trp Lys Lys Arg Ser Leu Leu Glu Pro Val Glu Ser Glu Leu Ala
    290                 295                 300

Gln Val Ser Ile Arg Cys Tyr Ser Ala Met Tyr Ala Asp Ala Leu Ala
305                 310                 315                 320

Thr Ala Ser Leu Ile Lys Arg Asp Ile Lys Lys Val Arg Gln Met Leu
                325                 330                 335

Glu Asp Trp Arg His Val Arg Asn Arg Val Thr Asn Tyr Val Thr Tyr
            340                 345                 350

Thr Arg Gln Gly Glu Arg Val Ala Arg Met Phe Glu Ile Ala Thr Asp
        355                 360                 365

Asn Ala Glu Ile Arg Lys Lys Arg Ile Ala Gly Ser Leu Pro Ala Arg
    370                 375                 380

Val Ile Val Val Gly Gly Gly Leu Ala Gly Leu Ser Ala Ala Ile Glu
385                 390                 395                 400

Ala Thr Ala Cys Gly Ala Gln Val Ile Leu Leu Glu Lys Glu Pro Lys
                405                 410                 415

Val Gly Gly Asn Ser Ala Lys Ala Thr Ser Gly Ile Asn Gly Trp Gly
            420                 425                 430

Thr Arg Ala Gln Ala Glu Gln Asp Val Tyr Asp Ser Gly Lys Tyr Phe
        435                 440                 445

Glu Arg Asp Thr His Lys Ser Gly Leu Gly Gly Ser Thr Asp Pro Gly
    450                 455                 460

Leu Val Arg Thr Leu Ser Val Lys Ser Gly Asp Ala Ile Ser Trp Leu
465                 470                 475                 480

Ser Ser Leu Gly Val Pro Leu Thr Val Leu Ser Gln Leu Gly Gly His
                485                 490                 495

Ser Arg Lys Arg Thr His Arg Ala Pro Asp Lys Ala Asp Gly Thr Pro
            500                 505                 510

Val Pro Ile Gly Phe Thr Ile Met Gln Thr Leu Glu Gln His Val Arg
        515                 520                 525

Thr Lys Leu Ala Asp Arg Val Thr Ile Met Glu Asn Thr Thr Val Thr
    530                 535                 540

Ser Leu Leu Ser Lys Ser Arg Val Arg His Asp Gly Ala Lys Gln Val
545                 550                 555                 560

Arg Val Tyr Gly Val Glu Val Leu Gln Asp Glu Gly Val Val Ser Arg
                565                 570                 575

Ile Leu Ala Asp Ala Val Ile Leu Ala Thr Gly Gly Phe Ser Asn Asp
            580                 585                 590

Lys Thr Pro Asn Ser Leu Leu Gln Glu Phe Ala Pro Gln Leu Ser Gly
        595                 600                 605

Phe Pro Thr Thr Asn Gly Pro Trp Ala Thr Gly Asp Gly Val Lys Leu
    610                 615                 620
```

```
Ala Arg Glu Leu Gly Val Lys Leu Val Asp Met Asp Lys Val Gln Leu
625                 630                 635                 640

His Pro Thr Gly Leu Ile Asp Pro Lys Asp Pro Ala Asn Pro Thr Lys
                645                 650                 655

Tyr Leu Gly Pro Glu Ala Leu Arg Gly Ser Gly Gly Val Leu Leu Asn
            660                 665                 670

Lys Lys Gly Glu Arg Phe Val Asn Glu Leu Asp Leu Arg Ser Val Val
        675                 680                 685

Ser Asn Ala Ile Ile Glu Gln Gly Asp Glu Tyr Pro Asp Ala Gly Gly
    690                 695                 700

Ser Lys Phe Ala Phe Cys Val Leu Asn Asp Ala Ala Val Lys Leu Phe
705                 710                 715                 720

Gly Val Asn Ser His Gly Phe Tyr Trp Lys Arg Leu Gly Leu Phe Val
                725                 730                 735

Lys Ala Asp Thr Val Glu Lys Leu Ala Ala Leu Ile Gly Cys Pro Val
            740                 745                 750

Glu Asn Val Arg Asn Thr Leu Gly Asp Tyr Glu Gln Leu Ser Lys Glu
        755                 760                 765

Asn Arg Gln Cys Pro Lys Thr Arg Lys Val Val Tyr Pro Cys Val Val
    770                 775                 780

Gly Pro Gln Gly Pro Phe Tyr Val Ala Phe Val Thr Pro Ser Ile His
785                 790                 795                 800

Tyr Thr Met Gly Gly Cys Leu Ile Ser Pro Ser Ala Glu Met Gln Leu
                805                 810                 815

Glu Glu Asn Thr Thr Ser Pro Phe Gly His Arg Arg Pro Ile Phe Gly
            820                 825                 830

Leu Phe Gly Ala Gly Glu Val Thr Gly Gly Val His Gly Gly Asn Arg
        835                 840                 845

Leu Gly Gly Asn Ser Leu Leu Glu Cys Val Val Phe Gly Arg Ile Ala
    850                 855                 860

Gly Asp Arg Ala Ala Thr Ile Leu Gln Lys Lys Pro Val Pro Leu Ser
865                 870                 875                 880

Phe Lys Thr Trp Thr Thr Val Ile Leu Arg Glu Val Arg Glu Gly Gly
                885                 890                 895

Met Tyr Gly Thr Gly Ser Arg Val Leu Arg Phe Asn Leu Pro Gly Ala
            900                 905                 910

Leu Gln Arg Ser Gly Leu Gln Leu Gly Gln Phe Ile Ala Ile Arg Gly
        915                 920                 925

Glu Trp Asp Gly Gln Gln Leu Ile Gly Tyr Tyr Ser Pro Ile Thr Leu
    930                 935                 940

Pro Asp Asp Leu Gly Val Ile Gly Ile Leu Ala Arg Ser Asp Lys Gly
945                 950                 955                 960

Thr Leu Lys Glu Trp Ile Ser Ala Leu Glu Pro Gly Asp Ala Val Glu
                965                 970                 975

Met Lys Gly Cys Gly Gly Leu Val Ile Glu Arg Arg Phe Ser Glu Arg
            980                 985                 990

Tyr Leu Tyr Phe Ser Gly His Ala  Leu Lys Lys Leu Cys  Leu Ile Ala
        995                 1000                1005

Gly Gly  Thr Gly Val Ala Pro  Met Leu Gln Ile Ile  Arg Ala Ala
    1010                1015                1020

Leu Lys  Lys Pro Phe Leu Glu  Asn Ile Glu Ser Ile  Arg Leu Ile
    1025                1030                1035

Tyr Ala  Ala Glu Asp Val Ser  Glu Leu Thr Tyr Arg  Glu Leu Leu
```

```
    1040                1045                1050

Glu His  His Gln Arg Asp Ser  Lys Gly Lys Phe Arg  Ser Ile Phe
    1055                1060                1065

Val Leu  Asn Arg Pro Pro Pro  Ile Trp Thr Asp Gly  Val Gly Phe
    1070                1075                1080

Ile Asp  Lys Lys Leu Leu Ser  Ser Ser Val Gln Pro  Pro Ala Lys
    1085                1090                1095

Asp Leu  Leu Val Ala Ile Cys  Gly Pro Pro Ile Met  Gln Arg Val
    1100                1105                1110

Val Lys  Thr Cys Leu Lys Ser  Leu Gly Tyr Asp Met  Gln Leu Val
    1115                1120                1125

Arg Thr  Val Asp Glu Val Glu  Thr Gln Asn Ser
    1130                1135


<210> SEQ ID NO 114
<211> LENGTH: 1144
<212> TYPE: PRT
<213> ORGANISM: Leishmania braziliensis

<400> SEQUENCE: 114

Met Ala Asp Gly Lys Thr Ser Ala Ser Val Val Ala Val Asp Pro Glu
1               5                   10                  15

Arg Ala Ala Lys Glu Arg Asp Ala Ala Ala Arg Ala Met Leu Gln Asp
            20                  25                  30

Gly Gly Val Ser Pro Val Gly Lys Ala Gln Leu Leu Lys Lys Gly Leu
        35                  40                  45

Ala Tyr Ala Val Pro Tyr Thr Leu Lys Ile Val Val Ala Asp Pro Lys
    50                  55                  60

Ala Met Glu Lys Thr Thr Ala Asp Val Glu Lys Val Leu Gln Thr Ala
65                  70                  75                  80

Phe Gln Val Val Asp Thr Leu Leu Asn Asn Phe Asn Glu Asn Ser Glu
                85                  90                  95

Val Ser Arg Ile Asn Arg Met Pro Val Gly Glu Glu His Gln Met Ser
            100                 105                 110

Ala Ala Leu Lys Arg Val Met Gly Cys Cys Gln Arg Val Tyr Asn Ser
        115                 120                 125

Ser Arg Gly Ala Phe Asp Pro Ala Val Gly Pro Leu Val Arg Glu Leu
    130                 135                 140

Arg Glu Ala Ala Arg Glu Gly Arg Thr Leu Pro Ala Glu Arg Ile Asn
145                 150                 155                 160

Ala Leu Leu Ser Lys Cys Thr Leu Asn Ile Ser Phe Ser Ile Asp Leu
                165                 170                 175

Asn Arg Gly Thr Ile Ala Arg Lys His Ala Asp Ala Met Leu Asp Leu
            180                 185                 190

Gly Gly Val Asn Lys Gly Tyr Gly Val Asp Tyr Val Val Glu His Leu
        195                 200                 205

Asn Asn Leu Gly Tyr Asp Asp Val Phe Phe Glu Trp Gly Gly Asp Val
    210                 215                 220

Arg Ala Ser Gly Lys Asn Pro Ser Asn Gln His Trp Val Val Gly Ile
225                 230                 235                 240

Ala Arg Pro Pro Ala Leu Ala Asp Ile Arg Thr Val Val Pro Gln Asp
                245                 250                 255

Lys Gln Ser Phe Ile Arg Val Val Cys Leu Asn Asp Glu Ala Ile Ala
            260                 265                 270
```

```
Thr Ser Gly Asp Tyr Glu Asn Leu Val Glu Gly Pro Gly Ser Lys Val
        275                 280                 285

Tyr Ser Ser Thr Phe Asn Ala Thr Ser Lys Ser Leu Leu Glu Pro Thr
    290                 295                 300

Glu Thr Asn Ile Ala Gln Val Ser Val Lys Cys Tyr Ser Cys Met Tyr
305                 310                 315                 320

Ala Asp Ala Leu Ala Thr Ala Ala Leu Leu Lys Asn Asn Pro Thr Ala
                325                 330                 335

Val Arg Arg Met Leu Asp Asn Trp Arg Tyr Val Arg Asp Thr Val Thr
            340                 345                 350

Asp Tyr Thr Thr Tyr Ser Arg Glu Gly Glu Arg Val Ala Lys Met Phe
        355                 360                 365

Glu Ile Ala Thr Glu Asp Lys Glu Met Arg Ala Lys Arg Ile Ser Gly
    370                 375                 380

Ser Leu Pro Ala Arg Val Ile Ile Val Gly Gly Gly Leu Ala Gly Cys
385                 390                 395                 400

Ser Ala Ala Ile Glu Ala Val Asn Cys Gly Ala Gln Val Ile Leu Leu
                405                 410                 415

Glu Lys Glu Ala Lys Ile Gly Gly Asn Ser Ala Lys Ala Thr Ser Gly
            420                 425                 430

Ile Asn Ala Trp Gly Thr Arg Ala Gln Ala Lys Gln Gly Val Met Asp
        435                 440                 445

Gly Gly Lys Phe Phe Glu Arg Asp Thr His Arg Ser Gly Lys Gly Gly
    450                 455                 460

His Cys Asp Pro Cys Leu Val Lys Thr Leu Ser Val Lys Ser Ser Asp
465                 470                 475                 480

Ala Val Lys Trp Leu Ser Glu Leu Gly Val Pro Leu Thr Val Leu Ser
                485                 490                 495

Gln Leu Gly Gly Ala Ser Arg Lys Arg Cys His Arg Ala Pro Asp Lys
            500                 505                 510

Ser Asp Gly Thr Pro Val Pro Ile Gly Phe Thr Ile Met Lys Thr Leu
        515                 520                 525

Glu Asn His Ile Ile Asn Asp Leu Ser His Gln Val Thr Val Met Thr
    530                 535                 540

Gly Ile Lys Val Thr Gly Leu Glu Ser Thr Ser His Ala Arg Pro Asp
545                 550                 555                 560

Gly Val Leu Val Lys His Val Thr Gly Val Arg Leu Ile Gln Gly Asp
                565                 570                 575

Gly Gln Ser Arg Val Leu Asn Ala Asp Ala Val Ile Leu Ala Thr Gly
            580                 585                 590

Gly Phe Ser Asn Asp His Thr Ala Asn Ser Leu Leu Gln Gln Tyr Ala
        595                 600                 605

Pro Gln Leu Ser Ser Phe Pro Thr Thr Asn Gly Val Trp Ala Thr Gly
    610                 615                 620

Asp Gly Val Lys Ala Ala Arg Glu Leu Gly Val Glu Leu Val Asp Met
625                 630                 635                 640

Asp Lys Val Gln Leu His Pro Thr Gly Leu Leu Asp Pro Lys Asp Pro
                645                 650                 655

Ser Asn Arg Thr Lys Tyr Leu Gly Pro Glu Ala Leu Arg Gly Ser Gly
            660                 665                 670

Gly Val Leu Leu Asn Lys Asn Gly Glu Arg Phe Val Asn Glu Leu Asp
        675                 680                 685

Leu Arg Ser Val Val Ser Gln Ala Ile Ile Glu Gln Asn Asn Val Tyr
```

```
    690                 695                 700

Pro Gly Ser Gly Gly Ser Lys Phe Ala Tyr Cys Val Leu Asn Glu Ala
705                 710                 715                 720

Ala Ala Lys Leu Phe Gly Lys Asn Phe Leu Gly Phe Tyr Trp His Arg
                725                 730                 735

Leu Gly Leu Phe Glu Lys Val Glu Asp Val Ala Gly Leu Ala Lys Leu
            740                 745                 750

Ile Gly Cys Pro Glu Glu Asn Val Thr Ala Thr Leu Lys Glu Tyr Lys
        755                 760                 765

Glu Leu Ser Ser Lys Lys Leu His Ala Cys Pro Leu Thr Asn Lys Asn
    770                 775                 780

Val Phe Pro Cys Thr Leu Gly Thr Glu Gly Pro Tyr Tyr Val Ala Phe
785                 790                 795                 800

Val Thr Pro Ser Ile His Tyr Thr Met Gly Gly Cys Leu Ile Ser Pro
                805                 810                 815

Ser Ala Glu Met Gln Thr Ile Asp Asn Thr Gly Val Thr Pro Val Arg
            820                 825                 830

Arg Pro Ile Leu Gly Leu Phe Gly Ala Gly Glu Val Thr Gly Gly Val
        835                 840                 845

His Gly Gly Asn Arg Leu Gly Gly Asn Ser Leu Leu Glu Cys Val Val
    850                 855                 860

Phe Gly Arg Ile Ala Gly Asp Arg Ala Ala Thr Ile Leu Gln Lys Lys
865                 870                 875                 880

Asn Ala Gly Leu Ser Met Thr Glu Trp Ser Thr Val Val Leu Arg Glu
                885                 890                 895

Val Arg Glu Gly Gly Val Tyr Gly Thr Gly Ser Arg Val Leu Arg Phe
            900                 905                 910

Asn Met Pro Gly Ala Leu Gln Lys Thr Gly Leu Ala Leu Gly Gln Phe
        915                 920                 925

Ile Ala Met Arg Gly Asp Trp Asp Gly Gln Gln Leu Leu Gly Tyr Tyr
    930                 935                 940

Ser Pro Ile Thr Leu Pro Asp Asp Ile Gly Val Ile Gly Ile Leu Ala
945                 950                 955                 960

Arg Ala Asp Lys Gly Arg Leu Ala Glu Trp Ile Ser Ala Leu Gln Pro
                965                 970                 975

Gly Asp Ala Val Glu Met Lys Ala Cys Gly Gly Leu Ile Ile His Arg
            980                 985                 990

Arg Phe Ala Ala Arg His Leu Phe  Phe Arg Ser His Lys  Ile Arg Lys
        995                 1000                1005

Leu Ala  Leu Ile Gly Gly Gly  Thr Gly Val Ala Pro  Met Leu Gln
    1010                1015                1020

Ile Val  Arg Ala Ala Val Lys  Lys Pro Phe Val Asp  Ser Ile Glu
    1025                1030                1035

Ser Ile  Gln Phe Ile Tyr Ala  Ala Glu Asp Val Ser  Glu Leu Thr
    1040                1045                1050

Tyr Arg  Thr Leu Leu Glu Ser  Tyr Glu Lys Glu Tyr  Gly Ser Gly
    1055                1060                1065

Lys Phe  Lys Cys His Phe Val  Leu Asn Asn Pro Pro  Ser Gln Trp
    1070                1075                1080

Thr Glu  Gly Val Gly Phe Val  Asp Thr Ala Leu Leu  Arg Ser Ala
    1085                1090                1095

Val Gln  Ala Pro Ser Asn Asp  Leu Leu Val Ala Ile  Cys Gly Pro
    1100                1105                1110
```

Pro Ile Met Gln Arg Ala Val Lys Ser Ala Leu Lys Gly Leu Gly
1115 1120 1125

Tyr Asn Met Asn Leu Val Arg Thr Val Asp Glu Pro Glu Pro Leu
1130 1135 1140

Ser

<210> SEQ ID NO 115
<211> LENGTH: 880
<212> TYPE: PRT
<213> ORGANISM: Mannheimia succiniproducens

<400> SEQUENCE: 115

Met Thr Glu Glu Tyr Leu Met Met Arg Asn Asn Ile Asn Met Leu Gly
1 5 10 15

Arg Phe Leu Gly Glu Thr Ile Gln Glu Ala Gln Gly Asp Asp Ile Leu
20 25 30

Glu Leu Ile Glu Asn Ile Arg Val Leu Ser Arg Asn Ser Arg Ser Gly
35 40 45

Asp Asp Lys Ala Arg Ala Ala Leu Leu Asp Thr Leu Ser Thr Ile Ser
50 55 60

Ala Asp Asn Ile Ile Pro Val Ala Arg Ala Phe Ser Gln Phe Leu Asn
65 70 75 80

Leu Thr Asn Val Ala Glu Gln Tyr Gln Thr Met Ser Arg Ser His Glu
85 90 95

Asp Lys Val Ser Ala Glu Arg Ser Thr Ala Ala Leu Phe Ala Arg Leu
100 105 110

Lys Glu Gln His Val Ser Gln Glu Glu Ile Ile Lys Thr Val Gln Lys
115 120 125

Leu Leu Ile Glu Ile Val Leu Thr Ala His Pro Thr Glu Val Thr Arg
130 135 140

Arg Ser Leu Met His Lys Gln Val Glu Ile Asn Lys Cys Leu Ala Gln
145 150 155 160

Leu Asp His Thr Asp Leu Thr Ala Glu Glu Gln Lys Asn Ile Glu Tyr
165 170 175

Lys Leu Leu Arg Leu Ile Ala Glu Ala Trp His Thr Asn Glu Ile Arg
180 185 190

Thr Asn Arg Pro Thr Pro Leu Glu Glu Ala Lys Trp Gly Phe Ala Val
195 200 205

Ile Glu Asn Ser Leu Trp Glu Gly Leu Pro Ala Phe Ile Arg Lys Leu
210 215 220

Asn Asp Ala Ala Val Glu His Leu Asn Tyr Ala Leu Pro Val Asp Leu
225 230 235 240

Thr Pro Val Arg Phe Ser Ser Trp Met Gly Gly Asp Arg Asp Gly Asn
245 250 255

Pro Phe Val Thr Ala Lys Ile Thr Arg Glu Ala Leu Gln Leu Ala Arg
260 265 270

Trp Lys Ala Ala Asp Leu Phe Leu Thr Asp Ile Gln Glu Leu Cys Asp
275 280 285

Glu Leu Ser Met Thr Gln Cys Thr Ala Glu Phe Arg Glu Lys Tyr Gly
290 295 300

Asp His Leu Glu Pro Tyr Arg Val Val Val Lys Asp Leu Arg Ser Lys
305 310 315 320

Leu Lys Asn Thr Leu Asp Tyr Tyr Asn Asp Ile Leu Ala Gly Arg Ile
325 330 335

```
Pro Pro Phe Lys Gln Asp Glu Ile Ile Ser Glu Asp Gln Gln Leu Trp
            340                 345                 350

Gln Pro Leu Tyr Asp Cys Tyr Gln Ser Leu Thr Ala Cys Gly Met Arg
        355                 360                 365

Ile Ile Ala Asn Gly Leu Leu Leu Asp Thr Leu Arg Arg Val Arg Cys
    370                 375                 380

Phe Gly Val Thr Leu Leu Arg Leu Asp Ile Arg Gln Glu Ser Thr Arg
385                 390                 395                 400

His Ser Asp Ala Ile Gly Glu Ile Thr Arg Tyr Ile Gly Leu Gly Asp
                405                 410                 415

Tyr Ser Gln Trp Thr Glu Asp Asp Lys Gln Ala Phe Leu Ile Arg Glu
            420                 425                 430

Leu Ser Ser Arg Arg Pro Leu Ile Pro His Asn Trp Thr Pro Ser Glu
        435                 440                 445

His Thr Arg Glu Ile Leu Asp Thr Cys Lys Val Ile Ala Lys Gln Pro
    450                 455                 460

Glu Gly Val Ile Ser Cys Tyr Ile Ile Ser Met Ala Arg Thr Ala Ser
465                 470                 475                 480

Asp Val Leu Ala Val His Leu Leu Leu Lys Glu Ala Gly Ile Ser Tyr
                485                 490                 495

His Leu Pro Val Val Pro Leu Phe Glu Thr Leu Asp Asp Leu Asp Ala
            500                 505                 510

Ser Lys Glu Val Met Thr Gln Leu Phe Asn Val Gly Trp Tyr Arg Gly
        515                 520                 525

Val Ile Lys Asn Arg Gln Met Ile Met Ile Gly Tyr Ser Asp Ser Ala
    530                 535                 540

Lys Asp Ala Gly Met Met Ala Ala Ser Trp Ala Gln Tyr Arg Ala Gln
545                 550                 555                 560

Asp Ala Leu Val Lys Leu Cys Glu Gln Thr Gly Ile Glu Leu Thr Leu
                565                 570                 575

Phe His Gly Arg Gly Gly Thr Val Gly Arg Gly Gly Ala Pro Ala His
            580                 585                 590

Ala Ala Leu Leu Ser Gln Pro Pro Arg Ser Leu Lys Asn Gly Leu Arg
        595                 600                 605

Val Thr Glu Gln Gly Glu Met Ile Arg Phe Lys Leu Gly Leu Pro Ala
    610                 615                 620

Ile Ala Ala Glu Ser Leu Asp Leu Tyr Ala Ser Ala Ile Leu Glu Ala
625                 630                 635                 640

Asn Leu Leu Pro Pro Pro Glu Pro Lys Ala Ser Trp Cys Arg Val Met
                645                 650                 655

Asp Glu Leu Ala Val Ala Ser Cys Glu Ile Tyr Arg Asn Val Val Arg
            660                 665                 670

Gly Asp Lys Asp Phe Val Pro Tyr Phe Arg Ser Ala Thr Pro Glu Gln
        675                 680                 685

Glu Leu Ala Lys Leu Pro Leu Gly Ser Arg Pro Ala Lys Arg Asn Pro
    690                 695                 700

Asn Gly Gly Val Glu Ser Leu Arg Ala Ile Pro Trp Ile Phe Ala Trp
705                 710                 715                 720

Met Gln Asn Arg Leu Met Leu Pro Ala Trp Leu Gly Ala Gly Ala Ser
                725                 730                 735

Ile Arg Gln Ala Met Glu Ser Gly Lys Ala Ala Val Ile Glu Glu Met
            740                 745                 750
```

```
Cys Asn His Trp Pro Phe Phe Asn Thr Arg Ile Gly Met Leu Glu Met
        755                 760                 765

Val Phe Ser Lys Thr Asp Ser Trp Leu Ser Glu Tyr Tyr Asp Gln Arg
    770                 775                 780

Leu Val Lys Lys Glu Leu Trp Tyr Leu Gly Glu Ser Leu Arg Lys Gln
785                 790                 795                 800

Leu Ser Glu Asp Ile Ala Thr Val Leu Arg Leu Ser Gly Lys Gly Asp
                805                 810                 815

Gln Leu Met Ser Asp Leu Pro Trp Val Ala Glu Ser Ile Ala Leu Arg
            820                 825                 830

Asn Val Tyr Thr Asp Pro Leu Asn Leu Leu Gln Val Glu Leu Leu Arg
        835                 840                 845

Arg Leu Arg Ala Asp Pro Glu His Pro Asn Pro Asp Ile Glu Gln Ala
    850                 855                 860

Leu Met Ile Thr Ile Thr Gly Ile Ala Ala Gly Met Arg Asn Thr Gly
865                 870                 875                 880


<210> SEQ ID NO 116
<211> LENGTH: 4171
<212> TYPE: DNA
<213> ORGANISM: Artificial
<220> FEATURE:
<223> OTHER INFORMATION: I. orientalis FUM gene integration fragment

<400> SEQUENCE: 116

aattctttga aggagcttgc caagaaacat aattttatga tttttgaaga tagaaaattt      60

gctgatattg gtaacactgt taaaaatcaa tataaatctg gtgtcttccg tattgccgaa     120

tgggctgaca tcactaatgc acatggtgta acgggtgcag gtattgtttc tggcttgaag     180

gaggcagccc aagaaacaac cagtgaacct agaggtttgc taatgcttgc tgagttatca     240

tcaaagggtt ctttagcata tggtgaatat acagaaaaaa cagtagaaat tgctaaatct     300

gataaagagt ttgtcattgg ttttattgcg caacacgata tgggcggtag agaagaaggt     360

tttgactgga tcattatgac tccaggggtt ggtttagatg acaaaggtga tgcacttggt     420

caacaatata gaactgttga tgaagttgta aagactggaa cggatatcat aattgttggt     480

agaggtttgt acggtcaagg aagagatcct atagagcaag ctaaaagata ccaacaagct     540

ggttggaatg cttatttaaa cagatttaaa tgattcttac acaaagattt gatacatgta     600

cactagttta aataagcatg aaaagaatta cacaagcaaa aaaaaaaaaa taaatgaggt     660

actttacgtt cacctacaac caaaaaaact agatagagta aaatcttaag atttagaaaa     720

agttgtttaa caaaggcttt agtatgtgaa tttttaatgt agcaaagcga taactaataa     780

acataaacaa aagtatggtt ttctttatca gtcaaatcat tatcgattga ttgttccgcg     840

tatctgcaga tagcctcatg aaatcagcca tttgcttttg ttcaacgatc ttttgaaatt     900

gttgttgttc ttggtagtta agttgatcca tcttggctta tgttgtgtgt atgttgtagt     960

tattcttagt atattcctgt cctgagttta gtgaaacata atatcgcctt gaaatgaaaa    1020

tgctgaaatt cgtcgacata caatttttca aactttttttt ttttcttggt gcacggacat    1080

gtttttaaag gaagtactct ataccagtta ttcttcacaa atttaattgc tggagaatag    1140

atcttcaacg cgtttcctcg acatttgctg caacggcaac atcaatgtcc acgtttacac    1200

acctacattt atatctatat ttatatttat atttatttat ttatgctact tagcttctat    1260

agttagttaa tgcactcacg atattcaaaa ttgacaccct tcaactactc cctactattg    1320

tctactactg tctactactc ctctttacta tagctgctcc caataggctc caccaatagg    1380
```

```
ctctgtcaat acattttgcg ccgccacctt tcaggttgtg tcactcctga aggaccatat   1440
tgggtaatcg tgcaatttct ggaagagagt ccgcgagaag tgaggccccc actgtaaatc   1500
ctcgaggggg catggagtat ggggcatgga ggatggagga tggggggggg ggggggggaaa  1560
ataggtagcg aaaggacccg ctatcacccc acccggagaa ctcgttgccg ggaagtcata   1620
tttcgacact ccggggagtc tataaaaggc gggttttgtc ttttgccagt tgatgttgct   1680
gagaggactt gtttgccgtt tcttccgatt taacagtata gaatcaacca ctgttaatta   1740
tacacgttat actaacacaa caaaaacaaa aacaacgaca acaacaacaa catctagata   1800
aaatgttagc tgctagatca ttaaaggcaa gaatgtcaac aagagctttc tcaactacct   1860
caattgcaaa aagaatcgaa aaagatgcat ttggtgacat tgaagtccca aatgagaaat   1920
attggggtgc tcaaactcaa agatctttac aaaatttcaa aattggtggt aagagagaag   1980
ttatgccaga accaatcatc aaatcttttg gtattttaaa gaaggctact gctaagatca   2040
atgctgagtc tggtgcttta gacccaaagt tatctgaagc catccaacaa gctgcaaccg   2100
aagtttatga aggtaaacta atggaccatt tcccattagt tgtctttcaa accggttctg   2160
gtactcaatc taacatgaat gccaatgaag tcatctctaa tagagcaatt gaaatcttgg   2220
gtggtgaatt aggctctaaa actccagtcc atcctaatga tcatgttaat atgtcccaat   2280
cttctaatga tactttccct actgtcatgc atattgcagc agttacagaa gtttcatccc   2340
atttattacc agaattaact gcactaagag atgcattgca aaagaaatcc gatgaattta   2400
agaatattat caaaatcggt agaacccatt tacaagatgc aactcccttta actttaggtc  2460
aagaattttc tggttatgtt caacaatgta ctaatggtat caaaagaatc gaaattgctc   2520
ttgaacattt gagatactta gctcaaggtg gtactgccgt tggtactggt cttaacacca   2580
agaaaggttt tgctgaaaag gttgcaaatg aagtcactaa attgactggt ttacaattct   2640
ataccgctcc aaataaattc gaagcccttg cagctcacga tgctgttgtt gaaatgtctg   2700
gtgctttgaa taccgttgca gtctcattat tcaaaatcgc tcaagatatc agatatttgg   2760
gttccggccc aagatgtggt tatggtgaat tggctttacc agaaaatgaa ccaggttctt   2820
ccatcatgcc gggtaaagtt aacccaactc aaaacgaagc tttgactatg ctttgtaccc   2880
aagtctttgg taaccactct tgtattacct ttgcaggtgc ttcaggtcaa ttcgaattga   2940
atgtctttaa gccagttatg atctccaact tgttatcttc tattaggtta ttaggtgatg   3000
gttgtaattc ttttagaatc cactgtgttg aaggtatcat tgcaaatacc gacaagattg   3060
ataaattact acatgaatct ctcatgttag ttactgcttt gaacccacac attggttacg   3120
ataaggcttc caagattgca aagaatgcac acaagaaggg cttgacattg aaacaatctg   3180
cattggaatt aggttacttg accgaagaac aattcaatga atgggttaga ccagaaaaca   3240
tgattggtcc aaaggattaa gttaattaac atctgaatgt aaaatgaaca ttaaaatgaa   3300
ttactaaact ttacgtctac tttacaatct ataaactttg tttaatcata taacgaaata   3360
cactaataca caatcctgta cgtatgtaat acttttatcc atcaaggatt gagaaaaaaa   3420
agtaatgatt ccctgggcca ttaaaactta gacccccaag cttggatagg tcactctcta   3480
ttttcgtttc tcccttccct gatagaaggg tgatatgtaa ttaagaataa tatataattt   3540
tataataaaa gcggccgcac caggggttta gtgaagtcac caattaagat tgttggtttg   3600
agtgagttgc caaagatcta tgaattgatg gagcaaggta agattttagg cagatatgtt   3660
gttgacactt cgaaatgatg ggctgacttg ggtgtactgg tgtgacgttt ttatgtgtat   3720
```

```
attgatatgc atgggggatg tatagtgatg aggagtagag tatataacga aatgaaatga   3780

aataatatga tatgataaga taagatgaga tcaatacgat aatataagat gcgacatgag   3840

gagttcaatg tagcatacta cacgatgctg cagtacaact ctgatacgct agactatact   3900

atacaaaact gtagtacact atacgttagt gtagtatcca gaaacaacac tgctttatag   3960

tacaatacaa ctctataata ctatagtata ctatgccaaa ccacgtaata ccataatatg   4020

ctccacgaca tggtacaatg tgctatactt catactatta taccatatat actccgatat   4080

attattgata tactatttta tactataata ccataccaca caacactaca ttacaacgag   4140

caaccttacc ataaatgtca gttatggccg c                                  4171


<210> SEQ ID NO 117
<211> LENGTH: 466
<212> TYPE: PRT
<213> ORGANISM: Escherichia coli

<400> SEQUENCE: 117

Met Pro His Ser Tyr Asp Tyr Asp Ala Ile Val Ile Gly Ser Gly Pro
1               5                   10                  15

Gly Gly Glu Gly Ala Ala Met Gly Leu Val Lys Gln Gly Ala Arg Val
            20                  25                  30

Ala Val Ile Glu Arg Tyr Gln Asn Val Gly Gly Gly Cys Thr His Trp
        35                  40                  45

Gly Thr Ile Pro Ser Lys Ala Leu Arg His Ala Val Ser Arg Ile Ile
    50                  55                  60

Glu Phe Asn Gln Asn Pro Leu Tyr Ser Asp His Ser Arg Leu Leu Arg
65                  70                  75                  80

Ser Ser Phe Ala Asp Ile Leu Asn His Ala Asp Asn Val Ile Asn Gln
                85                  90                  95

Gln Thr Arg Met Arg Gln Gly Phe Tyr Glu Arg Asn His Cys Glu Ile
            100                 105                 110

Leu Gln Gly Asn Ala Arg Phe Val Asp Glu His Thr Leu Ala Leu Asp
        115                 120                 125

Cys Pro Asp Gly Ser Val Glu Thr Leu Thr Ala Glu Lys Phe Val Ile
    130                 135                 140

Ala Cys Gly Ser Arg Pro Tyr His Pro Thr Asp Val Asp Phe Thr His
145                 150                 155                 160

Pro Arg Ile Tyr Asp Ser Asp Ser Ile Leu Ser Met His His Glu Pro
                165                 170                 175

Arg His Val Leu Ile Tyr Gly Ala Gly Val Ile Gly Cys Glu Tyr Ala
            180                 185                 190

Ser Ile Phe Arg Gly Met Asp Val Lys Val Asp Leu Ile Asn Thr Arg
        195                 200                 205

Asp Arg Leu Leu Ala Phe Leu Asp Gln Glu Met Ser Asp Ser Leu Ser
    210                 215                 220

Tyr His Phe Trp Asn Ser Gly Val Val Ile Arg His Asn Glu Glu Tyr
225                 230                 235                 240

Glu Lys Ile Glu Gly Cys Asp Asp Gly Val Ile Met His Leu Lys Ser
                245                 250                 255

Gly Lys Lys Leu Lys Ala Asp Cys Leu Leu Tyr Ala Asn Gly Arg Thr
            260                 265                 270

Gly Asn Thr Asp Ser Leu Ala Leu Gln Asn Ile Gly Leu Glu Thr Asp
        275                 280                 285

Ser Arg Gly Gln Leu Lys Val Asn Ser Met Tyr Gln Thr Ala Gln Pro
```

```
    290                 295                 300

His Val Tyr Ala Val Gly Asp Val Ile Gly Tyr Pro Ser Leu Ala Ser
305                 310                 315                 320

Ala Ala Tyr Asp Gln Gly Arg Ile Ala Ala Gln Ala Leu Val Lys Gly
                325                 330                 335

Glu Ala Thr Ala His Leu Ile Glu Asp Ile Pro Thr Gly Ile Tyr Thr
            340                 345                 350

Ile Pro Glu Ile Ser Ser Val Gly Lys Thr Glu Gln Gln Leu Thr Ala
        355                 360                 365

Met Lys Val Pro Tyr Glu Val Gly Arg Ala Gln Phe Lys His Leu Ala
    370                 375                 380

Arg Ala Gln Ile Val Gly Met Asn Val Gly Thr Leu Lys Ile Leu Phe
385                 390                 395                 400

His Arg Glu Thr Lys Glu Ile Leu Gly Ile His Cys Phe Gly Glu Arg
                405                 410                 415

Ala Ala Glu Ile Ile His Ile Gly Gln Ala Ile Met Glu Gln Lys Gly
            420                 425                 430

Gly Gly Asn Thr Ile Glu Tyr Phe Val Asn Thr Thr Phe Asn Tyr Pro
        435                 440                 445

Thr Met Ala Glu Ala Tyr Arg Val Ala Ala Leu Asn Gly Leu Asn Arg
    450                 455                 460

Leu Phe
465


<210> SEQ ID NO 118
<211> LENGTH: 466
<212> TYPE: PRT
<213> ORGANISM: Artificial
<220> FEATURE:
<223> OTHER INFORMATION: Codon optimized E. coli Stha enzyme

<400> SEQUENCE: 118

Met Pro His Ser Tyr Asp Tyr Asp Ala Ile Val Ile Gly Ser Gly Pro
1               5                   10                  15

Gly Gly Glu Gly Ala Ala Met Gly Leu Val Lys Gln Gly Ala Arg Val
            20                  25                  30

Ala Val Ile Glu Arg Tyr Gln Asn Val Gly Gly Gly Cys Thr His Trp
        35                  40                  45

Gly Thr Ile Pro Ser Lys Ala Leu Arg His Ala Val Ser Arg Ile Ile
    50                  55                  60

Glu Phe Asn Gln Asn Pro Leu Tyr Ser Asp His Ser Arg Leu Leu Arg
65                  70                  75                  80

Ser Ser Phe Ala Asp Ile Leu Asn His Ala Asp Asn Val Ile Asn Gln
                85                  90                  95

Gln Thr Arg Met Arg Gln Gly Phe Tyr Glu Arg Asn His Cys Glu Ile
            100                 105                 110

Leu Gln Gly Asn Ala Arg Phe Val Asp Glu His Thr Leu Ala Leu Asp
        115                 120                 125

Cys Pro Asp Gly Ser Val Glu Thr Leu Thr Ala Glu Lys Phe Val Ile
    130                 135                 140

Ala Cys Gly Ser Arg Pro Tyr His Pro Thr Asp Val Asp Phe Thr His
145                 150                 155                 160

Pro Arg Ile Tyr Asp Ser Asp Ser Ile Leu Ser Met His His Glu Pro
                165                 170                 175

Arg His Val Leu Ile Tyr Gly Ala Gly Val Ile Gly Cys Glu Tyr Ala
```

```
            180                 185                 190

Ser Ile Phe Arg Gly Met Asp Val Lys Val Asp Leu Ile Asn Thr Arg
        195                 200                 205

Asp Arg Leu Leu Ala Phe Leu Asp Gln Glu Met Ser Asp Ser Leu Ser
    210                 215                 220

Tyr His Phe Trp Asn Ser Gly Val Val Ile Arg His Asn Glu Glu Tyr
225                 230                 235                 240

Glu Lys Ile Glu Gly Cys Asp Asp Gly Val Ile Met His Leu Lys Ser
                245                 250                 255

Gly Lys Lys Leu Lys Ala Asp Cys Leu Leu Tyr Ala Asn Gly Arg Thr
            260                 265                 270

Gly Asn Thr Asp Ser Leu Ala Leu Gln Asn Ile Gly Leu Glu Thr Asp
        275                 280                 285

Ser Arg Gly Gln Leu Lys Val Asn Ser Met Tyr Gln Thr Ala Gln Pro
    290                 295                 300

His Val Tyr Ala Val Gly Asp Val Ile Gly Tyr Pro Ser Leu Ala Ser
305                 310                 315                 320

Ala Ala Tyr Asp Gln Gly Arg Ile Ala Ala Gln Ala Leu Val Lys Gly
                325                 330                 335

Glu Ala Thr Ala His Leu Ile Glu Asp Ile Pro Thr Gly Ile Tyr Thr
            340                 345                 350

Ile Pro Glu Ile Ser Ser Val Gly Lys Thr Glu Gln Gln Leu Thr Ala
        355                 360                 365

Met Lys Val Pro Tyr Glu Val Gly Arg Ala Gln Phe Lys His Leu Ala
    370                 375                 380

Arg Ala Gln Ile Val Gly Met Asn Val Gly Thr Leu Lys Ile Leu Phe
385                 390                 395                 400

His Arg Glu Thr Lys Glu Ile Leu Gly Ile His Cys Phe Gly Glu Arg
                405                 410                 415

Ala Ala Glu Ile Ile His Ile Gly Gln Ala Ile Met Glu Gln Lys Gly
            420                 425                 430

Gly Gly Asn Thr Ile Glu Tyr Phe Val Asn Thr Thr Phe Asn Tyr Pro
        435                 440                 445

Thr Met Ala Glu Ala Tyr Arg Val Ala Ala Leu Asn Gly Leu Asn Arg
    450                 455                 460

Leu Phe
465
```

<210> SEQ ID NO 119
<211> LENGTH: 464
<212> TYPE: PRT
<213> ORGANISM: Azotobacter vinelandii

<400> SEQUENCE: 119

```
Met Ala Val Tyr Asn Tyr Asp Val Val Val Ile Gly Thr Gly Pro Ala
1               5                   10                  15

Gly Glu Gly Ala Ala Met Asn Ala Val Lys Ala Gly Arg Lys Val Ala
            20                  25                  30

Val Val Asp Asp Arg Pro Gln Val Gly Gly Asn Cys Thr His Leu Gly
        35                  40                  45

Thr Ile Pro Ser Lys Ala Leu Arg His Ser Val Arg Gln Ile Met Gln
    50                  55                  60

Tyr Asn Asn Asn Pro Leu Phe Arg Gln Ile Gly Glu Pro Arg Trp Phe
65                  70                  75                  80
```

```
Ser Phe Ala Asp Val Leu Lys Ser Ala Glu Gln Val Ile Ala Lys Gln
                85                  90                  95

Val Ser Ser Arg Thr Gly Tyr Tyr Ala Arg Asn Arg Ile Asp Thr Phe
            100                 105                 110

Phe Gly Thr Ala Ser Phe Cys Asp Glu His Thr Ile Glu Val Val His
        115                 120                 125

Leu Asn Gly Met Val Glu Thr Leu Val Ala Lys Gln Phe Val Ile Ala
    130                 135                 140

Thr Gly Ser Arg Pro Tyr Arg Pro Ala Asp Val Asp Phe Thr His Pro
145                 150                 155                 160

Arg Ile Tyr Asp Ser Asp Thr Ile Leu Ser Leu Gly His Thr Pro Arg
                165                 170                 175

Arg Leu Ile Ile Tyr Gly Ala Gly Val Ile Gly Cys Glu Tyr Ala Ser
            180                 185                 190

Ile Phe Ser Gly Leu Gly Val Leu Val Asp Leu Ile Asp Asn Arg Asp
        195                 200                 205

Gln Leu Leu Ser Phe Leu Asp Asp Glu Ile Ser Asp Ser Leu Ser Tyr
    210                 215                 220

His Leu Arg Asn Asn Asn Val Leu Ile Arg His Asn Glu Glu Tyr Glu
225                 230                 235                 240

Arg Val Glu Gly Leu Asp Asn Gly Val Ile Leu His Leu Lys Ser Gly
                245                 250                 255

Lys Lys Ile Lys Ala Asp Ala Phe Leu Trp Ser Asn Gly Arg Thr Gly
            260                 265                 270

Asn Thr Asp Lys Leu Gly Leu Glu Asn Ile Gly Leu Lys Ala Asn Gly
        275                 280                 285

Arg Gly Gln Ile Gln Val Asp Glu His Tyr Arg Thr Glu Val Ser Asn
    290                 295                 300

Ile Tyr Ala Ala Gly Asp Val Ile Gly Trp Pro Ser Leu Ala Ser Ala
305                 310                 315                 320

Ala Tyr Asp Gln Gly Arg Ser Ala Ala Gly Ser Ile Thr Glu Asn Asp
                325                 330                 335

Ser Trp Arg Phe Val Asp Asp Val Pro Thr Gly Ile Tyr Thr Ile Pro
            340                 345                 350

Glu Ile Ser Ser Val Gly Lys Thr Glu Arg Glu Leu Thr Gln Ala Lys
        355                 360                 365

Val Pro Tyr Glu Val Gly Lys Ala Phe Phe Lys Gly Met Ala Arg Ala
    370                 375                 380

Gln Ile Ala Val Glu Lys Ala Gly Met Leu Lys Ile Leu Phe His Arg
385                 390                 395                 400

Glu Thr Leu Glu Ile Leu Gly Val His Cys Phe Gly Tyr Gln Ala Ser
                405                 410                 415

Glu Ile Val His Ile Gly Gln Ala Ile Met Asn Gln Lys Gly Glu Ala
            420                 425                 430

Asn Thr Leu Lys Tyr Phe Ile Asn Thr Thr Phe Asn Tyr Pro Thr Met
        435                 440                 445

Ala Glu Ala Tyr Arg Val Ala Ala Tyr Asp Gly Leu Asn Arg Leu Phe
    450                 455                 460
```

<210> SEQ ID NO 120
<211> LENGTH: 20
<212> TYPE: DNA
<213> ORGANISM: Artificial
<220> FEATURE:
<223> OTHER INFORMATION: Primer

<400> SEQUENCE: 120
cacagaggtg cagtaacgag 20

<210> SEQ ID NO 121
<211> LENGTH: 506
<212> TYPE: PRT
<213> ORGANISM: Issatchenkia orientalis

<400> SEQUENCE: 121

```
Met Gly Val Gln Phe Ile Glu Asn Thr Ile Ile Val Val Phe Gly Ala
1               5                   10                  15

Ser Gly Asp Leu Ala Lys Lys Lys Thr Phe Pro Ala Leu Phe Gly Leu
            20                  25                  30

Phe Arg Glu Gly Gln Leu Ser Glu Thr Thr Lys Ile Ile Gly Phe Ala
        35                  40                  45

Arg Ser Lys Leu Ser Asn Asp Asp Leu Arg Asn Arg Ile Lys Pro Tyr
    50                  55                  60

Leu Lys Leu Asn Lys Arg Thr Asp Ala Glu Arg Gln Ser Leu Glu Lys
65                  70                  75                  80

Phe Leu Gln Ile Leu Glu Tyr His Gln Ser Asn Tyr Asp Asp Ser Glu
                85                  90                  95

Gly Phe Glu Lys Leu Glu Lys Leu Ile Asn Lys Tyr Asp Asp Glu Ala
            100                 105                 110

Asn Val Lys Glu Ser His Arg Leu Tyr Tyr Leu Ala Leu Pro Pro Ser
        115                 120                 125

Val Phe Thr Thr Val Ala Thr Met Leu Lys Lys His Cys His Pro Gly
    130                 135                 140

Asp Ser Gly Ile Ala Arg Leu Ile Val Glu Lys Pro Phe Gly His Asp
145                 150                 155                 160

Leu Ser Ser Ser Arg Glu Leu Gln Lys Ser Leu Ala Pro Leu Trp Asn
                165                 170                 175

Glu Asp Glu Leu Phe Arg Ile Asp His Tyr Leu Gly Lys Glu Met Val
            180                 185                 190

Lys Asn Leu Ile Pro Leu Arg Phe Ser Asn Thr Phe Leu Ser Ser Ser
        195                 200                 205

Trp Asn Asn Gln Phe Ile Asp Thr Ile Gln Ile Thr Phe Lys Glu Asn
    210                 215                 220

Phe Gly Thr Glu Gly Arg Gly Gly Tyr Phe Asp Ser Ile Gly Ile Ile
225                 230                 235                 240

Arg Asp Val Ile Gln Asn His Leu Leu Gln Val Leu Thr Ile Val Leu
                245                 250                 255

Met Glu Lys Pro Ala Asp Phe Asn Gly Glu Ser Ile Arg Asp Glu Lys
            260                 265                 270

Val Lys Val Leu Lys Ala Ile Glu Gln Ile Asp Phe Asn Asn Val Leu
        275                 280                 285

Val Gly Gln Tyr Asp Lys Ser Glu Asp Gly Ser Lys Pro Gly Tyr Leu
    290                 295                 300

Asp Asp Asp Thr Val Asn Pro Asp Ser Lys Ala Val Thr Tyr Ala Ala
305                 310                 315                 320

Leu Val Leu Asn Val Ala Asn Glu Arg Trp Asn Asn Val Pro Ile Ile
                325                 330                 335

Leu Lys Ala Gly Lys Ala Leu Asn Gln Ser Lys Val Glu Ile Arg Ile
            340                 345                 350
```

```
Gln Phe Lys Pro Val Glu Asn Gly Ile Phe Lys Asn Ser Ala Arg Asn
        355                 360                 365

Glu Leu Val Ile Arg Ile Gln Pro Asn Glu Ala Met Tyr Leu Lys Met
    370                 375                 380

Asn Ile Lys Val Pro Gly Val Ser Asn Gln Val Ser Ile Ser Glu Met
385                 390                 395                 400

Asp Leu Thr Tyr Lys Asn Arg Tyr Ser Ser Glu Phe Tyr Ile Pro Glu
                405                 410                 415

Ala Tyr Glu Ser Leu Ile Lys Asp Ala Leu Met Asp Asp His Ser Asn
            420                 425                 430

Phe Val Arg Asp Asp Glu Leu Asp Ile Ser Trp Ala Leu Phe Thr Pro
        435                 440                 445

Leu Leu Glu His Ile Glu Gly Pro Asp Gly Pro Thr Pro Thr Lys Tyr
    450                 455                 460

Pro Tyr Gly Ser Arg Gly Pro Lys Glu Ile Asp Glu Phe Leu Arg Asn
465                 470                 475                 480

His Gly Tyr Val Lys Glu Pro Arg Glu Asn Tyr Gln Trp Pro Leu Thr
                485                 490                 495

Thr Pro Lys Glu Leu Asn Ser Ser Lys Phe
            500                 505
```

<210> SEQ ID NO 122
<211> LENGTH: 27
<212> TYPE: DNA
<213> ORGANISM: Artificial
<220> FEATURE:
<223> OTHER INFORMATION: Primer

<400> SEQUENCE: 122

```
gctggagaat agatcttcaa cgccccg                                          27
```

<210> SEQ ID NO 123
<211> LENGTH: 27
<212> TYPE: DNA
<213> ORGANISM: Artificial
<220> FEATURE:
<223> OTHER INFORMATION: Primer

<400> SEQUENCE: 123

```
catcactgtt aaaggaatgg gtaaatc                                          27
```

<210> SEQ ID NO 124
<211> LENGTH: 41
<212> TYPE: DNA
<213> ORGANISM: Artificial
<220> FEATURE:
<223> OTHER INFORMATION: Primer

<400> SEQUENCE: 124

```
gtaagctggc aaacctgcag gttagccggt attacgcata c                          41
```

<210> SEQ ID NO 125
<211> LENGTH: 4321
<212> TYPE: DNA
<213> ORGANISM: Artificial
<220> FEATURE:
<223> OTHER INFORMATION: I. orientalis FUM integration fragment

<400> SEQUENCE: 125

```
ttgaaggagc ttgccaagaa acataatttt atgatttttg aagatagaaa atttgctgat      60

attggtaaca ctgttaaaaa tcaatataaa tctggtgtct tccgtattgc cgaatgggct     120
```

```
gacatcacta atgcacatgg tgtaacgggt gcaggtattg tttctggctt gaaggaggca    180
gcccaagaaa caaccagtga acctagaggt ttgctaatgc ttgctgagtt atcatcaaag    240
ggttctttag catatggtga atatacagaa aaaacagtag aaattgctaa atctgataaa    300
gagtttgtca ttggttttat tgcgcaacac gatatgggcg gtagagaaga aggttttgac    360
tggatcatta tgactccagg ggttggttta gatgacaaag gtgatgcact tggtcaacaa    420
tatagaactg ttgatgaagt tgtaaagact ggaacggata tcataattgt tggtagaggt    480
ttgtacggtc aaggaagaga tcctatagag caagctaaaa gataccaaca agctggttgg    540
aatgcttatt taaacagatt taaatgattc ttacacaaag atttgataca tgtacactag    600
tttaaataag catgaaaaga attacacaag caaaaaaaaa aaaataaatg aggtacttta    660
cgttcaccta caaccaaaaa aactagatag agtaaaatct taagatttag aaaaagttgt    720
ttaacaaagg ctttagtatg tgaattttta atgtagcaaa gcgataacta ataaacataa    780
acaaaagtat ggttttcttt atcagtcaaa tcattatcga ttgattgttc cgcgtatctg    840
cagatagcct catgaaatca gccatttgct tttgttcaac gatcttttga aattgttgtt    900
gttcttggta gttaagttga tccatcttgg cttatgttgt gtgtatgttg tagttattct    960
tagtatattc ctgtcctgag tttagtgaaa cataaatatcg ccttgaaatg aaaatgctga  1020
aattcgtcga catacaattt ttcaaacttt tttttttct tggtgcacgg acatgttttt    1080
aaaggaagta ctctatacca gttattcttc acaaatttaa ttgctggaga atagatcttc   1140
aacgcgtttc ctcgacattt gctgcaacgg caacatcaat gtccacgttt acacacctac   1200
atttatatct atatttatat ttatatttat ttatttatgc tacttagctt ctatagttag   1260
ttaatgcact cacgatattc aaaattgaca cccttcaact actccctact attgtctact   1320
actgtctact actcctcttt actatagctg ctcccaatag gctccaccaa taggctctgt   1380
caatacattt tgcgccgcca cctttcaggt tgtgtcactc ctgaaggacc atattgggta   1440
atcgtgcaat ttctggaaga gagtccgcga gaagtgaggc ccccactgta aatcctcgag   1500
ggggcatgga gtatggggca tggaggatgg aggatggggg gggggggggg gaaaataggt   1560
agcgaaagga cccgctatca ccccacccgg agaactcgtt gccgggaagt catatttcga   1620
cactccgggg agtctataaa aggcgggttt tgtcttttgc cagttgatgt tgctgagagg   1680
acttgtttgc cgtttcttcc gatttaacag tatagaatca accactgtta attatacacg   1740
ttatactaac acaacaaaaa caaaaacaac gacaacaaca acaacatcta gataaaatgt   1800
tagctgctag atcattaaag gcaagaatgt caacaagagc tttctcaact acctcaattg   1860
caaaaagaat cgaaaaagat gcatttggtg acattgaagt cccaaatgag aaatattggg   1920
gtgctcaaac tcaaagatct ttacaaaatt tcaaaattgg tggtaagaga gaagttatgc   1980
cagaaccaat catcaaatct tttggtattt taaagaaggc tactgctaag atcaatgctg   2040
agtctggtgc tttagaccca aagttatctg aagccatcca acaagctgca accgaagttt   2100
atgaaggtaa actaatggac catttcccat tagttgtctt tcaaaccggt tctggtactc   2160
aatctaacat gaatgccaat gaagtcatct ctaatagagc aattgaaatc ttgggtggtg   2220
aattaggctc taaaactcca gtccatccta atgatcatgt taatatgtcc caatcttcta   2280
atgatacttt ccctactgtc atgcatattg cagcagttac agaagtttca tcccatttat   2340
taccagaatt aactgcacta agagatgcat tgcaaaagaa atccgatgaa tttaagaata   2400
ttatcaaaat cggtagaacc catttacaag atgcaactcc tttaacttta ggtcaagaat   2460
```

```
tttctggtta tgttcaacaa tgtactaatg gtatcaaaag aatcgaaatt gctcttgaac   2520

atttgagata cttagctcaa ggtggtactg ccgttggtac tggtcttaac accaagaaag   2580

gttttgctga aaaggttgca aatgaagtca ctaaattgac tggtttacaa ttctataccg   2640

ctccaaataa attcgaagcc cttgcagctc acgatgctgt tgttgaaatg tctggtgctt   2700

tgaataccgt tgcagtctca ttattcaaaa tcgctcaaga tatcagatat ttgggttccg   2760

gcccaagatg tggttatggt gaattggctt taccagaaaa tgaaccaggt tcttccatca   2820

tgccgggtaa agttaaccca actcaaaacg aagctttgac tatgctttgt acccaagtct   2880

ttggtaacca ctcttgtatt acctttgcag gtgcttcagg tcaattcgaa ttgaatgtct   2940

ttaagccagt tatgatctcc aacttgttat cttctattag gttattaggt gatggttgta   3000

attcttttag aatccactgt gttgaaggta tcattgcaaa taccgacaag attgataaat   3060

tactacatga atctctcatg ttagttactg ctttgaaccc acacattggt tacgataagg   3120

cttccaagat tgcaaagaat gcacacaaga agggcttgac attgaaacaa tctgcattgg   3180

aattaggtta cttgaccgaa gaacaattca atgaatgggt tagaccagaa aacatgattg   3240

gtccaaagga ttaagttaat taacatctga atgtaaaatg aacattaaaa tgaattacta   3300

aactttacgt ctactttaca atctataaac tttgtttaat catataacga aatacactaa   3360

tacacaatcc tgtacgtatg taatactttt atccatcaag gattgagaaa aaaaagtaat   3420

gattccctgg gccattaaaa cttagacccc caagcttgga taggtcactc tctattttcg   3480

tttctccctt ccctgataga agggtgatat gtaattaaga ataatatata attttataat   3540

aaaagcggcc gcctcccttc tctaaatgga ctgcttggat aacttggacc cccttcccat   3600

tttatagtca ttctcttccc cctcattttc ccactattcc caacaatgac catctctcca   3660

ccttgtttcc ccattcttcc tgctctacct ggtgggggtg tttcacccca ttaacggtcg   3720

gattccgctg tggagatggc tctggccttt ttcccattcc ttcccccccct caatcttctc   3780

catgcgggga aaaaaaaatt ttatccataa acaaccaaac cggcggctca acggggggtt   3840

tatactgaca gaaatggggt caatacaccc actgactgta cccgctctaa tcttaagctt   3900

tcccccccccc ctcctgtatt aacggcgcgg agtgcccgca gcgcccaatg gagaaggcgc   3960

gcagtggggg atgcccaggg aggggacagg tacacgcaca ggccatgcca acaccgcata   4020

gacgtgcgac ctcctctccc ccactgcaga gctgcccttt tcggacacac tccgtgcaag   4080

aggactcggc cggctcggct tttctgccga attcggcagc cctgatattg tcttacgtaa   4140

tacgaatgga gggggtgtct cattttccct gcgatttccc aattgggtag caatgtgcac   4200

acactgaaac agtgcagagt attggtgatt tgctaatgta tggtaatgta taatactttt   4260

ttagagtgta gtgcattgca gacagtatag tatccacttc tgggaatccc atcgaaacgg   4320

c                                                                   4321
```

<210> SEQ ID NO 126
<211> LENGTH: 34
<212> TYPE: DNA
<213> ORGANISM: Artificial
<220> FEATURE:
<223> OTHER INFORMATION: Primer

<400> SEQUENCE: 126

```
gatcgagctc caccttattt atgggagtta tttc                                 34
```

<210> SEQ ID NO 127
<211> LENGTH: 47

<212> TYPE: DNA
<213> ORGANISM: Artificial
<220> FEATURE:
<223> OTHER INFORMATION: Primer

<400> SEQUENCE: 127
ggataaaagt attacatacg tacaggattg tgtattagtg tatttcg 47

<210> SEQ ID NO 128
<211> LENGTH: 328
<212> TYPE: PRT
<213> ORGANISM: Rhizopus delemar

<400> SEQUENCE: 128

```
Met Val Lys Val Thr Val Cys Gly Ala Ala Gly Gly Ile Gly Gln Pro
1               5                   10                  15

Leu Ser Leu Leu Leu Lys Gln Ser Ser His Ile Thr His Leu Ser Leu
            20                  25                  30

Tyr Asp Ile Val Asn Thr Pro Gly Val Ala Ala Asp Leu Ser His Ile
        35                  40                  45

Asp Thr Lys Ser Lys Val Thr Gly His Val Gly Ala Ala Gln Leu Glu
    50                  55                  60

Glu Ala Ile Lys Asp Ser Asp Val Val Val Ile Pro Ala Gly Val Pro
65                  70                  75                  80

Arg Lys Pro Gly Met Thr Arg Asp Asp Leu Phe Lys Ile Asn Ala Gly
                85                  90                  95

Ile Val Arg Asp Leu Ala Thr Ala Ala Ala Lys Tyr Ala Pro Lys Ala
            100                 105                 110

Phe Met Cys Ile Ile Ser Asn Pro Val Asn Ser Thr Val Pro Ile Val
        115                 120                 125

Thr Glu Val Phe Lys Gln His Asn Val Tyr Asp Pro Lys Arg Ile Phe
    130                 135                 140

Gly Val Thr Thr Leu Asp Ile Val Arg Ala Ser Thr Phe Val Ser Glu
145                 150                 155                 160

Leu Ile Gly Gly Glu Pro Asn Ser Leu Arg Val Pro Val Ile Gly Gly
                165                 170                 175

His Ser Gly Val Thr Ile Leu Pro Leu Leu Ser Gln Val Pro Gly Ile
            180                 185                 190

Glu Lys Leu Asn Gln Glu Gln Ile Glu Lys Val Thr His Arg Ile Gln
        195                 200                 205

Phe Gly Gly Asp Glu Val Val Lys Ala Lys Asp Gly Ala Gly Ser Ala
    210                 215                 220

Thr Leu Ser Met Ala Tyr Ala Gly Ala Arg Phe Ala Thr Asn Ile Ile
225                 230                 235                 240

Glu Ala Ala Phe Ala Gly Lys Lys Gly Ile Val Glu Cys Thr Tyr Val
                245                 250                 255

Gln Leu Asp Ala Asp Lys Ser Gly Ala Gln Ser Val Lys Asp Leu Val
            260                 265                 270

Gly Ser Glu Leu Glu Tyr Phe Ser Val Pro Val Glu Leu Gly Pro Ser
        275                 280                 285

Gly Val Glu Lys Ile Leu Pro Ile Gly Asn Val Asn Glu Tyr Glu Lys
    290                 295                 300

Lys Leu Leu Asn Glu Ala Ser Pro Glu Leu Lys Thr Asn Ile Asp Lys
305                 310                 315                 320

Gly Cys Thr Phe Val Thr Glu Gly
                325
```

<210> SEQ ID NO 129
<211> LENGTH: 19
<212> TYPE: DNA
<213> ORGANISM: Artificial
<220> FEATURE:
<223> OTHER INFORMATION: Primer

<400> SEQUENCE: 129
tggcccaggg aatcattac 19

<210> SEQ ID NO 130
<211> LENGTH: 28
<212> TYPE: DNA
<213> ORGANISM: Artificial
<220> FEATURE:
<223> OTHER INFORMATION: Primer

<400> SEQUENCE: 130
tcaccacctg tcagtgacga gccacttc 28

<210> SEQ ID NO 131
<211> LENGTH: 20
<212> TYPE: DNA
<213> ORGANISM: Artificial
<220> FEATURE:
<223> OTHER INFORMATION: Primer

<400> SEQUENCE: 131
ggacccaatg cctcccaatc 20

<210> SEQ ID NO 132
<211> LENGTH: 21
<212> TYPE: DNA
<213> ORGANISM: Artificial
<220> FEATURE:
<223> OTHER INFORMATION: Primer

<400> SEQUENCE: 132
cgtttctccc ttccctgata g 21

<210> SEQ ID NO 133
<211> LENGTH: 6890
<212> TYPE: DNA
<213> ORGANISM: Artificial
<220> FEATURE:
<223> OTHER INFORMATION: E. coli SthA MEL integration fragment
<220> FEATURE:
<221> NAME/KEY: misc_feature
<222> LOCATION: (3973)..(3973)
<223> OTHER INFORMATION: n is a, c, g, or t

<400> SEQUENCE: 133
cggatttggt tggttcatag ctcttcttta gcgttgattg tagcctctgt tgcagaaaag 60
accttgtttt caagaaactg gttggtctga gtgttctgac accaatggtt atatttctag 120
ttgcaaacat gttggaataa tggtagtaat gttgatgctg gcagtgacag tagtgctagt 180
tcttgttctt gttctcgttc tcgttctcgt tctctttttt gtgctgtagc tgttactgta 240
ttggctactc tatataatat gcttgcaaag gaaaggaaat ctatgcaaac cactctctcc 300
tgcacaaacg ctagttcctt tgtcagggtt gaatgtagcc actctacgaa tgcgattcct 360
cttcccctct ctttcgcgtt gagcatattc aaaattgtga gaggtggcaa ggaaaaccat 420
acgattttcg gggtgcacgg atgcacagtg gacgtaagat ctgctctatt taagatacta 480

```
aagaaagtgg cagcgggaag accatcatgg aggacaacgt acatggacga ttccctgcta    540
gaaacaatga catgcaaacc cgtgcagtag gtagaagcag atttgctgag acagccatgc    600
caagtggaat tgttgtttaa ctctagtaga tattattgtt atagaaaaga tttatatata    660
agatccatgg agggggagg gaggtaagag aaatacgaaa aagaatgtgt aatgaatctt     720
aatgtagaca agtggaaatg cagctaaagg gggtcaaagg gaatgtgata atgcaaggtt    780
aggtttaaca agaatgggtt ggcggactcg tcaatggaga gtacaatgcc aaagttctcc    840
ctgaggttat tgcggccgcg gatccctcga gattggtagt tctttccccc tctcaagctg    900
gcgtgaaatg caaccttacg gcgtctacgt tactacaagg tccagaaagt gtaggtattg    960
ctactatttt tattttttat tggttctgga gaaatgcaga cagtcaatga acacaactgt   1020
ctcaatatgc atctatgcac atgcacacac acacacatca caggtacccc tacaaagaga   1080
ggtctcttga taatgtttca ttaccacgtg gcatcccccc cccccccccc aataaacaag   1140
tggccgagtt cccctgttgc agaggaggac aaaaaaaccg ctggtgttgg taccattatg   1200
cagcaactag cacaacaaac aaccgaccca gacatacaaa tcaacaacac ttcgccaaag   1260
acaccctttc cagggaggat ccactcccaa cgtctctcca taatgtctct gttggcccat   1320
gtctctgtcg ttgacaccgt aaccacacca accaacccgt ccattgtact gggatggtcg   1380
tccatagaca cctctccaac ggggaacacc tcattcgtaa accgccaagg ttaccgttcc   1440
tcctgactcg ccccgttgtt gatgctgcgc acctgtggtt gcccaacatg gttgtatatc   1500
gtgtaaccac accaacacat gtgcagcaca tgtgtttaaa agagtgtcat ggaggtggat   1560
catgatggaa gtggacttta ccacttggga actgtctcca ctcccgggaa gaaaagaccc   1620
ggcgtatcac gcggttgcct caatggggca atttggaagg agaaatatag ggaaaatcac   1680
gtcgctctcg gacggggaag agttccagac tatgaggggg gggggtggta tataaagaca   1740
ggagatgtcc acccccagag agaggaagaa gttggaactt tagaagagag agataacttt   1800
ccccagtgtc catcaataca caaccaaaca caaactctat atttacacat ataacccccct  1860
ctctagaatg ccacattcct atgactacga tgccattgtc attggttccg gtccaggtgg   1920
tgaaggtgct gcaatgggct tagttaagca gggtgctaga gttgctgtca tcgaaagata   1980
tcaaaatgtt ggtggtggtt gtactcactg ggtacaatt ccatctaagg cattgagaca    2040
tgcagtttcc agaattattg agtttaacca aaaccccttta tactctgatc attcaagatt  2100
gttgagatca tcttttgctg atattttgaa ccatgctgac aacgtcatca accaacaaac   2160
tcgtatgcgt caaggcttct atgagagaaa tcattgtgag attttacaag gtaacgctag   2220
atttgtcgat gagcatactc ttgcattaga ctgtccagac ggttccgttg agactcttac   2280
cgctgaaaaa ttcgttattg cttgtggttc cagaccatac cacccaaccg atgtcgattt   2340
cactcaccct cgtatctacg attccgattc tattttgtct atgcatcatg aaccaagaca   2400
tgttttgatt tatggtgctg gtgttatcgg ttgtgaatat gcttctattt tcagaggtat   2460
ggatgttaag gttgacttga ttaatacaag agacagatta ttagctttcc ttgatcagga   2520
aatgtctgat tccctttcct accatttttg gaactccggt gtcgtcatca gacacaacga   2580
ggaatatgaa aagattgaag gttgtgatga cggcgttatt atgcacctta agtctggtaa   2640
aaagttaaaa gcagattgct tgttatatgc aaatggtaga accggtaaca cagactcctt   2700
ggctttacaa aacattggtt tagaaaccga ttcaagaggt caattaaagg tcaattcaat   2760
gtatcaaact gcacaaccac acgtttacgc agttggtgac gttattggtt acccttcatt   2820
ggcatctgcc gcttacgatc aaggtagaat cgccgctcaa gcacttgtta agggtgaagc   2880
```

```
aactgcacac ttaatcgaag atatccctac cggtatctac actatcccag aaatctcttc   2940
tgttggcaag actgaacaac aattaaccgc aatgaaggtt ccatacgaag tcggtcgtgc   3000
ccagttcaag catttggcta gagcacaaat tgttggtatg aatgttggta ctttgaaaat   3060
cttgtttcac agagaaacaa aggaaatctt gggcattcac tgtttcggcg aaagagctgc   3120
agagattatt cacatcggtc aagccattat ggaacaaaaa ggcggtggta ataccattga   3180
atatttcgtt aataccacct tcaactaccc aacaatggcc gaagcatata gagtcgctgc   3240
tttaaacggt ttaaacagat tgttttaatt aacatctgaa tgtaaaatga acattaaaat   3300
gaattactaa actttacgtc tactttacaa tctataaact ttgtttaatc atataacgaa   3360
atacactaat acacaatcct gtacgtatgt aatacttta tccatcaagg attgagaaaa   3420
aaaagtaatg attccctggg ccattaaaac ttagaccccc aagcttggat aggtcactct   3480
ctattttcgt ttctcccttc cctgatagaa gggtgatatg taattaagaa taatatataa   3540
ttttataata aaagaattcg cccttacctg cagggataac ttcgtataat gtatgctata   3600
cgaagttatg ctgcaacggc aacatcaatg tccacgttta cacacctaca tttatatcta   3660
tatttatatt tatatttatt tatttatgct acttagcttc tatagttagt taatgcactc   3720
acgatattca aaattgacac ccttcaacta ctccctacta ttgtctacta ctgtctacta   3780
ctcctcttta ctatagctgc tcccaatagg ctccaccaat aggctctgtc aatacatttt   3840
gcgccgccac ctttcaggtt gtgtcactcc tgaaggacca tattgggtaa tcgtgcaatt   3900
tctggaagag agtgccgcga gaagtgaggc ccccactgta aatcctcgag gggcatgga   3960
gtatggggca tgnaggatgg aggatggggg gggggggga aaataggtag cgaaaggacc   4020
cgctatcacc ccacccggag aactcgttgc cgggaagtca tatttcgaca ctccggggag   4080
tctataaaag gcgggttttg tcttttgcca gttgatgttg ctgagaggac ttgtttgccg   4140
tttcttccga tttaacagta tagaatcaac cactgttaat tatacacgtt atactaacac   4200
aacaaaaaca aaaacaacga caacaacaac aacaatgttt gctttctact ttctcaccgc   4260
atgcaccact ttgaagggtg ttttcggagt ttctccgagt tacaatggtc ttggtctcac   4320
cccacagatg ggttgggaca gctggaatac gtttgcctgc gatgtcagtg aacagctact   4380
tctagacact gctgatagaa tttctgactt ggggctaaag gatatgggtt acaagtatgt   4440
catcctagat gactgttggt ctagcggcag ggattccgac ggtttcctcg ttgcagacaa   4500
gcacaaattt cccaacggta tgggccatgt tgcagaccac ctgcataata acagctttct   4560
tttcggtatg tattcgtctg ctggtgagta cacctgtgct gggtaccctg ggtctctggg   4620
gcgtgaggaa gaagatgctc aattctttgc aaataaccgc gttgactact tgaagtatga   4680
taattgttac aataaaggtc aatttggtac accagacgtt tcttaccacc gttacaaggc   4740
catgtcagat gctttgaata aaactggtag gcctattttc tattctctat gtaactgggg   4800
tcaggatttg acattttact ggggctctgg tatcgccaat tcttggagaa tgagcggaga   4860
tattactgct gagttcaccc gtccagatag cagatgtccc tgtgacggtg acgaatatga   4920
ttgcaagtac gccggtttcc attgttctat tatgaatatt cttaacaagg cagctccaat   4980
ggggcaaaat gcaggtgttg gtggttggaa cgatctggac aatctagagg tcggagtcgg   5040
taatttgact gacgatgagg aaaaggccca tttctctatg tgggcaatgg taaagtcccc   5100
acttatcatt ggtgccgacg tgaatcactt aaaggcatct tcgtactcga tctacagtca   5160
agcctctgtc atcgcaatta atcaagatcc aaagggtatt ccagccacaa gagtctggag   5220
```

```
atattatgtt tcagacaccg atgaatatgg acaaggtgaa attcaaatgt ggagtggtcc   5280

gcttgacaat ggtgaccaag tggttgcttt attgaatgga ggaagcgtag caagaccaat   5340

gaacacgacc ttggaagaga ttttctttga cagcaatttg ggttcaaagg aactgacatc   5400

gacttgggat atttacgact tatgggccaa cagagttgac aactctacgg cgtctgctat   5460

ccttgaacag aataaggcag ccaccggtat tctctacaat gctacagagc agtcttataa   5520

agacggtttg tctaagaatg atacaagact gtttggccag aaaattggta gtctttctcc   5580

aaatgctata cttaacacaa ctgttccagc tcatggtatc gccttctata ggttgagacc   5640

ctcggcttaa gctcaatgtt gagcaaagca ggacgagaaa aaaaaaaata atgattgtta   5700

agaagttcat gaaaaaaaaa aggaaaaata ctcaaatact tataacagag tgattaaata   5760

ataaacggca gtataccta tcaggtattg agatagtttt atttttgtag gtatataatc    5820

tgaagccttt gaactatttt ctcgtatata tcatggagta tacattgcat tagcaacatt   5880

gcatactagt tcataacttc gtataatgta tgctatacga agttattaat taacaagggc   5940

gaattccttg atttatatac acctttgcca accgcttgtt acttgataag gaaaagatag   6000

atttctaaag tgcaggaaaa gaaacgccac tacgtcatga aacaaaagaa atgaaacact   6060

ctgcaaaagg gaaaaccaat gacgccttca aaacgtactg actttccgcc tccttttctg   6120

cctttttttt ttctccctca atttgccaat tcccctttcc gctaatttta catcaccttt   6180

ttgtttgttt ccccttttcgg ccaagttttc catttctttt ttcggctgag cccttctttg  6240

gcgtcgacgt aatttctcgg catgtggcca atgtatattg acagtagatg aagtagacgt   6300

tcttagtaac tgttagggtg agattgccac ccccccttcc ttcttttact atctgtaata   6360

ccatcaccat agcaatagtt taaccatgtt ggagctggaa atacaacgtc tatagaggga   6420

agtcatcata ttacgccatt ttacggacca gggacaccct gtagtgtgtt tcctctcttg   6480

tagaggtagg ttttcaaatg gactctggcg tcgatttcca gcaagtcatt cccgtggttc   6540

accatttcta ctttttgcgc tacctctctt gacacagaaa tgaatgatga cgtgtaaatt   6600

acccgtccga gacctggact ccggagaaac tgtattaatt acgcgccaaa caagacaggt   6660

gtcggataaa cgtgcatgta cagactgcga gccgaaaacg gaagggggga aagaaaacag   6720

tggagtccca ttgttgttcc ggaaatggaa aacgggaact ggcggaaaag aaacgaaaca   6780

aaacaaaaga aaaagaggaa aaaaaagaaa aaaaaaagaa aaagacactg cacgtgattg   6840

ctggtgtgtg ctgcgtaacc gcggcacttt atttcgtaaa tgaaggggcc              6890
```

<210> SEQ ID NO 134
<211> LENGTH: 1656
<212> TYPE: DNA
<213> ORGANISM: Saccharomyces cerevisiae

<400> SEQUENCE: 134

```
atgtttgctt tctactttct caccgcatgc accactttga agggtgtttt cggagtttct     60

ccgagttaca atggtcttgg tctcacccca cagatgggtt gggacagctg gaatacgttt    120

gcctgcgatg tcagtgaaca gctacttcta gacactgctg atagaatttc tgacttgggg    180

ctaaaggata tgggttacaa gtatgtcatc ctagatgact gttggtctag cggcagggat    240

tccgacggtt tcctcgttgc agacaagcac aaatttccca acggtatggg ccatgttgca    300

gaccacctgc ataataacag ctttctttc ggtatgtatt cgtctgctgg tgagtacacc     360

tgtgctgggt accctgggtc tctggggcgt gaggaagaag atgctcaatt ctttgcaaat    420

aaccgcgttg actacttgaa gtatgataat tgttacaata aaggtcaatt tggtacacca    480
```

```
gacgtttctt accaccgtta caaggccatg tcagatgctt tgaataaaac tggtaggcct    540

attttctatt ctctatgtaa ctggggtcag gatttgacat tttactgggg ctctggtatc    600

gccaattctt ggagaatgag cggagatatt actgctgagt tcacccgtcc agatagcaga    660

tgtccctgtg acggtgacga atatgattgc aagtacgccg gtttccattg ttctattatg    720

aatattctta acaaggcagc tccaatgggg caaaatgcag gtgttggtgg ttggaacgat    780

ctggacaatc tagaggtcgg agtcggtaat ttgactgacg atgaggaaaa ggcccatttc    840

tctatgtggg caatggtaaa gtccccactt atcattggtg ccgacgtgaa tcacttaaag    900

gcatcttcgt actcgatcta cagtcaagcc tctgtcatcg caattaatca agatccaaag    960

ggtattccag ccacaagagt ctggagatat tatgtttcag acaccgatga atatggacaa   1020

ggtgaaattc aaatgtggag tggtccgctt gacaatggtg accaagtggt tgctttattg   1080

aatggaggaa gcgtagcaag accaatgaac acgaccttgg aagagatttt ctttgacagc   1140

aatttgggtt caaaggaact gacatcgact tgggatattt acgacttatg ggccaacaga   1200

gttgacaact ctacggcgtc tgctatcctt gaacagaata aggcagccac cggtattctc   1260

tacaatgcta cagagcagtc ttataaagac ggtttgtcta agaatgatac aagactgttt   1320

ggccagaaaa ttggtagtct ttctccaaat gctatactta acacaactgt tccagctcat   1380

ggtatcgcct tctataggtt gagaccctcg gcttaagctc aatgttgagc aaagcaggac   1440

gagaaaaaaa aaaataatga ttgttaagaa gttcatgaaa aaaaaaagga aaaatactca   1500

aatacttata acagagtgat taaataataa acggcagtat accctatcag gtattgagat   1560

agttttattt ttgtaggtat ataatctgaa gcctttgaac tattttctcg tatatatcat   1620

ggagtataca ttgcattagc aacattgcat actagt                             1656
```

<210> SEQ ID NO 135
<211> LENGTH: 6279
<212> TYPE: DNA
<213> ORGANISM: Artificial
<220> FEATURE:
<223> OTHER INFORMATION: E. coli SthA URA integration fragment

<400> SEQUENCE: 135

```
ggccccttca tttacgaaat aaagtgccgc ggttacgcag cacacaccag caatcacgtg     60

cagtgtcttt ttcttttttt tttctttttt ttcctctttt tcttttgttt tgtttcgttt    120

cttttccgcc agttcccgtt ttccatttcc ggaacaacaa tgggactcca ctgttttctt    180

tcccccctc cgttttcggc tcgcagtctg tacatgcacg tttatccgac acctgtcttg    240

tttggcgcgt aattaataca gtttctccgg agtccaggtc tcggacgggt aatttacacg    300

tcatcattca tttctgtgtc aagagaggta gcgcaaaaag tagaaatggt gaaccacggg    360

aatgacttgc tggaaatcga cgccagagtc catttgaaaa cctacctcta caagagagga    420

aacacactac agggtgtccc tggtccgtaa aatggcgtaa tatgatgact tccctctata    480

gacgttgtat ttccagctcc aacatggtta aactattgct atggtgatgg tattacagat    540

agtaaaagaa ggaagggggg gtggcaatct caccctaaca gttactaaga acgtctactt    600

catctactgt caatatacat tggccacatg ccgagaaatt acgtcgacgc caaagaaggg    660

ctcagccgaa aaaagaaatg gaaaacttgg ccgaaaaggg aaacaaacaa aaaggtgatg    720

taaaattagc ggaaagggga attggcaaat tgagggagaa aaaaaaaagg cagaaaagga    780

ggcggaaagt cagtacgttt tgaaggcgtc attggttttc ccttttgcag agtgtttcat    840
```

```
ttcttttgtt tcatgacgta gtggcgtttc ttttcctgca ctttagaaat ctatcttttc     900
cttatcaagt aacaagcggt tggcaaaggt gtatataaat caaggaattc ccactttgaa     960
ccctttgaat tttgatatcg tttattttaa atttatttgc ggccgcggat ccctcgagat    1020
tggtagttct ttcccctct caagctggcg tgaaatgcaa ccttacggcg tctacgttac    1080
tacaaggtcc agaaagtgta ggtattgcta ctatttttat tttttattgg ttctggagaa    1140
atgcagacag tcaatgaaca caactgtctc aatatgcatc tatgcacatg cacacacaca    1200
cacatcacag gtacccctac aaagagaggt ctcttgataa tgtttcatta ccacgtggca    1260
tccccccccc cccccccaat aaacaagtgg ccgagttccc ctgttgcaga ggaggacaaa    1320
aaaaccgctg gtgttggtac cattatgcag caactagcac aacaaacaac cgacccagac    1380
atacaaatca acaacacttc gccaaagaca ccctttccag ggaggatcca ctcccaacgt    1440
ctctccataa tgtctctgtt ggcccatgtc tctgtcgttg acaccgtaac cacaccaacc    1500
aacccgtcca ttgtactggg atggtcgtcc atagacacct ctccaacggg gaacacctca    1560
ttcgtaaacc gccaaggtta ccgttcctcc tgactcgccc cgttgttgat gctgcgcacc    1620
tgtggttgcc caacatggtt gtatatcgtg taaccacacc aacacatgtg cagcacatgt    1680
gtttaaaaga gtgtcatgga ggtggatcat gatggaagtg gactttacca cttgggaact    1740
gtctccactc ccgggaagaa aagacccggc gtatcacgcg gttgcctcaa tggggcaatt    1800
tggaaggaga aatataggga aaatcacgtc gctctcggac ggggaagagt tccagactat    1860
gagggggggg ggtggtatat aaagacagga gatgtccacc cccagagaga ggaagaagtt    1920
ggaactttag aagagagaga taactttccc cagtgtccat caatacacaa ccaaacacaa    1980
actctatatt tacacatata accccctctc tagaatgcca cattcctatg actacgatgc    2040
cattgtcatt ggttccggtc caggtggtga aggtgctgca atgggcttag ttaagcaggg    2100
tgctagagtt gctgtcatcg aaagatatca aaatgttggt ggtggttgta ctcactgggg    2160
tacaattcca tctaaggcat tgagacatgc agtttccaga attattgagt ttaaccaaaa    2220
ccctttatac tctgatcatt caagattgtt gagatcatct tttgctgata ttttgaacca    2280
tgctgacaac gtcatcaacc aacaaactcg tatgcgtcaa ggcttctatg agagaaatca    2340
ttgtgagatt ttacaaggta acgctagatt tgtcgatgag catactcttg cattagactg    2400
tccagacggt tccgttgaga ctcttaccgc tgaaaaattc gttattgctt gtggttccag    2460
accataccac ccaaccgatg tcgatttcac tcaccctcgt atctacgatt ccgattctat    2520
tttgtctatg catcatgaac caagacatgt tttgatttat ggtgctggtg ttatcggttg    2580
tgaatatgct tctattttca gaggtatgga tgttaaggtt gacttgatta atacaagaga    2640
cagattatta gctttccttg atcaggaaat gtctgattcc ctttcctacc atttttggaa    2700
ctccggtgtc gtcatcagac acaacgagga atatgaaaag attgaaggtt gtgatgacgg    2760
cgttattatg caccttaagt ctggtaaaaa gttaaaagca gattgcttgt tatatgcaaa    2820
tggtagaacc ggtaacacag actccttggc tttacaaaac attggtttag aaaccgattc    2880
aagaggtcaa ttaaaggtca attcaatgta tcaaactgca caaccacacg tttacgcagt    2940
tggtgacgtt attggttacc cttcattggc atctgccgct tacgatcaag gtagaatcgc    3000
cgctcaagca cttgttaagg gtgaagcaac tgcacactta atcgaagata tccctaccgg    3060
tatctacact atcccagaaa tctcttctgt tggcaagact gaacaacaat taaccgcaat    3120
gaaggttcca tacgaagtcg gtcgtgccca gttcaagcat ttggctagag cacaaattgt    3180
tggtatgaat gttggtactt tgaaaatctt gtttcacaga gaaacaaagg aaatcttggg    3240
```

```
cattcactgt ttcggcgaaa gagctgcaga gattattcac atcggtcaag ccattatgga   3300
acaaaaaggc ggtggtaata ccattgaata tttcgttaat accaccttca actacccaac   3360
aatggccgaa gcatatagag tcgctgcttt aaacggttta aacagattgt tttaattaac   3420
atctgaatgt aaaatgaaca ttaaaatgaa ttactaaact ttacgtctac tttacaatct   3480
ataaactttg tttaatcata taacgaaata cactaataca caatcctgta cgtatgtaat   3540
acttttatcc atcaaggatt gagaaaaaaa agtaatgatt ccctgggcca ttaaaactta   3600
gacccccaag cttggatagg tcactctcta ttttcgtttc tcccttccct gatagaaggg   3660
tgatatgtaa ttaagaataa tatataattt tataataaaa gaattcatag cctcatgaaa   3720
tcagccattt gcttttgttc aacgatcttt tgaaattgtt gttgttcttg gtagttaagt   3780
tgatccatct tggcttatgt tgtgtgtatg ttgtagttat tcttagtata ttcctgtcct   3840
gagtttagtg aaacataata tcgccttgaa atgaaaatgc tgaaattcgt cgacatacaa   3900
tttttcaaac tttttttttt tcttggtgca cggacatgtt tttaaaggaa gtactctata   3960
ccagttattc ttcacaaatt taattgctgg agaatagatc ttcaacgctt taataaagta   4020
gtttgtttgt caaggatggc gtcatacaaa gaaagatcag aatcacacac ttcccctgtt   4080
gctaggagac ttttctccat catggaggaa aagaagtcta acctttgtgc atcattggat   4140
attactgaaa ctgaaaagct tctctctatt ttggacacta ttggtcctta catctgtcta   4200
gttaaaacac acatcgatat tgtttctgat tttacgtatg aaggaactgt gttgcctttg   4260
aaggagcttg ccaagaaaca taattttatg atttttgaag atagaaaatt tgctgatatt   4320
ggtaacactg ttaaaaatca atataaatct ggtgtcttcc gtattgccga atgggctgac   4380
atcactaatg cacatggtgt aacgggtgca ggtattgttt ctggcttgaa ggaggcagcc   4440
caagaaacaa ccagtgaacc tagaggtttg ctaatgcttg ctgagttatc atcaaagggt   4500
tctttagcat atggtgaata tacagaaaaa acagtagaaa ttgctaaatc tgataaagag   4560
tttgtcattg gttttattgc gcaacacgat atgggcggta gagaagaagg ttttgactgg   4620
atcattatga ctccaggggt tggtttagat gacaaaggtg atgcacttgg tcaacaatat   4680
agaactgttg atgaagttgt aaagactgga acggatatca taattgttgg tagaggtttg   4740
tacggtcaag gaagagatcc tatagagcaa gctaaaagat accaacaagc tggttggaat   4800
gcttatttaa acagatttaa atgattctta cacaaagatt tgatacatgt acactagttt   4860
aaataagcat gaaaagaatt acacaagcaa aaaaaaaaaa ataaatgagg tactttacgt   4920
tcacctacaa ccaaaaaaac tagatagagt aaaatcttaa gatttagaaa aagttgttta   4980
acaaaggctt tagtatgtga atttttaatg tagcaaagcg ataactaata aacataaaca   5040
aaagtatggt tttctttatc agtcaaatca ttatcgattg attgttccgc gtatctgcag   5100
atagcctcat gaaatcagcc atttgctttt gttcaacgat cttttgaaat tgttgttgtt   5160
cttggtagtt aagttgatcc atcttggctt atgttgtgtg tatgttgtag ttattcttag   5220
tatattcctg tcctgagttt agtgaaacat aatatcgcct tgaaatgaaa atgctgaaat   5280
tcgtcgacat acaatttttc aaactttttt tttttcttgg tgcacggaca tgtttttaaa   5340
ggaagtactc tataccagtt attcttcaca aatttaattg ctggagaata gatcttcaac   5400
gccccggggg atctggatcc gcggccgcaa taacctcagg gagaactttg gcattgtact   5460
ctccattgac gagtccgcca acccattctt gttaaaccta accttgcatt atcacattcc   5520
ctttgacccc ctttagctgc atttccactt gtctacatta agattcatta cacattcttt   5580
```

```
ttcgtatttc tcttacctcc ctccccctc catggatctt atatataaat cttttctata   5640

acaataatat ctactagagt taaacaacaa ttccacttgg catggctgtc tcagcaaatc   5700

tgcttctacc tactgcacgg gtttgcatgt cattgtttct agcagggaat cgtccatgta   5760

cgttgtcctc catgatggtc ttcccgctgc cactttcttt agtatcttaa atagagcaga   5820

tcttacgtcc actgtgcatc cgtgcacccc gaaaatcgta tggttttcct tgccacctct   5880

cacaattttg aatatgctca acgcgaaaga gaggggaaga ggaatcgcat tcgtagagtg   5940

gctacattca accctgacaa aggaactagc gtttgtgcag gagagagtgg tttgcataga   6000

tttcctttcc tttgcaagca tattatatag agtagccaat acagtaacag ctacagcaca   6060

aaaaagagaa cgagaacgag aacgagaaca agaacaagaa ctagcactac tgtcactgcc   6120

agcatcaaca ttactaccat tattccaaca tgtttgcaac tagaaatata accattggtg   6180

tcagaacact cagaccaacc agtttcttga aaacaaggtc ttttctgcaa cagaggctac   6240

aatcaacgct aaagaagagc tatgaaccaa ccaaatccg                           6279


<210> SEQ ID NO 136
<211> LENGTH: 6888
<212> TYPE: DNA
<213> ORGANISM: Artificial
<220> FEATURE:
<223> OTHER INFORMATION: A. vinelandii MEL integration fragment
<220> FEATURE:
<221> NAME/KEY: misc_feature
<222> LOCATION: (2914)..(2914)
<223> OTHER INFORMATION: n is a, c, g, or t

<400> SEQUENCE: 136

ccttcattta cgaaataaag tgccgcggtt acgcagcaca caccagcaat cacgtgcagt     60

gtctttttct tttttttttc tttttttcc tctttttctt ttgttttgtt tcgtttcttt    120

tccgccagtt cccgttttcc atttccggaa caacaatggg actccactgt tttctttccc    180

cccttccgtt ttcggctcgc agtctgtaca tgcacgttta tccgacacct gtcttgtttg    240

gcgcgtaatt aatacagttt ctccggagtc caggtctcgg acgggtaatt tacacgtcat    300

cattcatttc tgtgtcaaga gaggtagcgc aaaaagtaga aatggtgaac cacgggaatg    360

acttgctgga aatcgacgcc agagtccatt tgaaaaccta cctctacaag agaggaaaca    420

cactacaggg tgtccctggt ccgtaaaatg gcgtaatatg atgacttccc tctatagacg    480

ttgtatttcc agctccaaca tggttaaact attgctatgg tgatggtatt acagatagta    540

aaagaaggaa ggggggtgg caatctcacc ctaacagtta ctaagaacgt ctacttcatc    600

tactgtcaat atacattggc cacatgccga gaaattacgt cgacgccaaa gaagggctca    660

gccgaaaaaa gaaatggaaa acttggccga aaagggaaac aaacaaaaag gtgatgtaaa    720

attagcggaa aggggaattg gcaaattgag ggagaaaaaa aaaaggcaga aaaggaggcg    780

gaaagtcagt acgttttgaa ggcgtcattg gttttccctt ttgcagagtg tttcatttct    840

tttgtttcat gacgtagtgg cgtttctttt cctgcacttt agaaatctat cttttcctta    900

tcaagtaaca agcggttggc aaaggtgtat ataaatcaag gaattcgccc ttgttaatta    960

ataacttcgt atagcataca ttatacgaag ttatgaacta gtatgcaatg ttgctaatgc   1020

aatgtatact ccatgatata tacgagaaaa tagttcaaag gcttcagatt atatacctac   1080

aaaaataaaa ctatctcaat acctgatagg gtatactgcc gtttattatt taatcactct   1140

gttataagta tttgagtatt tttcttttt tttttcatga acttcttaac aatcattatt   1200

ttttttttc tcgtcctgct ttgctcaaca ttgagcttaa gccgagggtc tcaacctata   1260
```

```
gaaggcgata ccatgagctg gaacagttgt gttaagtata gcatttggag aaagactacc   1320
aattttctgg ccaaacagtc ttgtatcatt cttagacaaa ccgtctttat aagactgctc   1380
tgtagcattg tagagaatac cggtggctgc cttattctgt tcaaggatag cagacgccgt   1440
agagttgtca actctgttgg cccataagtc gtaaatatcc caagtcgatg tcagttcctt   1500
tgaacccaaa ttgctgtcaa agaaaatctc ttccaaggtc gtgttcattg gtcttgctac   1560
gcttcctcca ttcaataaag caaccacttg gtcaccattg tcaagcggac cactccacat   1620
ttgaatttca ccttgtccat attcatcggt gtctgaaaca taatatctcc agactcttgt   1680
ggctggaata ccctttggat cttgattaat tgcgatgaca gaggcttgac tgtagatcga   1740
gtacgaagat gcctttaagt gattcacgtc ggcaccaatg ataagtgggg actttaccat   1800
tgcccacata gagaaatggg ccttttcctc atcgtcagtc aaattaccga ctccgacctc   1860
tagattgtcc agatcgttcc aaccaccaac acctgcattt tgccccattg gagctgcctt   1920
gttaagaata ttcataatag aacaatggaa accggcgtac ttgcaatcat attcgtcacc   1980
gtcacaggga catctgctat ctggacgggt gaactcagca gtaatatctc cgctcattct   2040
ccaagaattg gcgataccag agccccagta aaatgtcaaa tcctgacccc agttacatag   2100
agaatagaaa ataggcctac cagttttatt caaagcatct gacatggcct tgtaacggtg   2160
gtaagaaacg tctggtgtac caaattgacc tttattgtaa caattatcat acttcaagta   2220
gtcaacgcgg ttatttgcaa agaattgagc atcttcttcc tcacgcccca gagacccagg   2280
gtacccagca caggtgtact caccagcaga cgaatacata ccgaaaagaa agctgttatt   2340
atgcaggtgg tctgcaacat ggcccatacc gttgggaaat ttgtgcttgt ctgcaacgag   2400
gaaaccgtcg gaatccctgc cgctagacca acagtcatct aggatgacat acttgtaacc   2460
catatccttt agccccaagt cagaaattct atcagcagtg tctagaagta gctgttcact   2520
gacatcgcag gcaaacgtat tccagctgtc ccaacccatc tgtggggtga gaccaagacc   2580
attgtaactc ggagaaactc cgaaaacacc cttcaaagtg gtgcatgcgg tgagaaagta   2640
gaaagcaaac attgttgttg ttgttgtcgt tgtttttgtt tttgttgtgt tagtataacg   2700
tgtataatta acagtggttg attctatact gttaaatcgg aagaaacggc aaacaagtcc   2760
tctcagcaac atcaactggc aaaagacaaa acccgccttt tatagactcc ccggagtgtc   2820
gaaatatgac ttcccggcaa cgagttctcc gggtggggtg atagcgggtc ctttcgctac   2880
ctattttccc cccccccccc catcctccat cctncatgcc ccatactcca tgccccctcg   2940
aggatttaca gtgggggcct cacttctcgc ggcactctct tccagaaatt gcacgattac   3000
ccaatatggt ccttcaggag tgacacaacc tgaaaggtgg cggcgcaaaa tgtattgaca   3060
gagcctattg gtggagccta ttgggagcag ctatagtaaa gaggagtagt agacagtagt   3120
agacaatagt agggagtagt tgaagggtgt caattttgaa tatcgtgagt gcattaacta   3180
actatagaag ctaagtagca taaataaata aatataaata taaatataga tataaatgta   3240
ggtgtgtaaa cgtggacatt gatgttgccg ttgcagcata acttcgtata gcatacatta   3300
tacgaagtta tccctgcagg taagggcgaa ttcttttatt ataaaattat atattattct   3360
taattacata tcacccttct atcagggaag ggagaaacga aaatagagag tgacctatcc   3420
aagcttgggg gtctaagttt taatggccca gggaatcatt actttttttt ctcaatcctt   3480
gatggataaa agtattacat acgtacagga ttgtgtatta gtgtatttcg ttatatgatt   3540
aaacaaagtt tatagattgt aaagtagacg taaagtttag taattcattt taatgttcat   3600
```

```
tttacattca gatgttaatt aattagaaca atctgttcaa accatcgtac gcagccactc   3660
tatatgcttc tgccattgta ggataattga atgtagtatt aatgaaatac ttcaaagtgt   3720
tggcttcacc cttttggttc ataattgctt gaccgatgtg cacaatttca gatgcttgat   3780
aaccaaaaca atggacgcct aagatttcga gtgtttctct gtgaaacaaa atctttaaca   3840
tgcctgcctt ttcaacagca atctgggctc ttgccatacc tttgaaaaag gccttaccaa   3900
cctcgtatgg aacttttgcc tgagtaagtt ctctttctgt cttaccaaca ctggaaattt   3960
ctggaatggt gtagataccg gtagggacat cgtcaacaaa tctccaggag tcgttttcag   4020
tgatggagcc agcagcggat ctaccttgat cgtaagcagc agatgccaaa gatggccaac   4080
caataacatc accagcagcg tagatgttgg aaacttcggt tctataatgc tcatcgactt   4140
gaatttgacc tctaccatta gcctttaaac caatgttttc aagacccaac ttatcagtgt   4200
taccggttct accgttggac caaaggaatg catctgcctt gatcttttta ccagacttca   4260
aatgtaaaat gacaccgttg tcgaggcctt caactctttc gtactcctcg ttatgtctga   4320
ttaagacatt gttattcctt aagtgataag acaatgagtc ggaaatttcg tcatcgagaa   4380
aagatagtaa ttgatcacga ttgtcaatca aatcgactaa aacacctagt cctgagaaaa   4440
tacttgcgta ttcgcaaccg ataacaccag ctccgtagat aatcaaacgt cttggagtat   4500
gacccaaaga taagatagta tcagaatcgt agatcctagg gtgagtaaag tccacatcgg   4560
ctggtctata aggtcttgaa ccggtagcaa taacaaattg ctttgcgacc aaggtttcga   4620
ccataccatt caaatgaacg acttcaatag tatgctcgtc acagaatgat gcggtaccga   4680
aaaaggtatc aattctgttt ctagcataat atccggttct ggaagagact tgcttcgcaa   4740
taacttgctc tgctgatttt agaacgtcag cgaaagagaa ccatcttggt tcaccaattt   4800
gacggaataa tgggttgttg ttgtactgca taatttgtct aacagagtgc cttaaagcct   4860
tacttgggat agtgcctaag tgcgtacaat taccgccaac ttgtggtcta tcatcaacaa   4920
ctgcaacttt tctaccagct ttgactgcat tcatagcggc accttcaccc gctggacctg   4980
taccgataac aacaacatca taattgtaaa cagccattct agagaggggg ttatatgtgt   5040
aaatatagag tttgtgtttg gttgtgtatt gatggacact ggggaaagtt atctctctct   5100
tctaaagttc caacttcttc ctctctctgg gggtggacat ctcctgtctt tatataccac   5160
cccccccct catagtctgg aactcttccc cgtccgagag cgacgtgatt ttccctatat   5220
ttctccttcc aaattgcccc attgaggcaa ccgcgtgata cgccgggtct tttcttcccg   5280
ggagtggaga cagttcccaa gtggtaaagt ccacttccat catgatccac ctccatgaca   5340
ctcttttaaa cacatgtgct gcacatgtgt tggtgtggtt acacgatata caaccatgtt   5400
gggcaaccac aggtgcgcag catcaacaac ggggcgagtc aggaggaacg gtaaccttgg   5460
cggtttacga atgaggtgtt ccccgttgga gaggtgtcta tggacgacca tcccagtaca   5520
atggacgggt tggttggtgt ggttacggtg tcaacgacag agacatgggc caacagagac   5580
attatggaga gacgttggga gtggatcctc cctggaaagg gtgtctttgg cgaagtgttg   5640
ttgatttgta tgtctgggtc ggttgtttgt tgtgctagtt gctgcataat ggtaccaaca   5700
ccagcggttt ttttgtcctc ctctgcaaca ggggaactcg gccacttgtt tattgggggg   5760
gggggggggg atgccacgtg gtaatgaaac attatcaaga gacctctctt tgtaggggta   5820
cctgtgatgt gtgtgtgtgt gcatgtgcat agatgcatat tgagacagtt gtgttcattg   5880
actgtctgca tttctccaga accaataaaa aataaaaata gtagcaatac ctacactttc   5940
tggaccttgt agtaacgtag acgccgtaag gttgcatttc acgccagctt gagaggggga   6000
```

```
aagaactacc aatctcgagg gatccgcggc cgcaataacc tcagggagaa ctttggcatt   6060
gtactctcca ttgacgagtc cgccaaccca ttcttgttaa acctaacctt gcattatcac   6120
attccctttg accccccttta gctgcatttc cacttgtcta cattaagatt cattacacat   6180
tctttttcgt atttctctta cctccctccc ccctccatgg atcttatata taaatctttt   6240
ctataacaat aatatctact agagttaaac aacaattcca cttggcatgg ctgtctcagc   6300
aaatctgctt ctacctactg cacgggtttg catgtcattg tttctagcag ggaatcgtcc   6360
atgtacgttg tcctccatga tggtcttccc gctgccactt tctttagtat cttaaataga   6420
gcagatctta cgtccactgt gcatccgtgc accccgaaaa tcgtatggtt ttccttgcca   6480
cctctcacaa ttttgaatat gctcaacgcg aaagagaggg gaagaggaat cgcattcgta   6540
gagtggctac attcaaccct gacaaaggaa ctagcgtttg tgcaggagag agtggtttgc   6600
atagatttcc tttcctttgc aagcatatta tatagagtag ccaatacagt aacagctaca   6660
gcacaaaaaa gagaacgaga acgagaacga gaacaagaac aagaactagc actactgtca   6720
ctgccagcat caacattact accattattc caacatgttt gcaactagaa atataaccat   6780
tggtgtcaga acactcagac caaccagttt cttgaaaaca aggtcttttc tgcaacagag   6840
gctacaatca acgctaaaga agagctatga accaaccaaa tccgagct                6888
```

<210> SEQ ID NO 137
<211> LENGTH: 6276
<212> TYPE: DNA
<213> ORGANISM: Artificial
<220> FEATURE:
<223> OTHER INFORMATION: A. vinelandii URA integration fragment

<400> SEQUENCE: 137

```
ggccccttca tttacgaaat aaagtgccgc ggttacgcag cacacaccag caatcacgtg     60
cagtgtcttt ttcttttttt tttctttttt ttcctctttt tcttttgttt tgtttcgttt    120
cttttccgcc agttcccgtt ttccatttcc ggaacaacaa tgggactcca ctgttttctt    180
tccccccttc cgttttcggc tcgcagtctg tacatgcacg tttatccgac acctgtcttg    240
tttggcgcgt aattaataca gtttctccgg agtccaggtc tcggacgggt aatttacacg    300
tcatcattca tttctgtgtc aagagaggta gcgcaaaaag tagaaatggt gaaccacggg    360
aatgacttgc tggaaatcga cgccagagtc catttgaaaa cctacctcta caagagagga    420
aacacactac agggtgtccc tggtccgtaa aatggcgtaa tatgatgact tccctctata    480
gacgttgtat ttccagctcc aacatggtta aactattgct atggtgatgg tattacagat    540
agtaaaagaa ggaagggggg gtggcaatct caccctaaca gttactaaga acgtctactt    600
catctactgt caatatacat tggccacatg ccgagaaatt acgtcgacgc caaagaaggg    660
ctcagccgaa aaaagaaatg gaaaacttgg ccgaaaaggg aaacaaacaa aaaggtgatg    720
taaaattagc ggaaagggga attggcaaat tgagggagaa aaaaaaaagg cagaaaagga    780
ggcggaaagt cagtacgttt tgaaggcgtc attggttttc ccttttgcag agtgtttcat    840
ttcttttgtt tcatgacgta gtggcgtttc ttttcctgca ctttagaaat ctatcttttc    900
cttatcaagt aacaagcggt tggcaaaggt gtatataaat caaggaattc ccactttgaa    960
ccctttgaat tttgatatcg tttattttaa atttatttgc ggccgcggat ccctcgagat   1020
tggtagttct ttccccctct caagctggcg tgaaatgcaa ccttacggcg tctacgttac   1080
tacaaggtcc agaaagtgta ggtattgcta ctatttttat tttttattgg ttctggagaa   1140
```

```
atgcagacag tcaatgaaca caactgtctc aatatgcatc tatgcacatg cacacacaca   1200
cacatcacag gtacccctac aaagagaggt ctcttgataa tgtttcatta ccacgtggca   1260
tccccccccc cccccccaat aaacaagtgg ccgagttccc ctgttgcaga ggaggacaaa   1320
aaaaccgctg gtgttggtac cattatgcag caactagcac aacaaacaac cgacccagac   1380
atacaaatca acaacacttc gccaaagaca ccctttccag ggaggatcca ctcccaacgt   1440
ctctccataa tgtctctgtt ggcccatgtc tctgtcgttg acaccgtaac cacaccaacc   1500
aacccgtcca ttgtactggg atggtcgtcc atagacacct ctccaacggg gaacacctca   1560
ttcgtaaacc gccaaggtta ccgttcctcc tgactcgccc cgttgttgat gctgcgcacc   1620
tgtggttgcc caacatggtt gtatatcgtg taaccacacc aacacatgtg cagcacatgt   1680
gtttaaaaga gtgtcatgga ggtggatcat gatggaagtg gactttacca cttgggaact   1740
gtctccactc ccgggaagaa aagacccggc gtatcacgcg gttgcctcaa tggggcaatt   1800
tggaaggaga aatataggga aaatcacgtc gctctcggac ggggaagagt tccagactat   1860
gaggggggggg ggtggtatat aaagacagga gatgtccacc cccagagaga ggaagaagtt   1920
ggaactttag aagagagaga taactttccc cagtgtccat caatacacaa ccaaacacaa   1980
actctatatt tacacatata accccctctc tagaatggct gtttacaatt atgatgttgt   2040
tgttatcggt acaggtccag cgggtgaagg tgccgctatg aatgcagtca aagctggtag   2100
aaaagttgca gttgttgatg atagaccaca agttggcggt aattgtacgc acttaggcac   2160
tatcccaagt aaggctttaa ggcactctgt tagacaaatt atgcagtaca acaacaaccc   2220
attattccgt caaattggtg aaccaagatg gttctctttc gctgacgttc taaaatcagc   2280
agagcaagtt attgcgaagc aagtctcttc cagaaccgga tattatgcta gaaacagaat   2340
tgataccttt ttcggtaccg catcattctg tgacgagcat actattgaag tcgttcattt   2400
gaatggtatg gtcgaaacct tggtcgcaaa gcaatttgtt attgctaccg gttcaagacc   2460
ttatagacca gccgatgtgg actttactca ccctaggatc tacgattctg atactatctt   2520
atctttgggt catactccaa gacgtttgat tatctacgga gctggtgtta tcggttgcga   2580
atacgcaagt attttctcag gactaggtgt tttagtcgat ttgattgaca atcgtgatca   2640
attactatct tttctcgatg acgaaatttc cgactcattg tcttatcact taaggaataa   2700
caatgtctta atcagacata acgaggagta cgaaagagtt gaaggcctcg acaacggtgt   2760
cattttacat ttgaagtctg gtaaaaagat caaggcagat gcattccttt ggtccaacgg   2820
tagaaccggt aacactgata agttgggtct tgaaaacatt ggtttaaagg ctaatggtag   2880
aggtcaaatt caagtcgatg agcattatag aaccgaagtt tccaacatct acgctgctgg   2940
tgatgttatt ggttggccat ctttggcatc tgctgcttac gatcaaggta gatccgctgc   3000
tggctccatc actgaaaacg actcctggag atttgttgac gatgtcccta ccggtatcta   3060
caccattcca gaaatttcca gtgttggtaa gacagaaaga gaacttactc aggcaaaagt   3120
tccatacgag gttggtaagg ccttttttcaa aggtatggca agagcccaga ttgctgttga   3180
aaaggcaggc atgttaaaga ttttgtttca cagagaaaca ctcgaaatct taggcgtcca   3240
ttgttttggt tatcaagcat ctgaaattgt gcacatcggt caagcaatta tgaaccaaaa   3300
gggtgaagcc aacactttga agtatttcat taatactaca ttcaattatc ctacaatggc   3360
agaagcatat agagtggctg cgtacgatgg tttgaacaga ttgttctaat taattaacat   3420
ctgaatgtaa aatgaacatt aaaatgaatt actaaacttt acgtctactt tacaatctat   3480
aaactttgtt taatcatata acgaaataca ctaatacaca atcctgtacg tatgtaatac   3540
```

```
ttttatccat caaggattga gaaaaaaaag taatgattcc ctgggccatt aaaacttaga   3600
cccccaagct tggataggtc actctctatt ttcgtttctc ccttccctga tagaagggtg   3660
atatgtaatt aagaataata tataatttta taataaaaga attcatagcc tcatgaaatc   3720
agccatttgc ttttgttcaa cgatcttttg aaattgttgt tgttcttggt agttaagttg   3780
atccatcttg gcttatgttg tgtgtatgtt gtagttattc ttagtatatt cctgtcctga   3840
gtttagtgaa acataatatc gccttgaaat gaaaatgctg aaattcgtcg acatacaatt   3900
tttcaaactt tttttttttc ttggtgcacg gacatgtttt taaaggaagt actctatacc   3960
agttattctt cacaaattta attgctggag aatagatctt caacgcttta ataaagtagt   4020
ttgtttgtca aggatggcgt catacaaaga aagatcagaa tcacacactt cccctgttgc   4080
taggagactt ttctccatca tggaggaaaa gaagtctaac ctttgtgcat cattggatat   4140
tactgaaact gaaaagcttc tctctatttt ggacactatt ggtccttaca tctgtctagt   4200
taaaacacac atcgatattg tttctgattt tacgtatgaa ggaactgtgt tgcctttgaa   4260
ggagcttgcc aagaaacata attttatgat tttgaagat agaaaatttg ctgatattgg    4320
taacactgtt aaaaatcaat ataaatctgg tgtcttccgt attgccgaat gggctgacat   4380
cactaatgca catggtgtaa cgggtgcagg tattgtttct ggcttgaagg aggcagccca   4440
agaaacaacc agtgaaccta gaggtttgct aatgcttgct gagttatcat caaagggttc   4500
tttagcatat ggtgaatata cagaaaaaac agtagaaatt gctaaatctg ataaagagtt   4560
tgtcattggt tttattgcgc aacacgatat gggcggtaga gaagaaggtt ttgactggat   4620
cattatgact ccaggggttg gtttagatga caaaggtgat gcacttggtc aacaatatag   4680
aactgttgat gaagttgtaa agactggaac ggatatcata attgttggta gaggtttgta   4740
cggtcaagga agagatccta tagagcaagc taaaagatac caacaagctg gttggaatgc   4800
ttatttaaac agatttaaat gattcttaca caaagatttg atacatgtac actagtttaa   4860
ataagcatga aaagaattac acaagcaaaa aaaaaaaaat aaatgaggta ctttacgttc   4920
acctacaacc aaaaaaacta gatagagtaa aatcttaaga tttagaaaaa gttgtttaac   4980
aaaggcttta gtatgtgaat ttttaatgta gcaaagcgat aactaataaa cataaacaaa   5040
agtatggttt tctttatcag tcaaatcatt atcgattgat tgttccgcgt atctgcagat   5100
agcctcatga aatcagccat ttgcttttgt tcaacgatct tttgaaattg ttgttgttct   5160
tggtagttaa gttgatccat cttggcttat gttgtgtgta tgttgtagtt attcttagta   5220
tattcctgtc ctgagtttag tgaaacataa tatcgccttg aaatgaaaat gctgaaattc   5280
gtcgacatac aatttttcaa actttttttt tttcttggtg cacggacatg tttttaaagg   5340
aagtactcta taccagttat tcttcacaaa tttaattgct ggagaataga tcttcaacgc   5400
cccgggggat ctggatccgc ggccgcaata acctcaggga gaactttggc attgtactct   5460
ccattgacga gtccgccaac ccattcttgt taaacctaac cttgcattat cacattccct   5520
ttgaccccct ttagctgcat ttccacttgt ctacattaag attcattaca cattcttttt   5580
cgtatttctc ttacctccct ccccctcca tggatcttat atataaatct tttctataac    5640
aataatatct actagagtta aacaacaatt ccacttggca tggctgtctc agcaaatctg   5700
cttctaccta ctgcacgggt ttgcatgtca ttgtttctag cagggaatcg tccatgtacg   5760
ttgtcctcca tgatggtctt cccgctgcca ctttctttag tatcttaaat agagcagatc   5820
ttacgtccac tgtgcatccg tgcaccccga aaatcgtatg gttttccttg ccacctctca   5880
```

```
caattttgaa tatgctcaac gcgaaagaga ggggaagagg aatcgcattc gtagagtggc   5940

tacattcaac cctgacaaag gaactagcgt ttgtgcagga gagagtggtt tgcatagatt   6000

tcctttcctt tgcaagcata ttatatagag tagccaatac agtaacagct acagcacaaa   6060

aaagagaacg agaacgagaa cgagaacaag aacaagaact agcactactg tcactgccag   6120

catcaacatt actaccatta ttccaacatg tttgcaacta gaaatataac cattggtgtc   6180

agaacactca gaccaaccag tttcttgaaa acaaggtctt ttctgcaaca gaggctacaa   6240

tcaacgctaa agaagagcta tgaaccaacc aaatcc                             6276
```

<210> SEQ ID NO 138
<211> LENGTH: 6892
<212> TYPE: DNA
<213> ORGANISM: Artificial
<220> FEATURE:
<223> OTHER INFORMATION: Pseudomonas fluoresens SthA MEL integration fragment
<220> FEATURE:
<221> NAME/KEY: misc_feature
<222> LOCATION: (3975)..(3975)
<223> OTHER INFORMATION: n is a, c, g, or t

<400> SEQUENCE: 138

```
cggatttggt tggttcatag ctcttcttta gcgttgattg tagcctctgt tgcagaaaag     60

accttgtttt caagaaactg gttggtctga gtgttctgac accaatggtt atatttctag    120

ttgcaaacat gttggaataa tggtagtaat gttgatgctg gcagtgacag tagtgctagt    180

tcttgttctt gttctcgttc tcgttctcgt tctctttttt gtgctgtagc tgttactgta    240

ttggctactc tatataatat gcttgcaaag gaaaggaaat ctatgcaaac cactctctcc    300

tgcacaaacg ctagttcctt tgtcagggtt gaatgtagcc actctacgaa tgcgattcct    360

cttcccctct ctttcgcgtt gagcatattc aaaattgtga gaggtggcaa ggaaaaccat    420

acgatttcg gggtgcacgg atgcacagtg gacgtaagat ctgctctatt taagatacta    480

aagaaagtgg cagcgggaag accatcatgg aggacaacgt acatggacga ttccctgcta    540

gaaacaatga catgcaaacc cgtgcagtag gtagaagcag atttgctgag acagccatgc    600

caagtggaat tgttgtttaa ctctagtaga tattattgtt atagaaaaga tttatatata    660

agatccatgg aggggggagg gaggtaagag aaatacgaaa aagaatgtgt aatgaatctt    720

aatgtagaca agtggaaatg cagctaaagg gggtcaaagg gaatgtgata atgcaaggtt    780

aggtttaaca agaatgggtt ggcggactcg tcaatggaga gtacaatgcc aaagttctcc    840

ctgaggttat tgcggccgcg gatccctcga gattggtagt tctttccccc tctcaagctg    900

gcgtgaaatg caaccttacg gcgtctacgt tactacaagg tccagaaagt gtaggtattg    960

ctactatttt tattttttat tggttctgga gaaatgcaga cagtcaatga acacaactgt   1020

ctcaatatgc atctatgcac atgcacacac acacacatca caggtacccc tacaaagaga   1080

ggtctcttga taatgtttca ttaccacgtg gcatcccccc cccccccccc aataaacaag   1140

tggccgagtt cccctgttgc agaggaggac aaaaaaaccg ctggtgttgg taccattatg   1200

cagcaactag cacaacaaac aaccgaccca gacatacaaa tcaacaacac ttcgccaaag   1260

acaccctttc cagggaggat ccactcccaa cgtctctcca taatgtctct gttggcccat   1320

gtctctgtcg ttgacaccgt aaccacacca accaacccgt ccattgtact gggatggtcg   1380

tccatagaca cctctccaac ggggaacacc tcattcgtaa accgccaagg ttaccgttcc   1440

tcctgactcg ccccgttgtt gatgctgcgc acctgtggtt gcccaacatg gttgtatatc   1500
```

```
gtgtaaccac accaacacat gtgcagcaca tgtgtttaaa agagtgtcat ggaggtggat   1560
catgatggaa gtggacttta ccacttggga actgtctcca ctcccgggaa gaaaagaccc   1620
ggcgtatcac gcggttgcct caatggggca atttggaagg agaaatatag ggaaaatcac   1680
gtcgctctcg gacggggaag agttccagac tatgaggggg gggggtggta tataaagaca   1740
ggagatgtcc acccccagag agaggaagaa gttggaactt tagaagagag agataacttt   1800
ccccagtgtc catcaataca caaccaaaca caaactctat atttacacat ataacccccct   1860
ctctagataa aatggctgtt tataactacg acgttgttgt tttgggttct ggtccagcag   1920
gcgaaggtgc tgctatgaat gcagctaaag caggcagaaa agttgctatg gttgattcac   1980
gtagacaagt cggtggtaac tgtacccact taggtactat tccttctaag gctttgagac   2040
actctgttcg tcaaatcatg caattcaaca ctaatccaat gttcagagcc attggcgaac   2100
caagatggtt ctcctttcca gatgttttaa agtctgcaga aaaggttatt tccaagcaag   2160
tcgcttctcg taccggctat tacgctagaa acagagttga tttgtttttc ggtactggtt   2220
ccttcgcaga tgaacagact gttgaagtcg tttgtgcaaa tggtgttgtc gagaagttag   2280
ttgctaagca tattatcatc gccacaggtt ccagacctta cagaccagca gacatcgatt   2340
tccatcatcc acgtatctac gactctgata ccatcttatc tttaggccac acccctagaa   2400
agttgattat ctacggtgcc ggtgttatcg gttgcgagta tgcttctatc ttttcaggtt   2460
tgggtgtctt agtcgagttg gtcgataaca gagatcaact tttgtccttt ttagactctg   2520
aaatttctca agctctttcc tatcactttt ctaataacaa cattacagtt agacataatg   2580
aggaatacga cagagtcgaa ggtttagata acggtgttat tttgcatttg aagtccggta   2640
aaaagattaa ggccgatgca ttgttatggt gtaacggtag aactggtaat actgacaagt   2700
taggtatgga aaacattggt gttaaggtca actccagagg tcaaattgaa gttgacgaga   2760
attacagaac ctgtgtcaca aacatttatg gtgctggtga tgttattggt tggccatcac   2820
ttgcctcagc agctcacgac caaggtagat cagcagctgg ctctatcgtt gataatggtt   2880
cctggagata tgtcaacgat gttccaaccg gtatctacac tattccagaa atttcctcaa   2940
ttggtaaaaa tgaacacgaa ttgactaaag ctaaggttcc ttatgaggtc ggtaaagcct   3000
ttttcaagtc tatggcaaga gcacaaattg ctggtgaacc acagggtatg cttaaaatct   3060
tattccatag agaaacttta gaagtcttag gtgttcactg ttttggttat caagcatccg   3120
aaattgttca tattggccag gcaattatga accaaccagg tgaacaaaat actcttaagt   3180
acttcgtcaa taccaccttc aactacccaa caatggctga agcatataga gttgcagctt   3240
acgatggttt gaacagattg ttctaattaa ttaacatctg aatgtaaaat gaacattaaa   3300
atgaattact aaactttacg tctactttac aatctataaa ctttgtttaa tcatataacg   3360
aaatacacta atacacaatc ctgtacgtat gtaatacttt tatccatcaa ggattgagaa   3420
aaaaaagtaa tgattccctg ggccattaaa acttagaccc ccaagcttgg ataggtcact   3480
ctctattttc gtttctccct tccctgatag aagggtgata tgtaattaag aataatatat   3540
aattttataa taaaagaatt cgcccttacc tgcagggata acttcgtata atgtatgcta   3600
tacgaagtta tgctgcaacg gcaacatcaa tgtccacgtt tacacaccta catttatatc   3660
tatatttata tttatattta tttatttatg ctacttagct tctatagtta gttaatgcac   3720
tcacgatatt caaaattgac acccttcaac tactccctac tattgtctac tactgtctac   3780
tactcctctt tactatagct gctcccaata ggctccacca ataggctctg tcaatacatt   3840
ttgcgccgcc acctttcagg ttgtgtcact cctgaaggac catattgggt aatcgtgcaa   3900
```

```
tttctggaag agagtgccgc gagaagtgag gcccccactg taaatcctcg agggggcatg   3960
gagtatgggg catgnaggat ggaggatggg gggggggggg gaaaataggt agcgaaagga   4020
cccgctatca ccccacccgg agaactcgtt gccgggaagt catatttcga cactccgggg   4080
agtctataaa aggcgggttt tgtcttttgc cagttgatgt tgctgagagg acttgtttgc   4140
cgtttcttcc gatttaacag tatagaatca accactgtta attatacacg ttatactaac   4200
acaacaaaaa caaaaacaac gacaacaaca acaacaatgt ttgctttcta ctttctcacc   4260
gcatgcacca ctttgaaggg tgttttcgga gtttctccga gttacaatgg tcttggtctc   4320
accccacaga tgggttggga cagctggaat acgtttgcct gcgatgtcag tgaacagcta   4380
cttctagaca ctgctgatag aatttctgac ttggggctaa aggatatggg ttacaagtat   4440
gtcatcctag atgactgttg gtctagcggc agggattccg acggtttcct cgttgcagac   4500
aagcacaaat ttcccaacgg tatgggccat gttgcagacc acctgcataa taacagcttt   4560
cttttcggta tgtattcgtc tgctggtgag tacacctgtg ctgggtaccc tgggtctctg   4620
gggcgtgagg aagaagatgc tcaattcttt gcaaataacc gcgttgacta cttgaagtat   4680
gataattgtt acaataaagg tcaatttggt acaccagacg tttcttacca ccgttacaag   4740
gccatgtcag atgctttgaa taaaactggt aggcctattt tctattctct atgtaactgg   4800
ggtcaggatt tgacatttta ctggggctct ggtatcgcca attcttggag aatgagcgga   4860
gatattactg ctgagttcac ccgtccagat agcagatgtc cctgtgacgg tgacgaatat   4920
gattgcaagt acgccggttt ccattgttct attatgaata ttcttaacaa ggcagctcca   4980
atggggcaaa atgcaggtgt tggtggttgg aacgatctgg acaatctaga ggtcggagtc   5040
ggtaatttga ctgacgatga ggaaaaggcc catttctcta tgtgggcaat ggtaaagtcc   5100
ccacttatca ttggtgccga cgtgaatcac ttaaaggcat cttcgtactc gatctacagt   5160
caagcctctg tcatcgcaat taatcaagat ccaaagggta ttccagccac aagagtctgg   5220
agatattatg tttcagacac cgatgaatat ggacaaggtg aaattcaaat gtggagtggt   5280
ccgcttgaca atggtgacca agtggttgct ttattgaatg gaggaagcgt agcaagacca   5340
atgaacacga ccttggaaga gattttcttt gacagcaatt tgggttcaaa ggaactgaca   5400
tcgacttggg atatttacga cttatgggcc aacagagttg acaactctac ggcgtctgct   5460
atccttgaac agaataaggc agccaccggt attctctaca atgctacaga gcagtcttat   5520
aaagacggtt tgtctaagaa tgatacaaga ctgtttggcc agaaaattgg tagtctttct   5580
ccaaatgcta tacttaacac aactgttcca gctcatggta tcgccttcta taggttgaga   5640
ccctcggctt aagctcaatg ttgagcaaag caggacgaga aaaaaaaaaa taatgattgt   5700
taagaagttc atgaaaaaaa aaaggaaaaa tactcaaata cttataacag agtgattaaa   5760
taataaacgg cagtataccc tatcaggtat tgagatagtt ttatttttgt aggtatataa   5820
tctgaagcct ttgaactatt ttctcgtata tatcatggag tatacattgc attagcaaca   5880
ttgcatacta gttcataact tcgtataatg tatgctatac gaagttatta attaacaagg   5940
gcgaattcct tgatttatat acacctttgc caaccgcttg ttacttgata aggaaaagat   6000
agatttctaa agtgcaggaa aagaaacgcc actacgtcat gaaacaaaag aaatgaaaca   6060
ctctgcaaaa gggaaaacca atgacgcctt caaaacgtac tgactttccg cctccttttc   6120
tgcctttttt ttttctccct caatttgcca attccccttt ccgctaattt tacatcacct   6180
ttttgtttgt ttccctttc ggccaagttt tccatttctt ttttcggctg agcccttctt   6240
```

```
tggcgtcgac gtaatttctc ggcatgtggc caatgtatat tgacagtaga tgaagtagac   6300
gttcttagta actgttaggg tgagattgcc acccccccctt ccttctttta ctatctgtaa   6360
taccatcacc atagcaatag tttaaccatg ttggagctgg aaatacaacg tctatagagg   6420
gaagtcatca tattacgcca ttttacggac cagggacacc ctgtagtgtg tttcctctct   6480
tgtagaggta ggttttcaaa tggactctgg cgtcgatttc cagcaagtca ttcccgtggt   6540
tcaccatttc tactttttgc gctacctctc ttgacacaga aatgaatgat gacgtgtaaa   6600
ttacccgtcc gagacctgga ctccggagaa actgtattaa ttacgcgcca aacaagacag   6660
gtgtcggata aacgtgcatg tacagactgc gagccgaaaa cggaaggggg gaaagaaaac   6720
agtggagtcc cattgttgtt ccggaaatgg aaaacgggaa ctggcggaaa agaaacgaaa   6780
caaaacaaaa gaaaaagagg aaaaaaaaga aaaaaaaaag aaaaagacac tgcacgtgat   6840
tgctggtgtg tgctgcgtaa ccgcggcact ttatttcgta aatgaagggg cc           6892
```

```
<210> SEQ ID NO 139
<211> LENGTH: 1395
<212> TYPE: DNA
<213> ORGANISM: Pseudomonas fluorescens

<400> SEQUENCE: 139

ttagaacaat ctgttcaaac catcgtaagc tgcaactcta tatgcttcag ccattgttgg     60
gtagttgaag gtggtattga cgaagtactt aagagtattt tgttcacctg gttggttcat    120
aattgcctgg ccaatatgaa caatttcgga tgcttgataa ccaaaacagt gaacacctaa    180
gacttctaaa gtttctctat ggaataagat tttaagcata ccctgtggtt caccagcaat    240
ttgtgctctt gccatagact tgaaaaaggc tttaccgacc tcataaggaa ccttagcttt    300
agtcaattcg tgttcatttt taccaattga ggaaatttct ggaatagtgt agataccggt    360
tggaacatcg ttgacatatc tccaggaacc attatcaacg atagagccag ctgctgatct    420
accttggtcg tgagctgctg aggcaagtga tggccaacca ataacatcac cagcaccata    480
aatgtttgtg acacaggttc tgtaattctc gtcaacttca atttgacctc tggagttgac    540
cttaacacca atgttttcca tacctaactt gtcagtatta ccagttctac cgttacacca    600
taacaatgca tcggccttaa tctttttacc ggacttcaaa tgcaaaataa caccgttatc    660
taaaccttcg actctgtcgt attcctcatt atgtctaact gtaatgttgt tattagaaaa    720
gtgataggaa agagcttgag aaatttcaga gtctaaaaag gacaaaagtt gatctctgtt    780
atcgaccaac tcgactaaga cacccaaacc tgaaaagata gaagcatact cgcaaccgat    840
aacaccggca ccgtagataa tcaactttct aggggtgtgg cctaaagata agatggtatc    900
agagtcgtag atacgtggat gatggaaatc gatgtctgct ggtctgtaag gtctggaacc    960
tgtggcgatg ataatatgct tagcaactaa cttctcgaca acaccatttg cacaaacgac   1020
ttcaacagtc tgttcatctg cgaaggaacc agtaccgaaa aacaaatcaa ctctgtttct   1080
agcgtaatag ccggtacgag aagcgacttg cttggaaata acctttctg cagactttaa   1140
aacatctgga aaggagaacc atcttggttc gccaatggct ctgaacattg gattagtgtt   1200
gaattgcatg atttgacgaa cagagtgtct caaagcctta gaaggaatag tacctaagtg   1260
ggtacagtta ccaccgactt gtctacgtga atcaaccata gcaacttttc tgcctgcttt   1320
agctgcattc atagcagcac cttcgcctgc tggaccagaa cccaaaacaa caacgtcgta   1380
gttataaaca gccat                                                    1395
```

<210> SEQ ID NO 140
<211> LENGTH: 6281
<212> TYPE: DNA
<213> ORGANISM: Artificial
<220> FEATURE:
<223> OTHER INFORMATION: Pseudomonas fluorescens URA integration fragment

<400> SEQUENCE: 140

```
cggatttggt tggttcatag ctcttcttta gcgttgattg tagcctctgt tgcagaaaag     60
accttgtttt caagaaactg gttggtctga gtgttctgac accaatggtt atatttctag    120
ttgcaaacat gttggaataa tggtagtaat gttgatgctg gcagtgacag tagtgctagt    180
tcttgttctt gttctcgttc tcgttctcgt tctctttttt gtgctgtagc tgttactgta    240
ttggctactc tatataatat gcttgcaaag gaaaggaaat ctatgcaaac cactctctcc    300
tgcacaaacg ctagttcctt tgtcagggtt gaatgtagcc actctacgaa tgcgattcct    360
cttcccctct ctttcgcgtt gagcatattc aaaattgtga gaggtggcaa ggaaaaccat    420
acgattttcg ggtgcacgg atgcacagtg gacgtaagat ctgctctatt taagatacta    480
aagaaagtgg cagcgggaag accatcatgg aggacaacgt acatggacga ttccctgcta    540
gaaacaatga catgcaaacc cgtgcagtag gtagaagcag atttgctgag acagccatgc    600
caagtggaat tgttgtttaa ctctagtaga tattattgtt atagaaaaga tttatatata    660
agatccatgg aggggggagg gaggtaagag aaatacgaaa aagaatgtgt aatgaatctt    720
aatgtagaca agtggaaatg cagctaaagg gggtcaaagg gaatgtgata atgcaaggtt    780
aggtttaaca agaatgggtt ggcggactcg tcaatggaga gtacaatgcc aaagttctcc    840
ctgaggttat tgcggccgcg gatccagatc ccccggggcg ttgaagatct attctccagc    900
aattaaattt gtgaagaata actggtatag agtacttcct ttaaaaacat gtccgtgcac    960
caagaaaaaa aaaaagtttg aaaaattgta tgtcgacgaa tttcagcatt ttcatttcaa   1020
ggcgatatta tgtttcacta aactcaggac aggaatatac taagaataac tacaacatac   1080
acacaacata agccaagatg gatcaactta actaccaaga acaacaacaa tttcaaaaga   1140
tcgttgaaca aaagcaaatg gctgatttca tgaggctatc tgcagatacg cggaacaatc   1200
aatcgataat gatttgactg ataaagaaaa ccatactttt gtttatgttt attagttatc   1260
gctttgctac attaaaaatt cacatactaa agcctttgtt aaacaacttt ttctaaatct   1320
taagatttta ctctatctag tttttttggt tgtaggtgaa cgtaaagtac ctcatttatt   1380
ttttttttt tgcttgtgta attcttttca tgcttattta aactagtgta catgtatcaa   1440
atctttgtgt aagaatcatt taaatctgtt taaataagca ttccaaccag cttgttggta   1500
tcttttagct tgctctatag gatctcttcc ttgaccgtac aaacctctac caacaattat   1560
gatatccgtt ccagtcttta caacttcatc aacagttcta tattgttgac caagtgcatc   1620
acctttgtca tctaaaccaa cccctggagt cataatgatc cagtcaaaac cttcttctct   1680
accgcccata tcgtgttgcg caataaaacc aatgacaaac tctttatcag atttagcaat   1740
ttctactgtt ttttctgtat attcaccata tgctaaagaa ccctttgatg ataactcagc   1800
aagcattagc aaacctctag gttcactggt tgtttcttgg gctgcctcct tcaagccaga   1860
aacaatacct gcacccgtta caccatgtgc attagtgatg tcagcccatt cggcaatacg   1920
gaagacacca gatttatatt gatttttaac agtgttacca atatcagcaa attttctatc   1980
ttcaaaaatc ataaaattat gtttcttggc aagctccttc aaaggcaaca cagttccttc   2040
atacgtaaaa tcagaaacaa tatcgatgtg tgttttaact agacagatgt aaggaccaat   2100
```

```
agtgtccaaa atagagagaa gcttttcagt ttcagtaata tccaatgatg cacaaaggtt   2160
agacttcttt tcctccatga tggagaaaag tctcctagca acaggggaag tgtgtgattc   2220
tgatctttct ttgtatgacg ccatccttga caaacaaact actttattaa agcgttgaag   2280
atctattctc cagcaattaa atttgtgaag aataactggt atagagtact tcctttaaaa   2340
acatgtccgt gcaccaagaa aaaaaaaaag tttgaaaaat tgtatgtcga cgaatttcag   2400
cattttcatt tcaaggcgat attatgtttc actaaactca ggacaggaat atactaagaa   2460
taactacaac atacacacaa cataagccaa gatggatcaa cttaactacc aagaacaaca   2520
acaatttcaa aagatcgttg aacaaaagca aatggctgat ttcatgaggc tatgaattct   2580
tttattataa aattatatat tattcttaat tacatatcac ccttctatca gggaagggag   2640
aaacgaaaat agagagtgac ctatccaagc ttgggggtct aagttttaat ggcccaggga   2700
atcattactt tttttctca atccttgatg gataaaagta ttacatacgt acaggattgt   2760
gtattagtgt atttcgttat atgattaaac aaagtttata gattgtaaag tagacgtaaa   2820
gtttagtaat tcattttaat gttcatttta cattcagatg ttaattaatt agaacaatct   2880
gttcaaacca tcgtaagctg caactctata tgcttcagcc attgttgggt agttgaaggt   2940
ggtattgacg aagtacttaa gagtattttg ttcacctggt tggttcataa ttgcctggcc   3000
aatatgaaca atttcggatg cttgataacc aaaacagtga acacctaaga cttctaaagt   3060
ttctctatgg aataagattt taagcatacc ctgtggttca ccagcaattt gtgctcttgc   3120
catagacttg aaaaaggctt taccgacctc ataaggaacc ttagctttag tcaattcgtg   3180
ttcattttta ccaattgagg aaatttctgg aatagtgtag ataccggttg gaacatcgtt   3240
gacatatctc caggaaccat tatcaacgat agagccagct gctgatctac cttggtcgtg   3300
agctgctgag gcaagtgatg gccaaccaat aacatcacca gcaccataaa tgtttgtgac   3360
acaggttctg taattctcgt caacttcaat ttgacctctg gagttgacct taacaccaat   3420
gttttccata cctaacttgt cagtattacc agttctaccg ttacaccata acaatgcatc   3480
ggccttaatc tttttaccgg acttcaaatg caaaataaca ccgttatcta aaccttcgac   3540
tctgtcgtat tcctcattat gtctaactgt aatgttgtta ttagaaaagt gataggaaag   3600
agcttgagaa atttcagagt ctaaaaagga caaaagttga tctctgttat cgaccaactc   3660
gactaagaca cccaaacctg aaaagataga agcatactcg caaccgataa caccggcacc   3720
gtagataatc aactttctag ggtgtggcc taaagataag atggtatcag agtcgtagat   3780
acgtggatga tggaaatcga tgtctgctgg tctgtaaggt ctggaacctg tggcgatgat   3840
aatatgctta gcaactaact tctcgacaac accatttgca caaacgactt caacagtctg   3900
ttcatctgcg aaggaaccag taccgaaaaa caaatcaact ctgtttctag cgtaatagcc   3960
ggtacgagaa gcgacttgct tggaaataac cttttctgca gactttaaaa catctggaaa   4020
ggagaaccat cttggttcgc caatggctct gaacattgga ttagtgttga attgcatgat   4080
ttgacgaaca gagtgtctca aagccttaga aggaatagta cctaagtggg tacagttacc   4140
accgacttgt ctacgtgaat caaccatagc aacttttctg cctgctttag ctgcattcat   4200
agcagcacct tcgcctgctg gaccagaacc caaaacaaca acgtcgtagt tataaacagc   4260
cattttatct agagaggggg ttatatgtgt aaatatagag tttgtgtttg gttgtgtatt   4320
gatggacact ggggaaagtt atctctctct tctaaagttc caacttcttc ctctctctgg   4380
gggtggacat ctcctgtctt tatataccac ccccccccct catagtctgg aactcttccc   4440
```

```
cgtccgagag cgacgtgatt ttccctatat ttctccttcc aaattgcccc attgaggcaa   4500
ccgcgtgata cgccgggtct tttcttcccg ggagtggaga cagttcccaa gtggtaaagt   4560
ccacttccat catgatccac ctccatgaca ctcttttaaa cacatgtgct gcacatgtgt   4620
tggtgtggtt acacgatata caaccatgtt gggcaaccac aggtgcgcag catcaacaac   4680
ggggcgagtc aggaggaacg gtaaccttgg cggtttacga atgaggtgtt ccccgttgga   4740
gaggtgtcta tggacgacca tcccagtaca atggacgggt tggttggtgt ggttacggtg   4800
tcaacgacag agacatgggc caacagagac attatggaga gacgttggga gtggatcctc   4860
cctggaaagg gtgtctttgg cgaagtgttg ttgatttgta tgtctgggtc ggttgtttgt   4920
tgtgctagtt gctgcataat ggtaccaaca ccagcggttt ttttgtcctc ctctgcaaca   4980
ggggaactcg gccacttgtt tattgggggg gggggggggg atgccacgtg gtaatgaaac   5040
attatcaaga gacctctctt tgtaggggta cctgtgatgt gtgtgtgtgt gcatgtgcat   5100
agatgcatat tgagacagtt gtgttcattg actgtctgca tttctccaga accaataaaa   5160
aataaaaata gtagcaatac ctacactttc tggaccttgt agtaacgtag acgccgtaag   5220
gttgcatttc acgccagctt gagaggggga aagaactacc aatctcgagg gatccgcggc   5280
cgcaaataaa tttaaaataa acgatatcaa aattcaaagg gttcaaagtg ggaattcctt   5340
gatttatata cacctttgcc aaccgcttgt tacttgataa ggaaaagata gatttctaaa   5400
gtgcaggaaa agaaacgcca ctacgtcatg aaacaaaaga aatgaaacac tctgcaaaag   5460
ggaaaaccaa tgacgccttc aaaacgtact gactttccgc ctccttttct gccttttttt   5520
tttctccctc aatttgccaa ttccccttc cgctaatttt acatcacctt tttgtttgtt   5580
tcccttttcg gccaagtttt ccatttcttt tttcggctga gcccttcttt ggcgtcgacg   5640
taatttctcg gcatgtggcc aatgtatatt gacagtagat gaagtagacg ttcttagtaa   5700
ctgttagggt gagattgcca cccccccttc cttcttttac tatctgtaat accatcacca   5760
tagcaatagt ttaaccatgt tggagctgga aatacaacgt ctatagaggg aagtcatcat   5820
attacgccat tttacggacc agggacaccc tgtagtgtgt ttcctctctt gtagaggtag   5880
gttttcaaat ggactctggc gtcgatttcc agcaagtcat tcccgtggtt caccatttct   5940
actttttgcg ctacctctct tgacacagaa atgaatgatg acgtgtaaat tacccgtccg   6000
agacctggac tccggagaaa ctgtattaat tacgcgccaa acaagacagg tgtcggataa   6060
acgtgcatgt acagactgcg agccgaaaac ggaagggggg aaagaaaaca gtggagtccc   6120
attgttgttc cggaaatgga aaacgggaac tggcggaaaa gaaacgaaac aaaacaaaag   6180
aaaaagagga aaaaaaagaa aaaaaaaaga aaaagacact gcacgtgatt gctggtgtgt   6240
gctgcgtaac cgcggcactt tatttcgtaa atgaaggggc c                        6281
```

<210> SEQ ID NO 141
<211> LENGTH: 34
<212> TYPE: DNA
<213> ORGANISM: Artificial
<220> FEATURE:
<223> OTHER INFORMATION: Primer

<400> SEQUENCE: 141

```
aaagggttaa ttaattagaa caatctgttc aaac                                  34
```

<210> SEQ ID NO 142
<211> LENGTH: 20
<212> TYPE: DNA
<213> ORGANISM: Artificial

<220> FEATURE:
<223> OTHER INFORMATION: Primer

<400> SEQUENCE: 142
ctgttcaaac catcgtaagc 20

<210> SEQ ID NO 143
<211> LENGTH: 30
<212> TYPE: DNA
<213> ORGANISM: Artificial
<220> FEATURE:
<223> OTHER INFORMATION: Primer

<400> SEQUENCE: 143
gtagttgaag gtggtattaa cgaaatattc 30

<210> SEQ ID NO 144
<211> LENGTH: 18
<212> TYPE: DNA
<213> ORGANISM: Artificial
<220> FEATURE:
<223> OTHER INFORMATION: Primer

<400> SEQUENCE: 144
ggaactgtgt tgcctttg 18

<210> SEQ ID NO 145
<211> LENGTH: 32
<212> TYPE: DNA
<213> ORGANISM: Artificial
<220> FEATURE:
<223> OTHER INFORMATION: Primer

<400> SEQUENCE: 145
gaataaaact ggtaggccta ttttctattc tc 32

<210> SEQ ID NO 146
<211> LENGTH: 464
<212> TYPE: PRT
<213> ORGANISM: Pseudomonas fluorescens

<400> SEQUENCE: 146

```
Met Ala Val Tyr Asn Tyr Asp Val Val Val Leu Gly Ser Gly Pro Ala
1               5                   10                  15

Gly Glu Gly Ala Ala Met Asn Ala Ala Lys Ala Gly Arg Lys Val Ala
            20                  25                  30

Met Val Asp Ser Arg Arg Gln Val Gly Gly Asn Cys Thr His Leu Gly
        35                  40                  45

Thr Ile Pro Ser Lys Ala Leu Arg His Ser Val Arg Gln Ile Met Gln
    50                  55                  60

Phe Asn Thr Asn Pro Met Phe Arg Ala Ile Gly Glu Pro Arg Trp Phe
65                  70                  75                  80

Ser Phe Pro Asp Val Leu Lys Ser Ala Glu Lys Val Ile Ser Lys Gln
                85                  90                  95

Val Ala Ser Arg Thr Gly Tyr Tyr Ala Arg Asn Arg Val Asp Leu Phe
            100                 105                 110

Phe Gly Thr Gly Ser Phe Ala Asp Glu Gln Thr Val Glu Val Val Cys
        115                 120                 125

Ala Asn Gly Val Val Glu Lys Leu Val Ala Lys His Ile Ile Ile Ala
    130                 135                 140

Thr Gly Ser Arg Pro Tyr Arg Pro Ala Asp Ile Asp Phe His His Pro
```

-continued

```
145                 150                 155                 160

Arg Ile Tyr Asp Ser Asp Thr Ile Leu Ser Leu Gly His Thr Pro Arg
                165                 170                 175

Lys Leu Ile Ile Tyr Gly Ala Gly Val Ile Gly Cys Glu Tyr Ala Ser
            180                 185                 190

Ile Phe Ser Gly Leu Gly Val Leu Val Glu Leu Val Asp Asn Arg Asp
        195                 200                 205

Gln Leu Leu Ser Phe Leu Asp Ser Glu Ile Ser Gln Ala Leu Ser Tyr
    210                 215                 220

His Phe Ser Asn Asn Asn Ile Thr Val Arg His Asn Glu Glu Tyr Asp
225                 230                 235                 240

Arg Val Glu Gly Leu Asp Asn Gly Val Ile Leu His Leu Lys Ser Gly
                245                 250                 255

Lys Lys Ile Lys Ala Asp Ala Leu Leu Trp Cys Asn Gly Arg Thr Gly
            260                 265                 270

Asn Thr Asp Lys Leu Gly Met Glu Asn Ile Gly Val Lys Val Asn Ser
        275                 280                 285

Arg Gly Gln Ile Glu Val Asp Glu Asn Tyr Arg Thr Cys Val Thr Asn
    290                 295                 300

Ile Tyr Gly Ala Gly Asp Val Ile Gly Trp Pro Ser Leu Ala Ser Ala
305                 310                 315                 320

Ala His Asp Gln Gly Arg Ser Ala Ala Gly Ser Ile Val Asp Asn Gly
                325                 330                 335

Ser Trp Arg Tyr Val Asn Asp Val Pro Thr Gly Ile Tyr Thr Ile Pro
            340                 345                 350

Glu Ile Ser Ser Ile Gly Lys Asn Glu His Glu Leu Thr Lys Ala Lys
        355                 360                 365

Val Pro Tyr Glu Val Gly Lys Ala Phe Phe Lys Ser Met Ala Arg Ala
    370                 375                 380

Gln Ile Ala Gly Glu Pro Gln Gly Met Leu Lys Ile Leu Phe His Arg
385                 390                 395                 400

Glu Thr Leu Glu Val Leu Gly Val His Cys Phe Gly Tyr Gln Ala Ser
                405                 410                 415

Glu Ile Val His Ile Gly Gln Ala Ile Met Asn Gln Pro Gly Glu Gln
            420                 425                 430

Asn Thr Leu Lys Tyr Phe Val Asn Thr Thr Phe Asn Tyr Pro Thr Met
        435                 440                 445

Ala Glu Ala Tyr Arg Val Ala Ala Tyr Asp Gly Leu Asn Arg Leu Phe
    450                 455                 460
```